US008697360B2

(12) United States Patent
Thorlacius et al.

(10) Patent No.: US 8,697,360 B2
(45) Date of Patent: Apr. 15, 2014

(54) GENETIC VARIANTS ON CHR 11Q AND 6Q AS MARKERS FOR PROSTATE AND COLORECTAL CANCER PREDISPOSITION

(75) Inventors: Steinunn Thorlacius, Reykjavik (IS); Patrick Sulem, Reyjavik (IS); Julius Gudmundsson, Reyjavik (IS)

(73) Assignee: deCODE Genetics ehf., Reykjavík (IS)

( * ) Notice: Subject to any disclaimer, the term of this patent is extended or adjusted under 35 U.S.C. 154(b) by 446 days.

(21) Appl. No.: 12/315,114

(22) Filed: Nov. 26, 2008

(65) Prior Publication Data
US 2011/0053281 A1  Mar. 3, 2011

(30) Foreign Application Priority Data

Nov. 30, 2007  (IS) .............................................. 8696

(51) Int. Cl.
*C12Q 1/68* (2006.01)
(52) U.S. Cl.
CPC ........ *C12Q 1/6886* (2013.01); *C12Q 2600/156* (2013.01)
USPC ...................................................... 435/6.11
(58) Field of Classification Search
None
See application file for complete search history.

(56) References Cited

U.S. PATENT DOCUMENTS

| | | | |
|---|---|---|---|
| 4,376,110 A | 3/1983 | David et al. | |
| 4,851,330 A | 7/1989 | Kohne | |
| 5,223,409 A | 6/1993 | Ladner et al. | |
| 5,288,611 A | 2/1994 | Kohne | |
| 5,288,644 A | 2/1994 | Beavis et al. | |
| 5,445,934 A | 8/1995 | Fodor et al. | |
| 5,700,637 A | 12/1997 | Southern | |
| 5,744,305 A | 4/1998 | Fodor et al. | |
| 5,945,334 A | 8/1999 | Besemer et al. | |
| 6,054,270 A | 4/2000 | Southern | |
| 6,300,063 B1 | 10/2001 | Lipshutz et al. | |
| 6,429,027 B1 | 8/2002 | Chee et al. | |
| 6,733,977 B2 | 5/2004 | Besemer et al. | |
| 6,858,394 B1 | 2/2005 | Chee et al. | |
| 6,872,533 B2 * | 3/2005 | Toland et al. ................. | 435/6.17 |
| 7,364,858 B2 | 4/2008 | Barany et al. | |
| 2009/0317799 A1 | 12/2009 | Amundadottir et al. | |
| 2010/0041037 A1 | 2/2010 | Gudmundsson et al. | |
| 2010/0129799 A1 | 5/2010 | Guomundsson et al. | |

FOREIGN PATENT DOCUMENTS

| | | |
|---|---|---|
| EP | 0 373 293 | 6/1990 |
| EP | 0 619 321 | 1/1999 |
| WO | WO 90/02809 | 3/1990 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 93/01288 | 1/1993 |
| WO | WO 93/22456 | 11/1993 |
| WO | WO-2006/123369 A1 | 11/2006 |
| WO | WO-2008/050356 A1 | 5/2008 |
| WO | WO-2008/096375 A2 | 8/2008 |

OTHER PUBLICATIONS

Andiappan (BMC Genetics. 2010. 11: 36).*
International HapMap project, Showing 100 kbp from chr11, positions 68714690 to 68814689, printed from http://hapmap.ncbi.nlm.nih.gov/cgi-perl/gbrowse/hapmap27_B36/ on Aug. 24, 2011. eight pages.*
Sotos et al. Statistics Education Research Journal Nov. 2009, 8(2):33-55.*
Terwilliger and Hiekkalinna European Journal of Human Genetics (2006) 14, 426-437. doi:10.1038/sj.ejhg.5201583; published online Feb. 15, 2006.*
Langdahl (Journal of Bone and Mineral Research 2000 vol. 15, No. 3, pp. 402-414).*
Wall (Nature Reviews Genetics (2003) vol. 4, pp. 587-597).*
NCBI dbSNP database record ss18943924. Obtained from http://www.ncbi.nlm.nih.gov/projects/SNP/snp_ss.cgi?subsnp_id=18943924 on Jun. 12, 2012. seven pages.*
Jemal A., et al., "Cancer Statistics, 2002," *CA Cancer J. Clin.* 52:23-47 (Jan. 2002).
Peschel, R.E. and J.W. Colberg, "Surgery, Brachytherapy, and External-Beam Radiotherapy for Early Prostate Cancer," *Lancet*, 4:233-241 (Apr. 2003).
Nelson, W.G., et al., "Mechanisms of Disease: Prostate Cancer," *N. Engl. J. Med.*, 349(4):366-381 (Jul. 2003).
Simard, J., et al., "Perspective: Prostate Cancer Susceptibility Genes," *Endocrinology*, 143(6):2029-2040 (Jun. 2002).
Lichtenstein, P., et al., "Environmental and Heritable Factors in the Causation of Cancer—Analyses of Cohorts of Twins from Sweden, Denmark, and Finland," *N. Engl. J. Med.*, 343(2):78-85 (Jul. 2000).
Amundadottir, et al., "Cancer as a Complex Phenotype: Pattern of Cancer Distribution Within and Beyond the Nuclear Family," *PLoS Medicine*, 1(3):e65 (Dec. 2004).
Ries, L.A.G., et al., "Cancer Incidence and Survival Among Children and Adolescents: United States Seer Program 1975-1995," *NIH Pub.* No. 99-4649 (1999) (month not available).
Punglia, et al. "Effect of Verification Bias on Screening for Prostate Cancer by Measurement of Prostate-Specific Antigen," *N. Engl. J. Med.*, 349(4):335-342 (Jul. 2003).
Cookson, M.S., "Prostate Cancer: Screening and Early Detection," *Cancer Control*, 8(2):133-140 (Mar. 2001).
Thompson, I.M., et al., "Prevalence of Prostate Cancer among Men with a Prostate-Specific Antigen Level 4.0 ng per Milliliter," *N. Engl. J. Med.*, 350:2239-2246 (May 2004).

(Continued)

*Primary Examiner* — Juliet Switzer
(74) *Attorney, Agent, or Firm* — Marshall, Gerstein & Borun LLP

(57) ABSTRACT

It has been discovered that certain polymorphic markers on chromosome 6 and chromosome 11 are indicative of a susceptibility to prostate cancer and colon cancer. The invention describes diagnostic applications for determining a susceptibility to cancer using such markers, as well as kits for use in such applications.

35 Claims, 1 Drawing Sheet

(56) References Cited

OTHER PUBLICATIONS

Mistry, K.J., "Meta-Analysis of Prostate-Specific Antigen and Digital Rectal Examination as Screening Tests for Prostate Carcinoma," *Am. Board Fam. Pract.*, 16(2):95-101 (Mar. 2003).
Nwosu, V., et al., "Population Genomics: a Bridge From Evolutionary History to Genetic Medicine," *Hum. Mol. Genet.*, 10(20):2313-2318 (Oct. 2001).
Ostrander, E.A. and J.L. Stanford, "Genetics of Prostate Cancer: Too Many Loci, Too Few Genes," *Am. J. Hum. Genet.*, 67:1367-1375 (Dec. 2000).
Actane Consortium, "Results of a Genome-Wide Linkage Analysis in Prostate Cancer Families Ascertained Through the Actane Consortium," *Prostate*, 1;57(4) 270-279 (Jul. 2003).
Carpten, J., et al., "Germline Mutations in the Ribonuclease L Gene in Families Showing Linkage With HPC1," *Nat. Genet.*, 30:181-184 (Jan. 2002).
Casey, G., et al., "RNASEL Arg462Gln Variant Is Implicated in up to 13% of Prostate Cancer Cases," *Nat. Genet.*, 32(4)-581-583 (Dec. 2002).
Rokman, A., et al., "Germline Alterations of the RNASEL Gene, a Candidate HPC1 Gene at 1q25, in Patients and Families with Prostate Cancer," *Am. J. Hum. Genet.*, 70:1299-1304 (May 2002).
Rennert, H., et al., "A Novel Founder Mutation in the RNASEL Gene, 471delAAAG, Is Associated with Prostate Cancer in Ashkenazi Jews," *Am. J. Hum. Genet.*, 71:981-984 (Oct. 2002).
Stanford, J.L., "Association of HPC2/ELAC2 Polymorphisms with Risk of Prostate Cancer in a Population-based Study," *Cancer Epidemiol. Biomarkers Prev.*, 12(9):876-881 (Sep. 2003).
Wang, L., et al., "Analysis of the RNASEL Gene in Familial and Sporadic Prostate Cancer," *Am. J. Hum. Genet.*, 71:116-123 (Jul. 2002).
Wiklund, F., et al., "Genetic Analysis of the RNASEL Gene in Hereditary, Familial, and Sporadic Prostate Cancer," *Clin. Cancer Res.*, 10(21):7150-7156 (Nov. 2004).
Maier, C., et al., "Mutation Screening and Association Study of RNASEL As a Prostate Cancer Susceptibility Gene," *Br. J. Cancer,* 92(6):1159-1164 (Mar. 2005).
Xu, J., et al., "Germline Mutations and Sequence Variants of the Macrophage Scavenger Receptor 1 Gene are Associated With Prostate Cancer Risk," *Nat. Genet.*, 32:321-325 (Oct. 2002).
Lindmark, F., et al., "Analysis of the Macrophage Scavenger Receptor 1 Gene in Swedish Hereditary and Sporadic Prostate Cancer ," *Prostate*, 59(2):132-140 (2004) (month not available).
Seppala, E.H., et al., "Germ-Line Alterations in MSR1 Gene and Prostate Cancer Risk," *Clin. Cancer Res.*, 9(14):5252-5256 (Nov. 2003).
Wang, L., et al., "No Association of Germline Alteration of MSR1 With Prostate Cancer Risk," *Nat. Genet.*, 35(2):128-129 (Oct. 2003).
Miller, D.C., et al., "Germ-line Mutations of the Macrophage Scavenger Receptor 1 Gene: Association with Prostate Cancer Risk in African-American Men," *Cancer Res.*, 63(13):3486-3489 (Jul. 2003).
Tavtigian, S.V., et al., "A Candidate Prostate Cancer Susceptibility Gene at Chromosome 17p," *Nat. Genet.*, 27(2):172-180 (Feb. 2001).
Rebbeck, T.R., et al., "Association of HPC2/ELAC2 Genotypes and Prostate Cancer," *Am. J. Hum. Genet.*, 67(4):1014-1019 (Oct. 2000).
Wang, L., et al., "Role of HPC2/ELAC2 in Hereditary Prostate Cancer," *Cancer Res.*, 61(17):6494-6499 (Sep. 2001).
Vesprini, D., et al., "HPC2 Variants and Screen-Detected Prostate Cancer," *Am. J. Hum. Genet.*, 68(4):912-917 (Apr. 2001).
Shea, P.R., et al., "ELAC2 and Prostate Cancer Risk in Afro-Caribbeans of Tobago," *Hum. Genet.*, 111(4-5):398-400 (Jul. 2002).
Suarez, B.K., et al., "Polymorphisms in the Prostate Cancer Susceptibility Gene HPC2/ELAC2 in Multiplex Families and Healthy Controls," *Cancer Res.* 61(13):4982-4984 (Jul. 2001).
Severi, G., et al., "ELAC2/HPC2 Polymorphisms, Prostate-Specific Antigen Levels, and Prostate Cancer," *J. Natl. Cancer Inst.*, 95(11):818-824 (Jun. 2003).
Fujiwara, H., et al., "Association of Common Missense Changes in ELAC2 (HPC2) With Prostate Cancer in a Japanese Case-Control Series," *J. Hum. Genet.*, 47(12):641-648 (Oct. 2002).
Camp, N.J., et al., "Meta-Analysis of Associations of the Ser217Leu and Ala541Thr Variants in ELAC2 (HPC2) and Prostate Cancer," *Am. J. Hum. Genet.*, 71(6):1475-1478 (Dec. 2002).
Chang, B., et al, "Linkage and Association of CYP17 Gene in Hereditary and Sporadic Prostate Cancer," *Int. J. Cancer,* 95:354-359 (Jun. 2001).
Makridakis, N.M., et al., "Association of Mis-Sense Substitution in SRD5A2 Gene with Prostate Cancer in African-American and Hispanic Men in Los Angeles, USA," *Lancet*, 354:975-978 (Sep. 1999).
Nam, R.K., et al., "V89L Polymorphism of the Type-2, 5-Alpha Reductase Enzyme Gene (SRD5A2) Predicts Prostate Cancer Development and Progression," *Urology,* 57:199-204 (Jan. 2001).
Amundadottir, L.T., "A Common Variant Associated With Prostate Cancer in European and African Populations," *Nature Genet.*, 38(6):652-658 (Jun. 2006).
Parkin, D.M., et al., "Global cancer statistics, 2002," *CA Cancer J. Clin.*, 55:74-108 (Mar. 2005).
Jemal, A., et al., "Cancer Statistics, 2006," *CA Cancer J. Clin.*, 56:106-130 (Mar. 2006).
Peto, J., and T.M. Mack, "High Constant Incidence in Twins and Other Relatives of Women With Breast Cancer," *Nat. Genet.*, 26:411-414 (Dec. 2000).
Risch, N., "The Genetic Epidemiology of Cancer: Interpreting Family and Twin Studies and Their Implications for Molecular Genetic Approaches," *Cancer Epidemiol Biomarkers Prev.*, 10:733-741 (Jul. 2001).
de la Chapelle, A., "The Incidence of Lynch Syndrome," *Fam Cancer,* 4:233-237 (2005) (month not available).
Latil, A., et al., "Oncogene Amplifications in Early-Stage Human Prostate Carcinomas," *Int. J. Cancer,* 59(5):637-638 (Dec. 1994).
El Gedaily, A., et al., "Discovery of New DNA Amplification Loci in Prostate Cancer by Comparative Genomic Hybridization," *Prostate,* 46(3):184-190 (Feb. 2001).
Paris, P.L., et al., "Whole Genome Scanning Identifies Genotypes Associated with Recurrence and Metastasis in Prostate Tumors," *Hum. Mol. Genet.*, 13(13):1303-1313 (May 2004).
Kasahara, K., et al., "Genetic Changes in Localized Prostate Cancer of Japanese Patients Shown by Comparative Genomic Hybridization," *Cancer Genet. Cytogenet.*, 159(1):84-88 (May 2005).
Das, K., et al., "Chromosomal Changes in Prostate Cancer: a Fluorescence in situ Hybridization Study," *Clin. Genet.*, 68(1):40-47 (Mar. 2005).
Paris, P.L., et al., "An Oncogenic Role for the Multiple Endocrine Neoplasia Type 1 Gene in Prostate Cancer," *Prostate Cancer Prostatic Dis.*, [Epub ahead of print] (Sep. 2008).
Kobayashi, M., et al., "Molecular Analysis of Multifocal Prostate Cancer by Comparative Genomic Hybridization," *Prostate,* 68(16):1715-1724 (Dec. 2008).
Dong, X.Y., et al., "SnoRNA U50 is a Candidate Tumor-Suppressor Gene at 6q14.3 With a Mutation Associated With Clinically Significant Prostate Cancer," *Hum. Mol. Genet.*, 17(7):1031-1042 (Epub Jan. 2008).
Verhagen, P.C., "Deletion of Chromosomal Region 6q14-16 in Prostate Cancer," *Int. J. Cancer,* 102(2):142-147 (Nov. 2002).
Bläker, H., et al., "Recurrent Deletions at 6q in Early Age of Onset Non-HNPCC- and Non-FAP-Associated Intestinal Carcinomas. Evidence for a Novel Cancer Susceptibility Locus at 6q14-q22," *Genes Chromosomes Cancer,* 47(2):159-164 (Feb. 2008).
Nakao, M., et al., "Identification of DNA Copy Number Aberrations Associated With Metastases of Colorectal Cancer Using Array CGH Profiles," *Cancer Genet. Cytogenet..*, 188(2):70-76 (Jan. 2009).
Song, H., et al., "Association Study of Prostate Cancer Susceptibility Variants With Risks of Invasive Ovarian, Breast, and Colorectal Cancer," *Cancer Res.*, 68(21):8837-8842 (Nov. 2008).
"A Catalog of Published Genome-Wide Association Studies," National Human Genome Research Institute, summary page, published/maintained at http://www.genome.gov/gwastudies/ (printed Feb. 12, 2013).
"Genetic Information and Voluntary Life Insurance," Issue Brief: American Academy of Actuators, (1998).

(56) References Cited

OTHER PUBLICATIONS

"Good Laboratory Practices for Molecular Genetic Testing for Heritable Diseases and Conditions," Morbidity and Mortality Weekly Report, vol. 58, No. RR-6, Department of Health and Human Services Centers for Disease Control and Prevention (Jun. 12, 2009).
Altshuler et al., "Guilt Beyond a Reasonable Doubt," *Nature Genet.*, 39:813-815 (2007).
Barrett et al., "Haploview: Analysis and Visualization of LD and Haplotype Maps," *Bioinformatics*, 21(2):263-265 (2005).
Bitton et al., "The Framingham Heart Study's Impact on Global Risk," *Prog Cardiovasc Dis.*, 53(1):68-78 (2010).
Bowcock, "Guild by Association," *Nature*, 447:645-646 (2007).
Breyer et al., "Genetic Variants and Prostate Cancer Risk: Candidate Replication and Exploration of Viral Restriction Genes," *Cancer Epidemiol Biomarkers Prev*, 18:2137-2144 (2009).
Easton et al., "Genome-Wide Association Study Identifies Novel Breast Cancer Susceptibility Loci," *Nature*, 447:1087-1093 (2007).
Frayling et al., "A Common Variant in the *FTO* Gene is Associated with Body Mass Index and Predisposes to Childhood and Adult Obesity," *Science*, 316:889-894 (2007).
Frayling, "Genome-Wide Association Studies Provide New Insights into Type 2 Diabetes Aetiology," *Nature Reviews Genet.*, 8:657-662 (2007).
Grys et al., "Actuarial Considerations on Genetic Testing," *Phil. Trans. R. Soc. Lond. B*, 352:1057-1061 (1997).
Gudmundsson et al., "Genome-Wide Association Study Identifies a Second Prostate Cancer Susceptibility Variant at 8q24," *Nat. Gen.*, 39:631-637 (2007).
Haiman et al., "Multiple Regions within 8q24 Independently Affect Risk for Prostate Cancer," *Nat. Genet.*, 39(5):638-644 (2007).
Hunter et al., "A Genome-Wide Association Study Identifies Alleles in *FGFR2* Associated with Risk of Sporadic Postmenopausal Breast Cancer," *Nat. Genet.*, 39:870-874 (2007).
Kingsmore et al., "Genome-Wide Association Studies: Progress and Potential for Drug Discovery and Development," *Nature Reviews Genet.*, 7:221-230 (2008).
Klein et al., "Complement Factor H Polymorphism in Age-Related Macular Degeneration," *Science*, 308:385-389 (2005).
McGuire et al., "Association of Prostate Cancer Risk Alleles with Unfabourable Pathological Characteristics in Potential Candidates for Active Surveillance," *BJU Internatoinal*, 110:338-343 (2011).
Summary of Build Statistics for NCBI dbSNP Short Genetic Variations, published at http://www.ncbi.nlm.nih.gov/SNP/snp_summary.cgi (printed Feb. 12, 2013).
Pearson et al., "How to Interpret a Genome-Wide Association Study," *JAMA*, 299(11):1335-1344 (2008).
Saxena et al., "Genome-Wide Association Analysis Identifies Loci for Type 2 Diabetes and Triglyceride Levels," *Science*, 316:1331-1336 (2007).
Silberberg, Chemistry: The Molecular Nature of Matter and Changes, Fourth Edition, pp. G-12, McGraw Hill Co. (2006).
Spencer et al., "Designing Genome-Wide Association Studies: Sample Size, Power, Imputation, and the Choice of Genotyping Chip," *PLoS Genet.*, 5(5):1-13 (2009).
Stacey et al., "Common Variants on Chromosomes 2q35 and 16q12 Confer Susceptibility to Estrogen Receptor-Positive Breast Cancer," *Nat. Genet.*, 39:865-869 (2007).
Sulem et al., "Identification of Low-Frequency Variants Associated with Gout and Serum Uric Acid Levels," *Nature Genet.*, 43(11):1127-1131 (2011).
The International HapMap Consortium, "A Haplotype Map of the Human Genome," *Nature*, 437:1299-1320 (2005).
Witte, "Multiple Prostate Cancer Risk Variants on 8q24," *Nat. Genet.*, 39(5):579-580 (2007).
Yeager et al., "Genome-Wide Association Study of Prostate Cancer Identifies a Second Risk Locus at 8q24," *Nat. Gen.*, 39:645-649 (2007).
Zick et al., "Genetic Testing for Alzheimer's Disease and its Impact on Insurance Purchasing Behavior," *Health Affairs*, 24(2):483-490 (2005).

\* cited by examiner

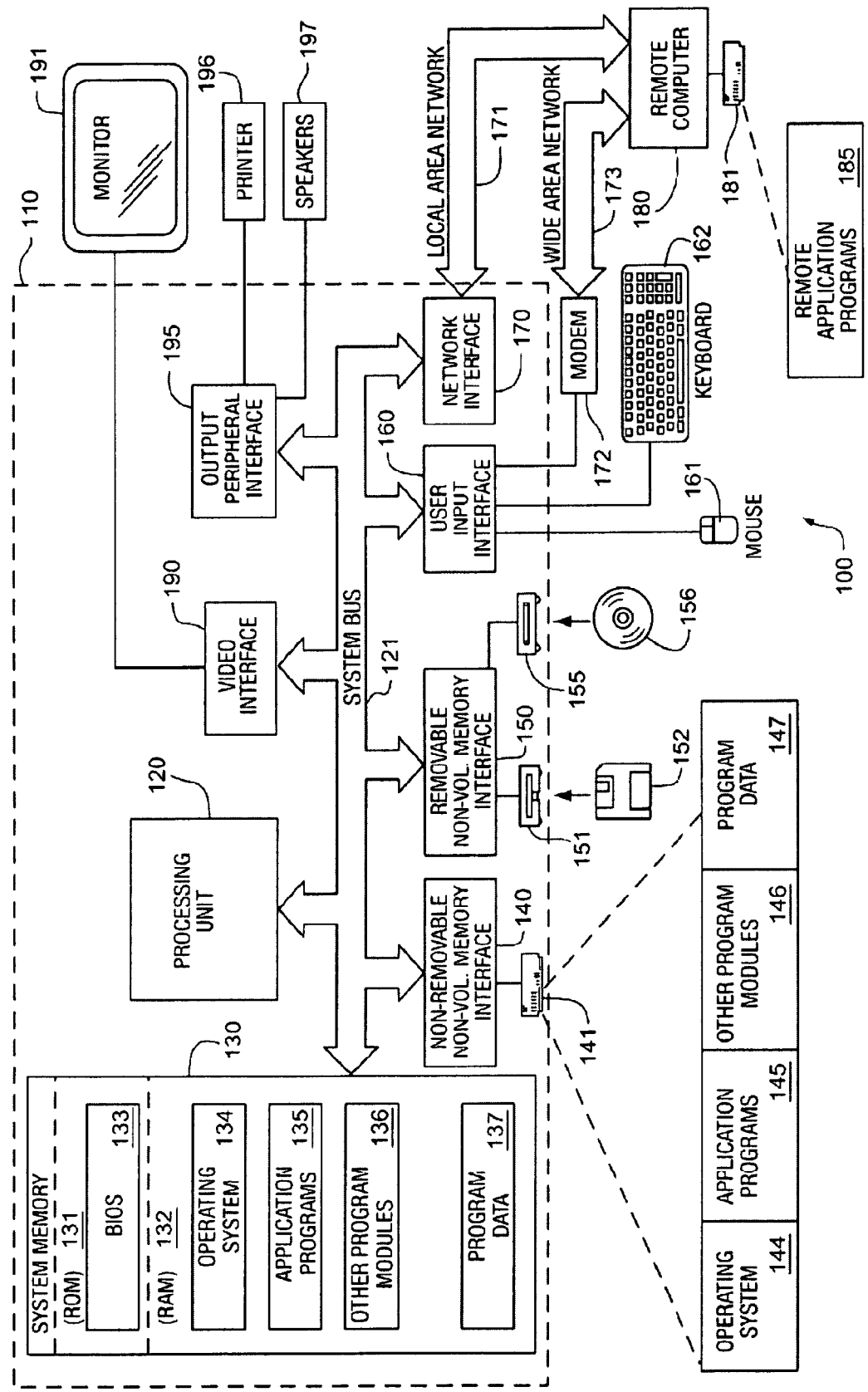

GENETIC VARIANTS ON CHR 11Q AND 6Q AS MARKERS FOR PROSTATE AND COLORECTAL CANCER PREDISPOSITION

RELATED APPLICATION

This application claims priority under 35 U.S.C. §119 or 365 to Iceland, Application No. 8696, filed Nov. 30, 2007. The entire teachings of the above application are incorporated herein by reference.

BACKGROUND OF THE INVENTION

Cancer, the uncontrolled growth of malignant cells, is a major health problem of the modern medical era and is one of the leading causes of death in developed countries. In the United States, one in four deaths is caused by cancer (Jemal, A. et al., *CA Cancer J. Clin.* 52:23-47 (2002)).

The incidence of prostate cancer has dramatically increased over the last decades and prostate cancer is now a leading cause of death in the United States and Western Europe (Peschel, R. E. and J. W. Colberg, *Lancet* 4:233-41 (2003); Nelson, W. G. et al., *N. Engl. J. Med.* 349(4):366-81 (2003)). Prostate cancer is the most frequently diagnosed noncutaneous malignancy among men in industrialized countries, and in the United States, 1 in 8 men will develop prostate cancer during his life (Simard, J. et al., *Endocrinology* 143(6):2029-40 (2002)). Although environmental factors, such as dietary factors and lifestyle-related factors, contribute to the risk of prostate cancer, genetic factors have also been shown to play an important role. Indeed, a positive family history is among the strongest epidemiological risk factors for prostate cancer, and twin studies comparing the concordant occurrence of prostate cancer in monozygotic twins have consistently revealed a stronger hereditary component in the risk of prostate cancer than in any other type of cancer (Nelson, W. G. et al., *N. Engl. J. Med.* 349(4):366-81 (2003); Lichtenstein P. et. al., *N. Engl. J. Med.* 343(2):78-85 (2000)). In addition, an increased risk of prostate cancer is seen in $1^{st}$ to $5^{th}$ degree relatives of prostate cancer cases in a nation wide study on the familiality of all cancer cases diagnosed in Iceland from 1955-2003 (Amundadottir et. al., *PLoS Medicine* 1(3):e65 (2004)). The genetic basis for this disease, emphasized by the increased risk among relatives, is further supported by studies of prostate cancer among particular populations: for example, African Americans have among the highest incidence of prostate cancer and mortality rate attributable to this disease: they are 1.6 times as likely to develop prostate cancer and 2.4 times as likely to die from this disease than European Americans (Ries, L. A. G. et al., *NIH Pub. No.* 99-4649 (1999)).

An average 40% reduction in life expectancy affects males with prostate cancer. If detected early, prior to metastasis and local spread beyond the capsule, prostate cancer can be cured (e.g., using surgery). However, if diagnosed after spread and metastasis from the prostate, prostate cancer is typically a fatal disease with low cure rates. While prostate-specific antigen (PSA)-based screening has aided early diagnosis of prostate cancer, it is neither highly sensitive nor specific (Punglia et. al., *N Engl J Med.* 349(4):335-42 (2003)). This means that a high percentage of false negative and false positive diagnoses are associated with the test. The consequences are both many instances of missed cancers and unnecessary follow-up biopsies for those without cancer. As many as 65 to 85% of individuals (depending on age) with prostate cancer have a PSA value less than or equal to 4.0 ng/mL, which has traditionally been used as the upper limit for a normal PSA level (Punglia et. al., *N Engl J Med.* 349(4):335-42 (2003); Cookston, M. S., *Cancer Control* 8(2):133-40 (2001); Thompson, I. M. et. al., *N Engl J Med.* 350:2239-46 (2004)). A significant fraction of those cancers with low PSA levels are scored as Gleason grade 7 or higher, which is a measure of an aggressive prostate cancer.

In addition to the sensitivity problem outlined above, PSA testing also has difficulty with specificity and predicting prognosis. PSA levels can be abnormal in those without prostate cancer. For example, benign prostatic hyperplasia (BPH) is one common cause of a false-positive PSA test. In addition, a variety of noncancer conditions may elevate serum PSA levels, including urinary retention, prostatitis, vigorous prostate massage and ejaculation.

Subsequent confirmation of prostate cancer using needle biopsy in patients with positive PSA levels is difficult if the tumor is too small to see by ultrasound. Multiple random samples are typically taken but diagnosis of prostate cancer may be missed because of the sampling of only small amounts of tissue. Digital rectal examination (DRE) also misses many cancers because only the posterior lobe of the prostate is examined. As early cancers are nonpalpable, cancers detected by DRE may already have spread outside the prostate (Mistry K. J., *Am. Board Fam. Pract.* 16(2):95-101 (2003)).

Thus, there is clearly a great need for improved diagnostic procedures that would facilitate early-stage prostate cancer detection and prognosis, as well as aid in preventive and curative treatments of the disease. In addition, there is a need to develop tools to better identify those patients who are more likely to have aggressive forms of prostate cancer from those patients that are more likely to have more benign forms of prostate cancer that remain localized within the prostate and do not contribute significantly to morbidity or mortality. This would help to avoid invasive and costly procedures for patients not at significant risk.

The incidence of prostate cancer has dramatically increased over the last decades. Prostate cancer is a multifactorial disease with genetic and environmental components involved in its etiology. It is characterized by heterogeneous growth patterns that range from slow growing tumors to very rapid highly metastatic lesions.

Although genetic factors are among the strongest epidemiological risk factors for prostate cancer, the search for genetic determinants involved in the disease has been challenging. Studies have revealed that linking candidate genetic markers to prostate cancer has been more difficult than identifying susceptibility genes for other cancers, such as breast, ovary and colorectal cancer. Several reasons have been proposed for this increased difficulty including: the fact that prostate cancer is often diagnosed at a late age thereby often making it difficult to obtain DNA samples from living affected individuals for more than one generation; the presence within high-risk pedigrees of phenocopies that are associated with a lack of distinguishing features between hereditary and sporadic forms; and the genetic heterogeneity of prostate cancer and the accompanying difficulty of developing appropriate statistical transmission models for this complex disease (Simard, J. et al., *Endocrinology* 143(6):2029-40 (2002)).

Various genome scans for prostate cancer-susceptibility genes have been conducted and several prostate cancer susceptibility loci have been reported. For example, HPC1 (1q24-q25), PCAP (1q42-q43), HCPX (Xq27-q28), CAPB (1p36), HPC20 (20q13), HPC2/ELAC2 (17p11) and 16q23 have been proposed as prostate cancer susceptibility loci (Simard, J. et al., *Endocrinology* 143(6):2029-40 (2002); Nwosu, V. et al., *Hum. Mol. Genet.* 10(20):2313-18 (2001)).

In a genome scan conducted by Smith et al., the strongest evidence for linkage was at HPC1, although two-point analysis also revealed a LOD score of ≥1.5 at D4S430 and LOD scores ≥1.0 at several loci, including markers at Xq27-28 (Ostrander E. A. and J. L. Stanford, *Am. J. Hum. Genet.* 67:1367-75 (2000)). In other genome scans, two-point LOD scores of ≥1.5 for chromosomes 10q, 12q and 14q using an autosomal dominant model of inheritance, and chromosomes 1q, 8q, 10q and 16p using a recessive model of inheritance, have been reported, as well as nominal evidence for linkage to chr 2q, 12p, 15q, 16q and 16p. A genome scan for prostate cancer predisposition loci using a small set of Utah high risk prostate cancer pedigrees and a set of 300 polymorphic markers provided evidence for linkage to a locus on chromosome 17p (Simard, J. et al., *Endocrinology* 143(6):2029-40 (2002)). Eight new linkage analyses were published in late 2003, which depicted remarkable heterogeneity. Eleven peaks with LOD scores higher than 2.0 were reported, none of which overlapped (see Actane consortium, Schleutker et. al., Wiklund et. al., Witte et. al., Janer Xu et. al., Lange et. al., Cunningham et al.; all of which appear in *Prostate*, vol. 57 (2003)).

As described above, identification of particular genes involved in prostate cancer has been challenging. One gene that has been implicated is RNASEL, which encodes a widely expressed latent endoribonuclease that participates in an interferon-inducible RNA-decay pathway believed to degrade viral and cellular RNA, and has been linked to the HPC locus (Carpten, J. et al., *Nat. Genet.* 30:181-84 (2002); Casey, G. et al., *Nat. Genet.* 32(4):581-83 (2002)). Mutations in RNASEL have been associated with increased susceptibility to prostate cancer. For example, in one family, four brothers with prostate cancer carried a disabling mutation in RNASEL, while in another family, four of six brothers with prostate cancer carried a base substitution affecting the initiator methionine codon of RNASEL. Other studies have revealed mutant RNASEL alleles associated with an increased risk of prostate cancer in Finnish men with familial prostate cancer and an Ashkenazi Jewish population (Rokman, A. et al., *Am J. Hum. Genet.* 70:1299-1304 (2002); Rennert, H. et al., *Am J. Hum. Genet.* 71:981-84 (2002)). In addition, the Ser217Leu genotype has been proposed to account for approximately 9% of all sporadic cases in Caucasian Americans younger than 65 years (Stanford, J. L., *Cancer Epidemiol. Biomarkers Prev.* 12(9):876-81 (2003)). In contrast to these positive reports, however, some studies have failed to detect any association between RNASEL alleles with inactivating mutations and prostate cancer (Wang, L. et al., *Am. J. Hum. Genet.* 71:116-23 (2002); Wiklund, F. et al., *Clin. Cancer Res.* 10(21):7150-56 (2004); Maier, C. et. al., *Br. J. Cancer* 92(6):1159-64 (2005)).

The macrophage-scavenger receptor 1 (MSR1) gene, which is located at 8p22, has also been identified as a candidate prostate cancer-susceptibility gene (Xu, J. et al., *Nat. Genet.* 32:321-25 (2002)). A mutant MSR1 allele was detected in approximately 3% of men with nonhereditary prostate cancer but only 0.4% of unaffected men. However, not all subsequent reports have confirmed these initial findings (see, e.g., Lindmark, F. et al., *Prostate* 59(2):132-40 (2004); Seppala, E. H. et al., *Clin. Cancer Res.* 9(14):5252-56 (2003); Wang, L. et al., *Nat. Genet.* 35(2):128-29 (2003); Miller, D. C. et al., *Cancer Res.* 63(13):3486-89 (2003)). MSR1 encodes subunits of a macrophage-scavenger receptor that is capable of binding a variety of ligands, including bacterial lipopolysaccharide and lipoteicholic acid, and oxidized high-density lipoprotein and low-density lipoprotein in serum (Nelson, W. G. et al., *N. Engl. J. Med.* 349(4):366-81 (2003)).

The ELAC2 gene on Chr17p was the first prostate cancer susceptibility gene to be cloned in high risk prostate cancer families from Utah (Tavtigian, S. V., et al., *Nat. Genet.* 27(2): 172-80 (2001)). A frameshift mutation (1641InsG) was found in one pedigree. Three additional missense changes: Ser217Leu; Ala541Thr; and Arg781His, were also found to associate with an increased risk of prostate cancer. The relative risk of prostate cancer in men carrying both Ser217Leu and Ala541Thr was found to be 2.37 in a cohort not selected on the basis of family history of prostate cancer (Rebbeck, T. R., et al., *Am. J. Hum. Genet.* 67(4):1014-19 (2000)). Another study described a new termination mutation (Glu216X) in one high incidence prostate cancer family (Wang, L., et al., *Cancer Res.* 61(17):6494-99 (2001)). Other reports have not demonstrated strong association with the three missense mutations, and a recent metaanalysis suggests that the familial risk associated with these mutations is more moderate than was indicated in initial reports (Vesprini, D., et al., *Am. J. Hum. Genet.* 68(4):912-17 (2001); Shea, P. R., et al., *Hum. Genet.* 111(4-5):398-400 (2002); Suarez, B. K, et al., *Cancer Res.* 61(13):4982-84 (2001); Severi, G., et al., *J. Natl. Cancer Inst.* 95(11):818-24 (2003); Fujiwara, H., et al., *J. Hum. Genet.* 47(12):641-48 (2002); Camp, N. J., et al., *Am. J. Hum. Genet.* 71(6):1475-78 (2002)).

Polymorphic variants of genes involved in androgen action (e.g., the androgen receptor (AR) gene, the cytochrome P-450c17 (CYP17) gene, and the steroid-5-α-reductase type II (SRD5A2) gene), have also been implicated in increased risk of prostate cancer (Nelson, W. G. et al., *N. Engl. J. Med.* 349(4):366-81 (2003)). With respect to AR, which encodes the androgen receptor, several genetic epidemiological studies have shown a correlation between an increased risk of prostate cancer and the presence of short androgen-receptor polyglutamine repeats, while other studies have failed to detect such a correlation. Linkage data has also implicated an allelic form of CYP17, an enzyme that catalyzes key reactions in sex-steroid biosynthesis, with prostate cancer (Chang, B. et al., *Int. J. Cancer* 95:354-59 (2001)). Allelic variants of SRD5A2, which encodes the predominant isozyme of 5-α-reductase in the prostate and functions to convert testosterone to the more potent dihydrotestosterone, have been associated with an increased risk of prostate cancer and with a poor prognosis for men with prostate cancer (Makridakis, N. M. et al., *Lancet* 354:975-78 (1999); Nam, R. K. et al., *Urology* 57:199-204 (2001)).

In short, despite the effort of many groups around the world, the genes that account for a substantial fraction of prostate cancer risk have not been identified. Although twin studies have implied that genetic factors are likely to be prominent in prostate cancer, only a handful of genes have been identified as being associated with an increased risk for prostate cancer, and these genes account for only a low percentage of cases. Thus, it is clear that the majority of genetic risk factors for prostate cancer remain to be found. It is likely that these genetic risk factors will include a relatively high number of low-to-medium risk genetic variants. These low-to-medium risk genetic variants may, however, be responsible for a substantial fraction of prostate cancer, and their identification, therefore, a great benefit for public health. Furthermore, none of the published prostate cancer genes have been reported to predict a greater risk for aggressive prostate cancer than for less aggressive prostate cancer.

Extensive genealogical information for a population containing cancer patients has in a recent study been combined with powerful gene sharing methods to map a locus on chromosome 8q24.21, which has been demonstrated to play a major role in cancer. Various cancer patients and their relatives were genotyped with a genome-wide marker set including 1100 microsatellite markers, with an average marker density of 3-4 cM. (Amundadottir L. T., *Nature Genet.* 38(6): 652-658 (2006)). Association was detected to a single LD block within the locus between positions 128.414 and 128.506 Mb (NCBI build 34) in Utah CEPH HapMap samples.

Colorectal Cancer (CRC) is one of the most commonly diagnosed cancers and one of the leading causes of cancer mortality (Parkin D M, et. al. *CA Cancer J Clin,* 55:74-108 (2005)). Cancers of the colon and rectum accounted for about 1 million new cases in 2002 (9.4% of cancer cases worldwide) and it affects men and women almost equally. The average lifetime risk for an individual in the US to develop CRC is 6% (Jemal A, et al. CA Cancer J Clin., 56:106-30 (2006)). The prognosis is strongly associated with the stage of the disease at diagnosis; therefore, CRC screening presents an opportunity for early cancer detection and cancer prevention.

Colorectal cancer is a consequence of environmental exposures acting upon a background of genetically determined susceptibility. Studies indicate that 30-35% of colorectal cancer risk could be explained by genetic factors (Lichtenstein P, et. al. *N Engl J Med,* 343:78-85 (2000);) Peto J and Mack T M. *Nat Genet,* 26:411-4 (2000); Risch N. *Cancer Epidemiol Biomarkers Prev,* 10:733-41 (2001)). The analysis of cancer occurrence in relatives of cancer patients also lends strong evidence for genetic factors that increase the risk of cancer.

At present only a small percentage of the heritable risk of CRC is identified, usually through the investigation of rare cancer syndromes. High-penetrance mutations in several genes have been identified in rare hereditary colorectal cancer syndromes. The most common of these are the familial adenomatous polyposis (FAP) syndrome and hereditary non-polyposis colorectal cancer (HNPCC) or Lynch syndrome (LS). FAP, caused by mutations in the APC gene, is an autosomal dominant syndrome, characterized by early onset of multiple adenomatous polyps in the colon that eventually progress to cancer. LS is caused by mutations in DNA mismatch repair (MMR) genes and is considered to be the most common hereditary CRC syndrome, comprising approximately 3-5% of all CRCs (de la Chapelle, A. *Fam Cancer,* 4:233-7 (2005)).

The search for additional highly-penetrant CRC genes has not been fruitful and accumulating evidence supports the notion that no single susceptibility gene is likely to explain a large proportion of highly familial or early onset CRC. This has led to the currently favored hypothesis that most of the inherited CRC risk is due to multiple, low genetic risk variants. Each such variant would be expected to carry a small increase in risk; however, if the variant is common, it may contribute significantly to the population attributable risk (PAR).

SUMMARY OF THE INVENTION

The present invention relates to the use of polymorphic markers in diagnostic methods, kits and apparatus for determining susceptibility to prostate cancer and colorectal cancer.

In one aspect, the present invention relates to a method for determining a susceptibility to a cancer selected from prostate cancer and colorectal cancer in a human individual, comprising determining the presence or absence of at least one allele of at least one polymorphic marker in a nucleic acid sample obtained from the individual, or in a genotype dataset from the individual, wherein the at least one polymorphic marker is selected from markers selected from the group consisting of markers within LD Block C11 and LD Block C06, and wherein the presence of the at least one allele is indicative of a susceptibility to the cancer.

In another aspect, the present invention relates to a method for determining a susceptibility to a cancer selected from prostate cancer and colorectal cancer in a human individual, comprising determining the presence or absence of at least one allele of at least one polymorphic marker in a nucleic acid sample obtained from the individual, or in a genotype dataset from the individual, wherein the at least one polymorphic marker is selected from the group consisting of the markers set forth in Table 5 and Table 6, and markers in linkage disequilibirium therewith, and wherein the presence of the at least one allele is indicative of a susceptibility to the cancer. Determining a susceptibility comprises in one embodiment a diagnosis of a susceptibility. Diagnosis may be made by a medical professional, or other professional that provides information about disease risk. Alternatively, diagnosis of a susceptibility is provided by a genotype provider, or by an individual or organization that interprets genotype data for an individual or groups of individuals.

The genotype dataset comprises in one embodiment information about marker identity and the allelic status of the individual for at least one allele of a marker, i.e. information about the identity of at least one allele of the marker in the individual. The genotype dataset may comprise allelic information (information about allelic status) about one or more marker, including two or more markers, three or more markers, five or more markers, ten or more markers, one hundred or more markers, an so on. In some embodiments, the genotype dataset comprises genotype information from a whole-genome assessment of the individual, that may include hundreds of thousands of markers, or even one million or more markers spanning the entire genome of the individual.

Another aspect relates to a method of determining a susceptibility to a cancer selected from prostate cancer and colorectal cancer in a human individual, comprising determining whether at least one at-risk allele in at least one polymorphic marker is present in a genotype dataset derived from the individual, wherein the at least one polymorphic marker is selected from the group consisting of the markers set forth in Tables 5 and 6, and markers in linkage disequilibrium therewith, and wherein determination of the presence of the at least one at-risk allele is indicative of increased susceptibility to cancer.

Another aspect of the invention relates to a method of determining a susceptibility to prostate cancer, the method comprising: obtaining nucleic acid sequence data about a human individual identifying at least one allele of at least one polymorphic marker, wherein different alleles of the at least one polymorphic marker are associated with different susceptibilities to prostate cancer in humans, and determining a susceptibility to prostate cancer from the nucleic acid sequence data, wherein the at least one polymorphic marker is selected from the group consisting of rs10896450, and markers in linkage disequilibirium therewith.

In general, polymorphic genetic markers lead to alternate sequences at the nucleic acid level. If the nucleic acid marker changes the codon of a polypeptide encoded by the nucleic acid, then the marker will also result in alternate sequence at the amino acid level of the encoded polypeptide (polypeptide markers). Determination of the identity of particular alleles at polymorphic markers in a nucleic acid or particular alleles at polypeptide markers comprises whether particular alleles are present at a certain position in the sequence. Sequence data identifying a particular allele at a marker comprises sufficient sequence to detect the particular allele. For single nucleotide polymorphisms (SNPs) or amino acid polymorphisms described herein, sequence data can comprise sequence at a single position, i.e. the identity of a nucleotide or amino acid at a single position within a sequence. The sequence data can optionally include information about sequence flanking the polymorphic site, which in the case of SNPs spans a single nucleotide.

In certain embodiments, it may be useful to determine the nucleic acid sequence for at least two polymorphic markers. In other embodiments, the nucleic acid sequence for at least three, at least four or at least five or more polymorphic markers is determined. Haplotype information can be derived from an analysis of two or more polymorphic markers. Thus, in certain embodiments, a further step is performed, whereby haplotype information is derived based on sequence data for at least two polymorphic markers.

The invention also provides a method of determining a susceptibility to a cancer selected from prostate cancer and colorectal cancer in a human individual, the method comprising obtaining nucleic acid sequence data about a human individual identifying both alleles of at least two polymorphic markers selected from the markers listed in Table 3 and Table 4, and markers in linkage disequilibrium therewith, determine the identity of at least one haplotype based on the sequence data, and determine a susceptibility to the cancer from the haplotype data.

In certain embodiments, determination of a susceptibility comprises comparing the nucleic acid sequence data to a database containing correlation data between the at least one polymorphic marker and susceptibility to cancer. In some embodiments, the database comprises at least one risk measure of susceptibility to cancer for the at least one marker. The sequence database can for example be provided as a look-up table that contains data that indicates the susceptibility of cancer for any one, or a plurality of, particular polymorphisms. The database may also contain data that indicates the susceptibility for a particular haplotype that comprises at least two polymorphic markers.

Obtaining nucleic acid sequence data can in certain embodiments comprise obtaining a biological sample from the human individual and analyzing sequence of the at least one polymorphic marker in nucleic acid in the sample. Analyzing sequence can comprise determining the presence or absence of at least one allele of the at least one polymorphic marker. Determination of the presence of a particular susceptibility allele (e.g., an at-risk allele) is indicative of susceptibility to cancer in the human individual. Determination of the absence of a particular susceptibility allele is indicative that the particular susceptibility due to the at least one polymorphism is not present in the individual.

In some embodiments, obtaining nucleic acid sequence data comprises obtaining nucleic acid sequence information from a preexisting record. The preexisting record can for example be a computer file or database containing sequence data, such as genotype data, for the human individual, for at least one polymorphic marker.

Susceptibility determined by the diagnostic methods of the invention can be reported to a particular entity. In some embodiments, the at least one entity is selected from the group consisting of the individual, a guardian of the individual, a genetic service provider, a physician, a medical organization, and a medical insurer.

In certain embodiments, genetic markers associated with risk of prostate cancer and/or colorectal cancer as described herein are indicative of different response rates to particular treatment modalities for the cancer. Thus, in certain embodiments, the presence of the marker or haplotype is indicative of a different response rate of the subject to a particular treatment modality.

Another aspect of the invention relates to a method of identification of a marker for use in assessing susceptibility to prostate cancer, the method comprising identifying at least one polymorphic marker within LD Block C06 or LD Block C11, or at least one polymorphic marker in linkage disequilibrium therewith;

determining the genotype status of a sample of individuals diagnosed with, or having a susceptibility to, prostate cancer; and determining the genotype status of a sample of control individuals;

wherein a significant difference in frequency of at least one allele in at least one polymorphism in individuals diagnosed with, or having a susceptibility to, prostate cancer, as compared with the frequency of the at least one allele in the control sample is indicative of the at least one polymorphism being useful for assessing susceptibility to prostate cancer.

The invention also relates, in another aspect, to a method of identification of a marker for use in assessing susceptibility to colorectal cancer, the method comprising identifying at least one polymorphic marker within The LD Block C11 genomic region, or at least one polymorphic marker in linkage disequilibrium therewith;

determining the genotype status of a sample of individuals diagnosed with, or having a susceptibility to, colorectal cancer; and determining the genotype status of a sample of control individuals;

wherein a significant difference in frequency of at least one allele in at least one polymorphism in individuals diagnosed with, or having a susceptibility to, colorectal cancer, as compared with the frequency of the at least one allele in the control sample is indicative of the at least one polymorphism being useful for assessing susceptibility to colorectal cancer. In one embodiment, an increase in frequency of the at least one allele in the at least one polymorphism in individuals diagnosed with, or having a susceptibility to, the cancer, as compared with the frequency of the at least one allele in the control sample is indicative of the at least one polymorphism being useful for assessing increased susceptibility to the cancer. In another embodiment, a decrease in frequency of the at least one allele in the at least one polymorphism in individuals diagnosed with, or having a susceptibility to, the cancer, as compared with the frequency of the at least one allele in the control sample is indicative of the at least one polymorphism being useful for assessing decreased susceptibility to, or protection against, the cancer.

The invention, in another aspect, also relates to a method of genotyping a nucleic acid sample obtained from a human individual at risk for, or diagnosed with, a cancer selected from prostate cancer and colorectal cancer, comprising determining the presence or absence of at least one allele of at least one polymorphic marker in the sample, wherein the at least one marker is selected from the markers set forth in Table 3 and Table 4, and markers in linkage disequilibrium therewith, and wherein the presence of the at least one allele is indicative of a susceptibility to the cancer. In one embodiment, genotyping comprises amplifying a segment of a nucleic acid that comprises the at least one polymorphic marker by Polymerase Chain Reaction (PCR), using a nucleotide primer pair flanking the at least one polymorphic marker. In another embodiment, genotyping is performed using a process selected from allele-specific probe hybridization, allele-specific primer extension, allele-specific amplification, nucleic acid sequencing, 5'-exonuclease digestion, molecular beacon assay, oligonucleotide ligation assay, size analysis, and single-stranded conformation analysis. In one preferred embodiment, the process comprises allele-specific probe hybridization. In another preferred embodiment, the process comprises DNA sequencing. In yet another preferred embodiment, genotyping comprises the steps of contacting copies of the nucleic acid with a detection oligonucleotide probe and an enhancer oligonucleotide probe under conditions for specific hybridization of the oligonucleotide probe with the nucleic acid;

wherein the detection oligonucleotide probe is from 5-100 nucleotides in length and specifically hybridizes to a first segment of the nucleic acid whose nucleotide sequence is given by SEQ ID NO:2 that comprises at least one polymorphic site;

the detection oligonucleotide probe comprises a detectable label at its 3' terminus and a quenching moiety at its 5' terminus;

the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid; and a single base gap exists between the first segment and the second segment, such that when the oligonucleotide probe and the enhancer oligonucleotide probe are both hybridized to the nucleic acid, a single base gap exists between the oligonucleotides;

treating the nucleic acid with an endonuclease that will cleave the detectable label from the 3' terminus of the detection probe to release free detectable label when the detection probe is hybridized to the nucleic acid; and measuring free detectable label, wherein the presence of the free detectable label indicates that the detection probe specifically hybridizes to the first segment of the nucleic acid, and indicates the sequence of the polymorphic site as the complement of the detection probe. The copies of the nucleic acid are preferably provided by amplification by Polymerase Chain Reaction (PCR).

Another aspect relates to a method of assessing an individual for probability of response to a therapeutic agent for preventing and/or ameliorating symptoms associated with cancer, comprising: determining the presence or absence of at least one allele of at least one polymorphic marker in a nucleic acid sample obtained from the individual, wherein the at least one polymorphic marker is selected from the group consisting of the polymorphic markers set forth in Table 3 and Table 4, and markers in linkage disequilibrium therewith, wherein the presence of the at least one allele of the at least one marker is indicative of a probability of a positive response to a cancer therapeutic agent.

Another aspect relates to a method of predicting prognosis of an individual diagnosed with a cancer selected from prostate cancer and colorectal cancer, the method comprising determining the presence or absence of at least one allele of at least one polymorphic marker in a nucleic acid sample obtained from the individual, wherein the at least one polymorphic marker is selected from the group consisting of the polymorphic markers listed in Table 3 and Table 4, and markers in linkage disequilibrium therewith, wherein the presence of the at least one allele is indicative of a worse prognosis of the cancer in the individual.

Yet another aspect relates to a method of monitoring progress of a treatment of an individual undergoing treatment for a cancer selected from prostate cancer and colorectal cancer, the method comprising determining the presence or absence of at least one allele of at least one polymorphic marker in a nucleic acid sample obtained from the individual, wherein the at least one polymorphic marker is selected from the group consisting of the polymorphic markers listed in Table 3 and Table 4, and markers in linkage disequilibrium therewith, wherein the presence of the at least one allele is indicative of the treatment outcome of the individual.

The invention in another aspect relates to a kit for assessing susceptibility to a cancer selected from prostate cancer and colorectal cancer in a human individual, the kit comprising reagents for selectively detecting at least one allele of at least one polymorphic marker in the genome of the individual, wherein the polymorphic marker is selected from the group consisting of the polymorphic markers set forth in Table 5 and Table 6, and markers in linkage disequilibrium therewith, and a collection of data comprising correlation data between the polymorphic markers assessed by the kit and susceptibility to prostate cancer and/or colorectal cancer. In one embodiment, the reagents comprise at least one contiguous oligonucleotide that hybridizes to a fragment of the genome of the individual comprising the at least one polymorphic marker, a buffer and a detectable label. In another embodiment, the reagents comprise at least one pair of oligonucleotides that hybridize to opposite strands of a genomic nucleic acid segment obtained from the subject, wherein each oligonucleotide primer pair is designed to selectively amplify a fragment of the genome of the individual that includes one polymorphic marker, and wherein the fragment is at least 30 base pairs in size. In yet another embodiment, the at least one oligonucleotide is completely complementary to the genome of the individual. In one embodiment, the oligonucleotide is about 18 to about 50 nucleotides in length. In another embodiment, the oligonucleotide is 20-30 nucleotides in length.

In one preferred embodiment, the kit comprises:

a detection oligonucleotide probe that is from 5-100 nucleotides in length;

an enhancer oligonucleotide probe that is from 5-100 nucleotides in length; and an endonuclease enzyme;

wherein the detection oligonucleotide probe specifically hybridizes to a first segment of the nucleic acid whose nucleotide sequence is given by SEQ ID NO: 201 that comprises at least one polymorphic site; and wherein the detection oligonucleotide probe comprises a detectable label at its 3' terminus and a quenching moiety at its 5' terminus;

wherein the enhancer oligonucleotide is from 5-100 nucleotides in length and is complementary to a second segment of the nucleotide sequence that is 5' relative to the oligonucleotide probe, such that the enhancer oligonucleotide is located 3' relative to the detection oligonucleotide probe when both oligonucleotides are hybridized to the nucleic acid;

wherein a single base gap exists between the first segment and the second segment, such that when the oligonucleotide probe and the enhancer oligonucleotide probe are both hybridized to the nucleic acid, a single base gap exists between the oligonucleotides; and wherein treating the nucleic acid with the endonuclease will cleave the detectable label from the 3' terminus of the detection probe to release free detectable label when the detection probe is hybridized to the nucleic acid.

Another aspect of the invention relates to the use of an oligonucleotide probe in the manufacture of a diagnostic reagent for diagnosing and/or assessing susceptibility to a cancer selected from prostate cancer and colorectal cancer in a human individual, wherein the probe hybridizes to a segment of a nucleic acid within LD Block C06 or LD Block C11 that comprises at least one polymorphic site, wherein the fragment is 15-500 nucleotides in length.

The invention also provides computer-implemented aspects. In one such aspect, the invention provides a computer-readable medium having computer executable instructions for determining susceptibility to a cancer selected from prostate cancer and colorectal cancer in an individual, the computer readable medium comprising:

data representing at least one polymorphic marker; and a routine stored on the computer readable medium and adapted to be executed by a processor to determine susceptibility to the cancer in an individual based on the allelic status of at least one allele of said at least one polymorphic marker in the individual.

In one embodiment, said data representing at least one polymorphic marker comprises at least one parameter indicative of the susceptibility to the cancer linked to said at least one polymorphic marker. In another embodiment, said data representing at least one polymorphic marker comprises data indicative of the allelic status of at least one allele of said at least one allelic marker in said individual. In another embodiment, said routine is adapted to receive input data indicative of the allelic status for at least one allele of said at least one allelic marker in said individual. In a preferred embodiment, the at least one marker is selected from rs10896450 and rs10943605, and markers in linkage disequilibrium therewith. In another preferred embodiment, the at least one polymorphic marker is selected from the markers set forth in Table 3 and Table 4.

The invention further provides an apparatus for determining a genetic indicator for a cancer selected from prostate cancer and colorectal cancer in a human individual, comprising:

a processor, a computer readable memory having computer executable instructions adapted to be executed on the processor to analyze marker and/or haplotype information for at least one human individual with respect to a cancer selected from prostate cancer and colorectal cancer, and generate an output based on the marker or haplotype information, wherein the output comprises a risk measure of the at least one marker or haplotype as a genetic indicator of the cancer for the human individual.

In one embodiment, the computer readable memory comprises data indicative of the frequency of at least one allele of at least one polymorphic marker or at least one haplotype in a plurality of individuals diagnosed with prostate cancer and/or colorectal cancer, and data indicative of the frequency of at the least one allele of at least one polymorphic marker or at least one haplotype in a plurality of reference individuals, and wherein a risk measure is based on a comparison of the at least one marker and/or haplotype status for the human individual to the data indicative of the frequency of the at least one marker and/or haplotype information for the plurality of individuals diagnosed with the cancer. In one embodiment, the computer readable memory further comprises data indicative of a risk of developing prostate cancer and/or colorectal cancer associated with at least one allele of at least one polymorphic marker or at least one haplotype, and wherein a risk measure for the human individual is based on a comparison of the at least one marker and/or haplotype status for the human individual to the risk associated with at least one allele of the at least one polymorphic marker or the at least one haplotype. In another embodiment, the computer readable memory further comprises data indicative of the frequency of at least one allele of at least one polymorphic marker or at least one haplotype in a plurality of individuals diagnosed with a cancer selected from prostate cancer and colorectal cancer, and data indicative of the frequency of at the least one allele of at least one polymorphic marker or at least one haplotype in a plurality of reference individuals, and wherein risk of developing the cancer is based on a comparison of the frequency of the at least one allele or haplotype in individuals diagnosed with the cancer, and reference individuals. In a preferred embodiment, the at least one marker is selected from rs10943605 and rs10896450, and markers in linkage disequilibrium therewith. In another preferred embodiment, the at least one polymorphic marker is selected from the markers set forth in Table 3 and Table 4.

Different embodiments of the various aspects of the invention relate to specific use of the polymorphic variants described herein to be associated with prostate cancer and colorectal cancer, or variants (polymorphic markers) in linkage disequilibrium therewith. In one embodiment of the invention, the at least one marker is selected from the markers within LD Block C06 and/or LD Block C11, as defined herein, and markers in linkage disequilibrium therewith. In one such embodiment, the at least one marker is selected from markers within LD Block C06 and/or LD Block C11. In one embodiment, the at least one polymorphic marker is selected from the markers set forth in Table 5 and Table 6. In another embodiment, the at least one polymorphic marker comprises at least one marker selected from the group of markers set forth in Table 3 and Table 4, and markers in linkage disequilibrium therewith. One embodiment relates to at least one marker selected from the group consisting of marker rs10896450, marker rs11228565, marker rs7947353 and marker rs10943605, and markers in linkage disequilibrium therewith. One embodiment relates to marker rs10896450, and markers in linkage disequilibrium therewith. One embodiment relates to marker rs11228565, and markers in linkage disequilibrium therewith. One embodiment relates to marker rs10943605, and markers in linkage disequilibrium therewith. One embodiment relates to marker rs10896450. Another embodiment relates to marker rs11228565. Another embodiment relates to marker rs10943605. In certain embodiments, the cancer assessed by the invention is prostate cancer. In certain other embodiments, the cancer is colorectal cancer. In one such embodiment, the at least one polymorphic marker is selected from the group of markers set forth in Table 3. In another embodiment, the marker is rs10943605, and markers in linkage disequilibrium therewith.

Some embodiments of the invention, further comprise assessing the frequency of at least one haplotype in the individual.

The methods of the invention comprise, in some embodiments, an additional step of assessing at least one biomarker in a sample from the individual. The sample can be a blood sample or a cancer biopsy sample, or any other biological sample derived from an individual that is suitable for assessing the presence or absence, or for quantitative determination, of at least one biomarker. The biomarker is preferably a biological molecule that represents directly or indirectly the disease state in question, i.e. prostate cancer or colorectal cancer. An exemplary biomarker is PSA. Other embodiments of the methods of the invention further comprise analyzing non-genetic information to make risk assessment, diagnosis, or prognosis of the individual. The non-genetic information is in some embodiments selected from age, gender, ethnicity, socioeconomic status, previous disease diagnosis, medical history of subject, family history of cancer, biochemical measurements, and clinical measurements.

Other genetic risk factors for cancer, e.g., prostate cancer and/or colorectal cancer, can be assessed in combination with the markers of the present invention found to be predictive of these cancers, for providing overall risk assessment of prostate cancer and/or colorectal cancer. Thus, in one embodiment, the methods of the invention relate to further steps comprising assessing the presence of absence of at least one additional genetic risk factor for prostate cancer or colorectal cancer in the individual. In certain embodiments, the additional genetic risk factor is not associated, defined by values of $r^2$ of at least 0.2 and/or values of |D'| of at least 0.8, to markers set forth in Tables 3 and 4, in particular marker rs10896450, marker rs11228565, marker rs7947353 and marker rs10943605. Such additional risk factor are in certain embodiments risk factors for a particular type of cancer, i.e. cancer at a particular site (e.g., prostate cancer and/or colorectal cancer). In certain other embodiments, such additional risk factors are susceptibility variants for multiple forms of cancer.

Thus, in certain embodiments, a further step is included, comprising determining whether at least one at-risk allele of at least one at-risk variant for a cancer selected from prostate cancer and colorectal cancer not in linkage disequilibrium with any one of the markers rs10896450, rs11228565, rs7947353 and rs10943605 are present in a sample comprising genomic DNA from a human individual or a genotype dataset derived from a human individual. In other words, genetic markers in other locations in the genome can be useful in combination with the markers of the present invention, so as to determine overall risk of the cancer based on multiple genetic variants. In one embodiment, the at least one at-risk variant for cancer is not in linkage disequilibrium with marker rs10896450. Selection of markers that are not in linkage disequilibrium (not in LD) can be based on a suitable measure for linkage disequilibrium, as described further herein. In certain embodiments, markers that are not in linkage disequilibrium have values for the LD measure $r^2$ correlating the markers of less than 0.2. In certain other embodiments, markers that are not in LD have values for $r^2$ correlating the markers of less than 0.15, including less than 0.10, less than 0.05, less than 0.02 and less than 0.01. Other suitable numerical values for establishing that markers are not in LD are contemplated, including values bridging any of the above-mentioned values.

The risk factors are in one embodiment selected from rs1447295, rs4430796, rs1859962, rs5945572, rs6983267, rs16901979 and rs10505483, and markers in linkage disequilibrium therewith. In another embodiment, the additional genetic risk factor is selected from the group consisting of rs2710646 allele A, rs16901979 allele A, rs1447295 allele A, rs6983267 allele G, rs10896450 allele G, rs1859962 allele G, rs4430796 allele A and rs5945572 allele A. In other embodiments, the additional genetic risk factor is selected from markers in linkage disequilibrium with any of the markers rs2710646, rs16901979, rs1447295, rs6983267, rs10896450, rs1859962, rs4430796 and rs5945572. An overall risk for prostate cancer and/or colon cancer is in one embodiment calculated based on the genotype status of the individual.

In certain embodiments, the susceptibility is increased susceptibility. Increased susceptibility is in certain embodiments accompanied by an odds ratio (OR) or relative risk (RR) of at least 1.10. In other embodiments, the odds ratio or relative risk is at least 1.15. In other embodiments, the relative risk or odds ratio is at least 1.20. In one embodiment, the at least one marker or haplotype comprises marker rs10896450 allele G, marker rs7947353 allele A and marker rs10943605 allele G.

In certain other embodiments, the susceptibility is decreased susceptibility. The decreased susceptibility is in some embodiments accompanied by a relative risk or odds ratio of less than 0.9.

Certain embodiments of the invention relate to aggressive forms of prostate cancer. In some embodiments, the prostate cancer is an aggressive prostate cancer as defined by a combined Gleason score of 7(4+3)–10. In other embodiments, the prostate cancer is a less aggressive prostate cancer as defined by a combined Gleason score of 2-7(3+4).

In certain embodiments of the invention, the individual is of a specific ancestry. One embodiment relates to the ancestry being Caucasian ancestry. In other embodiments, the ancestry is African ancestry or African American ancestry. In another embodiment, the ancestry is European ancestry. The ancestry is in some embodiment self-reported. In other embodiments, the ancestry is determined by detecting at least one allele of at least one polymorphic marker in a sample from the individual, wherein the presence or absence of the allele is indicative of the ancestry of the individual.

In certain embodiments of the invention, linkage disequilibrium is determined using the linkage disequilibrium measures $r^2$ and |D'|, which give a quantitative measure of the extent of linkage disequilibrium (LD) between two genetic element (e.g., polymorphic markers). Certain numerical values of these measures for particular markers are indicative of the markers being in linkage disequilibrium, as described further herein. The higher the numerical value for the LD measures $r^2$ and |D'|, the stronger the LD between the genetic elements is, as further described herein. In one embodiment of the invention, linkage disequilibrium between marker (i.e., LD values indicative of the markers being in linkage disequilibrium) is defined as $r^2>0.1$. In another embodiment, linkage disequilibrium is defined as $r^2>0.2$. Other embodiments can include other definitions of linkage disequilibrium, such as $r^2>0.25$, $r^2>0.3$, $r^2>0.35$, $r^2>0.4$, $r^2>0.45$, $r^2>0.5$, $r^2>0.55$, $r^2>0.6$, $r^2>0.65$, $r^2>0.7$, $r^2>0.75$, $r^2>0.8$, $r^2>0.85$, $r^2>0.9$, $r^2>0.95$, $r^2>0.96$, $r^2>0.97$, $r^2>0.98$, or $r^2>0.99$. Linkage disequilibrium can in certain embodiments also be defined as |D'|>0.2, or as |D'|>0.3, |D'|>0.4, |D'|>0.5, |D'|>0.6, |D'|>0.7, |D'|>0.8, |D'|>0.9, |D'|>0.95, |D'|>0.98 or |D'|>0.99. In certain embodiments, linkage disequilibrium is defined as fulfilling two criteria of $r^2$ and |D'|, such as $r^2>0.2$ and/or |D'|>0.8. Other combinations of values for $r^2$ and |D'| are also possible and within scope of the present invention, including but not limited to the values for these parameters set forth in the above.

It should be understood that all combinations of features described herein are contemplated, even if the combination of feature is not specifically found in the same sentence or paragraph herein. This includes, but is not limited to, the use of all markers disclosed herein, alone or in combination, for analysis individually or in haplotypes, in all aspects of the invention as described herein.

BRIEF DESCRIPTION OF THE DRAWINGS

The foregoing and other objects, features and advantages of the invention will be apparent from the following more particular description of preferred embodiments of the invention.

The FIGURE provides a diagram illustrating a computer-implemented system utilizing risk variants as described herein.

DETAILED DESCRIPTION OF THE INVENTION

The present invention discloses polymorphic variants and haplotypes that have been found to be associated with prostate and colorectal cancer. Such markers and haplotypes are useful for diagnostic purposes, as described in further detail herein.

Definitions

Unless otherwise indicated, nucleic acid sequences are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by the ordinary person skilled in the art to which the invention pertains.

The following terms shall, in the present context, have the meaning as indicated:

A "polymorphic marker", sometimes referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including SNPs, mini- or microsatellites, translocations and copy number variations (insertions, deletions, duplications). Polymorphic markers can be of any measurable frequency in the population. For mapping of disease genes, polymorphic markers with population frequency higher than 5-10% are in general most useful. However, polymorphic markers may also have lower population frequencies, such as 1-5% frequency, or even lower frequency, in particular copy number variations (CNVs). The term shall, in the present context, be taken to include polymorphic markers with any population frequency.

An "allele" refers to the nucleotide sequence of a given locus (position) on a chromosome. A polymorphic marker allele thus refers to the composition (i.e., sequence) of the marker on a chromosome. Genomic DNA from an individual contains two alleles for any given polymorphic marker, representative of each copy of the marker on each chromosome. Sequence codes for nucleotides used herein are: A=1, C=2, G=3, T=4. For microsatellite alleles, the CEPH sample (Centre d'Etudes du Polymorphisme Humain, genomics repository, CEPH sample 1347-02) is used as a reference, the shorter allele of each microsatellite in this sample is set as 0 and all other alleles in other samples are numbered in relation to this reference. Thus, e.g., allele 1 is 1 bp longer than the shorter allele in the CEPH sample, allele 2 is 2 bp longer than the shorter allele in the CEPH sample, allele 3 is 3 bp longer than the lower allele in the CEPH sample, etc., and allele −1 is 1 bp shorter than the shorter allele in the CEPH sample, allele −2 is 2 bp shorter than the shorter allele in the CEPH sample, etc.

Sequence conucleotide ambiguity as described herein is as proposed by IUPAC-IUB. These codes are compatible with the codes used by the EMBL, GenBank, and PIR databases.

| IUB code | Meaning |
|---|---|
| A | Adenosine |
| C | Cytidine |
| G | Guanine |
| T | Thymidine |
| R | G or A |
| Y | T or C |
| K | G or T |
| M | A or C |

| IUB code | Meaning |
|---|---|
| S | G or C |
| W | A or T |
| B | C, G or T |
| D | A, G or T |
| H | A, C or T |
| V | A, C or G |
| N | A, C, G or T (Any base) |

A nucleotide position at which more than one sequence is possible in a population (either a natural population or a synthetic population, e.g., a library of synthetic molecules) is referred to herein as a "polymorphic site".

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population.

An "indel" is a common form of polymorphism comprising a small insertion or deletion that is typically only a few nucleotides long.

A "haplotype," as described herein, refers to a segment of genomic DNA within one strand of DNA that is characterized by a specific combination of alleles arranged along the segment. For diploid organisms such as humans, a haplotype comprises one member of the pair of alleles for each polymorphic marker or locus along the segment. In a certain embodiment, the haplotype can comprise two or more alleles, three or more alleles, four or more alleles, or five or more alleles. Haplotypes are described herein in the context of the marker name and the allele of the marker in that haplotype, e.g., "3 rs10896450" refers to the 3 allele of marker rs10896450 being in the haplotype, and is equivalent to "rs10896450 allele 3". Furthermore, allelic codes in haplotypes are as for individual markers, i.e. 1=A, 2=C, 3=G and 4=T.

The term "susceptibility", as described herein, encompasses both increased susceptibility and decreased susceptibility. Thus, particular polymorphic markers and/or haplotypes of the invention may be characteristic of increased susceptibility (i.e., increased risk) of prostate cancer, as characterized by a relative risk (RR) or odds ratio (OR) of greater than one for the particular allele or haplotype. Alternatively, the markers and/or haplotypes of the invention are characteristic of decreased susceptibility (i.e., decreased risk) of prostate cancer, as characterized by a relative risk of less than one.

The term "and/or" shall in the present context be understood to indicate that either or both of the items connected by it are involved. In other words, the term herein shall be taken to mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or the can contain information about multiple markers, and they may also comprise other factors, such as particulars about diseases diagnoses, racial information, biomarkers, biochemical measurements, therapeutic methods or drugs, etc.

A "computer-readable medium", is an information storage medium that can be accessed by a computer using a commercially available or custom-made interface. Exemplary compute-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample", as described herein, refer to a sample obtained from an individual that contains nucleic acid (DNA or RNA). In certain embodiments, i.e. the detection of specific polymorphic markers and/or haplotypes, the nucleic acid sample comprises genomic DNA. Such a nucleic acid sample can be obtained from any source that contains genomic DNA, including as a blood sample, sample of amniotic fluid, sample of cerebrospinal fluid, or tissue sample from skin, muscle, buccal or conjunctival mucosa, placenta, gastrointestinal tract or other organs.

The term "prostate cancer therapeutic agent" and "colorectal cancer therapeutic agent", as described herein, refers to an agent that can be used to ameliorate or prevent symptoms associated with prostate cancer and colorectal cancer, respectively.

The term "prostate cancer-associated nucleic acid" and "colorectal cancer-associated nucleic acid", as described herein, refers to a nucleic acid that has been found to be associated to prostate and/or colorectal cancer. This includes, but is not limited to, the markers and haplotypes described herein and markers and haplotypes in strong linkage disequilibrium (LD) therewith. In one embodiment, a prostate and/or colon cancer-associated nucleic acid refers to an LD-block found to be associated with prostate and/or colorectal cancer through at least one polymorphic marker located within the LD block C06 or associated with the LD block C11.

"Aggressive prostate cancer", as described herein, refers to prostate cancer with combined Gleason grades of 7 or higher OR stage T3 or higher OR node positive OR metastasis positive disease OR death because of prostate cancer. Note that it is sufficient to have one of these criteria to be determined aggressive prostate cancer. These clinical parameters are well known surrogates for increased aggressiveness of the disease.

The term "LD block 06", as described herein, refers to the Linkage Disequilibrium (LD) block on Chromosome 6 between positions 79,300,773 and 79,917,888 of NCBI (National Center for Biotechnology Information) Build 36, spanning the region flanked by the SNP markers rs611737 and rs9294130.

The term "LD block C11", as described herein, refers to the Linkage Disequilibrium (LD) block on Chromosome 11 between positions 68,709,630 and 68,782,375 of NCBI (National Center for Biotechnology Information) Build 36, spanning the region flanked by the SNP markers rs7128814 and rs3884627. The LD block C11 has the sequence as set forth in SEQ ID NO:201 herein, based on NCBI Build 36 of the human genome sequence assembly.

A genome-wide search for variants associated with prostate and/or colorectal cancer has identified two genomic regions associated with these cancers. Markers rs10896450 and rs7947353 on Chr 11q13.3, within a region herein called LD Block C11, were identified as contributing to risk of prostate cancer (see Table 1). The two markers are fully correlated (D'=1 and $r^2$=1; see footnote of Table 1) and do therefore essentially represent the same association signal. The G allele of SNP marker rs10896450 confers increased risk of prostate cancer, with an odds ratio (OR) of 1.17 in the Icelandic samples (P=6.6×10$^{-5}$). The initial discovery in an Icelandic prostate cancer cohort was validated by analysis of marker rs7947353, which is perfectly correlated (i.e., a perfect surrogate marker) to rs10896450, in prostate cancer cohorts from the Netherlands, Spain and US (Chicago, Ill.). The results for these additional cohorts are comparable to the results for the Icelandic discovery cohort, showing that the initial observation represents a true association signal. Overall, the association is significant with a p-value of 1.43×10$^{-6}$.

A follow-up analysis revealed that marker rs11228565, located within LD Block C11, shows that this marker associated very significantly with prostate cancer, with an OR of 1.23 for all cohorts and an overall P-value of 6.7×10$^{-12}$ (Table 7).

A second region on Chromosome 6 (LD Block C06) was identified as a prostate cancer susceptibility region, as shown in Table 2a. The association of the G allele of the rs10943605 SNP marker observed in the Icelandic cohort was replicated in Dutch and Spanish cohort, both which gave increased risk conferred by the G allele, although only the replication in the Dutch cohort is statistically significant. Surprisingly, the G allele of the rs10943605 SNP marker was also found to be associated with increased risk of developing colorectal cancer, with an OR of 1.14 in the Icelandic colorectal cancer samples (P=4.8×10$^{-3}$) (Table 2b).

Accordingly, the present invention provides methods for determining a susceptibility to prostate cancer and colorectal cancer, by assessing for the presence or absence of particular alleles of polymorphic markers within the LD Block C06 and/or LD Block C11 genomic segments that are indicative of risk of prostate cancer and colorectal cancer. Determination of the presence of such marker alleles is indicative of risk of prostate cancer and/or colorectal cancer in the individual.

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have occurred in a single mutational event, and therefore there are usually two possible alleles possible at each SNP site; the original allele and the mutated allele. Due to natural genetic drift and possibly also selective pressure, the original mutation has resulted in a polymorphism characterized by a particular frequency of its alleles in any given population. Many other types of sequence variants are found in the human genome, including mini- and microsatellites, and insertions, deletions and inversions (also called copy number variations (CNVs)). A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention.

Due to their abundance, SNPs account for a majority of sequence variation in the human genome. Over 6 million SNPs have been validated to date (ncbi.nlm.nih.gov/projects/SNP/snp_summary.cgi). However, CNVs are receiving increased attention. These large-scale polymorphisms (typically 1 kb or larger) account for polymorphic variation affecting a substantial proportion of the assembled human genome; known CNVs cover over 15% of the human genome sequence (Estivill, X., Armengol; L., *PloS Genetics* 3:1787-99 (2007). A http://projects.tcag.ca/variation/). Most of these polymorphisms are however very rare, and on average affect only a fraction of the genomic sequence of each individual. CNVs are known to affect gene expression, phenotypic variation and adaptation by disrupting gene dosage, and are also known to cause disease (microdeletion and microduplication disorders) and confer risk of common complex diseases, including HIV-1 infection and glomerulonephritis (Redon, R., et al. *Nature* 23:444-454 (2006)). It is thus possible that either previously described or unknown CNVs represent causative variants in linkage disequilibrium with the markers described herein to be associated with prostate and colorectal cancer. Methods for detecting CNVs include comparative genomic hybridization (CGH) and genotyping, including use of genotyping arrays, as described by Carter (*Nature Genetics* 39:S16-S21 (2007)). The Database of Genomic Variants (http://projects.tcag.ca/variation/) contains updated information about the location, type and size of described CNVs. The database currently contains data for over 15,000 CNVs.

In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realise that by assaying or reading the opposite DNA strand, the complementary allele can in each case be measured. Thus, for a polymorphic site (polymorphic marker) characterized by an A/G polymorphism, the assay employed may be designed to specifically detect the presence of one or both of the two bases possible, e.g. A and G. Alternatively, by designing an assay that is designed to detect the complimentary strand on the DNA template, the presence of the complementary bases T and C can be measured. Quantitatively (for example, in terms of risk estimates), identical results would be obtained from measurement of either DNA strand (+ strand or − strand).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Additional variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (Chen, X. et al., *Genome Res.* 9(5): 492-98 (1999); Kutyavin et al., *Nucleic Acid Res.* 34:e128 (2006)), utilizing PCR, LCR, Nested PCR and other techniques for nucleic acid amplification. Specific methodologies available for SNP genotyping include, but are not limited to, TaqMan genotyping assays and SNPlex platforms (Applied Biosystems), mass spectrometry (e.g., MassARRAY system from Sequenom), minisequencing methods, real-time PCR, BioPlex system (BioRad), CEQ and SNPstream systems (Beckman), Molecular Inversion Probe array technology (e.g., Affymetrix GeneChip), and BeadArray Technologies (e.g., Illumina GoldenGate and Infinium assays). By these or other methods available to the person skilled in the art, one or more alleles at polymorphic markers, including microsatellites, SNPs or other types of polymorphic markers, can be identified.

In the present context, and individual who is at an increased susceptibility (i.e., increased risk) for a disease, is an individual in whom at least one specific allele at one or more polymorphic marker or haplotype conferring increased susceptibility (increased risk) for the disease is identified (i.e., at-risk marker alleles or haplotypes). The at-risk marker or haplotype is one that confers an increased risk (increased susceptibility) of the disease. In one embodiment, significance associated with a marker or haplotype is measured by a relative risk (RR). In another embodiment, significance associated with a marker or haplotye is measured by an odds ratio (OR). In a further embodiment, the significance is measured by a percentage. In one embodiment, a significant increased risk is measured as a risk (relative risk and/or odds ratio) of at least 1.2, including but not limited to: at least 1.2, at least 1.3, at least 1.4, at least 1.5, at least 1.6, at least 1.7, 1.8, at least 1.9, at least 2.0, at least 2.5, at least 3.0, at least 4.0, and at least 5.0. In a particular embodiment, a risk (relative risk and/or odds ratio) of at least 1.2 is significant. In another particular embodiment, a risk of at least 1.3 is significant. In yet another embodiment, a risk of at least 1.4 is significant. In a further embodiment, a relative risk of at least 1.5 is significant. In another further embodiment, a significant increase in risk is at least 1.7 is significant. However, other cutoffs are also contemplated, e.g., at least 1.15, 1.25, 1.35, and so on, and such cutoffs are also within scope of the present invention. In other embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 20%. In other embodiments, a significant increase in risk is at least 30%, at least 40%, at least 50%, at least 60%, at least 70%, at least 80%, at least 90% and at least 100%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype of the present invention is one where at least one allele of at least one marker or haplotype is more frequently present in an individual at risk for the disease or trait (affected), compared to the frequency of its presence in a comparison group (control), and wherein the presence of the marker or haplotype is indicative of susceptibility to the disease or trait. The control group may in one embodiment be a population sample, i.e. a random sample from the general population. In another embodiment, the control group is represented by a group of individuals who are disease-free. Such disease-free control may in one embodiment be characterized by the absence of one or more specific disease-associated symptoms. In another embodiment, the disease-free control group is characterized by the absence of one or more disease-specific risk factors. Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In another embodiment, the risk factors are at least one genetic risk factor.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes.

In other embodiments of the invention, an individual who is at a decreased susceptibility (i.e., at a decreased risk) for a disease or trait is an individual in whom at least one specific allele at one or more polymorphic marker or haplotype conferring decreased susceptibility for the disease or trait is identified. The marker alleles and/or haplotypes conferring decreased risk are also said to be protective. In one aspect, the protective marker or haplotype is one that confers a significant decreased risk (or susceptibility) of the disease or trait. In one embodiment, significant decreased risk is measured as a relative risk of less than 0.9, including but not limited to less than 0.9, less than 0.8, less than 0.7, less than 0.6, less than 0.5, less than 0.4, less than 0.3, less than 0.2 and less than 0.1. In one particular embodiment, significant decreased risk is less than 0.7. In another embodiment, significant decreased risk is less than 0.5. In yet another embodiment, significant decreased risk is less than 0.3. In another embodiment, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. In one particular embodiment, a significant decrease in risk is at least about 30%. In another embodiment, a significant decrease in risk is at least about 50%. In another embodiment, the decrease in risk is at least about 70%. Other cutoffs or ranges as deemed suitable by the person skilled in the art to characterize the invention are however also contemplated, and those are also within scope of the present invention.

The person skilled in the art will appreciate that for markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

A genetic variant associated with a disease or a trait can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes $k=3^n \times 2^p$; where n is the number autosomal loci and p the number of gonosomal (sex chromosomal) loci. Overall risk assessment calculations for a plurality of risk variants usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk—is the product of the locus specific risk values—and which also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider variants in eight regions (loci) that have been described to associate with prostate cancer (Gudmundsson, J., et al., *Nat Genet* 39:631-7 (2007), Gudmundsson, J., et al., *Nat Genet* 39:977-83 (2007); Yeager, M., et al, *Nat Genet* 39:645-49 (2007), Amundadottir, L., et al., *Nat Genet* 38:652-8 (2006); Haiman, C. A., et al., *Nat Genet* 39:638-44 (2007)). Seven of these loci are on autosomes, and the remaining locus is on chromosome X. The total number of theoretical genotypic combinations is then $3^7 \times 2^1 = 4374$. Some of those genotypic classes are very rare, but are still possible, and should be considered for overall risk assessment. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Accordingly, in certain embodiments, therefore, the markers shown herein to be predictive of risk of prostate cancer in humans can be used in combination with any one, or a combination of, rs2710646 allele A, rs16901979 allele A, rs1447295 allele A, rs6983267 allele G, rs10896450 allele G, rs1859962 allele G, rs4430796 allele A and rs5945572 allele A. In a preferred embodiment, the at-risk markers for prostate cancer as described herein are assessed together with rs2710646 allele A, rs16901979 allele A, rs1447295 allele A, rs6983267 allele G, rs10896450 allele G, rs1859962 allele G, rs4430796 allele A and rs5945572 allele A to determine overall risk of prostate cancer in an individual.

The skilled person will realize that the markers presented herein may also be assessed in combination with any other genetic risk factors for prostate cancer and/or colorectal cancer, so as to determine overall risk of the cancer in an individual.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet.* 29:217-222 (2001); May, C. A., et al., *Nature Genet* 31:272-275 (2002)).

Linkage Disequilibrium (LD) refers to a non-random assortment of two genetic elements. For example, if a particular genetic element (e.g., an allele of a polymorphic marker, or a haplotype) occurs in a population at a frequency of 0.50 (50%) and another element occurs at a frequency of 0.50 (50%), then the predicted occurrance of a person's having both elements is 0.25 (25%), assuming a random distribution of the elements. However, if it is discovered that the two elements occur together at a frequency higher than 0.25, then the elements are said to be in linkage disequilibrium, since they tend to be inherited together at a higher rate than what their independent frequencies of occurrence (e.g., allele or haplotype frequencies) would predict. Roughly speaking, LD is generally correlated with the frequency of recombination events between the two elements. Allele or haplotype frequencies can be determined in a population by genotyping individuals in a population and determining the frequency of the occurence of each allele or haplotype in the population. For populations of diploids, e.g., human populations, individuals will typically have two alleles for each genetic element (e.g., a marker, haplotype or gene).

Many different measures have been proposed for assessing the strength of linkage disequilibrium (LD; reviewed in Devlin, B. & Risch, N., *Genomics* 29:311-22 (1995))). Most capture the strength of association between pairs of biallelic sites. Two important pairwise measures of LD are $r^2$ (sometimes denoted $\Delta^2$) and |D'| (Lewontin, R., *Genetics* 49:49-67 (1964); Hill, W. G. & Robertson, A. *Theor. Appl. Genet.* 22:226-231 (1968)). Both measures range from 0 (no disequilibrium) to 1 ('complete' disequilibrium), but their interpretation is slightly different. |D'| is defined in such a way that it is equal to 1 if just two or three of the possible haplotypes are present, and it is <1 if all four possible haplotypes are present. Therefore, a value of |D'| that is <1 indicates that historical recombination may have occurred between two sites (recurrent mutation can also cause |D'| to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, 0.99 or 1.0. In one preferred embodiment, the significant $r^2$ value can be at least 0.2. Alternatively, linkage disequilibrium as described herein, refers to linkage disequilibrium characterized by values of |D'| of at least 0.2, such as 0.3, 0.4, 0.5, 0.6, 0.7, 0.8, 0.85, 0.9, 0.95, 0.96, 0.97, 0.98, 0.99. Thus, linkage disequilibrium represents a correlation between alleles of distinct markers. It is measured by correlation coefficient or |D'| ($r^2$ up to 1.0 and |D'| up to 1.0). In certain embodiments, linkage disequilibrium is defined in terms of values for both the $r^2$ and |D'| measures. In one such embodiment, a significant linkage disequilibrium is defined as $r^2>0.2$ and/or |D'|>0.8. In another embodiment, a significant linkage disequilibrium is defined as $r^2>0.2$ and/or |D'|>0.9. Other combinations and permutations of values of $r^2$ and |D'| for determining linkage disequilibrium are also possible, and within the scope of the invention. Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http://www.hapmap.org). In one such embodiment, LD is determined in the CEU population of the HapMap samples. In another embodiment, LD is determined in the YRI population. In yet another embodiment, LD is determined in samples from the Icelandic population.

If all polymorphisms in the genome were identical at the population level, then every single one of them would need to be investigated in association studies. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, Science 273:1516-1517 (1996); Maniatis, N., et al., Proc Natl Acad Sci USA 99:2228-2233 (2002); Reich, D E et al, Nature 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., Nature Reviews Genetics 4:587-597 (2003); Daly, M. et al., Nature Genet. 29:229-232 (2001); Gabriel, S. B. et al., Science 296:2225-2229 (2002); Patil, N. et al., Science 294: 1719-1723 (2001); Dawson, E. et al., Nature 418:544-548 (2002); Phillips, M. S. et al., Nature Genet. 33:382-387 (2003)).

There are two main methods for defining these haplotype blocks: blocks can be defined as regions of DNA that have limited haplotype diversity (see, e.g., Daly, M. et al., Nature Genet. 29:229-232 (2001); Patil, N. et al., Science 294:1719-1723 (2001); Dawson, E. et al., Nature 418:544-548 (2002); Zhang, K. et al., Proc. Natl. Acad. Sci. USA 99:7335-7339 (2002)), or as regions between transition zones having extensive historical recombination, identified using linkage disequilibrium (see, e.g., Gabriel, S. B. et al., Science 296:2225-2229 (2002); Phillips, M. S. et al., Nature Genet. 33:382-387 (2003); Wang, N. et al., Am. J. Hum. Genet. 71:1227-1234 (2002); Stumpf, M. P., and Goldstein, D. B., Curr. Biol. 13:1-8 (2003)). More recently, a fine-scale map of recombination rates and corresponding hotspots across the human genome has been generated (Myers, S., et al., Science 310: 321-32324 (2005); Myers, S. et al., Biochem Soc Trans 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait, and as such are useful for use in the methods and kits of the present invention. One or more causative (functional) variants or mutations may reside within the region found to be associating to the disease or trait. The functional variant may be another SNP, a tandem repeat polymorphism (such as a minisatellite or a microsatellite), a transposable element, or a copy number variation, such as an inversion, deletion or insertion. Such variants in LD with the variants described herein may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. An example of such an embodiment would be a rare, or relatively rare (such as <10% allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc. B*, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a linkage region, for example, association of all possible combinations of genotyped markers is studied, provided those markers span a practical region. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of a significant marker and/or haplotype association.

Haplotype Analysis

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics*, 60(2):368-75 (2004)) as a natural extension of information measures defined for linkage analysis, and is implemented in NEMO.

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due to the relatedness of patients who were recruited as families, first and second-degree relatives can be eliminated from the patient list. Furthermore, the test can be repeated for association correcting for any remaining relatedness among the patients, by extending a variance adjustment procedure described in Risch, N. & Teng, J. (*Genome Res.*, 8:1273-1288 (1998)), DNA pooling (ibid) for sibships so that it can be applied to general familial relationships, and present both adjusted and unadjusted p-values for comparison. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

An association signal detected in one association study may be replicated in a second cohort, ideally from a different population (e.g., different region of same country, or a different country) of the same or different ethnicity. The advantage of replication studies is that the number of tests performed in the replication study is usually quite small, and hence the less stringent the statistical measure that needs to be applied. For example, for a genome-wide search for susceptibility variants for a particular disease or trait using 300,000 SNPs, a correction for the 300,000 tests performed (one for each SNP) can be performed. Since many SNPs on the arrays typically used are correlated (i.e., in LD), they are not independent. Thus, the correction is conservative. Nevertheless, applying this correction factor requires an observed P-value of less than $0.05/300,000=1.7\times10^{-7}$ for the signal to be considered significant applying this conservative test on results from a single study cohort. Obviously, signals found in a genome-wide association study with P-values less than this conservative threshold are a measure of a true genetic effect, and replication in additional cohorts is not necessarily from a statistical point of view. Importantly, however, signals with P-values that are greater than this threshold may also be due to a true genetic effect. Thus, since the correction factor depends on the number of statistical tests performed, if one signal (one SNP) from an initial study is replicated in a second case-control cohort, the appropriate statistical test for significance is that for a single statistical test, i.e., P-value less than 0.05. Replication studies in one or even several additional case-control cohorts have the added advantage of providing assessment of the association signal in additional populations, thus simultaneously confirming the initial finding and providing an assessment of the overall significance of the genetic variant(s) being tested in human populations in general.

The results from several case-control cohorts can also be combined to provide an overall assessment of the underlying effect. The methodology commonly used to combine results from multiple genetic association studies is the Mantel-Haenszel model (Mantel and Haenszel, *J Natl Cancer Inst* 22:719-48 (1959)). The model is designed to deal with the situation where association results from different populations, with each possibly having a different population frequency of the genetic variant, are combined. The model combines the results assuming that the effect of the variant on the risk of the disease, a measured by the OR or RR, is the same in all populations, while the frequency of the variant may differ between the populations. Combining the results from several populations has the added advantage that the overall power to detect a real underlying association signal is increased, due to the increased statistical power provided by the combined cohorts. Furthermore, any deficiencies in individual studies, for example due to unequal matching of cases and controls or population stratification will tend to balance out when results from multiple cohorts are combined, again providing a better estimate of the true underlying genetic effect.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different genotype. For a disease, a relative risk of 2 means that one group has twice the chance of developing a disease as the other group. The risk presented is usually the relative risk for a person, or a specific genotype of a person, compared to the population with matched gender and ethnicity. Risks of two individuals of the same gender and ethnicity could be compared in a simple manner. For example, if, compared to the population, the first individual has relative risk 1.5 and the second has relative risk 0.5, then the risk of the first individual compared to the second individual is 1.5/0.5=3.

As described herein, certain polymorphic markers and haplotypes comprising such markers are found to be useful for risk assessment of prostate cancer and colorectal cancer. Risk assessment can involve the use of the markers for diagnosing a susceptibility to prostate cancer and/or colorectal cancer. Particular alleles of polymorphic markers are found more frequently in individuals with prostate cancer and/or colorectal cancer, than in individuals without diagnosis of prostate cancer and/or colorectal cancer. Therefore, these marker alleles have predictive value for detecting prostate cancer and/or colorectal cancer, or a susceptibility to prostate cancer and/or colorectal cancer, in an individual. Tagging markers in linkage disequilibrium with the at-risk variants (or protective variants) described herein can be used as surrogates for these markers (and/or haplotypes). Such surrogate markers can be located within a particular haplotype block or LD block, e.g. LD Block C11 or LD Block C06. Such surrogate markers can also sometimes be located outside the physical boundaries of such a haplotype block or LD block, either in close vicinity of the LD block/haplotype block, but possibly also located in a more distant genomic location.

Long-distance LD can for example arise if particular genomic regions (e.g., genes) are in a functional relationship. For example, if two genes encode proteins that play a role in a shared metabolic pathway, then particular variants in one gene may have a direct impact on observed variants for the other gene. Let us consider the case where a variant in one gene leads to increased expression of the gene product. To counteract this effect and preserve overall flux of the particular pathway, this variant may have led to selection of one (or more) variants at a second gene that confers decreased expression levels of that gene. These two genes may be located in different genomic locations, possibly on different chromosomes, but variants within the genes are in apparent LD, not because of their shared physical location within a region of high LD, but rather due to evolutionary forces. Such LD is also contemplated and within scope of the present invention. The skilled person will appreciate that many other scenarios of functional gene-gene interaction are possible, and the particular example discussed here represents only one such possible scenario.

Markers with values of $r^2$ equal to 1 are perfect surrogates for the at-risk variants, i.e. genotypes for one marker perfectly predicts genotypes for the other. Markers with smaller values of $r^2$ than 1 can also be surrogates for the at-risk variant, or alternatively represent variants with relative risk values as high as or possibly even higher than the at-risk variant. The at-risk variant identified may not be the functional variant itself, but is in this instance in linkage disequilibrium with the true functional variant. The functional variant may for example be a tandem repeat, such as a minisatellite or a microsatellite, a transposable element (e.g., an Alu element), or a structural alteration, such as a deletion, insertion or inversion (sometimes also called copy number variations, or CNVs). The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation genotype surrogate markers in linkage disequilibrium with the markers and/or haplotypes as described herein. The tagging or surrogate markers in LD with the at-risk variants detected, also have predictive value for detecting association to prostate cancer and/or colorectal cancer, or a susceptibility to prostate cancer and/or colorectal cancer, in an individual. These tagging or surrogate markers that are in LD with the markers of the present invention can also include other markers that distinguish among haplotypes, as these similarly have predictive value for detecting susceptibility to prostate cancer and/or colorectal cancer.

The present invention can in certain embodiments be practiced by assessing a sample comprising genomic DNA from an individual for the presence of variants described herein to be associated with cancer. Such assessment typically steps that detect the presence or absence of at least one allele of at least one polymorphic marker, using methods well known to the skilled person and further described herein, and based on the outcome of such assessment, determine whether the individual from whom the sample is derived is at increased or decreased risk (increased or decreased susceptibility) of cancer. Detecting particular alleles of polymorphic markers can in certain embodiments be done by obtaining nucleic acid sequence data for a particular human individual, that identifies at least one allele of at least one polymorphic marker. Different alleles of the at least one marker are associated with different susceptibility to the disease in humans. Obtaining nucleic acid sequence data can comprise nucleic acid sequence at a single nucleotide position, which is sufficient to identify alleles at polymorphic markers, such as SNPs and microsatellites. The nucleic acid sequence data can also comprise sequence at any other number of nucleotide positions, in particular for genetic markers that comprise multiple nucleotide positions, and can be anywhere from two to hundreds of thousands, possibly even millions, of nucleotides (in particular, in the case of copy number variations (CNVs)).

In certain embodiments, the invention can be practiced utilizing a dataset comprising information about the genotype status of at least one polymorphic marker associated with prostate and/or colorectal cancer (or markers in linkage disequilibrium with at least one marker associated with these diseases). In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with risk of prostate cancer and colorectal cancer. A positive result for a variant (e.g., marker allele) associated with the cancer is indicative of the individual from which the dataset is derived is at increased susceptibility (increased risk) of the cancer.

In certain embodiments of the invention, a polymorphic marker is correlated to the cancer by referencing genotype data for the polymorphic marker to a look-up table that comprises correlations between at least one allele of the polymorphism and the cancer. In some embodiments, the table comprises a correlation for one polymorphism. In other embodiments, the table comprises a correlation for a plurality of polymorphisms. In both scenarios, by referencing to a look-up table that gives an indication of a correlation between a marker and the cancer, a risk for the cancer, or a susceptibility to the cancer, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

The markers of the invention, e.g., the markers presented in Tables 1-6, may be useful for risk assessment and diagnostic purposes for prostate cancer and/or colorectal cancer, either alone or in combination. Thus, even in cases where the increase in risk by individual markers is relatively modest, i.e. on the order of 10-30%, the association may have significant implications. Thus, relatively common variants may have significant contribution to the overall risk (Population Attributable Risk is high), or combination of markers can be used to define groups of individual who, based on the combined risk of the markers, is at significant combined risk of developing the disease.

Thus, in one embodiment of the invention, a plurality of variants (genetic markers, biomarkers and/or haplotypes) is used for overall risk assessment. These variants are in one embodiment selected from the variants as disclosed herein. Other embodiments include the use of the variants of the present invention in combination with other variants known to be useful for diagnosing a susceptibility to prostate cancer and/or colorectal cancer. In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as multivariate analyses or joint risk analyses, may subsequently be used to determine the overall risk conferred based on the genotype status at the multiple loci. Assessment of risk based on such analysis may subsequently be used in the methods and kits of the invention, as described herein.

In certain embodiments of risk assessment of prostate cancer, the variants described herein to be associated with prostate cancer risk are assessed in combination with at least one marker selected from the group consisting of rs2710646, rs16901979, rs1447295, rs6983267, rs10896450, rs1859962, rs4430796 and rs5945572. Any combination of these markers, or surrogate markers in linkage disequilibrium therewith, with any of the variants described herein for risk assessment of prostate cancer is contemplated.

As described in the above, the haplotype block structure of the human genome has the effect that a large number of variants (markers and/or haplotypes) in linkage disequilibrium with the variant originally associated with a disease or trait may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein (e.g., LD block C11 and/or LD block C06), or by other methods known to the person skilled in the art. However, sometimes marker and haplotype association is found to extend beyond the physical boundaries of the haplotype block as defined. Such markers and/or haplotypes may in those cases be also used as surrogate markers and/or haplotypes for the markers and/or haplotypes physically residing within the haplotype block as defined. As a consequence, markers and haplotypes in LD (typically characterized by $r^2$ greater than 0.1, such as $r^2$ greater than 0.2, including $r^2$ greater than 0.3, also including $r^2$ greater than 0.4) with the markers and haplotypes of the present invention are also within the scope of the invention, even if they are physically located beyond the boundaries of the haplotype block as defined. This includes markers that are described herein (e.g., Tables 1-6, e.g. Tables 3-4), but may also include other markers that are in strong LD (e.g., characterized by $r^2$ greater than 0.1 or 0.2 and/or $|D'|>0.8$) with one or more of the markers listed in Tables 1-6.

For the SNP markers described herein, the opposite allele to the allele found to be in excess in patients (at-risk allele) is found in decreased frequency in prostate cancer and/or colorectal cancer. These markers and haplotypes in LD and/or comprising such markers, are thus protective for prostate cancer and/or colorectal cancer, i.e. they confer a decreased risk or susceptibility of individuals carrying these markers and/or haplotypes developing prostate cancer and/or colorectal cancer.

Certain variants of the present invention, including certain haplotypes comprise, in some cases, a combination of various genetic markers, e.g., SNPs and microsatellites. Detecting haplotypes can be accomplished by methods known in the art and/or described herein for detecting sequences at polymorphic sites. Furthermore, correlation between certain haplotypes or sets of markers and disease phenotype can be verified using standard techniques. A representative example of a simple test for correlation would be a Fisher-exact test on a two by two table.

In specific embodiments, a marker allele or haplotype found to be associated with prostate cancer and/or colorectal cancer, (e.g., marker alleles as listed in Tables 1-6) is one in which the marker allele or haplotype is more frequently present in an individual at risk for prostate cancer and/or colorectal cancer (affected), compared to the frequency of its presence in a healthy individual (control), wherein the presence of the marker allele or haplotype is indicative of prostate cancer and/or colorectal cancer or a susceptibility to prostate cancer and/or colorectal cancer. In other embodiments, at-risk markers in linkage disequilibrium with one or more markers found to be associated with prostate cancer and/or colorectal cancer (e.g., marker alleles as listed in Tables 1-6) are tagging markers that are more frequently present in an individual at risk for prostate cancer and/or colorectal cancer (affected), compared to the frequency of their presence in a healthy individual (control), wherein the presence of the tagging markers is indicative of increased susceptibility to prostate cancer and/or colorectal cancer. In a further embodiment, at-risk markers alleles (i.e. conferring increased susceptibility) in linkage disequilibrium with one or more markers found to be associated with prostate cancer and/or colorectal cancer (e.g., marker alleles as listed in Table 1-6), are markers comprising one or more allele that is more frequently present in an individual at risk for prostate cancer and/or colorectal cancer, compared to the frequency of their presence in a healthy individual (control), wherein the presence of the markers is indicative of increased susceptibility to.

Study Population

In a general sense, the methods and kits of the invention can be utilized from samples containing genomic DNA from any source, i.e. any individual. In preferred embodiments, the individual is a human individual. The individual can be an adult, child, or fetus. The present invention also provides for assessing markers and/or haplotypes in individuals who are members of a target population. Such a target population is in one embodiment a population or group of individuals at risk of developing the disease, based on other genetic factors, biomarkers, biophysical parameters (e.g., weight, BMD, blood pressure), or general health and/or lifestyle parameters (e.g., history of prostate and/or colorectal cancer or other cancers, previous diagnosis of prostate and/or colorectal cancer, family history of prostate cancer and/or colorectal cancer).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or age 30. Other embodiments relate to individuals with age at onset of the disease in any of the age ranges described in the above. It is also contemplated that a range of ages may be relevant in certain embodiments, such as age at onset at more than age 45 but less than age 60. Other age ranges are however also contemplated, including all age ranges bracketed by the age values listed in the above. The invention furthermore relates to individuals of either gender, males or females.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Styrkarsdottir, U., et al. *N Engl J Med Apr.* 29, 2008 (Epub ahead of print); Thorgeirsson, T., et al. *Nature* 452:638-42 (2008); Gudmundsson, J., et al. *Nat Genet.* 40:281-3 (2008); Stacey, S, N., et al., *Nat Genet.* 39:865-69 (2007); Helgadottir, A., et al., *Science* 316:1491-93 (2007); Steinthorsdottir, V., et al., *Nat Genet.* 39:770-75 (2007); Gudmundsson, J., et al., *Nat Genet.* 39:631-37 (2007); Frayling, T M, *Nature Reviews Genet* 8:657-662 (2007); Amundadottir, L. T., et al., *Nat Genet.* 38:652-58 (2006); Grant, S. F., et al., *Nat Genet.* 38:320-23 (2006)). Thus, genetic findings in the Icelandic population have in general been replicated in other populations, including populations from Africa and Asia.

It is thus believed that the markers of the present invention found to be associated with risk of prostate cancer and colorectal cancer to show similar association in other human populations. Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portugues, Italian, Polish, Bulgarian, Slavic, Serbian, Bosnian, Chech, Greek and Turkish populations. The invention furthermore in other embodiments can be practiced in specific human populations that include Bantu, Mandenk, Yoruba, San, Mbuti Pygmy, Orcadian, Adygel, Russian, Sardinian, Tuscan, Mozabite, Bedouin, Druze, Palestinian, Balochi, Brahui, Makrani, Sindhi, Pathan, Burusho, Hazara, Uygur, Kalash, Han, Dai, Daur, Hezhen, Lahu, Miao, Orogen, She, Tujia, Tu, Xibo, Yi, Mongolan, Naxi, Cambodian, Japanese, Yakut, Melanesian, Papuan, Karitianan, Surui, Colmbian, Maya and Pima.

In one preferred embodiment, the invention relates to populations that include black African ancestry such as populations comprising persons of African descent or lineage. Black African ancestry may be determined by self reporting as African-Americans, Afro-Americans, Black Americans, being a member of the black race or being a member of the negro race. For example, African Americans or Black Americans are those persons living in North America and having origins in any of the black racial groups of Africa. In another example, self-reported persons of black African ancestry may have at least one parent of black African ancestry or at least one grandparent of black African ancestry.

The racial contribution in individual subjects may also be determined by genetic analysis. Genetic analysis of ancestry may be carried out using unlinked microsatellite markers such as those set out in Smith et al. (*Am J Hum Genet* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, have different population frequency in different populations, or are polymorphic in one population but not in another. The person skilled in the art will however apply the methods available and as thought herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Utility of Genetic Testing

The person skilled in the art will appreciate and understand that the variants described herein in general do not, by themselves, provide an absolute identification of individuals who will develop a particular disease. The variants described herein do however indicate increased and/or decreased likelihood that individuals carrying the at-risk or protective variants of the invention will develop symptoms associated with prostate cancer and/or colorectal cancer. This information is however extremely valuable in itself, as outlined in more detail in the below, as it can be used to, for example, initiate preventive measures at an early stage, perform regular physical and/or mental exams to monitor the progress and/or appearance of symptoms, or to schedule exams at a regular interval to identify the condition in question, so as to be able to apply treatment at an early stage.

The knowledge of a genetic variant that confers a risk of developing cancer offers the opportunity to apply a genetic-test to distinguish between individuals with increased risk of developing the cancer (i.e. carriers of the at-risk variant) and those with decreased risk of developing the cancer (i.e. carriers of the protective variant, or non-carriers of the at-risk variant). The core values of genetic testing, for individuals belonging to both of the above mentioned groups, are the possibilities of being able to diagnose the cancer at an early stage and provide information to the clinician about prognosis/aggressiveness of the disease in order to be able to apply the most appropriate treatment. For example, the application of a genetic test for cancer (e.g., colorectal cancer or prostate cancer (including aggressive or high Gleason grade prostate cancer, less aggressive or low Gleason grade prostate cancer)) can provide an opportunity for the detection of the cancer at an earlier stage which may lead to the application of therapeutic measures at an earlier stage, and thus can minimize the deleterious effects of the symptoms and serious health consequences conferred by cancer. Some advantages of genetic tests for prostate cancer include:

1. To Aid Early Detection

The application of a genetic test for prostate cancer can provide an opportunity for the detection of the disease at an earlier stage which leads to higher cure rates, if found locally, and increases survival rates by minimizing regional and distant spread of the tumor. For prostate cancer, a genetic test will most likely increase the sensitivity and specificity of the already generally applied Prostate Specific Antigen (PSA) test and Digital Rectal Examination (DRE). This can lead to lower rates of false positives (thus minimize unnecessary procedures such as needle biopsies) and false negatives (thus increasing detection of occult disease and minimizing morbidity and mortality due to PCA).

2. To Determine Aggressiveness

Genetic testing can provide information about pre-diagnostic prognostic indicators and enable the identification of individuals at high or low risk for aggressive tumor types that can lead to modification in screening strategies. For example, an individual determined to be a carrier of a high risk allele for the development of aggressive prostate cancer will likely undergo more frequent PSA testing, examination and have a lower threshold for needle biopsy in the presence of an abnormal PSA value.

Furthermore, identifying individuals that are carriers of high or low risk alleles for aggressive tumor types will lead to modification in treatment strategies. For example, if prostate cancer is diagnosed in an individual that is a carrier of an allele that confers increased risk of developing an aggressive form of prostate cancer, then the clinician would likely advise a more aggressive treatment strategy such as a prostatectomy instead of a less aggressive treatment strategy.

As is known in the art, Prostate Specific Antigen (PSA) is a protein that is secreted by the epithelial cells of the prostate gland, including cancer cells. An elevated level in the blood indicates an abnormal condition of the prostate, either benign or malignant. PSA is used to detect potential problems in the prostate gland and to follow the progress of prostate cancer therapy. PSA levels above 4 ng/ml are indicative of the presence of prostate cancer (although as known in the art and described herein, the test is neither very specific nor sensitive).

In one embodiment, the method of the invention is performed in combination with (either prior to, concurrently or after) a PSA assay. In a particular embodiment, the presence of an at-risk marker or haplotype, in conjunction with the subject having a PSA level greater than 4 ng/ml, is indicative of a more aggressive prostate cancer and/or a worse prognosis. As described herein, particular markers and haplotypes are associated with high Gleason (i.e., more aggressive) prostate cancer. In another embodiment, the presence of a marker or haplotype, in a patient who has a normal PSA level (e.g., less than 4 ng/ml), is indicative of a high Gleason (i.e., more aggressive) prostate cancer and/or a worse prognosis. A "worse prognosis" or "bad prognosis" occurs when it is more likely that the cancer will grow beyond the boundaries of the prostate gland, metastasize, escape therapy and/or kill the host.

In one embodiment, the presence of a marker or haplotype is indicative of a predisposition to a somatic rearrangement (e.g., one or more of an amplification, a translocation, an insertion and/or deletion) in a tumor or its precursor. The somatic rearrangement itself may subsequently lead to a more aggressive form of prostate cancer (e.g., a higher histologic grade, as reflected by a higher Gleason score or higher stage at diagnosis, an increased progression of prostate cancer (e.g., to a higher stage), a worse outcome (e.g., in terms of morbidity, complications or death)). As is known in the art, the Gleason grade is a widely used method for classifying prostate cancer tissue for the degree of loss of the normal glandular architecture (size, shape and differentiation of glands). A grade from 1-5 is assigned successively to each of the two most predominant tissue patterns present in the examined tissue sample and are added together to produce the total or combined Gleason grade (scale of 2-10). High numbers indicate poor differentiation and therefore more aggressive cancer.

Aggressive prostate cancer is cancer that grows beyond the prostate, metastasizes and eventually kills the patient. As described herein, one surrogate measure of aggressiveness is a high combined Gleason grade. The higher the grade on a scale of 2-10 the more likely it is that a patient has aggressive disease.

The present invention furthermore relates to risk assessment for prostate cancer and colorectal cancer, including diagnosing whether an individual is at risk for developing prostate cancer and/or colorectal cancer. The polymorphic markers of the present invention can be used alone or in combination, as well as in combination with other factors, including other genetic risk factors or biomarkers, for risk assessment of an individual for prostate cancer and/or colorectal cancer. Certain factors known to affect the predisposition of an individual towards developing risk of developing common disease, including prostate cancer and/or colorectal cancer are known to the person skilled in the art and can be utilized in such assessment. These include, but are not limited to, age, gender, smoking status, family history of cancer, previously diagnosed cancer, colonic adenomas, chronic inflammatory bowel disease and diet. Methods known in the art can be used for such assessment, including multivariate analyses or logistic regression.

Methods

Methods for risk assessment of and risk management of prostate cancer and/or colorectal cancer are described herein and are encompassed by the invention. The invention also encompasses methods of assessing an individual for probability of response to a therapeutic agent for prostate cancer and/or colorectal cancer, as well as methods for predicting the effectiveness of a therapeutic agent for prostate cancer and/or colorectal cancer. Kits for assaying a sample from a subject to detect susceptibility to prostate cancer and/or colorectal cancer are also encompassed by the invention.

Diagnostic and Screening Methods

In certain embodiments, the present invention pertains to methods of diagnosing, or aiding in the diagnosis of, prostate cancer and/or colorectal cancer or a susceptibility to prostate cancer and/or colorectal cancer, by detecting particular alleles at genetic markers that appear more frequently in prostate cancer and/or colorectal cancer subjects or subjects who are susceptible to prostate cancer and/or colorectal cancer. In a particular embodiment, the invention is a method of diagnosing a susceptibility to prostate cancer and/or colorectal cancer by detecting at least one allele of at least one polymorphic marker (e.g., the markers described herein). The present invention describes methods whereby detection of particular alleles of particular markers or haplotypes is indicative of a susceptibility to prostate cancer and/or colorectal cancer. Such prognostic or predictive assays can also be used to determine prophylactic treatment of a subject prior to the onset of symptoms of prostate cancer and/or colorectal cancer.

The present invention pertains in some embodiments to methods of clinical applications of diagnosis, e.g., diagnosis performed by a medical professional. In other embodiments, the invention pertains to methods of diagnosis performed by a layman. The layman can be the customer of a genotyping service. The layman may also be a genotype service provider, who performs genotype analysis on a DNA sample from an individual, in order to provide service related to genetic risk factors for particular traits or diseases, based on the genotype status of the individual (i.e., the customer). Recent technological advances in genotyping technologies, including high-throughput genotyping of SNP markers, such as Molecular Inversion Probe array technology (e.g., Affymetrix Gene-Chip), and BeadArray Technologies (e.g., Illumina Golden-Gate and Infinium assays) have made it possible for individuals to have their own genome assessed for up to one million SNPs simultaneously, at relatively little cost. The resulting genotype information, made available to the customer can be compared to information from the public literature about disease or trait risk associated with various SNPs. The diagnostic application of disease-associated alleles as described herein, can thus be performed either by the individual, through analysis of his/her genotype data, or by a health professional based on results of a clinical test. In other words, the diagnosis or assessment of a susceptibility based on genetic risk can be made by health professionals, genetic counselors or by the layman, based on information about his/her genotype and publications on various risk factors. In the present context, the term "diagnosing", and "diagnose a susceptibility", is meant to refer to any available diagnostic method, including those mentioned above.

In certain embodiments, a sample containing genomic DNA from an individual is collected. Such sample can for example be a buccal swab, a saliva sample, a blood sample, or other suitable samples containing genomic DNA, as described further herein. The genomic DNA is then analyzed using any common technique available to the skilled person, such as high-throughput array technologies. Results from such genotyping are stored in a convenient data storage unit, such as a data carrier, including computer databases, data storage disks, or by other convenient data storage means. In certain embodiments, the computer database is an object database, a relational database or a post-relational database. The genotype data is subsequently analyzed for the presence of certain variants known to be susceptibility variants for a particular human conditions, such as the genetic variants described herein. Genotype data can be retrieved from the data storage unit using any convenient data query method. Calculating risk conferred by a particular genotype for the individual can be based on comparing the genotype of the individual to previously determined risk (expressed as a relative risk (RR) or and odds ratio (OR), for example) for the genotype, for example for an heterozygous carrier of an at-risk variant for a particular disease or trait (such as prostate cancer and colorectal cancer). The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. Using the population average may in certain embodiments be more convenient, since it provides a measure which is easy to interpret for the user, i.e. a measure that gives the risk for the individual, based on his/her genotype, compared with the average in the population. The calculated risk estimated can be made available to the customer via a website, preferably a secure website.

In certain embodiments, a service provider will include in the provided service all of the steps of isolating genomic DNA from a sample provided by the customer, performing genotyping of the isolated DNA, calculating genetic risk based on the genotype data, and report the risk to the customer. In some other embodiments, the service provider will include in the service the interpretation of genotype data for the individual, i.e., risk estimates for particular genetic variants based on the genotype data for the individual. In some other embodiments, the service provider may include service that includes genotyping service and interpretation of the genotype data, starting from a sample of isolated DNA from the individual (the customer).

Custom sequencing service can also be used to assess genotype status of individuals. Targeted sequencing or whole genome sequencing technologies can be used to determine the identity of nucleotides at certain polymorphic sites. Determination of such identity defines the allelic status of the individual at the site, i.e. provides genotype information. Such sequencing services can thus also be utilized to realize the present invention. As whole-genome sequencing technologies become economically feasible on a large scale, utilization of genotype information based on such technologies may become preferable. Certain embodiments of the invention encompass genotyping performed by such sequencing technologies.

In addition, in certain other embodiments, the present invention pertains to methods of diagnosing, or aiding in the diagnosis of, a decreased susceptibility to prostate cancer and/or colorectal cancer, by detecting particular genetic marker alleles or haplotypes that appear less frequently in prostate cancer and/or colorectal cancer patients than in individual not diagnosed with prostate cancer and/or colorectal cancer or in the general population.

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

As described and exemplified herein, particular marker alleles or haplotypes (e.g. the markers and haplotypes as listed in Tables 1-6) are associated with prostate cancer and colorectal cancer. In one embodiment, the marker allele or haplotype is one that confers a significant risk or susceptibility to prostate cancer and/or colorectal cancer. In another embodiment, the invention relates to a method of determining or diagnosing a susceptibility to prostate cancer and/or colorectal cancer in a human individual, the method comprising determining the presence or absence of at least one allele of at least one polymorphic marker in a nucleic acid sample obtained from the individual, wherein the at least one polymorphic marker is selected from the group consisting of the polymorphic markers listed in Table 5 and 6, and markers in linkage disequilibrium (e.g., defined as $r^2>0.2$) therewith. In another embodiment, the invention pertains to methods of diagnosing or determining a susceptibility to prostate cancer and/or colorectal cancer in a human individual, by screening for at least one marker allele as listed in Table 3 and Table 4 or markers in linkage disequilibrium therewith. In another embodiment, the invention relates to methods of diagnosing or determining a susceptibility to colorectal cancer in a human individual, by screening for at least one marker as listed in Table 4. In another embodiment, the marker allele or haplotype is more frequently present in a subject having, or who is susceptible to, prostate cancer and/or colorectal cancer (affected), as compared to the frequency of its presence in a healthy subject (control, such as population controls). In certain embodiments, the significance of association of the at least one marker allele or haplotype is characterized by a p value <0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to prostate cancer and/or colorectal cancer. These diagnostic methods involve detecting the presence or absence of at least one marker allele or haplotype that is associated with prostate cancer and/or colorectal cancer. The haplotypes described herein include combinations of alleles at various genetic markers (e.g., SNPs, microsatellites). The detection of the particular genetic marker alleles that make up the particular haplotypes can be performed by a variety of methods described herein and/or known in the art. For example, genetic markers can be detected at the nucleic acid level (e.g., by direct nucleotide sequencing or by other means known to the skilled in the art) or at the amino acid level if the genetic marker affects the coding sequence of a protein encoded by a cancer (prostate cancer or colorectal cancer)-associated nucleic acid (e.g., by protein sequencing or by immunoassays using antibodies that recognize such a protein). The marker alleles or haplotypes of the present invention correspond to fragments of a genomic DNA sequence associated with prostate cancer and/or colorectal cancer. Such fragments encompass the DNA sequence of the polymorphic marker or haplotype in question, but may also include DNA segments in strong LD (linkage disequilibrium) with the marker or haplotype. In one embodiment, such segments comprises segments in LD with the marker or haplotype as determined by a value of $r^2$ greater than 0.1 and/or |D'|>0.8).

In one embodiment, diagnosis of a susceptibility to prostate cancer and/or colorectal cancer can be accomplished using hybridization methods, such as Southern analysis, Northern analysis, and/or in situ hybridizations (see Current Protocols in Molecular Biology, Ausubel, F. et al., eds., John Wiley & Sons, including all supplements). The presence of a specific marker allele can be indicated by sequence-specific hybridization of a nucleic acid probe specific for the particular allele. The presence of more than specific marker allele or a specific haplotype can be indicated by using several sequence-specific nucleic acid probes, each being specific for a particular allele. In one embodiment, a haplotype can be indicated by a single nucleic acid probe that is specific for the specific haplotype (i.e., hybridizes specifically to a DNA strand comprising the specific marker alleles characteristic of the haplotype). A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample.

To diagnose a susceptibility to prostate cancer and/or colorectal cancer, a hybridization sample is formed by contacting the test sample containing a prostate cancer and/or colorectal cancer-associated nucleic acid, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. For example, the nucleic acid probe can comprise all or a portion of the nucleotide sequence of LD Block C06 or LD Block C11, as described herein, optionally comprising at least one allele of a marker described herein, or the probe can be the complementary sequence of such a sequence. In a particular embodiment, the nucleic acid probe is a portion of the nucleotide sequence of LD Block C06 or LD Block C11, as described herein, optionally comprising at least one allele of a marker described herein, or at least one allele of one polymorphic marker or haplotype comprising at least one polymorphic marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the present invention, or markers that make up a haplotype of the present invention, or multiple probes can be used concurrently to detect more than one, marker alleles at a time. It is also possible to design a single probe containing more than one marker alleles of a particular haplotype (e.g., a probe containing alleles complementary to 2, 3, 4, 5 or all of the markers that make up a particular haplotype). Detection of the particular markers of the haplotype in the sample is indicative that the source of the sample has the particular haplotype (e.g., a haplotype) and therefore is susceptible to prostate cancer and/or colorectal cancer.

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In another hybridization method, Northern analysis (see Current Protocols in Molecular Biology, Ausubel, F. et al., eds., John Wiley & Sons, supra) is used to identify the presence of a polymorphism associated with prostate cancer and/or colorectal cancer. For Northern analysis, a test sample of RNA is obtained from the subject by appropriate means. As described herein, specific hybridization of a nucleic acid probe to RNA from the subject is indicative of a particular allele complementary to the probe. For representative examples of use of nucleic acid probes, see, for example, U.S. Pat. Nos. 5,288,611 and 4,851,330.

Additionally, or alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more of the marker alleles or haplotypes that are associated with prostate cancer and/or colorectal cancer. Hybridization of the PNA probe is thus diagnostic for prostate cancer and/or colorectal cancer or a susceptibility to prostate cancer and/or colorectal cancer In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype associated with prostate cancer and/or colorectal cancer, can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis using quantitative PCR (kinetic thermal cycling). This technique can, for example, utilize commercially available technologies, such as TaqMan®

(Applied Biosystems, Foster City, Calif.). The technique can assess the presence of an alteration in the expression or composition of a polypeptide or splicing variant(s) that is encoded by a nucleic acid associated with prostate cancer and/or colorectal cancer. Further, the expression of the variant(s) can be quantified as physically or functionally different.

In another embodiment of the methods of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles or haplotypes associated with prostate cancer and/or colorectal cancer (e.g. the polymorphic markers of Tables 4 and 5, and markers in linkage disequilibrium therewith). Therefore, in one embodiment, determination of the presence or absence of a particular marker alleles or haplotypes comprises sequence analysis of a test sample of DNA or RNA obtained from a subject or individual. PCR or other appropriate methods can be used to amplify a portion of a nucleic acid associated with prostate cancer and/or colorectal cancer, and the presence of a specific allele can then be detected directly by sequencing the polymorphic site (or multiple polymorphic sites in a haplotype) of the genomic DNA in the sample.

Allele-specific oligonucleotides can also be used to detect the presence of a particular allele in a nucleic acid associated with prostate cancer and/or colorectal cancer (e.g. the polymorphic markers of Tables 3 and 4, and markers in linkage disequilibrium therewith), through the use of dot-blot hybridization of amplified oligonucleotides with allele-specific oligonucleotide (ASO) probes (see, for example, Saiki, R. et al., *Nature,* 324:163-166 (1986)). An "allele-specific oligonucleotide" (also referred to herein as an "allele-specific oligonucleotide probe") is an oligonucleotide of approximately 10-50 base pairs or approximately 15-30 base pairs, that specifically hybridizes to a nucleic acid associated with prostate cancer and/or colorectal cancer, and which contains a specific allele at a polymorphic site (e.g., a marker or haplotype as described herein). An allele-specific oligonucleotide probe that is specific for one or more particular a nucleic acid associated with prostate cancer and/or colorectal cancer can be prepared using standard methods (see, e.g., Current Protocols in Molecular Biology, supra). PCR can be used to amplify the desired region. The DNA containing the amplified region can be dot-blotted using standard methods (see, e.g., Current Protocols in Molecular Biology, supra), and the blot can be contacted with the oligonucleotide probe. The presence of specific hybridization of the probe to the amplified region can then be detected. Specific hybridization of an allele-specific oligonucleotide probe to DNA from the subject is indicative of a specific allele at a polymorphic site associated with DISEASE (see, e.g., Gibbs, R. et al., *Nucleic Acids Res.,* 17:2437-2448 (1989) and WO 93/22456).

In another embodiment, arrays of oligonucleotide probes that are complementary to target nucleic acid sequence segments from a subject, can be used to identify particular alleles at polymorphic sites. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light directed synthesis methods that incorporate a combination of photolithographic methods and solid phase oligonucleotide synthesis methods, or by other methods known to the person skilled in the art (see, e.g., Bier, F. F., et al. *Adv Biochem Eng Biotechnol* 109:433-53 (2008); Hoheisel, J. D., *Nat Rev Genet.* 7:200-10 (2006); Fan, J. B., et al. *Methods Enzymol* 410:57-73 (2006); Raqoussis, J. & Elvidge, G., *Expert Rev Mol Diagn* 6:145-52 (2006); Mockler, T. C., et al *Genomics* 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. No. 6,858,394, U.S. Pat. No. 6,429,027, U.S. Pat. No. 5,445,934, U.S. Pat. No. 5,700,637, U.S. Pat. No. 5,744,305, U.S. Pat. No. 5,945,334, U.S. Pat. No. 6,054,270, U.S. Pat. No. 6,300,063, U.S. Pat. No. 6,733,977, U.S. Pat. No. 7,364,858, EP 619 321, and EP 373 203, the entire teachings of which are incorporated by reference herein.

Other methods of nucleic acid analysis that are available to those skilled in the art can be used to detect a particular allele at a polymorphic site associated with prostate cancer and/or colorectal cancer (e.g. the polymorphic markers of Tables 3 and 4, and markers in linkage disequilibrium therewith). Representative methods include, for example, direct manual sequencing (Church and Gilbert, *Proc. Natl. Acad. Sci. USA,* 81: 1991-1995 (1988); Sanger, F., et al., *Proc. Natl. Acad. Sci. USA,* 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA,* 86:232-236 (1989)), mobility shift analysis (Orita, M., et al., *Proc. Natl. Acad. Sci. USA,* 86:2766-2770 (1989)), restriction enzyme analysis (Flavell, R., et al., *Cell,* 15:25-41 (1978); Geever, R., et al., *Proc. Natl. Acad. Sci. USA,* 78:5081-5085 (1981)); heteroduplex analysis; chemical mismatch cleavage (CMC) (Cotton, R., et al., *Proc. Natl. Acad. Sci. USA,* 85:4397-4401 (1985)); RNase protection assays (Myers, R., et al., *Science,* 230:1242-1246 (1985); use of polypeptides that recognize nucleotide mismatches, such as *E. coli* mutS protein; and allele-specific PCR.

In another embodiment of the invention, diagnosis of prostate cancer and/or colorectal cancer or a susceptibility to prostate cancer and/or colorectal cancer can be made by examining expression and/or composition of a polypeptide encoded by a nucleic acid associated with prostate cancer and/or colorectal cancer in those instances where the genetic marker(s) or haplotype(s) of the present invention result in a change in the composition or expression of the polypeptide. Thus, diagnosis of a susceptibility to prostate cancer and/or colorectal cancer can be made by examining expression and/or composition of one of these polypeptides, or another polypeptide encoded by a nucleic acid associated with prostate cancer and/or colorectal cancer, in those instances where the genetic marker or haplotype of the present invention results in a change in the composition or expression of the polypeptide. The haplotypes and markers of the present invention that show association to prostate cancer and/or colorectal cancer may play a role through their effect on one or more of these nearby genes. Possible mechanisms affecting these genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) of the invention showing association to prostate cancer and/or colorectal cancer affect the expression of a nearby gene. It is well known that regulatory element affecting gene expression may be located far away, even as far as tenths or hundreds of kilobases away, from the promoter region of a gene. By assaying for the presence or absence of at least one allele of at least one polymorphic marker of the present invention, it is thus possible to assess the expression level of such nearby genes.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a nucleic acid associated with prostate cancer and/or colorectal cancer. An alteration in expression of a polypeptide encoded by a nucleic acid associated with prostate cancer and/or colorectal cancer can be, for example, an alteration in the quantitative polypeptide expression (i.e., the amount of polypeptide produced). An alteration in the composition of a polypeptide encoded by a nucleic acid associated with prostate cancer and/or colorectal cancer is an alteration in the qualitative polypeptide expression (e.g., expression of a mutant polypeptide or of a different splicing variant). In one embodiment, diagnosis of a susceptibility to prostate cancer and/or colorectal cancer is made by detecting a particular splicing variant encoded by a nucleic acid associated with prostate cancer and/or colorectal cancer, or a particular pattern of splicing variants.

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, prostate cancer and/or colorectal cancer. In one embodiment, the control sample is from a subject that does not possess a marker allele or haplotype as described herein. Similarly, the presence of one or more different splicing variants in the test sample, or the presence of significantly different amounts of different splicing variants in the test sample, as compared with the control sample, can be indicative of a susceptibility to prostate cancer and/or colorectal cancer. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with prostate cancer and/or colorectal cancer can be used. Antibodies can be polyclonal or monoclonal. An intact antibody, or a fragment thereof (e.g., Fv, Fab, Fab', F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of polypeptide encoded by a nucleic acid associated with prostate cancer and/or colorectal cancer in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, the diagnosis of a susceptibility to prostate cancer and/or colorectal cancer is made by detecting at least one marker or haplotypes of the present invention (e.g., associated alleles of the markers listed in Tables 1-6, and markers in linkage disequilibrium therewith), in combination with an additional protein-based, RNA-based or DNA-based assay. The methods of the invention can also be used in combination with an analysis of a subject's family history and risk factors (e.g., environmental risk factors, lifestyle risk factors).

Kits

Kits useful in the methods of the invention comprise components useful in any of the methods described herein, including for example, primers for nucleic acid amplification, hybridization probes, restriction enzymes (e.g., for RFLP analysis), allele-specific oligonucleotides, antibodies that bind to an altered polypeptide encoded by a nucleic acid of the invention as described herein (e.g., a genomic segment comprising at least one polymorphic marker and/or haplotype of the present invention) or to a non-altered (native) polypeptide encoded by a nucleic acid of the invention as described herein, means for amplification of a nucleic acid associated with prostate cancer and/or colorectal cancer, means for analyzing the nucleic acid sequence of a nucleic acid associated with prostate cancer and/or colorectal cancer, means for analyzing the amino acid sequence of a polypeptide encoded by a nucleic acid associated with prostate cancer and/or colorectal cancer (e.g., a prostate cancer and/or colorectal cancer protein encoded by a prostate cancer and/or colorectal cancer-associated gene), etc. The kits can for example include necessary buffers, nucleic acid primers for amplifying nucleic acids of the invention (e.g., a nucleic acid segment comprising one or more of the polymorphic markers as described herein), and reagents for allele-specific detection of the fragments amplified using such primers and necessary enzymes (e.g., DNA polymerase). Additionally, kits can provide reagents for assays to be used in combination with the methods of the present invention, e.g., reagents for use with other prostate cancer and/or colorectal cancer diagnostic assays.

In one embodiment, the invention is a kit for assaying a sample from a subject to detect the presence of prostate cancer and/or colorectal cancer, symptoms associated with prostate cancer and/or colorectal cancer, or a susceptibility to prostate cancer and/or colorectal cancer in a subject, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism, wherein the polymorphism is selected from the group consisting of the polymorphisms as listed in Tables 1-6, and polymorphic markers in linkage disequilibrium therewith. In yet another embodiment the fragment is at least 20 base pairs in size. Such oligonucleotides or nucleic acids (e.g., oligonucleotide primers) can be designed using portions of the nucleic acid sequence flanking polymorphisms (e.g., SNPs or microsatellites) that are indicative of prostate cancer and/or colorectal cancer. In another embodiment, the kit comprises one or more labeled nucleic acids capable of allele-specific detection of one or more specific polymorphic markers or haplotypes associated with prostate cancer and/or colorectal cancer, and reagents for detection of the label. Suitable labels include, e.g., a radioisotope, a fluorescent label, an enzyme label, an enzyme co-factor label, a magnetic label, a spin label, an epitope label.

In particular embodiments, the polymorphic marker or haplotype to be detected by the reagents of the kit comprises one or more markers, two or more markers, three or more markers, four or more markers or five or more markers selected from the group consisting of the markers set forth in Tables 1-6. In another embodiment, the marker or haplotype to be detected comprises the markers set forth in Tables 3 and 4. In another embodiment, the marker or haplotype to be detected comprises at least one marker from the group of markers in strong linkage disequilibrium, as defined by values of $r^2$ greater than 0.2, to at least one of the group of markers listed in Tables 3 and 4. In another embodiment, the marker or haplotype to be detected is selected from the group consisting of rs10896450, rs7947353, rs11228565 and rs10943605.

In one preferred embodiment, the kit for detecting the markers of the invention comprises a detection oligonucleotide probe, that hybridizes to a segment of template DNA containing a SNP polymorphisms to be detected, an enhancer oligonucleotide probe and an endonuclease. As explained in the above, the detection oligonucleotide probe comprises a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

In one of such embodiments, determination of the presence of the marker or haplotype is indicative of a susceptibility (increased susceptibility or decreased susceptibility) to prostate cancer and/or colorectal cancer. In another embodiment, the presence of the marker or haplotype is indicative of response to a therapeutic agent for prostate cancer and/or colorectal cancer. In another embodiment, the presence of the marker or haplotype is indicative of prognosis of prostate cancer and/or colorectal cancer. In yet another embodiment, the presence of the marker or haplotype is indicative of progress of treatment of prostate cancer and/or colorectal cancer. Such treatment may include intervention by surgery, medication or by other means (e.g., lifestyle changes).

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or RNAi molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

In certain embodiments, the kit further comprises a set of instructions for using the reagents comprising the kit. In certain embodiments, the kit further comprises a collection of data comprising correlation data between the polymorphic markers assessed by the kit and susceptibility to prostate cancer and/or colorectal cancer.

Therapeutic Agents

Variants of the present invention (e.g., the markers of the invention, e.g., the markers listed in Tables 1-6, e.g., the markers set forth in Tables 3 and 4, and markers in linkage disequilibrium therewith, e.g., rs10896450, rs7947353, rs11228565 and rs10943605) can be used to identify novel therapeutic targets for prostate cancer and/or colorectal cancer. For example, genes containing, or in linkage disequilibrium with, variants (markers and/or haplotypes) associated with prostate cancer and/or colorectal cancer, or their products, as well as genes or their products that are directly or indirectly regulated by or interact with these variant genes or their products, can be targeted for the development of therapeutic agents to treat prostate cancer and/or colorectal cancer, or prevent or delay onset of symptoms associated with prostate cancer and/or colorectal cancer. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants of the invention, or nucleic acids comprising their complementary sequence, may be used as antisense constructs to control gene expression in cells, tissues or organs. The methodology associated with antisense techniques is well known to the skilled artisan, and is described and reviewed in *Antisense Drug Technology: Principles, Strategies, and Applications*, Crooke, ed., Marcel Dekker Inc., New York (2001). In general, antisense agents (antisense oligonucleotides) are comprised of single stranded oligonucleotides (RNA or DNA) that are capable of binding to a complimentary nucleotide segment. By binding the appropriate target sequence, an RNA-RNA, DNA-DNA or RNA-DNA duplex is formed. The antisense oligonucleotides are complementary to the sense or coding strand of a gene. It is also possible to form a triple helix, where the antisense oligonucleotide binds to duplex DNA.

Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today*, 7:912-917 (2002)). Antisense oligonucleotides are useful directly as therapeutic agents, and are also useful for determining and validating gene function, for example by gene knock-out or gene knock-down experiments. Antisense technology is further described in Layery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer. Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002).

In certain embodiments, the antisense agent is an oligonucleotide that is capable of binding to a nucleotide segment of the LD Block C11 or LD Block C06, as described herein. Antisense nucleotides can be from 5-500 nucleotides in length, including 5-200 nucleotides, 5-100 nucleotides, 8-50 nucleotides, and 8-30 nucleotides. In certain preferred embodiments, the antisense nucleotides is from 14-50 nucleotides in length, including 14-40 nucleotides and 14-30 nucleotides. In certain such embodiments, the antisense nucleotide is capable of binding to a nucleotide segment of LD Block C11 as set forth in SEQ ID NO:201.

The variants described herein can be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus protein expression, the molecules can be used to treat a disease or disorder, including prostate cancer and/or colorectal cancer. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today*, 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (*FEBS Lett.* 579:5974-81 (2005)). Chemically synthetic siRNAs and shRNAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., *Science* 296: 550-553 (2002)).

Since RNAi molecules, including siRNA, miRNA and shRNA, act in a sequence-dependent manner, the variants of the present invention (e.g., the markers set forth in Tables 1-6, e.g., the markers set forth in Tables 3 and 4) can be used to design RNAi reagents that recognize specific nucleic acid molecules comprising specific alleles and/or haplotypes (e.g., the alleles and/or haplotypes of the present invention), while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100:6343-6346 (2003), Vickers et al., *J. Biol. Chem.* 278:7108-7118 (2003), Agami, *Curr. Opin. Chem. Biol.* 6:829-834 (2002), Lavery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of a disease, such as prostate cancer and/or colorectal cancer, or a defect causing the disease, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the administered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat prostate cancer and/or colorectal cancer. Thus, the variants of the invention are useful as targets for the identification and/or development of therapeutic agents. Such methods may include assaying the ability of an agent or compound to modulate the activity and/or expression of a nucleic acid that includes at least one of the variants (markers and/or haplotypes) of the present invention, or the encoded product of the nucleic acid. This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for treating prostate cancer and/or colorectal cancer can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents, Methods of Monitoring Progress of Treatment and Methods of Treatment As is known in the art, individuals can have differential responses to a particular therapy (e.g., a therapeutic agent or therapeutic method). Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may determine the manner in which a therapeutic agent and/or method acts on the body, or the way in which the body metabolizes the therapeutic agent.

Accordingly, in one embodiment, the presence of a particular allele at a polymorphic site or haplotype is indicative of a different, e.g. a different response rate, to a particular treatment modality for prostate cancer and/or colorectal cancer. This means that a patient diagnosed with prostate cancer and/or colorectal cancer, and carrying a certain allele at a polymorphic or haplotype of the present invention (e.g., the at-risk and protective alleles and/or haplotypes of the invention) would respond better to, or worse to, a specific therapeutic, drug therapy and/or other therapy used to treat the disease. Therefore, the presence or absence of the marker allele or haplotype could aid in deciding what treatment should be used for a the patient. For example, for a newly diagnosed patient, the presence of a marker or haplotype of the present invention may be assessed (e.g., through testing DNA derived from a blood sample, as described herein). If the patient is positive for a marker allele or haplotype at (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

The present invention also relates to methods of monitoring progress or effectiveness of a treatment for a prostate cancer and/or colorectal cancer. This can be done based on the genotype and/or haplotype status of the markers and haplotypes of the present invention, i.e., by assessing the absence or presence of at least one allele of at least one polymorphic marker as disclosed herein, or by monitoring expression of genes that are associated with the variants (markers and haplotypes) of the present invention. The risk gene mRNA or the encoded polypeptide can be measured in a tissue sample (e.g., a peripheral blood sample, or a biopsy sample). Expression levels and/or mRNA levels can thus be determined before and during treatment to monitor its effectiveness. Alternatively, or concomitantly, the genotype and/or haplotype status of at least one risk variant for prostate cancer and/or colorectal cancer as presented herein is determined before and during treatment to monitor its effectiveness.

Alternatively, biological networks or metabolic pathways related to the markers and haplotypes of the present invention can be monitored by determining mRNA and/or polypeptide levels. This can be done for example, by monitoring expression levels or polypeptides for several genes belonging to the network and/or pathway, in samples taken before and during treatment. Alternatively, metabolites belonging to the biological network or metabolic pathway can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of at least one at-risk variant of the present invention, i.e. individuals who are carriers of at least one allele of at least one polymorphic marker conferring increased risk of developing prostate cancer and/or colorectal cancer may be more likely to respond to a particular treatment modality. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product. This application can improve the safety of clinical trials, but can also enhance the chance that a clinical trial will demonstrate statistically significant efficacy, which may be limited to a certain sub-group of the population. Thus, one possible outcome of such a trial is that carriers of certain genetic variants, e.g., the markers and haplotypes of the present invention, are statistically significantly likely to show positive response to the therapeutic agent, i.e. experience alleviation of symptoms associated with prostate cancer and/or colorectal cancer when taking the therapeutic agent or drug as prescribed.

In a further aspect, the markers and haplotypes of the present invention can be used for targeting the selection of pharmaceutical agents for specific individuals. Personalized selection of treatment modalities, lifestyle changes or combination of lifestyle changes and administration of particular treatment, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

The FIGURE illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method or apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices; and the like.

The steps of the claimed method and system may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to the FIGURE, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, the FIGURE illustrates operating system 134, application programs 135, other program modules 136, and program data 137.

The computer 110 may also include other removable/non-removable, volatile/nonvolatile computer storage media. By way of example only, the FIGURE illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in the FIGURE, provide storage of computer readable instructions, data structures, program modules and other data for the computer 110. In the FIGURE, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in the FIGURE. The logical connections depicted in FIGURE include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, the FIGURE illustrates remote application programs 185 as residing on memory device 181. It will be appreciated that the network connections shown are exemplary and other means of establishing a communications link between the computers may be used.

Although the forgoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

While the risk evaluation system and method, and other elements, have been described as preferably being implemented in software, they may be implemented in hardware, firmware, etc., and may be implemented by any other processor. Thus, the elements described herein may be implemented in a standard multi-purpose CPU or on specifically designed hardware or firmware such as an application-specific integrated circuit (ASIC) or other hard-wired device as desired, including, but not limited to, the computer 110 of the FIGURE. When implemented in software, the software routine may be stored in any computer readable memory such as on a magnetic disk, a laser disk, or other storage medium, in a RAM or ROM of a computer or processor, in any database, etc. Likewise, this software may be delivered to a user or a diagnostic system via any known or desired delivery method including, for example, on a computer readable disk or other transportable computer storage mechanism or over a communication channel such as a telephone line, the interne, wireless communication, etc. (which are viewed as being the same as or interchangeable with providing such software via a transportable storage medium).

Thus, many modifications and variations may be made in the techniques and structures described and illustrated herein without departing from the spirit and scope of the present invention. Thus, it should be understood that the methods and apparatus described herein are illustrative only and are not limiting upon the scope of the invention.

Accordingly, the invention relates to computer-implemented applications using the polymorphic markers and haplotypes described herein, and genotype and/or disease-association data derived therefrom. Such applications can be useful for storing, manipulating or otherwise analyzing genotype data that is useful in the methods of the invention. One example pertains to storing genotype information derived from an individual on readable media, so as to be able to provide the genotype information to a third party (e.g., the individual, a guardian of the individual, a health care provider or genetic analysis service provider), or for deriving information from the genotype data, e.g., by comparing the genotype data to information about genetic risk factors contributing to increased susceptibility to prostate and/or colorectal cancer, and reporting results based on such comparison.

In general terms, computer-readable media has capabilities of storing (i) identifier information for at least one polymorphic marker or a haplotype, as described herein; (ii) an indicator of the frequency of at least one allele of said at least one marker, or the frequency of a haplotype, in individuals with prostate cancer and/or colorectal cancer; and an indicator of the frequency of at least one allele of said at least one marker, or the frequency of a haplotype, in a reference population. The reference population can be a disease-free population of individuals. Alternatively, the reference population is a random sample from the general population, and is thus representative of the population at large. The frequency indicator may be a calculated frequency, a count of alleles and/or haplotype copies, or normalized or otherwise manipulated values of the actual frequencies that are suitable for the particular medium.

The markers and haplotypes described herein to be associated with increased susceptibility (e.g., increased risk) of prostate and colorectal cancer, are in certain embodiments useful for interpretation and/or analysis of genotype data. Thus in certain embodiments, an identification of an at-risk allele for prostate cancer and/or colorectal cancer, as shown herein, or an allele at a polymorphic marker in LD with any one of the markers shown herein to be associated with these cancers, is indicative of the individual from whom the genotype data originates is at increased risk of prostate cancer and/or colorectal cancer. In one such embodiment, genotype data is generated for at least one such polymorphic marker, or a marker in linkage disequilibrium therewith. The genotype data is subsequently made available to a third party, such as the individual from whom the data originates, his/her guardian or representative, a physician or health care worker, genetic counselor, or insurance agent, for example via a user interface accessible over the internet, together with an interpretation of the genotype data, e.g., in the form of a risk measure (such as an absolute risk (AR), risk ratio (RR) or odds ratio (OR)) for the disease. In another embodiment, at-risk markers identified in a genotype dataset derived from an individual are assessed and results from the assessment of the risk conferred by the presence of such at-risk variants in the dataset are made available to the third party, for example via a secure web interface, or by other communication means. The results of such risk assessment can be reported in numeric form (e.g., by risk values, such as absolute risk, relative risk, and/or an odds ratio, or by a percentage increase in risk compared with a reference), by graphical means, or by other means suitable to illustrate the risk to the individual from whom the genotype data is derived.

Nucleic Acids and Polypeptides

The nucleic acids and polypeptides described herein can be used in methods an kits of the present invention, as described in the above.

An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a marker or haplotype described herein). Such nucleic acid molecules can be detected and/or isolated by allele- or sequence-specific hybridization (e.g., under high stringency conditions). Stringency conditions and methods for nucleic acid hybridizations are well known to the skilled person (see, e.g., *Current Protocols in Molecular Biology*, Ausubel, F. et al, John Wiley & Sons, (1998), and Kraus, M. and Aaronson, S., *Methods Enzymol.*, 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions× 100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S, and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA,* 85:2444-48 (1988). In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, the nucleotide sequence of LD Block C06 and/or LD Block C11, as defined herein, or a nucleotide sequence comprising, or consisting of, the complement of the nucleotide sequence of LD Block C06 and/or LD Block C11, wherein the nucleotide sequence comprises at least one polymorphic allele contained in the markers and haplotypes described herein. The nucleic acid fragments of the invention are at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule. In one embodiment, the probe or primer comprises at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labeled (e.g., radiolabeled) and used as a probe for screening a cDNA library derived from human cells. The cDNA can be derived from mRNA and contained in a suitable vector. Corresponding clones can be isolated, DNA can obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

Antibodies

The invention also provides antibodies which bind to an epitope comprising either a variant amino acid sequence (e.g., comprising an amino acid substitution) encoded by a variant allele or the reference amino acid sequence encoded by the corresponding non-variant or wild-type allele. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology* (1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.* 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., *Bio/Technology* 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies may also be useful in pharmacogenomic analysis. In such embodiments, antibodies against variant proteins encoded by nucleic acids according to the invention, such as variant proteins that are encoded by nucleic acids that contain at least one polymorphic marker of the invention, can be used to identify individuals that require modified treatment modalities.

Antibodies can furthermore be useful for assessing expression of variant proteins in disease states, such as in active stages of a cancer, such as prostate cancer and/or colorectal cancer, or in an individual with a predisposition to a cancer related to the function of the protein, in particular prostate cancer and colorectal cancer. Antibodies specific for a variant protein of the present invention that is encoded by a nucleic acid that comprises at least one polymorphic marker or haplotype as described herein can be used to screen for the presence of the variant protein, for example to screen for a predisposition to prostate cancer and/or colorectal cancer, as indicated by the presence of the variant protein.

Antibodies can be used in other methods. Thus, antibodies are useful as diagnostic tools for evaluating proteins, such as variant proteins of the invention, in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting example.

EXEMPLIFICATION

Example 1

Identification of Markers and LD Block Regions Associated with Prostate Cancer Patients Involved in the Genetics Study A population based list of all prostate and colorectal cancer patients that were diagnosed in Iceland from 1955 to 2005 form the basis for this study. Patients have been invited to join the study since 2001 on an ongoing basis. As of June 2007, blood samples from 1,850 prostate cancer and 1,169 colorectal cancer patients have been recruited. Genomic DNA from those samples, as well as samples from over 27,000 control individuals was extracted and genotyped.

Genotyping

A genome-wide scan of 1,645 Icelandic individuals diagnosed with Prostate Cancer, 1,010 colorectal cancer patients and 27,049 population controls was performed using Infinium HumanHap300 SNP chips from Illumina for assaying approximately 317,000 single nucleotide polymorphisms (SNPs) on a single chip (Illumina, San Diego, Calif., USA). SNP genotyping for replication in other case-control cohorts was carried using the Centaurus platform (Nanogen).

Statistical Methods for Association and Haplotype Analysis

For single marker association to the disease, Fisher exact test was used to calculate a two-sided P-value for each individual allele. When presenting the results, we used allelic frequencies rather than carrier frequencies for SNPs and haplotypes. The program NEMO (NEsted Models; Gretarsdottir, et al., *Nat. Genet.* 2003 October; 35(2):131-8) was used both to study marker-marker association and to calculate linkage disequilibrium (LD) between markers. With NEMO, haplotype frequencies are estimated by maximum likelihood and the differences between patients and controls are tested using a generalized likelihood ratio test. The maximum likelihood estimates, likelihood ratios and P-values are computed with the aid of the EM-algorithm directly for the observed data, and hence the loss of information due to the uncertainty with phase and missing genotypes is automatically captured by the likelihood ratios, and under most situations, large sample theory can be used to reliably determine statistical significance. The relative risk (RR) of an allele or a haplotype, i.e., the risk of an allele compared to all other alleles of the same marker, is calculated assuming the multiplicative model (Terwilliger, J. D. & Ott, J. A haplotype-based 'haplotype relative risk' approach to detecting allelic associations. *Hum. Hered.* 42, 337-46 (1992) and Falk, C. T. & Rubinstein, P. Haplotype relative risks: an easy reliable way to construct a proper control sample for risk calculations. *Ann. Hum. Genet.* 51 (Pt 3), 227-33 (1987)), together with the population attributable risk (PAR). When controls are considered unaffected (i.e., disease-free), the relative risk is replaced by an estimate for the odds ratio (OR) of the particular marker allele or haplotype.

As a measure of LD, we use two standard definitions of LD, D' and $R^2$ (Lewontin, R., *Genetics*, 49:49-67 (1964) and Hill, W. G. and A. Robertson, *Theor. Appl. Genet.*, 22:226-231 (1968)) as they provide complementary information on the amount of LD. For the purpose of estimating D' and $R^2$, the frequencies of all two-marker allele combinations are estimated using maximum likelihood methods and the deviation from linkage disequilibrium is evaluated using a likelihood ratio test. The standard definitions of D' and $R^2$ are extended to include microsatellites by averaging over the values for all possible allele combinations of the two markers weighted by the marginal allele probabilities.

Results

Through analysis of over 300,000 markers across the genome, we identified two regions that are associated with prostate and colorectal cancer. In Table 1, we show results of association of markers rs10896450 and rs7947353 on Chr 11q13.3 to prostate cancer. The two markers are fully correlated (D'=1 and $r^2$=1; see footnote of Table 1) and do therefore essentially represent the same association signal The G allele of SNP marker rs10896450 confers increased risk of prostate cancer, with an odds ratio (OR) of 1.17 in the Icelandic samples (P=6.6×10$^{-5}$).

To validate the initial discovery, we attempted to genotype the rs10896450 SNP marker in prostate cancer cohorts from the Netherlands, Spain and US (Chicago, Ill.). However, the design of the Centaurus assay failed for this marker and we therefore selected a fully correlated SNP rs7947353 (D'=1 and $r^2$=1; see footnote of Table 1) for further genotyping and analysis in the replication samples. The results for allele A of SNP marker rs7947353 from the replication cohorts are shown in Table 1, and are comparable to the results for the Icelandic discovery cohort. The observed risk in the Spanish cohort is somewhat lower than in Iceland, while the US cohort has a higher risk. Overall, the association is significant with a p-value of 1.43×10$^6$.

A second association signal was detected on Chromosome 6 for prostate cancer (Table 2a). The signal was replicated in Dutch and Spanish cohort, both which gave increased risk conferred by the G allele of the rs10943605 SNP marker, although only the replication in the Dutch cohort is statistically significant. The G allele of the rs10943605 SNP marker was also found to be associated with increased risk of developing colorectal cancer, with an OR of 1.14 in the Icelandic colorectal cancer samples (P=4.8×10$^{-3}$) (Table 2b).

TABLE 1

Association results for 11q13.3 and prostate cancer in Iceland discovery cohort, and replication cohorts from The Netherlands, Spain, and the US

| Study population (N cases/N controls) Variant (allele) | Frequency | | OR | P value |
| --- | --- | --- | --- | --- |
| | Cases | Controls | | |
| Iceland (1,645/21,474) | | | | |
| rs10896450 (G)[a] | 0.505 | 0.466 | 1.17 | 6.6 × 10$^{-5}$ |
| rs7947353 (A)[a] | 0.505 | 0.466 | 1.17 | 6.6 × 10$^{-5}$ |
| The Netherlands (998/2,014) | | | | |
| rs7947353 (A) Spain (455/1,066) | 0.528 | 0.500 | 1.12 | 0.042 |
| rs7947353 (A) Chicago, Illinois (661/292) | 0.579 | 0.564 | 1.06 | 0.450 |
| rs7947353 (A) All above combined (3,759/24,846) | 0.545 | 0.493 | 1.23 | 0.035 |
| rs7947353 (A) | — | 0.506 | 1.15 | 1.43 × 10$^{-6}$ |

TABLE 1-continued

*Correlation between the two markers see below (results are based on analysis of 2,340 Icelanders:

| M1 | M2 | D' | r² |
|---|---|---|---|
| rs10896450 | rs7947353 | 1 | 1 |

TABLE 2a

Association results for 6q14.1 and prostate cancer in Icelandic discovery cohorts, and replication cohorts from The Netherlands and Spain.

| Study population (N cases/N controls) Variant (allele) | Frequency Cases | Controls | OR | P value |
|---|---|---|---|---|
| Iceland PrCa (1,645/21,472) | | | | |
| rs10943605 (G) | 0.597 | 0.557 | 1.18 | $2.72 \times 10^{-5}$ |
| The Netherlands PrCa (910/2,006) | | | | |
| rs10943605 (G) | 0.530 | 0.490 | 1.17 | $6.04 \times 10^{-3}$ |
| Spain PrCa (436/1,417) | | | | |
| rs10943605 (G) | 0.567 | 0.553 | 1.06 | 0.480 |

TABLE 2a-continued

Association results for 6q14.1 and prostate cancer in Icelandic discovery cohorts, and replication cohorts from The Netherlands and Spain.

| Study population (N cases/N controls) Variant (allele) | Frequency Cases | Controls | OR | P value |
|---|---|---|---|---|
| All above combined (2,991/24,895) | | | | |
| rs10943605 (G) | — | 0.533 | 1.16 | $9.35 \times 10^{-7}$ |

TABLE 2b

Association results for 6q14.1 and colorectal cancer in Iceland

| Study population (N cases/N controls) Variant (allele) | Frequency Cases | Controls | OR | P value |
|---|---|---|---|---|
| Iceland ColCa (1,010/27,033) | | | | |
| rs10943605 (G) | 0.591 | 0.558 | 1.14 | $4.8 \times 10^{-3}$ |

TABLE 3

SNP markers that are in linkage disequilibrium with marker rs10943605 on Chromosome 6. Linkage disequilibrium was calculated based on HapMap CEU population data (http://www.hapmap.org). Location of correlated markers is given with respect to NCBI Build 36 of the Human genome assembly.

| Marker 1 | Marker 2 | D' | r² | p-value | Marker 1 location | Seq ID No: |
|---|---|---|---|---|---|---|
| rs611737 | rs10943605 | 0.631963 | 0.293866 | 3.91E−09 | 79300773 | 1 |
| rs666982 | rs10943605 | 0.605842 | 0.284949 | 6.11E−09 | 79316431 | 2 |
| rs685245 | rs10943605 | 0.606322 | 0.29663 | 1.77E−08 | 79327502 | 3 |
| rs547472 | rs10943605 | 0.608391 | 0.291941 | 4.51E−09 | 79341083 | 4 |
| rs654628 | rs10943605 | 0.603324 | 0.288712 | 6.47E−09 | 79343805 | 5 |
| rs605697 | rs10943605 | 0.622444 | 0.296062 | 6.91E−09 | 79345910 | 6 |
| rs605264 | rs10943605 | 0.605842 | 0.284949 | 6.11E−09 | 79346003 | 7 |
| rs603964 | rs10943605 | 0.609097 | 0.293439 | 6.80E−09 | 79346271 | 8 |
| rs612489 | rs10943605 | 0.604036 | 0.290201 | 9.72E−09 | 79346309 | 9 |
| rs484582 | rs10943605 | 0.610497 | 0.30416 | 4.78E−09 | 79346824 | 10 |
| rs597283 | rs10943605 | 0.572594 | 0.27296 | 3.74E−08 | 79347449 | 11 |
| rs596810 | rs10943605 | 0.590052 | 0.272681 | 2.36E−08 | 79347562 | 12 |
| rs596337 | rs10943605 | 0.600542 | 0.282979 | 1.11E−08 | 79347676 | 13 |
| rs655566 | rs10943605 | 0.597614 | 0.277093 | 1.90E−08 | 79348564 | 14 |
| rs689389 | rs10943605 | 0.608391 | 0.291941 | 4.51E−09 | 79348661 | 15 |
| rs846452 | rs10943605 | 0.60564 | 0.286192 | 7.77E−09 | 79348887 | 16 |
| rs674105 | rs10943605 | 0.605842 | 0.284949 | 6.11E−09 | 79349688 | 17 |
| rs236867 | rs10943605 | 0.605842 | 0.284949 | 6.11E−09 | 79355383 | 18 |
| rs236872 | rs10943605 | 0.593491 | 0.304327 | 7.89E−09 | 79358008 | 19 |
| rs236873 | rs10943605 | 0.592785 | 0.282009 | 1.33E−08 | 79358580 | 20 |
| rs236877 | rs10943605 | 0.608391 | 0.291941 | 4.51E−09 | 79362203 | 21 |
| rs70478 | rs10943605 | 0.564166 | 0.209862 | 3.01E−06 | 79364899 | 22 |
| rs70480 | rs10943605 | 0.568404 | 0.216181 | 1.39E−06 | 79365324 | 23 |
| rs236882 | rs10943605 | 0.695923 | 0.256498 | 5.08E−08 | 79372832 | 24 |
| rs236884 | rs10943605 | 0.700831 | 0.26597 | 3.12E−08 | 79376244 | 25 |
| rs236888 | rs10943605 | 0.741063 | 0.286153 | 1.20E−08 | 79378960 | 26 |
| rs236861 | rs10943605 | 0.689267 | 0.264436 | 2.73E−07 | 79390866 | 27 |
| rs236862 | rs10943605 | 0.65937 | 0.248439 | 1.40E−07 | 79391691 | 28 |
| rs236855 | rs10943605 | 0.74615 | 0.29984 | 5.25E−09 | 79398610 | 29 |
| rs12210702 | rs10943605 | 0.886957 | 0.355449 | 2.28E−11 | 79426052 | 30 |
| rs9359338 | rs10943605 | 0.897621 | 0.450682 | 1.86E−13 | 79453470 | 31 |
| rs9352611 | rs10943605 | 0.89472 | 0.436416 | 7.36E−13 | 79453687 | 32 |
| rs10943567 | rs10943605 | 0.901397 | 0.4471 | 6.06E−14 | 79459170 | 33 |
| rs10943568 | rs10943605 | 0.898063 | 0.444367 | 5.16E−13 | 79460926 | 34 |
| rs9343786 | rs10943605 | 0.901397 | 0.4471 | 6.06E−14 | 79471447 | 35 |
| rs4706718 | rs10943605 | 0.901397 | 0.4471 | 6.06E−14 | 79473602 | 36 |
| rs9341739 | rs10943605 | 0.899434 | 0.433323 | 2.58E−13 | 79475795 | 37 |
| rs9352613 | rs10943605 | 0.901397 | 0.4471 | 6.06E−14 | 79481152 | 38 |
| rs13198615 | rs10943605 | 0.620748 | 0.264225 | 2.31E−08 | 79487271 | 39 |

TABLE 3-continued

SNP markers that are in linkage disequilibrium with marker rs10943605 on Chromosome 6. Linkage disequilibrium was calculated based on HapMap CEU population data (http://www.hapmap.org). Location of correlated markers is given with respect to NCBI Build 36 of the Human genome assembly.

| Marker 1 | Marker 2 | D' | $r^2$ | p-value | Marker 1 location | Seq ID No: |
|---|---|---|---|---|---|---|
| rs1180823 | rs10943605 | 0.786316 | 0.274692 | 3.17E−09 | 79489645 | 40 |
| rs1180828 | rs10943605 | 0.620748 | 0.264225 | 2.31E−08 | 79492141 | 41 |
| rs9343798 | rs10943605 | 0.620748 | 0.264225 | 2.31E−08 | 79512001 | 42 |
| rs7382016 | rs10943605 | 0.620748 | 0.264225 | 2.31E−08 | 79512500 | 43 |
| rs7759829 | rs10943605 | 1 | 0.257426 | 5.01E−10 | 79513725 | 44 |
| rs7759687 | rs10943605 | 0.910286 | 0.229805 | 3.16E−07 | 79513734 | 45 |
| rs9361426 | rs10943605 | 0.620748 | 0.264225 | 2.31E−08 | 79514269 | 46 |
| rs1158575 | rs10943605 | 0.620748 | 0.264225 | 2.31E−08 | 79515925 | 47 |
| rs9359344 | rs10943605 | 0.620748 | 0.264225 | 2.31E−08 | 79517752 | 48 |
| rs4141594 | rs10943605 | 0.502039 | 0.207557 | 9.50E−07 | 79517914 | 49 |
| rs9343820 | rs10943605 | 1 | 0.87395 | 2.70E−31 | 79537177 | 50 |
| rs1876389 | rs10943605 | 0.824869 | 0.421093 | 3.32E−13 | 79538651 | 51 |
| rs1021987 | rs10943605 | 1 | 0.21875 | 2.66E−09 | 79539884 | 52 |
| rs1507152 | rs10943605 | 0.83431 | 0.329234 | 2.01E−10 | 79540193 | 53 |
| rs1507153 | rs10943605 | 1 | 0.509466 | 2.18E−18 | 79541105 | 54 |
| rs9343824 | rs10943605 | 1 | 0.537205 | 1.54E−18 | 79554288 | 55 |
| rs1507149 | rs10943605 | 0.960507 | 0.683059 | 4.95E−22 | 79556805 | 56 |
| rs9343827 | rs10943605 | 1 | 0.967033 | 1.10E−35 | 79557755 | 57 |
| rs6926463 | rs10943605 | 0.942137 | 0.382849 | 1.82E−12 | 79559890 | 58 |
| rs9361448 | rs10943605 | 1 | 0.300546 | 1.55E−11 | 79579645 | 59 |
| rs12195716 | rs10943605 | 1 | 0.967033 | 1.10E−35 | 79592131 | 60 |
| rs6902294 | rs10943605 | 1 | 0.21875 | 2.66E−09 | 79593001 | 61 |
| rs1567168 | rs10943605 | 1 | 0.967033 | 1.10E−35 | 79593174 | 62 |
| rs2135767 | rs10943605 | 0.943831 | 0.389733 | 6.65E−13 | 79593386 | 63 |
| rs9352662 | rs10943605 | 0.939889 | 0.390142 | 2.32E−11 | 79598210 | 64 |
| rs1027813 | rs10943605 | 1 | 1 | 1.22E−37 | 79608837 | 65 |
| rs1567167 | rs10943605 | 1 | 1 | 1.14E−36 | 79610546 | 66 |
| rs12196485 | rs10943605 | 1 | 0.550265 | 1.01E−19 | 79613590 | 67 |
| rs9352663 | rs10943605 | 1 | 0.550265 | 1.01E−19 | 79614883 | 68 |
| rs971994 | rs10943605 | 1 | 1 | 9.93E−37 | 79616321 | 69 |
| rs4421161 | rs10943605 | 1 | 1 | 6.05E−38 | 79620938 | 70 |
| rs12176511 | rs10943605 | 1 | 0.715909 | 1.15E−25 | 79622440 | 71 |
| rs9352664 | rs10943605 | 1 | 1 | 6.05E−38 | 79622881 | 72 |
| rs9352666 | rs10943605 | 1 | 1 | 2.00E−36 | 79628903 | 73 |
| rs9352667 | rs10943605 | 1 | 1 | 6.05E−38 | 79629015 | 74 |
| rs9352668 | rs10943605 | 1 | 0.715909 | 2.11E−25 | 79629397 | 75 |
| rs9448584 | rs10943605 | 1 | 1 | 6.05E−38 | 79629518 | 76 |
| rs9361459 | rs10943605 | 1 | 0.715909 | 7.04E−25 | 79629641 | 77 |
| rs9341753 | rs10943605 | 1 | 0.361702 | 6.05E−14 | 79634515 | 78 |
| rs9352669 | rs10943605 | 1 | 1 | 2.00E−36 | 79640860 | 79 |
| rs9341754 | rs10943605 | 1 | 0.966443 | 8.10E−35 | 79641692 | 80 |
| rs9343844 | rs10943605 | 1 | 1 | 1.30E−37 | 79643182 | 81 |
| rs9350792 | rs10943605 | 1 | 0.550265 | 1.01E−19 | 79643892 | 82 |
| rs9361460 | rs10943605 | 1 | 1 | 6.05E−38 | 79646186 | 83 |
| rs9359354 | rs10943605 | 1 | 1 | 8.67E−36 | 79647104 | 84 |
| rs2174743 | rs10943605 | 1 | 1 | 1.30E−37 | 79648524 | 85 |
| rs6908105 | rs10943605 | 1 | 0.516024 | 7.87E−19 | 79651816 | 86 |
| rs12192086 | rs10943605 | 1 | 0.360294 | 5.04E−14 | 79657229 | 87 |
| rs2174742 | rs10943605 | 1 | 1 | 1.22E−37 | 79666820 | 88 |
| rs9352675 | rs10943605 | 1 | 1 | 2.30E−37 | 79669519 | 89 |
| rs1354832 | rs10943605 | 1 | 0.966849 | 1.92E−35 | 79670482 | 90 |
| rs4706079 | rs10943605 | 1 | 1 | 2.00E−36 | 79671927 | 91 |
| rs7756858 | rs10943605 | 1 | 1 | 2.45E−37 | 79676687 | 92 |
| rs9448594 | rs10943605 | 1 | 0.355054 | 2.69E−12 | 79679933 | 93 |
| rs12196457 | rs10943605 | 1 | 0.550265 | 1.01E−19 | 79684462 | 94 |
| rs9343853 | rs10943605 | 1 | 0.375 | 1.67E−14 | 79699300 | 95 |
| rs7740307 | rs10943605 | 1 | 0.525 | 2.34E−19 | 79710873 | 96 |
| rs10943605 | rs10943605 | 1 | 1 | — | 79712196 | 97 |
| rs2275291 | rs10943605 | 1 | 0.351955 | 9.65E−13 | 79713281 | 98 |
| rs2275290 | rs10943605 | 1 | 0.525 | 3.77E−19 | 79713289 | 99 |
| rs1984195 | rs10943605 | 1 | 1 | 1.30E−37 | 79714110 | 100 |
| rs2174739 | rs10943605 | 1 | 1 | 1.14E−37 | 79715889 | 101 |
| rs9448600 | rs10943605 | 1 | 0.525 | 2.34E−19 | 79719788 | 102 |
| rs3805746 | rs10943605 | 1 | 0.525 | 3.77E−19 | 79729157 | 103 |
| rs3805747 | rs10943605 | 1 | 1 | 1.22E−37 | 79729241 | 104 |
| rs10943608 | rs10943605 | 1 | 0.565217 | 6.62E−20 | 79731648 | 105 |
| rs9350797 | rs10943605 | 1 | 0.360294 | 5.04E−14 | 79732420 | 106 |
| rs11964204 | rs10943605 | 1 | 0.525 | 2.34E−19 | 79732781 | 107 |
| rs9343856 | rs10943605 | 1 | 1 | 1.30E−37 | 79734930 | 108 |
| rs1538235 | rs10943605 | 1 | 1 | 7.59E−37 | 79746169 | 109 |
| rs1572584 | rs10943605 | 1 | 1 | 6.05E−38 | 79747009 | 110 |
| rs1572585 | rs10943605 | 1 | 1 | 3.77E−36 | 79747295 | 111 |

TABLE 3-continued

SNP markers that are in linkage disequilibrium with marker rs10943605 on Chromosome 6. Linkage disequilibrium was calculated based on HapMap CEU population data (http://www.hapmap.org). Location of correlated markers is given with respect to NCBI Build 36 of the Human genome assembly.

| Marker 1 | Marker 2 | D' | r² | p-value | Marker 1 location | Seq ID No: |
|---|---|---|---|---|---|---|
| rs1890229 | rs10943605 | 1 | 1 | 6.05E−38 | 79751748 | 112 |
| rs3818839 | rs10943605 | 1 | 0.380941 | 1.44E−14 | 79757044 | 113 |
| rs9359360 | rs10943605 | 1 | 0.575195 | 7.14E−19 | 79759515 | 114 |
| rs9359361 | rs10943605 | 1 | 0.367498 | 1.07E−13 | 79762302 | 115 |
| rs9361477 | rs10943605 | 1 | 0.558824 | 9.59E−20 | 79767525 | 116 |
| rs9448607 | rs10943605 | 1 | 0.757211 | 5.03E−26 | 79772339 | 117 |
| rs9352683 | rs10943605 | 1 | 1 | 4.94E−36 | 79775514 | 118 |
| rs9443638 | rs10943605 | 1 | 1 | 2.00E−36 | 79777586 | 119 |
| rs4706747 | rs10943605 | 1 | 1 | 1.30E−37 | 79779358 | 120 |
| rs9361480 | rs10943605 | 1 | 1 | 2.89E−34 | 79781148 | 121 |
| rs1338023 | rs10943605 | 1 | 0.365871 | 4.42E−14 | 79785047 | 122 |
| rs2050660 | rs10943605 | 1 | 1 | 6.05E−38 | 79791445 | 123 |
| rs9448610 | rs10943605 | 1 | 0.733202 | 5.86E−26 | 79796341 | 124 |
| rs1538233 | rs10943605 | 1 | 1 | 6.05E−38 | 79800454 | 125 |
| rs9343861 | rs10943605 | 1 | 0.509466 | 2.18E−18 | 79801587 | 126 |
| rs10943613 | rs10943605 | 1 | 0.740385 | 5.66E−26 | 79801826 | 127 |
| rs11758432 | rs10943605 | 1 | 0.375 | 1.67E−14 | 79806313 | 128 |
| rs9361482 | rs10943605 | 1 | 0.733202 | 2.00E−25 | 79807104 | 129 |
| rs9343863 | rs10943605 | 1 | 1 | 6.05E−38 | 79809511 | 130 |
| rs2050663 | rs10943605 | 1 | 1 | 2.30E−37 | 79810113 | 131 |
| rs9448616 | rs10943605 | 1 | 0.360294 | 5.04E−14 | 79813653 | 132 |
| rs9352686 | rs10943605 | 1 | 1 | 2.45E−37 | 79814942 | 133 |
| rs2152951 | rs10943605 | 1 | 1 | 6.05E−38 | 79818891 | 134 |
| rs9343865 | rs10943605 | 1 | 0.368421 | 4.53E−14 | 79821914 | 135 |
| rs9343867 | rs10943605 | 1 | 0.364105 | 5.50E−14 | 79829072 | 136 |
| rs1547731 | rs10943605 | 1 | 1 | 1.14E−37 | 79832823 | 137 |
| rs9352688 | rs10943605 | 1 | 0.360294 | 5.04E−14 | 79832882 | 138 |
| rs10455120 | rs10943605 | 1 | 0.444999 | 1.18E−15 | 79836486 | 139 |
| rs9343869 | rs10943605 | 1 | 0.360294 | 7.16E−14 | 79841140 | 140 |
| rs9352691 | rs10943605 | 1 | 0.550265 | 1.01E−19 | 79842326 | 141 |
| rs7753531 | rs10943605 | 1 | 0.709974 | 7.37E−25 | 79846715 | 142 |
| rs7776138 | rs10943605 | 1 | 0.375 | 1.67E−14 | 79851212 | 143 |
| rs9359364 | rs10943605 | 0.947194 | 0.482034 | 1.37E−13 | 79852711 | 144 |
| rs9352693 | rs10943605 | 1 | 0.352274 | 3.20E−13 | 79854791 | 145 |
| rs7767100 | rs10943605 | 0.964821 | 0.930648 | 1.26E−29 | 79867252 | 146 |
| rs9443644 | rs10943605 | 0.937107 | 0.333308 | 3.02E−11 | 79867363 | 147 |
| rs12197385 | rs10943605 | 1 | 0.266602 | 4.88E−10 | 79872695 | 148 |
| rs9361489 | rs10943605 | 0.965965 | 0.933016 | 1.07E−31 | 79873504 | 149 |
| rs949846 | rs10943605 | 0.950814 | 0.497465 | 6.74E−16 | 79874315 | 150 |
| rs6916081 | rs10943605 | 0.941241 | 0.345568 | 4.80E−12 | 79874571 | 151 |
| rs1415310 | rs10943605 | 0.856953 | 0.419639 | 3.80E−13 | 79879033 | 152 |
| rs9443645 | rs10943605 | 0.931848 | 0.839777 | 1.03E−27 | 79879643 | 153 |
| rs10943616 | rs10943605 | 0.853077 | 0.40045 | 1.48E−12 | 79880260 | 154 |
| rs6940949 | rs10943605 | 0.876626 | 0.288616 | 1.29E−09 | 79880754 | 155 |
| rs7768535 | rs10943605 | 0.930436 | 0.292034 | 1.28E−09 | 79892231 | 156 |
| rs3920791 | rs10943605 | 0.869223 | 0.261765 | 6.14E−09 | 79893453 | 157 |
| rs1361043 | rs10943605 | 0.873498 | 0.269641 | 3.81E−09 | 79893786 | 158 |
| rs9343876 | rs10943605 | 0.806769 | 0.225158 | 1.01E−07 | 79901219 | 159 |
| rs9352701 | rs10943605 | 0.876903 | 0.28836 | 1.27E−09 | 79916596 | 160 |
| rs9361497 | rs10943605 | 0.876903 | 0.28836 | 1.27E−09 | 79916649 | 161 |
| rs9294130 | rs10943605 | 0.746969 | 0.282652 | 8.22E−09 | 79917888 | 162 |

TABLE 4

SNP markers that are in linkage disequilibrium with marker rs10896450 on Chromosome 11. Linkage disequilibrium was calculated based on HapMap CEU population data (http://www.hapmap.org). Location of correlated markers is given with respect to NCBI Build 36 of the Human genome assembly.

| Marker 1 | Marker 2 | D' | r² | p-value | Marker 1 location | Seq ID No: | Pos in Seq ID: 201 |
|---|---|---|---|---|---|---|---|
| rs7128814 | rs10896450 | 0.754033 | 0.328273 | 7.44E−09 | 68709630 | 163 | 300 |
| rs10896444 | rs10896450 | 0.950801 | 0.522291 | 5.93E−15 | 68723823 | 164 | 14493 |
| rs10896445 | rs10896450 | 0.951635 | 0.522873 | 3.85E−15 | 68724217 | 165 | 14887 |
| rs4255548 | rs10896450 | 1 | 0.620339 | 2.97E−22 | 68730546 | 166 | 21216 |
| rs7117034 | rs10896450 | 1 | 0.257642 | 2.43E−10 | 68731718 | 167 | 22388 |
| rs4495900 | rs10896450 | 1 | 0.606213 | 5.17E−21 | 68732695 | 168 | 23365 |
| rs11228563 | rs10896450 | 1 | 0.373812 | 1.43E−13 | 68733572 | 169 | 24242 |

TABLE 4-continued

SNP markers that are in linkage disequilibrium with marker rs10896450 on Chromosome 11. Linkage disequilibrium was calculated based on HapMap CEU population data (http://www.hapmap.org). Location of correlated markers is given with respect to NCBI Build 36 of the Human genome assembly.

| Marker 1 | Marker 2 | D' | r² | p-value | Marker 1 location | Seq ID No: | Pos in Seq ID: 201 |
|---|---|---|---|---|---|---|---|
| rs12281017 | rs10896450 | 1 | 0.295093 | 8.65E-11 | 68734077 | 170 | 24747 |
| rs11228565 | rs10896450 | 1 | 0.249586 | 7.96E-10 | 68735156 | 171 | 25826 |
| rs4620729 | rs10896450 | 1 | 1 | 4.70E-38 | 68736911 | 172 | 27581 |
| rs11821008 | rs10896450 | 1 | 0.329609 | 1.51E-12 | 68737211 | 173 | 27881 |
| rs11825796 | rs10896450 | 1 | 0.311982 | 7.96E-12 | 68737364 | 174 | 28034 |
| rs4451736 | rs10896450 | 1 | 0.964531 | 2.83E-34 | 68739279 | 175 | 29949 |
| rs12278923 | rs10896450 | 1 | 0.959809 | 3.04E-31 | 68740137 | 176 | 30807 |
| rs7929962 | rs10896450 | 1 | 1 | 4.70E-38 | 68742159 | 177 | 32829 |
| rs7109672 | rs10896450 | 1 | 0.967195 | 8.12E-36 | 68747686 | 178 | 38356 |
| rs10896448 | rs10896450 | 1 | 1 | 4.70E-38 | 68748325 | 179 | 38995 |
| rs12795301 | rs10896450 | 1 | 0.241803 | 5.99E-10 | 68748861 | 180 | 39531 |
| rs7122190 | rs10896450 | 1 | 0.967195 | 8.12E-36 | 68750364 | 181 | 41034 |
| rs6591374 | rs10896450 | 1 | 1 | 1.90E-37 | 68750408 | 182 | 41078 |
| rs7931342 | rs10896450 | 1 | 0.967195 | 1.58E-35 | 68751073 | 183 | 41743 |
| rs10896449 | rs10896450 | 1 | 1 | 4.70E-38 | 68751243 | 184 | 41913 |
| rs7130881 | rs10896450 | 1 | 0.241803 | 5.99E-10 | 68752534 | 185 | 43204 |
| rs12362678 | rs10896450 | 1 | 0.967195 | 8.12E-36 | 68752746 | 186 | 43416 |
| rs9787877 | rs10896450 | 1 | 1 | 4.70E-38 | 68753085 | 187 | 43755 |
| rs11603288 | rs10896450 | 1 | 0.242151 | 1.13E-09 | 68753358 | 188 | 44028 |
| rs4644650 | rs10896450 | 1 | 0.967195 | 8.12E-36 | 68754694 | 189 | 45364 |
| rs7950547 | rs10896450 | 0.953052 | 0.582711 | 4.00E-15 | 68755364 | 190 | 46034 |
| rs11228580 | rs10896450 | 1 | 0.229339 | 1.58E-09 | 68758918 | 191 | 49588 |
| rs7939250 | rs10896450 | 1 | 1 | 1.87E-37 | 68759526 | 192 | 50196 |
| rs7106762 | rs10896450 | 1 | 1 | 4.70E-38 | 68760282 | 193 | 50952 |
| rs12417087 | rs10896450 | 1 | 0.221577 | 3.17E-09 | 68760555 | 194 | 51225 |
| rs11228581 | rs10896450 | 1 | 0.337143 | 7.39E-13 | 68760586 | 195 | 51256 |
| rs7947353 | rs10896450 | 1 | 1 | 1.19E-35 | 68761559 | 196 | 52229 |
| rs10896450 | rs10896450 | 1 | 1 | — | 68764690 | 197 | 55360 |
| rs11228583 | rs10896450 | 1 | 0.965547 | 6.06E-35 | 68765690 | 198 | 56360 |
| rs12799883 | rs10896450 | 1 | 1 | 1.90E-37 | 68767227 | 199 | 57897 |
| rs3884627 | rs10896450 | 1 | 0.425723 | 6.96E-16 | 68782375 | 200 | 73045 |

TABLE 5

Polymorphic markers within the C11 region, between position 68,709,630 and 68,782,375 in NCBI Build 36. Shown is marker ID (rs-names), position in Build 36, strand and polymorphism type, where (—/N), N being any one nucleotide, or a plurality of nucleotides, corresponding to an insertion/deletion polymorphism (i.e. either the nucleotide(s) is present or not).

| Marker ID | Position Build 36 | Strand | Polymorphism |
|---|---|---|---|
| rs7128814 | 68709630 | + | A/G |
| rs34033330 | 68709734 | + | —/T |
| rs4993568 | 68709920 | + | G/T |
| rs4993567 | 68709926 | + | C/G |
| rs11228548 | 68710333 | + | C/T |
| rs11228549 | 68710384 | + | C/T |
| rs10896441 | 68710484 | + | A/G |
| rs10792027 | 68710514 | + | C/G |
| rs10792028 | 68710515 | + | C/T |
| rs11228550 | 68710833 | + | C/T |
| rs12294054 | 68711092 | + | A/G |
| rs11228551 | 68711570 | + | A/T |
| rs11228552 | 68711592 | + | C/T |
| rs10219207 | 68713596 | + | A/G |
| rs12809032 | 68713686 | + | C/T |
| rs11606280 | 68713966 | + | A/G |
| rs35691765 | 68715000 | + | —/G |
| rs4495899 | 68715236 | + | G/T |
| rs12800787 | 68715895 | + | C/T |
| rs4930664 | 68715976 | + | A/G |
| rs4930665 | 68715984 | + | A/T |
| rs4072598 | 68716265 | − | G/T |
| rs1128553 | 68716760 | + | G/T |
| rs10896442 | 68716789 | + | A/G |
| rs12223972 | 68716967 | + | A/G |
| rs12796709 | 68719501 | + | A/C |
| rs34461339 | 68719872 | + | —/G |
| rs12803641 | 68720487 | + | C/T |
| rs12808650 | 68720536 | + | C/G |
| rs12808185 | 68720581 | + | A/C |
| rs12808690 | 68720599 | + | C/G |
| rs12808846 | 68720638 | + | C/G |
| rs12808599 | 68720804 | + | A/T |
| rs12808603 | 68720810 | + | A/T |
| rs12785256 | 68720824 | + | A/G |
| rs11228554 | 68720854 | + | C/T |
| rs11602052 | 68721150 | + | C/G |
| rs11433399 | 68721158 | + | —/G |
| rs10896443 | 68722211 | + | G/T |
| rs11228555 | 68722341 | + | C/T |
| rs10792029 | 68723458 | + | A/G |
| rs4930666 | 68723812 | + | C/T |
| rs10896444 | 68723823 | + | A/C |
| rs34531633 | 68724028 | + | G/T |
| rs11228556 | 68724029 | + | G/T |
| rs10896445 | 68724217 | + | C/T |
| rs11228557 | 68724542 | + | A/G |
| rs10792030 | 68725391 | + | A/G |
| rs12417971 | 68726384 | + | C/T |
| rs11383798 | 68726876 | + | —/G |

TABLE 5-continued

Polymorphic markers within the C11 region, between position 68,709,630 and 68,782,375 in NCBI Build 36. Shown is marker ID (rs-names), position in Build 36, strand and polymorphism type, where (—/N), N being any one nucleotide, or a plurality of nucleotides, corresponding to an insertion/deletion polymorphism (i.e. either the nucleotide(s) is present or not).

| Marker ID | Position Build 36 | Strand | Polymorphism |
|---|---|---|---|
| rs7126286 | 68726993 | + | C/T |
| rs34210900 | 68727006 | + | —/G |
| rs3934653 | 68727096 | − | A/C |
| rs12049842 | 68727624 | + | G/T |
| rs9783326 | 68727749 | + | C/T |
| rs7927331 | 68729100 | + | A/G |
| rs7930375 | 68729233 | + | C/G |
| rs7945442 | 68729323 | + | C/T |
| rs9783278 | 68729551 | + | A/C |
| rs9783279 | 68729568 | + | A/C |
| rs9783280 | 68729612 | + | A/G |
| rs11824548 | 68729893 | + | A/G |
| rs7934295 | 68730254 | + | C/T |
| rs4255548 | 68730546 | + | A/G |
| rs7483742 | 68730628 | + | G/T |
| rs7949811 | 68730632 | + | G/T |
| rs12792553 | 68730645 | + | A/C |
| rs12792562 | 68730662 | + | A/C |
| rs12793009 | 68730931 | + | C/T |
| rs12793759 | 68731131 | + | A/G |
| rs9943593 | 68731168 | + | A/G |
| rs11228558 | 68731439 | + | C/T |
| rs10896446 | 68731695 | + | C/T |
| rs7117034 | 68731718 | + | C/T |
| rs11228559 | 68731861 | + | C/T |
| rs11228560 | 68731965 | + | C/T |
| rs7926098 | 68732100 | + | C/T |
| rs12287117 | 68732101 | + | C/G |
| rs7942465 | 68732362 | + | C/T |
| rs11228561 | 68732444 | + | C/G |
| rs7929389 | 68732558 | + | A/T |
| rs4495900 | 68732695 | + | C/T |
| rs11228562 | 68732747 | + | G/T |
| rs11228563 | 68733572 | + | A/G |
| rs10792031 | 68733592 | + | A/G |
| rs12418968 | 68733711 | + | C/T |
| rs12281017 | 68734077 | + | A/G |
| rs4930667 | 68734625 | + | C/T |
| rs12422130 | 68734751 | + | A/G |
| rs11228564 | 68735154 | + | C/T |
| rs11228565 | 68735156 | + | A/G |
| rs4357697 | 68735224 | + | G/T |
| rs7926037 | 68735253 | + | C/G |
| rs11228566 | 68735849 | + | C/T |
| rs11228567 | 68736126 | + | A/G |
| rs7937094 | 68736282 | + | C/T |
| rs11228568 | 68736438 | + | G/T |
| rs11228569 | 68736819 | + | C/T |
| rs4620729 | 68736911 | + | A/C |
| rs11821008 | 68737211 | + | A/G |
| rs11825791 | 68737337 | + | C/G |
| rs11825796 | 68737364 | + | A/G |
| rs4930668 | 68737404 | + | G/T |
| rs10896447 | 68737451 | + | A/C |
| rs4265599 | 68737642 | + | A/T |
| rs12275055 | 68737935 | + | A/G |
| rs4268514 | 68738060 | + | C/G |
| rs28613836 | 68738536 | + | C/T |
| rs9665814 | 68738604 | + | C/T |
| rs4930669 | 68738956 | + | C/T |
| rs4451736 | 68739279 | + | A/G |
| rs5792471 | 68739686 | + | —/C |
| rs4988608 | 68739767 | + | A/G |
| rs4988607 | 68739830 | + | G/T |
| rs12278923 | 68740137 | + | A/C |
| rs7939803 | 68740276 | + | C/T |
| rs10792032 | 68741178 | + | A/G |
| rs12294067 | 68741228 | + | A/G |
| rs11421935 | 68741320 | + | —/G |
| rs11228570 | 68741410 | + | C/T |
| rs11228571 | 68741445 | + | C/T |
| rs11351679 | 68742057 | + | —/T |
| rs7929962 | 68742159 | + | C/T |
| rs12282709 | 68742244 | + | A/C |
| rs28686842 | 68742981 | + | C/G |
| rs12790802 | 68743071 | + | A/C |
| rs11824985 | 68743246 | + | A/G |
| rs12785252 | 68743916 | + | A/C |
| rs12785424 | 68743958 | + | A/C |
| rs7941085 | 68744228 | + | G/T |
| rs11228572 | 68744280 | + | A/G |
| rs7119440 | 68744363 | + | A/G |
| rs35024453 | 68744479 | + | —/T |
| rs7119681 | 68744563 | + | A/G |
| rs7945227 | 68745639 | + | A/G |
| rs10792033 | 68745774 | + | A/G |
| rs28706904 | 68746828 | + | C/T |
| rs35911114 | 68746864 | + | —/A |
| rs7121816 | 68746871 | + | G/T |
| rs34326593 | 68746958 | + | —/C |
| rs7109672 | 68747686 | + | A/G |
| rs12270972 | 68748240 | + | A/G |
| rs10896448 | 68748325 | + | C/G |
| rs34655741 | 68748385 | + | —/T |
| rs35960410 | 68748742 | + | —/A |
| rs12795301 | 68748861 | + | A/C |
| rs11228573 | 68749659 | + | G/T |
| rs11228574 | 68750098 | + | A/T |
| rs35007842 | 68750196 | + | —/G |
| rs7122190 | 68750364 | + | C/T |
| rs6591374 | 68750408 | + | A/G |
| rs28367011 | 68750751 | + | C/T |
| rs36082692 | 68751072 | + | —/G |
| rs7931342 | 68751073 | + | G/T |
| rs10896449 | 68751243 | + | A/G |
| rs10750845 | 68751541 | + | A/G |
| rs35730578 | 68751818 | + | —/TG |
| rs11228575 | 68751854 | + | A/G |
| rs12365199 | 68751856 | + | A/G |
| rs11228576 | 68752122 | + | A/G |
| rs7130881 | 68752534 | + | A/G |
| rs12362678 | 68752746 | + | C/G |
| rs11603219 | 68753019 | + | A/G |
| rs9787877 | 68753085 | + | C/T |
| rs11603288 | 68753358 | + | A/G |
| rs11228577 | 68753390 | + | C/T |
| rs4644650 | 68754694 | + | C/T |
| rs5792472 | 68754765 | + | —/G |
| rs4569015 | 68754981 | + | C/T |
| rs7950547 | 68755364 | + | C/T |
| rs7935842 | 68755540 | + | G/T |
| rs4576823 | 68755685 | + | A/G |
| rs35572423 | 68755750 | + | —/A |
| rs7931312 | 68757543 | + | A/G |
| rs34699416 | 68757796 | + | —/C |
| rs4930670 | 68757828 | + | C/T |
| rs11605287 | 68758302 | + | G/T |
| rs11228579 | 68758793 | + | G/T |
| rs11228580 | 68758918 | + | C/T |
| rs7925434 | 68759208 | + | A/T |
| rs7939151 | 68759472 | + | A/G |
| rs7939250 | 68759526 | + | A/G |
| rs7118074 | 68759999 | + | G/T |
| rs12788188 | 68760157 | + | A/T |
| rs7106762 | 68760282 | + | C/T |
| rs34000592 | 68760510 | + | —/T |
| rs12417087 | 68760555 | + | A/T |
| rs11228581 | 68760586 | + | C/T |
| rs9667638 | 68760915 | + | A/T |
| rs28852414 | 68761492 | + | A/G |

TABLE 5-continued

Polymorphic markers within the C11 region, between position 68,709,630 and 68,782,375 in NCBI Build 36. Shown is marker ID (rs-names), position in Build 36, strand and polymorphism type, where (—/N), N being any one nucleotide, or a plurality of nucleotides, corresponding to an insertion/deletion polymorphism (i.e. either the nucleotide(s) is present or not).

| Marker ID | Position Build 36 | Strand | Polymorphism |
|---|---|---|---|
| rs28876082 | 68761493 | + | G/T |
| rs7947353 | 68761559 | + | A/G |
| rs7947298 | 68761677 | + | A/C |
| rs11826508 | 68762658 | + | A/G |
| rs34384086 | 68763007 | + | —/C |
| rs36091743 | 68763507 | + | —/T |
| rs11228582 | 68763813 | + | A/T |
| rs7104671 | 68763950 | + | C/G |
| rs12802068 | 68764310 | + | A/G |
| rs12802553 | 68764311 | + | A/G |
| rs36101702 | 68764356 | + | —/TT |
| rs10896450 | 68764690 | + | A/G |
| rs12808564 | 68765268 | + | A/G |
| rs11228583 | 68765690 | + | G/T |
| rs11228584 | 68766043 | + | A/G |
| rs10560769 | 68766333 | + | —/TT |
| rs12293259 | 68766814 | + | G/T |
| rs12799883 | 68767227 | + | G/T |
| rs4451737 | 68767444 | + | C/T |
| rs3925012 | 68767493 | + | C/T |
| rs4131929 | 68768714 | − | C/T |
| rs12270641 | 68768820 | + | A/T |
| rs35310215 | 68769540 | + | —/G |
| rs35836017 | 68769588 | + | —/C |
| rs34255287 | 68769711 | + | A/G |
| rs7127508 | 68770593 | + | C/T |
| rs7111780 | 68770972 | + | A/G |
| rs7111993 | 68771116 | + | A/G |
| rs7112311 | 68771118 | + | A/G |
| rs11603876 | 68771837 | + | A/T |
| rs12282656 | 68772304 | + | A/G |
| rs7119988 | 68772447 | + | A/G |
| rs36031129 | 68772686 | + | —/CC |
| rs11404080 | 68773007 | + | —/T |
| rs35921293 | 68773009 | + | —/T |
| rs10896451 | 68773469 | + | A/C |
| rs34887827 | 68774015 | + | C/T |
| rs12420858 | 68774110 | + | C/G |
| rs11228585 | 68774254 | + | C/T |
| rs10530250 | 68774509 | + | (LARGE DELETION)/— |
| rs11228586 | 68774667 | + | C/T |
| rs11228587 | 68774847 | + | A/G |
| rs4930671 | 68774950 | + | A/G |
| rs10896452 | 68775074 | + | C/T |
| rs11606813 | 68775164 | + | C/T |
| rs12225965 | 68775407 | + | A/G |
| rs34717487 | 68775561 | + | G/T |
| rs4930672 | 68775807 | + | A/G |
| rs12293276 | 68775830 | + | A/G |
| rs7118966 | 68775848 | + | C/T |
| rs7102758 | 68775981 | + | A/G |
| rs12421619 | 68775992 | + | C/T |
| rs35400111 | 68776233 | + | —/G |
| rs11228588 | 68776545 | + | A/G |
| rs34223044 | 68776551 | + | —/C |
| rs11828682 | 68776692 | + | A/G |
| rs7118204 | 68777260 | + | A/G |
| rs12806580 | 68777418 | + | C/T |
| rs35349840 | 68777566 | + | —/G |
| rs10896453 | 68777614 | + | A/G |
| rs10792034 | 68777793 | + | C/T |
| rs4531476 | 68778231 | + | C/G |
| rs11228589 | 68778253 | + | A/G |
| rs11228590 | 68778283 | + | C/T |
| rs11228591 | 68779388 | + | A/C |
| rs35087861 | 68779558 | + | —/G |
| rs11228593 | 68779604 | + | A/G |
| rs11228594 | 68779663 | + | A/G |
| rs11228595 | 68779946 | + | C/T |
| rs7127913 | 68780032 | + | C/G |
| rs10736673 | 68780073 | + | C/T |
| rs11228596 | 68780341 | + | A/G |
| rs11228597 | 68780850 | + | A/G |
| rs36061232 | 68781372 | + | —/A |
| rs11602505 | 68781617 | + | C/G |
| rs7928306 | 68781639 | + | C/T |
| rs11228598 | 68781757 | + | A/G |
| rs7121952 | 68781886 | + | C/T |
| rs12792211 | 68782129 | + | A/G |
| rs7122303 | 68782158 | + | C/T |
| rs3884627 | 68782375 | − | A/C |

TABLE 6

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs611737 | 79300773 | + | A/T |
| rs626819 | 79301359 | + | A/G |
| rs6910813 | 79302376 | + | C/T |
| rs12214422 | 79302660 | + | A/G |
| rs644560 | 79303061 | + | C/T |
| rs9352604 | 79303344 | + | A/G |
| rs9448457 | 79303808 | + | C/T |
| rs686492 | 79305307 | + | C/T |
| rs9448458 | 79305343 | + | A/G |
| rs6929235 | 79305516 | + | C/T |
| rs34452249 | 79305637 | + | —/A |
| rs7749430 | 79305957 | + | A/G |
| rs817878 | 79306182 | + | C/T |
| rs9443588 | 79306226 | + | A/G |
| rs9448459 | 79306228 | + | A/G |
| rs7749697 | 79306342 | + | C/T |
| rs768590 | 79306749 | + | C/T |
| rs9448460 | 79306888 | + | A/G |
| rs35921129 | 79307666 | + | —/G |
| rs586228 | 79308383 | + | C/T |
| rs34460368 | 79308541 | + | —/C |
| rs680095 | 79309251 | + | G/T |
| rs36120289 | 79309395 | + | —/T |
| rs681322 | 79309441 | + | A/G |
| rs681802 | 79309548 | + | A/C |
| rs36181646 | 79310146 | + | —/T |
| rs7742933 | 79310346 | + | C/G |
| rs7742862 | 79310526 | + | A/T |
| rs34040490 | 79311019 | + | —/A |
| rs9359329 | 79311380 | + | C/T |
| rs9294118 | 79311509 | + | A/T |
| rs9341737 | 79311928 | + | G/T |
| rs9443589 | 79312030 | + | C/G |
| rs1506767 | 79312288 | + | A/C |
| rs9448462 | 79312500 | + | A/G |
| rs9359330 | 79312505 | + | C/T |
| rs817881 | 79312760 | + | A/T |
| rs9448463 | 79312774 | + | A/G |
| rs817882 | 79312776 | + | A/G |
| rs4321794 | 79312812 | + | A/G |
| rs817883 | 79313522 | + | C/G |
| rs9448464 | 79313952 | + | A/C |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs590624 | 79314042 | − | A/C |
| rs9448465 | 79314256 | + | A/C |
| rs34720156 | 79314273 | + | —/C/T |
| rs9443590 | 79314631 | + | A/G |
| rs587503 | 79314716 | − | C/G |
| rs9448466 | 79315160 | + | A/G |
| rs682852 | 79315205 | + | A/T |
| rs9443591 | 79315537 | + | C/T |
| rs12183583 | 79315477 | + | C/T |
| rs12202264 | 79315943 | + | A/G |
| rs9443592 | 79316009 | + | A/G |
| rs35257893 | 79316335 | + | —/C |
| rs666982 | 79316431 | + | C/T |
| rs9443593 | 79316432 | + | C/T |
| rs34323328 | 79316810 | + | —/T |
| rs654652 | 79316879 | + | G/T |
| rs12528215 | 79316955 | + | A/C |
| rs34348581 | 79317371 | + | —/A |
| rs652356 | 79317426 | + | A/T |
| rs651900 | 79317529 | − | G/T |
| rs651894 | 79317535 | − | G/T |
| rs10565029 | 79317635 | + | —/AAA |
| rs10590702 | 79317656 | + | —/AAA |
| rs17823349 | 79318539 | + | C/T |
| rs35611717 | 79319004 | + | —/TTT |
| rs2024994 | 79319262 | + | C/T |
| rs34242911 | 79319291 | + | —/A |
| rs6932288 | 79319758 | + | G/T |
| rs16890129 | 79319993 | + | C/T |
| rs600913 | 79320040 | + | C/T |
| rs1625514 | 79320259 | + | C/T |
| rs10611862 | 79320291 | + | —/AC |
| rs10695566 | 79320376 | + | —/C/T/TA |
| rs28652972 | 79320377 | + | C/T |
| rs34108696 | 79320377 | + | —/TA |
| rs13214614 | 79320385 | + | C/G |
| rs13214617 | 79320392 | + | A/G |
| rs817886 | 79320395 | + | —/A/G/GT |
| rs28736801 | 79320394 | + | A/G |
| rs13214437 | 79320413 | + | C/T |
| rs13214632 | 79320425 | + | C/G |
| rs12200116 | 79320434 | + | A/G |
| rs12213654 | 79320441 | + | C/T |
| rs13200111 | 79320447 | + | C/T |
| rs9341738 | 79320646 | + | G/T |
| rs1616969 | 79320658 | − | A/C |
| rs12215356 | 79320880 | + | A/G |
| rs3063781 | 79321086 | + | —/GATA |
| rs616011 | 79321162 | + | C/T |
| rs685093 | 79321296 | + | C/T |
| rs1321599 | 79321507 | + | C/T |
| rs12195790 | 79321512 | + | A/T |
| rs12215690 | 79321527 | + | A/G |
| rs9448467 | 79321532 | + | A/G |
| rs10214428 | 79321604 | + | A/G |
| rs5877614 | 79321661 | + | —/ATGT |
| rs35273466 | 79321666 | + | —/TGTA |
| rs10214574 | 79321924 | + | C/T |
| rs12203729 | 79321949 | + | A/G |
| rs653092 | 79322088 | − | A/G |
| rs34332845 | 79322089 | + | CA/TG |
| rs653091 | 79322089 | − | C/T |
| rs12190592 | 79322474 | + | C/T |
| rs669241 | 79322487 | − | C/T |
| rs13328234 | 79322502 | + | C/T |
| rs11963866 | 79322524 | + | A/T |
| rs668305 | 79322704 | − | A/G |
| rs9448468 | 79322719 | + | C/T |
| rs656825 | 79322983 | − | A/T |
| rs656806 | 79322991 | − | C/T |
| rs656767 | 79323027 | − | C/T |
| rs636717 | 79323460 | − | C/T |
| rs623155 | 79324200 | − | A/G |
| rs1588045 | 79324435 | − | A/G |
| rs1588044 | 79324438 | − | A/G |
| rs12154026 | 79324811 | + | C/T |
| rs36029617 | 79324861 | + | A/C |
| rs627261 | 79324993 | − | A/T |
| rs9448469 | 79325158 | + | A/T |
| rs12196214 | 79325431 | + | C/T |
| rs625065 | 79325534 | + | C/T |
| rs625051 | 79325550 | + | G/T |
| rs623658 | 79325869 | − | A/G |
| rs611493 | 79326235 | + | A/G |
| rs34644016 | 79326358 | + | —/C |
| rs7762380 | 79326371 | + | C/T |
| rs2063044 | 79327042 | − | A/G |
| rs2057299 | 79327290 | + | C/T |
| rs685245 | 79327502 | + | G/T |
| rs9443594 | 79327549 | + | A/G |
| rs594889 | 79327616 | + | —/A/T |
| rs2321446 | 79328223 | + | C/G |
| rs2321447 | 79328224 | + | C/T |
| rs9294119 | 79328300 | + | A/G |
| rs12200457 | 79328690 | + | G/T |
| rs675860 | 79328980 | − | C/T |
| rs1395451 | 79329158 | + | A/C |
| rs5877615 | 79329487 | + | —/AG |
| rs33932619 | 79329488 | + | —/AG |
| rs2307940 | 79329492 | − | —/TC |
| rs9448471 | 79329660 | + | C/T |
| rs627504 | 79329799 | − | C/T |
| rs817874 | 79329815 | − | A/T |
| rs34927882 | 79330116 | + | —/C |
| rs4532413 | 79330118 | + | A/G |
| rs7755570 | 79330301 | + | A/G |
| rs624930 | 79330391 | − | A/G |
| rs7755650 | 79330536 | + | A/C |
| rs11321290 | 79330606 | + | —/A |
| rs4055943 | 79330613 | + | —/AA |
| rs5877616 | 79330615 | + | —/A/AA |
| rs623900 | 79330662 | + | A/C |
| rs35720273 | 79331059 | + | A/T |
| rs9448472 | 79331128 | + | C/T |
| rs1354783 | 79331316 | − | A/G |
| rs9448473 | 79332278 | + | A/C |
| rs9448474 | 79332375 | + | A/G |
| rs9448475 | 79332618 | + | C/T |
| rs10485132 | 79333000 | − | A/G |
| rs9448476 | 79333023 | + | G/T |
| rs9361409 | 79333075 | + | C/T |
| rs6936674 | 79333218 | + | A/C |
| rs599356 | 79333269 | + | C/G |
| rs9448477 | 79333362 | + | C/G |
| rs35610189 | 79333362 | + | —/C |
| rs9350762 | 79333552 | + | C/T |
| rs35356866 | 79333742 | + | —/A |
| rs9443595 | 79333782 | + | C/T |
| rs817873 | 79333940 | + | A/C |
| rs34056090 | 79334129 | + | —/G |
| rs35568407 | 79334141 | + | —/C |
| rs35329543 | 79334333 | + | —/G |
| rs1180729 | 79334524 | + | A/T |
| rs12203331 | 79334532 | + | C/T |
| rs11966608 | 79335281 | + | C/T |
| rs12527974 | 79335652 | + | C/T |
| rs2321448 | 79335824 | + | A/C |
| rs4357091 | 79335896 | + | A/T |
| rs35401847 | 79336555 | + | —/A |
| rs34962042 | 79336668 | + | —/G |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs34243415 | 79336793 | + | —/C |
| rs660115 | 79336811 | − | A/G |
| rs665915 | 79336879 | + | C/T |
| rs2321449 | 79337577 | + | A/C |
| rs10214706 | 79337707 | + | A/G |
| rs645217 | 79337828 | − | C/T |
| rs9448478 | 79338056 | + | A/T |
| rs1180712 | 79339059 | + | G/T |
| rs34586728 | 79339119 | + | A/C |
| rs34371761 | 79339519 | + | —/A |
| rs5877617 | 79339832 | + | —/C |
| rs12202205 | 79340216 | + | C/T |
| rs2022199 | 79340391 | − | C/T |
| rs5877618 | 79340404 | + | —/A |
| rs34256059 | 79340405 | + | —/A |
| rs5877619 | 79340411 | + | —/A |
| rs35771902 | 79340412 | + | —/A |
| rs2022198 | 79340494 | − | C/T |
| rs615980 | 79340588 | + | C/T |
| rs35269485 | 79340618 | + | —/A |
| rs2022197 | 79340630 | − | C/T |
| rs616526 | 79340734 | + | A/G |
| rs547472 | 79341083 | + | C/T |
| rs4706714 | 79341084 | + | A/C |
| rs9448479 | 79341414 | + | C/T |
| rs671940 | 79342180 | − | C/T |
| rs2321450 | 79342370 | + | C/G |
| rs662430 | 79342674 | + | C/T |
| rs12214043 | 79342882 | + | A/T |
| rs34757416 | 79342885 | + | —/CA |
| rs1853111 | 79342888 | + | C/T |
| rs34922104 | 79342890 | + | —/TT |
| rs12207739 | 79342893 | + | A/T |
| rs28643317 | 79342897 | + | A/T |
| rs28498695 | 79342903 | + | A/T |
| rs28394665 | 79342909 | + | A/T |
| rs10455117 | 79342926 | + | A/T |
| rs474764 | 79342934 | + | G/T |
| rs28436215 | 79342992 | + | A/C |
| rs10455118 | 79343162 | + | A/C |
| rs28662236 | 79343365 | + | A/G |
| rs34757274 | 79343581 | + | —/C |
| rs654628 | 79343805 | − | C/T |
| rs11755496 | 79343990 | + | C/G |
| rs528850 | 79344165 | + | C/G |
| rs16890160 | 79344345 | + | C/T |
| rs1033691 | 79344906 | + | C/T |
| rs1964131 | 79345300 | + | —/A/G |
| rs1964132 | 79345301 | + | A/G |
| rs627292 | 79345308 | − | A/G |
| rs627289 | 79345314 | − | C/G |
| rs7767332 | 79345618 | + | A/T |
| rs9448480 | 79345810 | + | C/T |
| rs605822 | 79345825 | + | A/G |
| rs605697 | 79345910 | + | A/G |
| rs605264 | 79346003 | + | C/T |
| rs603964 | 79346271 | − | A/G |
| rs612489 | 79346309 | − | G/T |
| rs484582 | 79346824 | + | G/T |
| rs35610422 | 79346949 | + | —/G |
| rs35763342 | 79347019 | + | —/T |
| rs9448481 | 79347164 | + | C/G |
| rs9448482 | 79347421 | + | C/T |
| rs597283 | 79347449 | − | C/G |
| rs596810 | 79347562 | − | C/T |
| rs596337 | 79347676 | − | C/T |
| rs34739094 | 79347711 | + | —/G |
| rs9448484 | 79347965 | + | C/T |
| rs655566 | 79348564 | − | A/G |
| rs581416 | 79348610 | − | C/G |
| rs689389 | 79348661 | − | A/G |
| rs846453 | 79348794 | − | C/G |
| rs846452 | 79348887 | − | A/G |
| rs11755342 | 79349385 | + | C/T |
| rs34223893 | 79349579 | + | —/G |
| rs674105 | 79349688 | − | A/G |
| rs9448485 | 79350112 | + | A/G |
| rs9443596 | 79350335 | + | A/G |
| rs12181074 | 79350315 | + | A/G |
| rs17225876 | 79350594 | + | C/T |
| rs11751885 | 79350686 | + | A/G |
| rs7746355 | 79351241 | + | A/C |
| rs7746614 | 79351279 | + | C/T |
| rs34541692 | 79351399 | + | —/A |
| rs699174 | 79351582 | − | A/G |
| rs9448486 | 79351645 | + | A/C |
| rs699175 | 79351931 | − | C/T |
| rs699176 | 79352012 | − | A/G |
| rs236863 | 79352234 | + | A/G |
| rs12207987 | 79352301 | + | G/T |
| rs13201882 | 79352366 | + | A/G |
| rs9448487 | 79352398 | + | G/T |
| rs9443597 | 79352413 | + | C/T |
| rs9448488 | 79352736 | + | C/T |
| rs9443598 | 79352745 | + | C/T |
| rs9448489 | 79352746 | + | A/G |
| rs3967379 | 79353019 | + | C/T |
| rs236864 | 79353190 | + | C/G |
| rs12209919 | 79353401 | + | A/G |
| rs12209974 | 79353466 | + | C/G |
| rs236865 | 79353475 | + | C/G |
| rs9443599 | 79354012 | + | A/G |
| rs236866 | 79354277 | − | A/G |
| rs1137258 | 79354328 | + | A/G |
| rs9448490 | 79354814 | + | A/C |
| rs17332393 | 79355181 | + | C/T |
| rs11759337 | 79355380 | + | A/G |
| rs236867 | 79355383 | + | C/T |
| rs9448491 | 79355466 | + | A/G |
| rs236868 | 79355488 | + | G/T |
| rs236869 | 79355706 | + | C/T |
| rs9443600 | 79356397 | + | G/T |
| rs236870 | 79356774 | + | C/T |
| rs236871 | 79356925 | + | C/T |
| rs16890184 | 79357098 | + | C/T |
| rs9443601 | 79357369 | + | A/G |
| rs9448492 | 79357532 | + | C/T |
| rs236872 | 79358008 | − | C/T |
| rs9448493 | 79358214 | + | C/T |
| rs7776020 | 79358245 | + | C/T |
| rs236873 | 79358580 | − | A/G |
| rs11753657 | 79358850 | + | A/C |
| rs34736990 | 79359228 | + | —/T |
| rs11461852 | 79359513 | + | —/T |
| rs9448495 | 79359564 | + | C/T |
| rs9448496 | 79359649 | + | A/G |
| rs9448497 | 79360057 | + | C/T |
| rs236874 | 79360347 | + | A/G |
| rs9443602 | 79360653 | + | C/T |
| rs192101 | 79360986 | + | A/G |
| rs35198424 | 79361056 | + | —/A |
| rs236875 | 79361403 | + | A/C |
| rs11366261 | 79361558 | + | —/A |
| rs236876 | 79362007 | + | C/G |
| rs12203300 | 79362176 | + | A/T |
| rs236877 | 79362203 | + | A/G |
| rs9448498 | 79362482 | + | A/G |
| rs11756326 | 79362950 | + | A/G |
| rs9448499 | 79363791 | + | A/C |
| rs9448500 | 79363928 | + | A/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs10485131 | 79364083 | − | C/T |
| rs7770444 | 79364354 | + | C/T |
| rs11757555 | 79364553 | + | A/C |
| rs236878 | 79364707 | − | G/T |
| rs910955 | 79364822 | + | A/G |
| rs70478 | 79364899 | + | C/T |
| rs70480 | 79365324 | + | A/G |
| rs5877620 | 79365398 | + | —/T |
| rs731449 | 79365401 | − | A/G/T |
| rs35967646 | 79365405 | + | —/A |
| rs9294120 | 79365528 | + | C/T |
| rs35822945 | 79365869 | + | —/T |
| rs9343779 | 79365908 | + | A/G |
| rs699178 | 79366002 | + | C/T |
| rs2750022 | 79366008 | + | A/C |
| rs699179 | 79366252 | + | A/G |
| rs699180 | 79366351 | + | C/T |
| rs9448502 | 79366447 | + | A/C |
| rs35286686 | 79366524 | + | —/T |
| rs9448503 | 79366694 | + | C/G |
| rs35383112 | 79367223 | + | —/A |
| rs699181 | 79367333 | + | C/T |
| rs7356833 | 79367828 | + | A/G |
| rs7356834 | 79367837 | + | A/G |
| rs34785800 | 79367950 | + | —/T |
| rs7356836 | 79367968 | + | A/G |
| rs5877621 | 79368047 | + | —/C |
| rs7356840 | 79368100 | + | A/G |
| rs7356843 | 79368150 | + | G/T |
| rs9294121 | 79368152 | + | G/T |
| rs7356844 | 79368157 | + | A/G |
| rs236879 | 79368578 | − | A/C |
| rs34335044 | 79368627 | + | —/C |
| rs9448504 | 79369400 | + | C/G |
| rs9448505 | 79369555 | + | C/T |
| rs9448506 | 79369618 | + | A/T |
| rs9359332 | 79369685 | + | G/T |
| rs236880 | 79369811 | − | A/T |
| rs9448507 | 79370086 | + | A/G |
| rs9448508 | 79370320 | + | A/G |
| rs9443603 | 79370631 | + | A/C |
| rs236881 | 79370661 | − | C/G |
| rs9448509 | 79371433 | + | A/G |
| rs11964133 | 79371604 | + | C/T |
| rs35268570 | 79371715 | + | —/G |
| rs498037 | 79371989 | − | A/G |
| rs1570075 | 79372076 | + | A/C |
| rs1567097 | 79372765 | − | A/T |
| rs1567096 | 79372799 | − | A/G |
| rs236882 | 79372832 | + | A/G |
| rs12200556 | 79372896 | + | C/T |
| rs10806133 | 79372949 | + | C/T |
| rs35217057 | 79373409 | + | —/TGGA |
| rs717364 | 79374159 | + | A/G |
| rs11757996 | 79374370 | + | C/T |
| rs1995650 | 79375007 | − | C/T |
| rs500391 | 79375065 | + | A/G |
| rs596057 | 79375070 | − | A/C |
| rs34948829 | 79375296 | + | G/T |
| rs2021855 | 79375397 | − | A/T |
| rs17226851 | 79375471 | + | A/G |
| rs984157 | 79375681 | − | C/T |
| rs1395447 | 79376010 | − | C/T |
| rs9361411 | 79376022 | + | A/G |
| rs236883 | 79376130 | − | A/C |
| rs236884 | 79376244 | + | C/G |
| rs9448510 | 79376314 | + | C/T |
| rs12197910 | 79376609 | + | C/T |
| rs2307943 | 79376998 | + | —/AA |
| rs10539915 | 79376999 | + | —/AA |
| rs4551135 | 79377021 | + | G/T |
| rs10943547 | 79378077 | + | A/G |
| rs236885 | 79378204 | + | A/G |
| rs236886 | 79378253 | + | A/C |
| rs10943548 | 79378357 | + | C/T |
| rs35488554 | 79378364 | + | A/C |
| rs236887 | 79378393 | − | A/T |
| rs16890218 | 79378495 | + | G/T |
| rs236888 | 79378960 | + | C/T |
| rs236889 | 79379130 | − | A/G |
| rs16890224 | 79379278 | + | A/T |
| rs1407102 | 79379719 | + | C/T |
| rs17825291 | 79379916 | + | C/T |
| rs34286917 | 79380641 | + | —/A |
| rs1012026 | 79381031 | + | A/G |
| rs236890 | 79381351 | + | A/C |
| rs236891 | 79381414 | + | C/T |
| rs1012027 | 79381592 | + | C/T |
| rs34331673 | 79382209 | + | —/G |
| rs9448511 | 79382811 | + | C/T |
| rs17227220 | 79382837 | + | A/G |
| rs16890230 | 79382886 | + | A/T |
| rs236892 | 79382966 | − | C/T |
| rs12189761 | 79382972 | + | A/T |
| rs12209692 | 79383101 | + | A/G |
| rs1395446 | 79383114 | − | A/C |
| rs34707756 | 79383315 | + | —/A |
| rs16890234 | 79383336 | + | A/G |
| rs2021251 | 79383492 | − | C/G |
| rs10943549 | 79383908 | + | C/T |
| rs699182 | 79384047 | + | G/T |
| rs3035341 | 79384211 | + | —/AAAAA |
| rs34681522 | 79384257 | + | —/T |
| rs1186428 | 79384269 | − | A/G |
| rs2022521 | 79384282 | − | G/T |
| rs817889 | 79384562 | − | A/G |
| rs6931841 | 79384660 | + | C/T |
| rs6932494 | 79384868 | + | A/G |
| rs9359333 | 79384897 | + | C/T |
| rs12213548 | 79385071 | + | G/T |
| rs12525083 | 79385670 | + | C/T |
| rs11970272 | 79385707 | + | C/T |
| rs10455349 | 79387663 | + | C/G |
| rs2063045 | 79388058 | − | A/G |
| rs11757737 | 79388316 | + | A/C |
| rs12197137 | 79388567 | + | A/G |
| rs9448512 | 79389055 | + | A/T |
| rs35065237 | 79389616 | + | —/T |
| rs10630134 | 79389747 | + | —/TA |
| rs34896371 | 79389748 | + | —/TA |
| rs34598417 | 79389756 | + | —/AT |
| rs236859 | 79389835 | − | C/T |
| rs6454064 | 79389958 | + | G/T |
| rs6454065 | 79390047 | + | G/T |
| rs41501448 | 79390057 | + | C/T |
| rs10640580 | 79390177 | + | —/CACA |
| rs34677786 | 79390178 | + | —/CACA |
| rs10565820 | 79390187 | + | —/CA |
| rs10542873 | 79390189 | + | —/CA |
| rs10536481 | 79390190 | + | —/AC |
| rs6454066 | 79390202 | + | C/T |
| rs6454067 | 79390311 | + | C/T |
| rs1567095 | 79390707 | − | C/T |
| rs1570001 | 79390750 | + | C/T |
| rs236860 | 79390814 | − | C/T |
| rs236861 | 79390866 | + | C/T |
| rs12530012 | 79390899 | + | C/T |
| rs9443604 | 79391001 | + | C/G |
| rs12530067 | 79391157 | + | C/T |
| rs12530068 | 79391178 | + | C/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs12530072 | 79391243 | + | C/T |
| rs4286729 | 79391508 | + | C/T |
| rs236862 | 79391691 | − | A/G |
| rs35710435 | 79391916 | + | —/G |
| rs5877622 | 79391938 | + | —/G |
| rs12190115 | 79392540 | + | A/G |
| rs699183 | 79392730 | + | A/G |
| rs34692849 | 79392774 | + | —/T |
| rs10943550 | 79392824 | + | G/T |
| rs10943551 | 79393059 | + | G/T |
| rs11413951 | 79393172 | + | —/A |
| rs35198419 | 79393180 | + | —/A |
| rs35839290 | 79393308 | + | C/T |
| rs11752300 | 79393726 | + | C/T |
| rs12200526 | 79393754 | + | C/T |
| rs12193597 | 79393898 | + | A/G |
| rs12524686 | 79394235 | + | C/G |
| rs35481326 | 79394369 | + | —/C |
| rs659108 | 79395159 | − | G/T |
| rs7775572 | 79395255 | + | C/T |
| rs7755578 | 79395265 | + | A/G |
| rs12195709 | 79395315 | + | A/G |
| rs7775782 | 79395445 | + | A/G |
| rs7755682 | 79395539 | + | C/T |
| rs12210711 | 79396008 | + | A/G |
| rs236853 | 79396185 | − | A/G |
| rs34570358 | 79396386 | + | —/T |
| rs35919105 | 79396567 | + | C/T |
| rs12530353 | 79396617 | + | A/G |
| rs6940529 | 79396666 | + | A/C |
| rs12530368 | 79396668 | + | A/G |
| rs6940555 | 79396714 | + | A/C |
| rs6941006 | 79396789 | + | A/G |
| rs6920658 | 79396993 | + | C/T |
| rs11755479 | 79397125 | + | A/T |
| rs12665819 | 79397185 | + | A/G |
| rs9448513 | 79397377 | + | A/G |
| rs12191138 | 79397842 | + | C/G |
| rs10615883 | 79397992 | + | —/TC |
| rs10563095 | 79397998 | + | —/TC |
| rs236854 | 79398400 | + | G/T |
| rs236855 | 79398610 | − | A/G |
| rs9443605 | 79398716 | + | C/T |
| rs497885 | 79398799 | + | G/T |
| rs2321764 | 79399237 | + | C/G |
| rs5018093 | 79399607 | + | C/T |
| rs12201840 | 79399748 | + | C/T |
| rs9448514 | 79399769 | + | A/C |
| rs34938165 | 79400028 | + | —/GA |
| rs35821097 | 79400053 | + | —/C |
| rs7774339 | 79400463 | + | C/T |
| rs236856 | 79400485 | + | A/G |
| rs236857 | 79401130 | + | C/T |
| rs9448515 | 79401281 | + | A/G |
| rs236858 | 79401284 | + | C/T |
| rs699184 | 79401788 | − | A/C |
| rs512778 | 79401865 | + | A/G |
| rs9361413 | 79401968 | + | A/G |
| rs3220157 | 79402127 | + | (CA)24/25/26/28/29/30/31/33 |
| rs36212818 | 79402095 | + | —/CACACACACA |
| rs5877623 | 79402087 | + | —/CACACACACA |
| rs33979908 | 79402121 | + | —/CACACACACA |
| rs9361414 | 79402167 | + | G/T |
| rs5877624 | 79402681 | + | —/G |
| rs541337 | 79402708 | + | A/G |
| rs2321765 | 79402846 | + | C/G |
| rs699185 | 79403177 | + | A/G |
| rs236848 | 79403803 | + | A/G |
| rs11965655 | 79403862 | + | A/G |
| rs236849 | 79403916 | − | A/G |
| rs10701196 | 79403945 | + | —/AA |
| rs35128239 | 79404539 | + | —/C |
| rs236850 | 79405375 | + | A/C |
| rs6904390 | 79405458 | + | A/T |
| rs6909051 | 79405613 | + | C/T |
| rs12206138 | 79405708 | + | C/T |
| rs34566789 | 79405761 | + | —/C |
| rs6909339 | 79405768 | + | C/G |
| rs6909644 | 79405797 | + | A/G |
| rs6909663 | 79405829 | + | G/T |
| rs6910018 | 79405963 | + | A/G |
| rs171050 | 79406031 | + | A/G |
| rs236851 | 79406471 | + | A/G |
| rs236852 | 79406611 | + | A/C |
| rs35683036 | 79406788 | + | —/C |
| rs7763429 | 79407488 | + | A/G |
| rs28797508 | 79407906 | + | A/T |
| rs34457432 | 79407905 | + | —/A |
| rs28845244 | 79407909 | + | A/T |
| rs11967330 | 79408002 | + | G/T |
| rs9766611 | 79408248 | + | C/G |
| rs9767153 | 79408285 | + | C/T |
| rs11967401 | 79408313 | + | G/T |
| rs34710160 | 79408331 | + | —/T |
| rs9767594 | 79408340 | + | A/G |
| rs9767160 | 79408362 | + | C/T |
| rs9766716 | 79408582 | + | C/T |
| rs9766717 | 79408597 | + | C/T |
| rs9767724 | 79408721 | + | A/G |
| rs9767248 | 79408857 | + | C/T |
| rs11755206 | 79408909 | + | C/T |
| rs11755256 | 79408948 | + | G/T |
| rs663954 | 79408987 | + | C/G |
| rs35768463 | 79409014 | + | C/G |
| rs2202590 | 79409231 | − | A/C |
| rs34750624 | 79409440 | + | —/AACA |
| rs125272367 | 9409757 | + | C/G |
| rs7740665 | 79410184 | + | C/T |
| rs4547970 | 79410315 | + | A/G |
| rs34273395 | 79410347 | + | —/T |
| rs10455350 | 79410646 | + | A/G |
| rs583747 | 79411314 | − | A/T |
| rs10455351 | 79411324 | + | G/T |
| rs34113682 | 79411805 | + | —/C |
| rs6936649 | 79411878 | + | A/T |
| rs6913931 | 79412046 | + | C/T |
| rs9343780 | 79412054 | + | C/T |
| rs1172263 | 79412098 | − | A/T |
| rs7751786 | 79412433 | + | A/T |
| rs1069028 | 79412764 | − | A/C |
| rs4706716 | 79412775 | + | G/T |
| rs7738229 | 79412794 | + | A/T |
| rs7756398 | 79412809 | + | A/C |
| rs7756411 | 79412884 | + | A/C |
| rs7756809 | 79412901 | + | A/G |
| rs7756442 | 79412946 | + | A/G |
| rs34345701 | 79412986 | + | G/T |
| rs9448517 | 79413089 | + | G/T |
| rs11753268 | 79413379 | + | A/G |
| rs2202589 | 79413464 | − | A/G |
| rs2202588 | 79413475 | − | C/T |
| rs11758439 | 79413558 | + | C/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs7761199 | 79413617 | + | A/G |
| rs11753781 | 79413684 | + | A/C |
| rs10455119 | 79413685 | + | A/G |
| rs4530796 | 79414858 | + | —/T |
| rs9448518 | 79414973 | + | A/G |
| rs9443606 | 79415015 | + | C/G |
| rs9443607 | 79415153 | + | C/T |
| rs13213955 | 79415197 | + | A/T |
| rs9350767 | 79415702 | + | A/C |
| rs7772851 | 79416038 | + | C/T |
| rs6454070 | 79416268 | + | A/C |
| rs7773660 | 79416279 | + | A/G |
| rs7773550 | 79416449 | + | A/G |
| rs9448519 | 79416456 | + | C/G |
| rs7773732 | 79416491 | + | A/C |
| rs9448520 | 79416508 | + | A/G |
| rs9361418 | 79416542 | + | C/T |
| rs7774017 | 79416543 | + | A/G |
| rs34978259 | 79416789 | + | —/C |
| rs13199250 | 79416845 | + | A/C |
| rs12528155 | 79417363 | + | A/G |
| rs12528140 | 79417430 | + | A/C |
| rs12524711 | 79417477 | + | A/G |
| rs12528168 | 79417483 | + | A/G |
| rs12529963 | 79417494 | + | A/T |
| rs12525058 | 79417555 | + | A/T |
| rs12528513 | 79417619 | + | C/G |
| rs35973698 | 79417626 | + | —/A |
| rs9448521 | 79418135 | + | C/T |
| rs13204264 | 79418289 | + | A/C |
| rs13204489 | 79418306 | + | G/T |
| rs13220434 | 79418337 | + | C/T |
| rs13204504 | 79418338 | + | A/G |
| rs13204411 | 79418403 | + | A/C |
| rs10943555 | 79418521 | + | A/G |
| rs12182690 | 79418612 | + | C/T |
| rs11758282 | 79418731 | + | A/G |
| rs10943556 | 79418749 | + | A/C |
| rs11758301 | 79418757 | + | G/T |
| rs12182714 | 79418795 | + | A/C |
| rs10943557 | 79418878 | + | G/T |
| rs10943558 | 79418957 | + | A/G |
| rs10943559 | 79418973 | + | A/C |
| rs12529060 | 79419023 | + | G/T |
| rs12529083 | 79419172 | + | A/G |
| rs12529066 | 79419210 | + | C/T |
| rs13208861 | 79419298 | + | C/G |
| rs35723058 | 79419309 | + | —/T |
| rs12524083 | 79419353 | + | C/T |
| rs4481395 | 79420009 | + | A/G |
| rs9359334 | 79420248 | + | C/G |
| rs12662183 | 79420296 | + | A/G |
| rs13202661 | 79421089 | + | G/T |
| rs2321767 | 79421453 | + | C/T |
| rs6921541 | 79421621 | + | C/T |
| rs11750986 | 79422024 | + | C/T |
| rs11755647 | 79422090 | + | A/C |
| rs35959932 | 79422201 | + | —/C |
| rs34291901 | 79422318 | + | A/T |
| rs9343782 | 79422366 | + | G/T |
| rs34044761 | 79424096 | + | —/G |
| rs11399404 | 79424247 | + | —/A |
| rs17234476 | 79425078 | + | G/T |
| rs5877625 | 79425313 | + | —/T |
| rs35681689 | 79425314 | + | —/T |
| rs34020492 | 79425316 | + | —/T |
| rs13220214 | 79425378 | + | G/T |
| rs12210702 | 79426052 | + | A/G |
| rs12525652 | 79426301 | + | A/C |
| rs1938554 | 79426313 | + | C/G |
| rs12525655 | 79426333 | + | C/T |
| rs35676724 | 79426360 | + | —/T |
| rs12525674 | 79426408 | + | C/T |
| rs12527490 | 79426534 | + | A/T |
| rs36020193 | 79426610 | + | —/T |
| rs12530352 | 79426691 | + | A/G |
| rs12526918 | 79426820 | + | A/G |
| rs12215953 | 79426831 | + | C/T |
| rs2154396 | 79426988 | + | C/T |
| rs10943560 | 79427137 | + | C/T |
| rs35902159 | 79427208 | + | —/AAT |
| rs6941828 | 79427531 | + | C/G |
| rs17234622 | 79427610 | + | A/G |
| rs10485130 | 79427659 | − | A/G |
| rs10485129 | 79427902 | − | C/T |
| rs17826325 | 79427930 | + | C/T |
| rs10485128 | 79428165 | − | A/C |
| rs9361420 | 79428649 | + | A/G |
| rs17826379 | 79428843 | + | A/C |
| rs9443608 | 79429038 | + | A/T |
| rs7768733 | 79429515 | + | C/T |
| rs12194701 | 79429556 | + | A/G |
| rs12528303 | 79429558 | + | A/C |
| rs7752431 | 79429626 | + | C/T |
| rs12524924 | 79429653 | + | C/T |
| rs12524949 | 79429719 | + | A/G |
| rs1938555 | 79430010 | + | A/G |
| rs1938556 | 79430133 | + | A/G |
| rs11962962 | 79430380 | + | C/G |
| rs35016983 | 79430502 | + | —/T |
| rs12661567 | 79430711 | + | C/T |
| rs9448524 | 79430774 | + | C/G |
| rs12196899 | 79431241 | + | A/G |
| rs7453195 | 79431988 | + | G/T |
| rs35095504 | 79432065 | + | C/T |
| rs11756592 | 79432239 | + | C/T |
| rs12198749 | 79432255 | + | C/T |
| rs11754162 | 79432324 | + | A/G |
| rs11964250 | 79432345 | + | C/T |
| rs11756635 | 79432372 | + | C/T |
| rs12198976 | 79432495 | + | C/G |
| rs11758823 | 79432516 | + | A/G |
| rs12526451 | 79432811 | + | A/G |
| rs35824053 | 79432979 | + | —/GT |
| rs9361422 | 79434457 | + | C/G |
| rs12527341 | 79434703 | + | C/T |
| rs34470324 | 79434880 | + | —/T |
| rs16890254 | 79435141 | + | G/T |
| rs11751443 | 79435191 | + | A/G |
| rs10943561 | 79435271 | + | A/G |
| rs34358078 | 79435272 | + | AT/GC |
| rs10943562 | 79435272 | + | C/T |
| rs11758593 | 79435318 | + | G/T |
| rs11759124 | 79435551 | + | A/T |
| rs17234902 | 79435793 | + | A/G |
| rs1954659 | 79436179 | − | G/T |
| rs9443609 | 79436197 | + | A/C |
| rs1954658 | 79436315 | − | G/T |
| rs11756825 | 79436318 | + | A/G |
| rs1954657 | 79436419 | − | A/G |
| rs34627531 | 79436474 | + | A/G |
| rs17826615 | 79436664 | + | C/T |
| rs17235062 | 79436828 | + | C/G |
| rs9359335 | 79436942 | + | C/T |
| rs16890261 | 79437480 | + | A/G |
| rs34327517 | 79437516 | + | —/C |
| rs17235125 | 79437555 | + | A/G |
| rs17235167 | 79437614 | + | C/G |
| rs17235209 | 79437636 | + | C/T |
| rs34645505 | 79437645 | + | —/C |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs17826801 | 79437741 | + | A/G |
| rs16890263 | 79438616 | + | C/T |
| rs2321768 | 79438791 | + | A/T |
| rs12201253 | 79439572 | + | G/T |
| rs34671943 | 79439692 | + | —/C |
| rs6914850 | 79439950 | + | C/G |
| rs12194506 | 79440009 | + | A/G |
| rs1938553 | 79440281 | − | A/C |
| rs1938552 | 79442027 | − | C/G |
| rs1938551 | 79442188 | − | A/G |
| rs1938550 | 79442759 | − | G/T |
| rs1938549 | 79442785 | − | C/G |
| rs4371819 | 79443838 | + | A/G |
| rs3207577 | 79443876 | + | G/T |
| rs2226283 | 79444234 | − | C/T |
| rs34263174 | 79444643 | + | —/C |
| rs9443610 | 79444913 | + | C/T |
| rs6901727 | 79444923 | + | A/G |
| rs9359337 | 79446035 | + | C/T |
| rs9352610 | 79446117 | + | A/G |
| rs4590226 | 79446611 | + | C/G |
| rs4568410 | 79448079 | + | A/G |
| rs4358581 | 79448365 | + | A/G |
| rs36159891 | 79448536 | + | —/G |
| rs12214797 | 79448885 | + | A/G |
| rs12203087 | 79449566 | + | C/T |
| rs1938548 | 79450052 | + | A/G |
| rs237114 | 79450160 | + | C/G |
| rs237113 | 79450255 | + | C/T |
| rs9448526 | 79450659 | + | A/G |
| rs9294124 | 79450941 | + | C/T |
| rs237112 | 79451719 | + | A/G |
| rs9443611 | 79451898 | + | C/T |
| rs28510272 | 79452108 | + | G/T |
| rs5877626 | 79452148 | + | —/T |
| rs28715651 | 79452155 | + | C/T |
| rs36084918 | 79452165 | + | —/T |
| rs237111 | 79452657 | + | A/C |
| rs9359338 | 79453470 | + | C/T |
| rs9352611 | 79453687 | + | C/T |
| rs9448528 | 79453785 | + | C/T |
| rs190210 | 79455101 | − | A/G |
| rs633117 | 79456053 | + | C/T |
| rs36071262 | 79456190 | + | —/T |
| rs578709 | 79456303 | + | C/T |
| rs9448529 | 79456446 | + | A/G |
| rs631308 | 79456494 | + | C/T |
| rs580694 | 79456568 | + | C/G |
| rs496269 | 79457094 | − | A/G |
| rs10678940 | 79457699 | + | —/AATG |
| rs35912544 | 79457700 | + | —/AATG |
| rs35640072 | 79457977 | + | —/C |
| rs639370 | 79458132 | + | C/T |
| rs2307947 | 79458723 | + | —/AAG |
| rs1180811 | 79458783 | + | A/G |
| rs10943567 | 79459170 | + | C/T |
| rs500306 | 79459437 | + | C/T |
| rs621121 | 79459440 | − | A/G |
| rs524008 | 79459763 | + | A/C |
| rs605868 | 79460512 | + | A/C |
| rs553313 | 79460609 | + | A/G |
| rs605016 | 79460685 | − | C/G |
| rs553545 | 79460686 | + | A/C |
| rs10943568 | 79460926 | + | G/T |
| rs557062 | 79461079 | + | C/T |
| rs9359339 | 79461851 | + | A/G |
| rs1099816 | 79461906 | + | A/G |
| rs1099817 | 79462027 | + | A/C |
| rs11760142 | 79462156 | + | A/G |
| rs36155678 | 79462155 | + | —/A |
| rs237117 | 79462475 | − | C/T |
| rs34503722 | 79462774 | + | —/T |
| rs36003173 | 79463000 | + | CAT/TGG |
| rs9352612 | 79463306 | + | C/T |
| rs35073587 | 79463953 | + | —/T |
| rs237116 | 79465318 | − | A/G |
| rs13219002 | 79465340 | + | G/T |
| rs36187425 | 79465396 | + | —/T |
| rs4116296 | 79465874 | + | A/C |
| rs9688758 | 79465988 | + | C/T |
| rs36167084 | 79466143 | + | —/A |
| rs11759842 | 79466549 | + | G/T |
| rs237115 | 79467111 | + | A/G |
| rs11751263 | 79467773 | + | C/T |
| rs10591157 | 79468622 | + | —/AGG |
| rs1180810 | 79468743 | + | C/G |
| rs12192387 | 79468754 | + | C/T |
| rs9361423 | 79468991 | + | G/T |
| rs13197296 | 79469397 | + | A/C |
| rs13197299 | 79469399 | + | A/C |
| rs13197312 | 79469415 | + | A/T |
| rs13197402 | 79469451 | + | A/C |
| rs13197429 | 79469504 | + | A/C |
| rs13197432 | 79469507 | + | A/C |
| rs237110 | 79469629 | − | C/G |
| rs35083334 | 79470193 | + | —/T |
| rs34384472 | 79470458 | + | —/C |
| rs35723904 | 79470956 | + | —/T |
| rs237109 | 79471413 | − | A/T |
| rs9343786 | 79471447 | + | A/C |
| rs34396685 | 79471699 | + | —/G |
| rs237108 | 79471734 | + | C/T |
| rs28526821 | 79472111 | + | A/G |
| rs9343787 | 79472325 | + | A/C |
| rs9343788 | 79472577 | + | A/G |
| rs237107 | 79472599 | + | A/G |
| rs11337252 | 79472738 | + | —/A |
| rs11322370 | 79472755 | + | —/A |
| rs9448533 | 79473558 | + | A/G |
| rs4706718 | 79473602 | + | A/G |
| rs7773448 | 79474075 | + | C/T |
| rs12662772 | 79474252 | + | C/G |
| rs34988548 | 79474267 | + | —/T |
| rs34521774 | 79474321 | + | —/A |
| rs16890280 | 79474935 | + | C/T |
| rs1180809 | 79474961 | + | A/G |
| rs35874347 | 79475533 | + | —/C |
| rs9341739 | 79475795 | + | C/G |
| rs10485127 | 79476149 | − | C/T |
| rs1782783 | 79476375 | − | A/G |
| rs34305826 | 79476572 | + | —/C |
| rs11758421 | 79477277 | + | A/G |
| rs1180829 | 79477495 | − | A/G |
| rs17642139 | 79477518 | + | C/T |
| rs11380286 | 79477603 | + | —/G |
| rs7748153 | 79477872 | + | C/T |
| rs9341740 | 79479508 | + | G/T |
| rs34794581 | 79480689 | + | —/G |
| rs10613222 | 79480812 | + | —/ATATATATAT |
| rs10613221 | 79480824 | + | —/AT |
| rs35653902 | 79480973 | + | —/G |
| rs9352613 | 79481152 | + | A/G |
| rs11363389 | 79481250 | + | —/A |
| rs10589550 | 79481315 | + | —/ATATATAT |
| rs34184424 | 79481323 | + | —/ATAT |
| rs1180812 | 79481799 | + | G/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs1180813 | 79482210 | + | C/T |
| rs1180814 | 79482234 | + | A/G |
| rs10455352 | 79482310 | + | A/G |
| rs1180815 | 79482567 | + | C/T |
| rs1185719 | 79483043 | + | A/G |
| rs1180816 | 79483108 | + | A/C |
| rs9343789 | 79483300 | + | A/G |
| rs9341741 | 79483557 | + | A/G |
| rs35281441 | 79483695 | + | A/C |
| rs1180817 | 79483705 | + | A/G |
| rs6923778 | 79483808 | + | A/G |
| rs1180818 | 79483938 | + | C/G |
| rs35304238 | 79484265 | + | —/A |
| rs28702778 | 79484289 | + | A/C |
| rs28667093 | 79484464 | + | A/G |
| rs12197635 | 79484466 | + | A/G |
| rs11403769 | 79484690 | + | —/A |
| rs33917829 | 79484698 | + | —/A |
| rs35564110 | 79484699 | + | —/A |
| rs1180819 | 79484743 | + | A/G |
| rs1180820 | 79485455 | + | A/G |
| rs1543481 | 79485804 | + | C/G |
| rs1543482 | 79485857 | + | A/G |
| rs1543483 | 79485890 | + | A/T |
| rs1180821 | 79486391 | + | A/G |
| rs9448534 | 79486474 | + | C/T |
| rs28831831 | 79486721 | + | C/T |
| rs2224461 | 79487062 | + | A/G |
| rs2208518 | 79487184 | + | G/T |
| rs13198615 | 79487271 | + | A/G |
| rs3920564 | 79487560 | + | G/T |
| rs6915548 | 79487586 | + | A/G |
| rs1180822 | 79487770 | + | A/G |
| rs35129774 | 79488647 | + | —/G |
| rs1180823 | 79489645 | + | A/G |
| rs13210865 | 79489811 | + | A/G |
| rs7746175 | 79489924 | + | A/T |
| rs11370388 | 79489978 | + | —/A |
| rs35746612 | 79489979 | + | —/A |
| rs35105486 | 79489988 | + | —/A |
| rs1180824 | 79490242 | + | A/G |
| rs1180825 | 79490569 | + | G/T |
| rs1180826 | 79491321 | + | C/G |
| rs1180827 | 79491347 | + | C/G |
| rs28634504 | 79491970 | + | A/G |
| rs1180828 | 79492141 | + | C/G |
| rs3035346 | 79492475 | + | —/G/GTG |
| rs35410463 | 79492476 | + | —/GTG |
| rs34535315 | 79492501 | + | —/G |
| rs35742744 | 79492502 | + | —/T |
| rs1184721 | 79492711 | + | C/T |
| rs1185343 | 79492909 | + | C/G |
| rs34508299 | 79492924 | + | —/T |
| rs2224462 | 79493658 | + | C/G |
| rs12192834 | 79493674 | + | C/T |
| rs7767460 | 79493730 | + | G/T |
| rs6454073 | 79494060 | + | A/G |
| rs7768079 | 79494100 | + | G/T |
| rs7747874 | 79494113 | + | C/T |
| rs7747911 | 79494214 | + | A/T |
| rs35940523 | 79494339 | + | —/A |
| rs9448536 | 79494391 | + | C/G |
| rs9448537 | 79494467 | + | A/G |
| rs10943570 | 79494466 | + | A/G |
| rs5877627 | 79494624 | + | —/CT |
| rs35909564 | 79494627 | + | —/CT |
| rs3035349 | 79494638 | + | —/CT/T |
| rs1570177 | 79494647 | + | C/T |
| rs2321769 | 79494679 | + | G/T |
| rs34358401 | 79494750 | + | A/G |
| rs7752898 | 79494868 | + | C/T |
| rs9448538 | 79495167 | + | G/T |
| rs2145685 | 79495471 | + | A/G |
| rs9341742 | 79496948 | + | C/T |
| rs9343792 | 79497004 | + | C/T |
| rs9343793 | 79497122 | + | C/T |
| rs12202166 | 79497374 | + | A/G |
| rs6901911 | 79497718 | + | A/G |
| rs35458046 | 79497892 | + | —/C |
| rs7740607 | 79498009 | + | C/T |
| rs9352615 | 79498212 | + | C/G |
| rs9352616 | 79498222 | + | C/T |
| rs9352617 | 79498373 | + | A/C |
| rs9448540 | 79498394 | + | G/T |
| rs7746203 | 79498898 | + | A/G |
| rs9352618 | 79499147 | + | C/T |
| rs9352619 | 79499433 | + | A/G |
| rs11752556 | 79499668 | + | C/T |
| rs7751066 | 79499807 | + | A/C |
| rs9352620 | 79500266 | + | G/T |
| rs11380936 | 79500730 | + | —/A |
| rs6900332 | 79501060 | + | C/T |
| rs9448542 | 79501084 | + | A/C |
| rs35258079 | 79501132 | + | —/C |
| rs9448543 | 79501153 | + | A/T |
| rs12661502 | 79501197 | + | C/T |
| rs9350769 | 79501280 | + | A/G |
| rs9448544 | 79501600 | + | C/T |
| rs9343794 | 79501644 | + | A/G |
| rs7450313 | 79501839 | + | C/T |
| rs4470810 | 79502002 | + | G/T |
| rs1080857 | 79502085 | + | C/T |
| rs4470811 | 79502097 | + | C/T |
| rs2321770 | 79502127 | + | C/T |
| rs7767636 | 79502775 | + | A/G |
| rs7768125 | 79503108 | + | A/G |
| rs9343796 | 79503266 | + | C/T |
| rs9443612 | 79503406 | + | C/T |
| rs12215204 | 79503784 | + | A/G |
| rs9448545 | 79504354 | + | C/T |
| rs9352621 | 79504806 | + | A/C |
| rs9341743 | 79504981 | + | A/G |
| rs9352622 | 79505238 | + | A/T |
| rs9352623 | 79505367 | + | A/C |
| rs7745733 | 79506026 | + | C/T |
| rs9359341 | 79506207 | + | C/T |
| rs7746057 | 79506232 | + | A/C |
| rs4706063 | 79506593 | + | A/G |
| rs4706721 | 79506594 | + | A/G |
| rs4706064 | 79506627 | + | C/T |
| rs4312941 | 79506920 | + | A/G |
| rs7382759 | 79507470 | + | A/C |
| rs6454075 | 79507724 | + | A/G |
| rs4498306 | 79507894 | + | C/T |
| rs36170402 | 79507898 | + | —/G |
| rs4299783 | 79508072 | + | C/T |
| rs7766318 | 79508234 | + | A/C |
| rs12213140 | 79508449 | + | A/G |
| rs4501390 | 79508621 | + | G/T |
| rs4543321 | 79508705 | + | C/T |
| rs4604236 | 79508754 | + | A/C |
| rs36170201 | 79508906 | + | —/C |
| rs9448546 | 79509562 | + | C/T |
| rs6900430 | 79510134 | + | A/G |
| rs9448548 | 79510151 | + | A/G |
| rs35040883 | 79510284 | + | —/C |
| rs6905141 | 79510644 | + | A/G |
| rs7743640 | 79510794 | + | A/G |
| rs7744731 | 79511190 | + | C/G |
| rs9361425 | 79511397 | + | C/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs9352625 | 79511473 | + | A/G |
| rs10428859 | 79511532 | + | C/T |
| rs2180910 | 79511716 | + | G/T |
| rs13199483 | 79511789 | + | G/T |
| rs9352626 | 79511810 | + | C/T |
| rs9343798 | 79512001 | + | A/G |
| rs9352627 | 79512305 | + | C/T |
| rs12528134 | 79512322 | + | A/G |
| rs7382016 | 79512500 | + | A/T |
| rs7382311 | 79512662 | + | A/G |
| rs7383685 | 79512701 | + | C/T |
| rs35420186 | 79512878 | + | —/CAA |
| rs9448549 | 79512991 | + | A/G |
| rs9350771 | 79513107 | + | C/T |
| rs9350772 | 79513288 | + | A/C |
| rs9350773 | 79513424 | + | A/C |
| rs9359343 | 79513450 | + | A/G |
| rs2145686 | 79513681 | + | A/C |
| rs7759829 | 79513725 | + | C/G |
| rs7759687 | 79513734 | + | A/G |
| rs7760429 | 79513941 | + | A/G |
| rs7760193 | 79514040 | + | A/C |
| rs9352628 | 79514166 | + | G/T |
| rs9361426 | 79514269 | + | A/C |
| rs9448551 | 79514294 | + | C/T |
| rs1998252 | 79514720 | + | C/T |
| rs10943576 | 79514771 | + | G/T |
| rs34981854 | 79514975 | + | —/G |
| rs34769649 | 79515326 | + | —/T |
| rs7766517 | 79515467 | + | C/T |
| rs7766791 | 79515472 | + | A/G |
| rs10559249 | 79515694 | + | —/GTGT |
| rs5877628 | 79515693 | + | —/TG |
| rs3035376 | 79515718 | + | —/GT |
| rs1319575 | 79515770 | + | C/T |
| rs3918524 | 79515816 | + | A/G |
| rs1158575 | 79515925 | + | C/T |
| rs4706066 | 79516496 | + | C/T |
| rs2145687 | 79516920 | + | C/T |
| rs2145688 | 79516936 | + | C/T |
| rs34523548 | 79517003 | + | —/T |
| rs35884007 | 79517112 | + | —/G |
| rs35363076 | 79517166 | + | —/G |
| rs961680 | 79517338 | + | A/T |
| rs9359344 | 79517752 | + | A/G |
| rs4141594 | 79517914 | + | A/C |
| rs9443614 | 79517919 | + | A/G |
| rs9350774 | 79518322 | + | A/G |
| rs9294125 | 79518365 | + | A/T |
| rs35542025 | 79518386 | + | —/A |
| rs12528472 | 79518434 | + | C/G |
| rs1475046 | 79518520 | + | A/G |
| rs9294126 | 79518524 | + | A/C |
| rs9352629 | 79518599 | + | A/T |
| rs10943577 | 79518602 | + | C/G |
| rs9343800 | 79518691 | + | A/G |
| rs9352630 | 79518911 | + | C/T |
| rs9352631 | 79518916 | + | A/G |
| rs9352632 | 79518945 | + | C/G |
| rs9343801 | 79518994 | + | A/G |
| rs12196839 | 79519152 | + | A/G |
| rs9352633 | 79519342 | + | C/G |
| rs9352634 | 79519344 | + | A/G |
| rs4706722 | 79519416 | + | C/T |
| rs4706723 | 79519455 | + | C/G |
| rs35622574 | 79519529 | + | —/C |
| rs4706724 | 79519540 | + | A/G |
| rs9448553 | 79520364 | + | G/T |
| rs9350775 | 79520504 | + | A/G |
| rs9350776 | 79520564 | + | A/G |
| rs4590227 | 79520629 | + | A/G |
| rs7451373 | 79520890 | + | C/T |
| rs9350777 | 79520900 | + | A/C |
| rs9361427 | 79521580 | + | A/T |
| rs2321771 | 79522159 | + | C/T |
| rs6454077 | 79522624 | + | A/G |
| rs4706725 | 79523110 | + | A/G |
| rs4706726 | 79523256 | + | C/G |
| rs4706727 | 79523430 | + | C/T |
| rs4706728 | 79523530 | + | G/T |
| rs4706729 | 79524311 | + | G/T |
| rs4706730 | 79524622 | + | A/G |
| rs35493328 | 79524755 | + | —/A |
| rs9343804 | 79524771 | + | A/G |
| rs9343805 | 79524845 | + | G/T |
| rs4706731 | 79525017 | + | C/T |
| rs6916201 | 79525202 | + | C/T |
| rs4706732 | 79525233 | + | A/C |
| rs4706733 | 79525331 | + | C/T |
| rs4706734 | 79525369 | + | C/T |
| rs4706067 | 79525544 | + | A/G |
| rs4706735 | 79525556 | + | C/T |
| rs4706068 | 79525824 | + | C/T |
| rs7758474 | 79525893 | + | C/G |
| rs7758382 | 79526025 | + | C/T |
| rs7758411 | 79526113 | + | A/G |
| rs7758668 | 79526149 | + | C/G |
| rs7758709 | 79526220 | + | A/C |
| rs9343809 | 79526430 | + | A/G |
| rs9352638 | 79526528 | + | A/G |
| rs9352639 | 79526557 | + | A/G |
| rs9352640 | 79526632 | + | C/T |
| rs9359345 | 79526635 | + | A/C |
| rs9361430 | 79526795 | + | C/T |
| rs9361431 | 79526796 | + | A/G |
| rs12215488 | 79526895 | + | A/G |
| rs4277969 | 79527116 | + | C/T |
| rs9343810 | 79527190 | + | C/G |
| rs9343811 | 79527285 | + | C/T |
| rs36159791 | 79527300 | + | —/G |
| rs6939408 | 79527324 | + | A/G |
| rs9361432 | 79527332 | + | A/G |
| rs9352641 | 79527639 | + | A/G |
| rs9361433 | 79527970 | + | A/G |
| rs9352642 | 79528071 | + | A/C |
| rs4706069 | 79528287 | + | C/T |
| rs11751339 | 79528440 | + | A/C |
| rs4706070 | 79528478 | + | A/G |
| rs36193003 | 79528479 | + | AA/GG |
| rs4706071 | 79528479 | + | A/G |
| rs9359346 | 79528869 | + | A/G |
| rs7746103 | 79529063 | + | C/T |
| rs9352645 | 79529280 | + | C/G |
| rs7746449 | 79529347 | + | A/C |
| rs9352646 | 79529377 | + | A/G |
| rs4419638 | 79529395 | + | C/G |
| rs36146147 | 79529439 | + | —/G |
| rs9341748 | 79529663 | + | A/G |
| rs9343814 | 79529792 | + | C/G |
| rs9448558 | 79529987 | + | C/G |
| rs10943581 | 79530174 | + | C/T |
| rs28716526 | 79530437 | + | A/G |
| rs11752708 | 79530459 | + | G/T |
| rs11752686 | 79530498 | + | C/T |
| rs6899455 | 79530697 | + | C/T |
| rs34374962 | 79530898 | + | A/C |
| rs9448559 | 79531201 | + | A/G |
| rs6920807 | 79531450 | + | A/T |
| rs2135769 | 79532044 | + | A/G |
| rs4706736 | 79532195 | + | A/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs4706072 | 79532210 | + | A/G |
| rs1588086 | 79532606 | + | C/T |
| rs1588087 | 79532636 | + | A/T |
| rs2321772 | 79532909 | + | G/T |
| rs9443616 | 79532925 | + | A/G |
| rs2321773 | 79532962 | + | A/G |
| rs2321774 | 79533169 | + | C/T |
| rs9443617 | 79533254 | + | A/G |
| rs34749198 | 79533559 | + | —/T |
| rs1073211 | 79533575 | − | C/T |
| rs28845538 | 79533674 | + | C/T |
| rs2135770 | 79533747 | + | A/C |
| rs9341750 | 79534203 | + | C/T |
| rs6938951 | 79534339 | + | A/C |
| rs6939263 | 79534367 | + | C/T |
| rs9359348 | 79534401 | + | A/T |
| rs6900794 | 79534563 | + | C/T |
| rs34763883 | 79534693 | + | —/A |
| rs6901015 | 79534742 | + | C/T |
| rs6924048 | 79534918 | + | C/T |
| rs36084053 | 79535093 | + | —/C |
| rs10943583 | 79535183 | + | C/G |
| rs35165607 | 79535238 | + | —/C |
| rs34534036 | 79535250 | + | —/C |
| rs11755934 | 79535340 | + | C/T |
| rs2321775 | 79535509 | + | C/T |
| rs9359350 | 79535870 | + | C/G |
| rs9361437 | 79536054 | + | C/T |
| rs9361438 | 79536280 | + | C/T |
| rs9352648 | 79536460 | + | A/G |
| rs9341751 | 79536555 | + | C/T |
| rs9448560 | 79536601 | + | A/G |
| rs9448561 | 79536715 | + | A/G |
| rs9343820 | 79537177 | + | A/T |
| rs11965322 | 79537414 | + | A/T |
| rs36082173 | 79537823 | + | —/T |
| rs6923812 | 79538338 | + | C/T |
| rs9350781 | 79538534 | + | A/T |
| rs1876389 | 79538651 | + | A/T |
| rs35000167 | 79538888 | + | —/T |
| rs11961822 | 79539174 | + | A/G |
| rs35722542 | 79539754 | + | —/A |
| rs12663824 | 79539849 | + | A/C |
| rs1021987 | 79539884 | + | C/G |
| rs1507151 | 79539965 | + | C/T |
| rs1507152 | 79540193 | + | C/T |
| rs1567169 | 79540652 | + | C/T |
| rs1507153 | 79541105 | + | A/C |
| rs35498910 | 79541112 | + | —/T |
| rs9448562 | 79541799 | + | G/T |
| rs1876390 | 79542282 | + | C/T |
| rs9448563 | 79543216 | + | A/G |
| rs9448564 | 79543231 | + | C/T |
| rs9448565 | 79543237 | + | C/T |
| rs16890304 | 79543377 | + | A/G |
| rs1876391 | 79543470 | + | C/T |
| rs6454082 | 79544001 | + | C/T |
| rs4555886 | 79544101 | + | A/T |
| rs34032635 | 79544308 | + | —/T |
| rs34806029 | 79544385 | + | —/G |
| rs11758151 | 79544940 | + | C/T |
| rs11758164 | 79544958 | + | G/T |
| rs6928279 | 79545677 | + | C/T |
| rs9361440 | 79546395 | + | A/C |
| rs9352649 | 79546502 | + | G/T |
| rs34850892 | 79547499 | + | —/C |
| rs9361441 | 79547685 | + | A/G |
| rs35665788 | 79547866 | + | —/T |
| rs35275890 | 79549004 | + | —/A |
| rs35562053 | 79549016 | + | A/T |
| rs6935486 | 79549211 | + | A/G |
| rs9359351 | 79549252 | + | A/G |
| rs11755568 | 79550337 | + | C/T |
| rs34268443 | 79550347 | + | —/C |
| rs6942344 | 79550522 | + | C/T |
| rs2321893 | 79550527 | + | C/T |
| rs9352650 | 79550613 | + | A/G |
| rs11751437 | 79550636 | + | A/G |
| rs9361442 | 79550764 | + | A/G |
| rs6904016 | 79550772 | + | C/T |
| rs4055608 | 79550977 | + | C/T |
| rs9350782 | 79551187 | + | A/G |
| rs9352652 | 79551451 | + | A/G |
| rs10806148 | 79551623 | + | A/G |
| rs34335705 | 79552378 | + | C/T |
| rs12181706 | 79552458 | + | C/G |
| rs9361443 | 79552769 | + | A/C |
| rs2874642 | 79552903 | + | A/G |
| rs12176501 | 79553029 | + | C/T |
| rs9343822 | 79553040 | + | A/T |
| rs7773850 | 79553042 | + | A/T |
| rs7773851 | 79553044 | + | A/T |
| rs11757519 | 79553160 | + | C/T |
| rs35940795 | 79553244 | + | —/C |
| rs35004706 | 79553408 | + | —/C |
| rs9352653 | 79553582 | + | A/G |
| rs9343823 | 79553825 | + | A/C |
| rs9343824 | 79554288 | + | A/G |
| rs35245361 | 79554378 | + | —/A/T |
| rs1507155 | 79554584 | + | A/G |
| rs2021541 | 79554588 | + | A/G |
| rs13210672 | 79554590 | + | A/G |
| rs9343826 | 79554632 | + | A/G |
| rs1507156 | 79554776 | + | A/G |
| rs34136836 | 79555385 | + | —/G |
| rs34958301 | 79556015 | + | —/G |
| rs9361444 | 79556792 | + | C/T |
| rs1507149 | 79556805 | − | C/G |
| rs9352654 | 79557000 | + | A/G |
| rs9343827 | 79557755 | + | A/G |
| rs9359352 | 79558729 | + | C/T |
| rs7757382 | 79558996 | + | C/G |
| rs10943585 | 79559128 | + | C/G |
| rs9361445 | 79559275 | + | C/T |
| rs5877629 | 79559295 | + | —/T |
| rs1827992 | 79559524 | − | A/G |
| rs7762022 | 79559578 | + | A/C |
| rs6926463 | 79559890 | + | A/G |
| rs6454083 | 79560137 | + | C/T |
| rs9352655 | 79560142 | + | A/T |
| rs1507154 | 79560419 | + | C/T |
| rs1476304 | 79560439 | + | C/T |
| rs1476305 | 79560605 | + | G/T |
| rs4628052 | 79560919 | + | A/G |
| rs13200035 | 79561004 | + | C/T |
| rs13214259 | 79561046 | + | A/C |
| rs13200136 | 79561064 | + | C/T |
| rs13214670 | 79561072 | + | A/G |
| rs13214372 | 79561084 | + | A/G |
| rs13200153 | 79561107 | + | C/T |
| rs13214383 | 79561121 | + | A/G |
| rs28781665 | 79561419 | + | A/G |
| rs1848194 | 79562087 | + | C/T |
| rs35374025 | 79562246 | + | —/T |
| rs1911513 | 79562355 | + | A/G |
| rs9448568 | 79562434 | + | A/G |
| rs7774691 | 79562517 | + | C/G |
| rs9352657 | 79562804 | + | C/G |
| rs7741245 | 79563215 | + | A/G |
| rs7741407 | 79563307 | + | A/G |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs7761613 | 79563435 | + | C/T |
| rs35613790 | 79563516 | + | —/A |
| rs6454084 | 79563604 | + | A/G |
| rs4446522 | 79564225 | + | A/T |
| rs6931419 | 79564240 | + | A/T |
| rs4334937 | 79564258 | + | C/T |
| rs12527806 | 79564386 | + | A/T |
| rs3967330 | 79564533 | + | A/C |
| rs9448572 | 79565438 | + | G/T |
| rs10943587 | 79565451 | + | C/T |
| rs9443619 | 79565631 | + | C/T |
| rs7756996 | 79566086 | + | A/C |
| rs11753266 | 79566107 | + | C/T |
| rs1857957 | 79566184 | − | C/G |
| rs28759673 | 79566270 | + | G/T |
| rs2321896 | 79566463 | + | C/G |
| rs41503746 | 79566463 | − | C/G |
| rs35414898 | 79566540 | + | —/A |
| rs34037147 | 79566911 | + | —/C |
| rs10943588 | 79567713 | + | A/C |
| rs11751036 | 79567797 | + | C/T |
| rs2202662 | 79568057 | − | G/T |
| rs2202661 | 79568299 | − | A/G |
| rs2202660 | 79568463 | − | G/T |
| rs9448573 | 79569097 | + | C/T |
| rs6913028 | 79570309 | + | C/T |
| rs6454085 | 79570611 | + | C/G |
| rs4706737 | 79570764 | + | A/G |
| rs35196425 | 79570832 | + | —/T |
| rs4706075 | 79570837 | + | C/G |
| rs4706076 | 79570871 | + | C/CA/T/TG |
| rs4706738 | 79570870 | + | A/G |
| rs2202659 | 79571328 | − | A/G |
| rs12662944 | 79571375 | + | A/T |
| rs9350784 | 79572125 | + | C/T |
| rs9350785 | 79572304 | + | C/T |
| rs9448574 | 79573020 | + | A/C |
| rs9448575 | 79573525 | + | G/T |
| rs1814219 | 79573704 | − | G/T |
| rs13216900 | 79573706 | + | A/G |
| rs34791687 | 79573717 | + | —/G |
| rs9350786 | 79574025 | + | G/T |
| rs35713298 | 79574030 | + | —/GGG |
| rs13217367 | 79574256 | + | A/T |
| rs9343834 | 79574390 | + | A/G |
| rs12203336 | 79575034 | + | G/T |
| rs35790661 | 79575375 | + | —/CA |
| rs2202658 | 79576388 | − | C/T |
| rs906320 | 79576561 | − | A/G |
| rs41269335 | 79576661 | + | G/T |
| rs34943334 | 79576824 | + | A/G |
| rs906319 | 79577408 | − | C/T |
| rs41269337 | 79577988 | + | A/G |
| rs6454086 | 79578882 | + | C/T |
| rs9361448 | 79579645 | + | G/T |
| rs9352659 | 79580583 | + | A/G |
| rs9448576 | 79580987 | + | C/G |
| rs2202663 | 79581585 | + | C/T |
| rs1395655 | 79581612 | + | C/T |
| rs7773491 | 79582941 | + | C/T |
| rs4640849 | 79583469 | + | A/G |
| rs35044999 | 79584659 | + | —/C |
| rs12524858 | 79586232 | + | G/T |
| rs2202664 | 79586366 | + | C/G |
| rs9448577 | 79586917 | + | C/G |
| rs28814638 | 79587149 | + | A/G |
| rs34428579 | 79587468 | + | —/A |
| rs12209635 | 79588934 | + | C/T |
| rs955765 | 79589329 | − | A/G |
| rs5877630 | 79589377 | + | —/G |
| rs9448578 | 79589928 | + | G/T |
| rs4706739 | 79590001 | + | C/T |
| rs12213359 | 79590746 | + | A/C |
| rs10556588 | 79592115 | + | —/AGAA |
| rs12195716 | 79592131 | + | C/T |
| rs6902294 | 79593001 | + | G/T |
| rs1567168 | 79593174 | + | A/C |
| rs2174740 | 79593284 | + | A/G |
| rs2135767 | 79593386 | + | C/T |
| rs6454088 | 79594398 | + | C/T |
| rs12194457 | 79595224 | + | A/G |
| rs35356883 | 79595302 | + | —/G |
| rs12194642 | 79595510 | + | A/G |
| rs9343838 | 79595869 | + | A/G |
| rs10639111 | 79596351 | + | —/GAGA |
| rs34962848 | 79596352 | + | —/GAGA |
| rs34665735 | 79596358 | + | —/AGAG |
| rs35366557 | 79596414 | + | —/G |
| rs16890324 | 79596828 | + | A/G |
| rs13217987 | 79597357 | + | A/G |
| rs1963638 | 79597835 | + | G/T |
| rs2013420 | 79597934 | + | A/G |
| rs16890325 | 79597947 | + | C/T |
| rs9352662 | 79598210 | + | A/G |
| rs28626679 | 79598705 | + | C/G |
| rs35393092 | 79598862 | + | —/T |
| rs16890326 | 79599251 | + | C/T |
| rs34305313 | 79600125 | + | —/A |
| rs33920803 | 79600126 | + | —/A |
| rs12110531 | 79600198 | + | C/G |
| rs6912683 | 79600211 | + | A/C |
| rs16890328 | 79600713 | + | A/C |
| rs7754715 | 79600777 | + | A/G |
| rs34253750 | 79601120 | + | —/G |
| rs13208855 | 79602240 | + | G/T |
| rs16890330 | 79602923 | + | A/C |
| rs1021986 | 79603853 | + | C/G |
| rs35242601 | 79604056 | + | —/T |
| rs13220688 | 79604565 | + | C/T |
| rs16890331 | 79605080 | + | C/T |
| rs1507150 | 79605316 | + | A/T |
| rs4706077 | 79605564 | + | A/G |
| rs10806150 | 79605891 | + | A/G |
| rs12664947 | 79606191 | + | A/T |
| rs1542977 | 79607026 | + | G/T |
| rs35949145 | 79607341 | + | —/A |
| rs2174741 | 79607599 | + | A/C |
| rs34567509 | 79608189 | + | —/C |
| rs9448579 | 79608431 | + | C/T |
| rs9448580 | 79608531 | + | C/G |
| rs1027813 | 79608837 | − | A/C |
| rs35909912 | 79609084 | + | C/T |
| rs34385822 | 79609087 | + | C/T |
| rs35544399 | 79609089 | + | C/T |
| rs34033174 | 79609112 | + | C/T |
| rs5877631 | 79609384 | + | —/T |
| rs35937908 | 79609385 | + | —/T |
| rs34696113 | 79609390 | + | —/T |
| rs33954612 | 79609391 | + | —/T |
| rs12664403 | 79610047 | + | G/T |
| rs2135766 | 79610075 | − | A/G |
| rs9448581 | 79610097 | + | A/G |
| rs35179848 | 79610136 | + | A/C |
| rs11332279 | 79610357 | + | —/A |
| rs1567167 | 79610546 | − | A/G |
| rs4415132 | 79610826 | + | C/T |
| rs6926537 | 79610912 | + | A/T |
| rs17741785 | 79610991 | + | A/G |
| rs1507148 | 79611110 | − | C/T |
| rs4409146 | 79611326 | + | C/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs34490997 | 79611333 | + | —/G |
| rs9361451 | 79611774 | + | C/T |
| rs16890334 | 79612885 | + | C/T |
| rs12196485 | 79613590 | + | A/G |
| rs4147183 | 79613765 | + | C/G |
| rs36024489 | 79614221 | + | G/T |
| rs9352663 | 79614883 | + | C/T |
| rs35934464 | 79615331 | + | —/C |
| rs971994 | 79616321 | − | C/G |
| rs7454053 | 79616439 | + | A/G |
| rs10223389 | 79616629 | + | A/G |
| rs12214796 | 79617787 | + | C/T |
| rs17798356 | 79618153 | + | A/G |
| rs12190108 | 79619374 | + | C/T |
| rs4421161 | 79620938 | + | A/G |
| rs12213652 | 79621099 | + | A/G |
| rs2321894 | 79621148 | + | A/G |
| rs9448583 | 79621405 | + | A/G |
| rs9361454 | 79621963 | + | —/G/T |
| rs12176511 | 79622440 | + | A/G |
| rs34132605 | 79622874 | + | —/G |
| rs9352664 | 79622881 | + | G/T |
| rs10455354 | 79622949 | + | A/G |
| rs2874643 | 79623036 | + | A/G |
| rs1960542 | 79623362 | + | C/T |
| rs9352665 | 79624438 | + | C/G |
| rs9361455 | 79624601 | + | A/G |
| rs34916187 | 79624764 | + | —/G |
| rs12661039 | 79625256 | + | C/T |
| rs4682456 | 79625580 | − | C/T |
| rs7449459 | 79625728 | + | C/T |
| rs6936109 | 79626595 | + | A/G |
| rs12201183 | 79626839 | + | A/G |
| rs6937465 | 79627064 | + | G/T |
| rs9361458 | 79627515 | + | C/T |
| rs11381253 | 79627547 | + | —/A |
| rs34502239 | 79627557 | + | —/A |
| rs9765849 | 79627608 | + | A/G |
| rs9352666 | 79628903 | + | C/G |
| rs9352667 | 79629015 | + | C/T |
| rs9352668 | 79629397 | + | A/G |
| rs9448584 | 79629518 | + | G/T |
| rs9448585 | 79629560 | + | A/G |
| rs9361459 | 79629641 | + | A/G |
| rs9343841 | 79630723 | + | C/G |
| rs6923327 | 79631594 | + | A/G |
| rs10943595 | 79632010 | + | C/G |
| rs34199187 | 79632011 | + | CC/GT |
| rs10943596 | 79632011 | + | C/T |
| rs34658311 | 79632386 | + | A/T |
| rs11444087 | 79632386 | + | —/T |
| rs7760883 | 79632388 | + | —/A/T |
| rs35635397 | 79632389 | + | —/A |
| rs16890347 | 79632927 | + | C/T |
| rs9443621 | 79633218 | + | A/G |
| rs41269339 | 79634131 | + | C/G |
| rs9350789 | 79634363 | + | A/C |
| rs9341753 | 79634515 | + | C/T |
| rs12153837 | 79635921 | + | A/C |
| rs12527589 | 79636178 | + | C/T |
| rs10455355 | 79636221 | + | C/T |
| rs34431699 | 79637008 | + | —/C |
| rs6941317 | 79637771 | + | A/C |
| rs7738062 | 79638242 | + | C/G |
| rs4706740 | 79639381 | + | A/C |
| rs34204884 | 79639456 | + | C/T |
| rs9443622 | 79639509 | + | C/T |
| rs4706078 | 79639525 | + | C/T |
| rs35373380 | 79639573 | + | C/T |
| rs12193104 | 79639633 | + | A/G |
| rs12660767 | 79639652 | + | C/T |
| rs35962544 | 79639717 | + | —/AA |
| rs12193319 | 79640156 | + | A/C |
| rs6454089 | 79640821 | + | C/T |
| rs9352669 | 79640860 | + | G/T |
| rs9352670 | 79641152 | + | A/G |
| rs9341754 | 79641692 | + | A/C |
| rs34538995 | 79641946 | + | —/GAAA |
| rs9448586 | 79642219 | + | A/G |
| rs34409101 | 79642323 | + | —/T |
| rs9343843 | 79642344 | + | C/T |
| rs35304712 | 79643086 | + | C/T |
| rs9343844 | 79643182 | + | A/T |
| rs9350792 | 79643892 | + | A/G |
| rs35439908 | 79645611 | + | —/G |
| rs9448587 | 79645751 | + | A/G |
| rs9341755 | 79645767 | + | C/G |
| rs9361460 | 79646186 | + | C/G |
| rs9448588 | 79646780 | + | G/T |
| rs9359354 | 79647104 | + | A/G |
| rs35560175 | 79647373 | + | —/A |
| rs34453824 | 79647874 | + | —/C |
| rs2174743 | 79648524 | − | C/T |
| rs2135772 | 79648767 | − | A/C |
| rs1021988 | 79649380 | − | A/G |
| rs35897423 | 79650428 | + | —/C |
| rs9352671 | 79651798 | + | A/C |
| rs6908105 | 79651816 | + | A/G |
| rs4055605 | 79651890 | + | —/TCTTA |
| rs35817888 | 79651891 | + | —/TCTTA |
| rs35754813 | 79652867 | + | —/A |
| rs2321895 | 79654080 | + | C/T |
| rs35355117 | 79654223 | + | —/C |
| rs9352672 | 79654253 | + | C/T |
| rs34228023 | 79654468 | + | —/A |
| rs35503114 | 79654971 | + | —/T |
| rs34717008 | 79655526 | + | C/T |
| rs36108843 | 79655546 | + | —/C |
| rs34900932 | 79655547 | + | —/T |
| rs34933654 | 79655550 | + | C/T |
| rs34963207 | 79656023 | + | —/A |
| rs9361462 | 79656183 | + | A/G |
| rs35606311 | 79656863 | + | —/A |
| rs12192086 | 79657229 | + | A/G |
| rs9448589 | 79657767 | + | G/T |
| rs9352673 | 79659462 | + | G/T |
| rs9359355 | 79659533 | + | A/G |
| rs9343845 | 79659752 | + | A/G |
| rs36114710 | 79659754 | + | A/G |
| rs9352674 | 79660060 | + | G/T |
| rs35774009 | 79662784 | + | —/A |
| rs36087293 | 79663083 | + | —/G |
| rs9448590 | 79663148 | + | C/G |
| rs9448591 | 79663209 | + | C/T |
| rs36004777 | 79663275 | + | —/A |
| rs4327648 | 79663334 | + | C/T |
| rs10525714 | 79664847 | + | —/ATATAT ATATATA TATATAT AT |
| rs35395481 | 79664848 | + | —/ATATAT ATATATA TATATAT AT |
| rs34482864 | 79664856 | + | —/AT |
| rs10700674 | 79664871 | + | —/AT |
| rs7776322 | 79666464 | + | A/T |
| rs2174742 | 79666820 | + | G/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs2135771 | 79667075 | + | C/T |
| rs6941107 | 79667642 | + | A/G |
| rs10943600 | 79668224 | + | A/G |
| rs9343846 | 79668848 | + | A/T |
| rs35533616 | 79669465 | + | —/A |
| rs9352675 | 79669519 | + | A/G |
| rs1354831 | 79670295 | + | C/T |
| rs1354832 | 79670482 | + | C/T |
| rs35112046 | 79671111 | + | —/C |
| rs9443623 | 79671372 | + | C/T |
| rs4706079 | 79671927 | + | A/G |
| rs4706742 | 79672269 | + | C/T |
| rs4706743 | 79672512 | + | G/T |
| rs2174744 | 79673008 | + | A/T |
| rs9448592 | 79673037 | + | C/G |
| rs35935416 | 79673657 | + | —/T |
| rs6915030 | 79674241 | + | C/T |
| rs9361466 | 79675071 | + | C/T |
| rs10806151 | 79676098 | + | C/T |
| rs11402304 | 79676284 | + | —/T |
| rs7756858 | 79676687 | + | A/G |
| rs9443624 | 79676995 | + | A/G |
| rs6921318 | 79677095 | + | A/G |
| rs7758407 | 79677426 | + | C/G |
| rs34373655 | 79677787 | + | —/T |
| rs9361467 | 79677817 | + | A/G |
| rs9343848 | 79677820 | + | C/T |
| rs9361468 | 79677933 | + | A/G |
| rs9448594 | 79679933 | + | A/T |
| rs9448595 | 79680349 | + | A/G |
| rs1963080 | 79681257 | + | A/G |
| rs5877633 | 79681440 | + | —/G |
| rs35590303 | 79682202 | + | —/C |
| rs2063124 | 79683041 | + | C/T |
| rs7756648 | 79683805 | + | A/T |
| rs35313944 | 79684092 | + | —/A |
| rs9343849 | 79684179 | + | A/G |
| rs12196457 | 79684462 | + | A/T |
| rs7767182 | 79685667 | + | A/C |
| rs35777909 | 79685724 | + | —/G |
| rs36012949 | 79685747 | + | —/C |
| rs9448596 | 79686148 | + | C/T |
| rs9443626 | 79686283 | + | C/G |
| rs9352676 | 79686718 | + | A/G |
| rs7750836 | 79688302 | + | C/G |
| rs9350794 | 79688561 | + | C/T |
| rs7755754 | 79689008 | + | A/G |
| rs36181347 | 79689691 | + | —/A |
| rs7760866 | 79689848 | + | C/G |
| rs9361472 | 79690160 | + | G/T |
| rs36132801 | 79690225 | + | —/G |
| rs9448597 | 79690306 | + | C/T |
| rs9689724 | 79690631 | + | A/G |
| rs9343851 | 79690827 | + | C/G |
| rs34433262 | 79690888 | + | —/C |
| rs9688928 | 79691098 | + | A/C |
| rs28826982 | 79691188 | + | A/G |
| rs34236947 | 79691189 | + | AC/GG |
| rs28811946 | 79691189 | + | C/G |
| rs9359358 | 79692407 | + | C/T |
| rs2089416 | 79692807 | + | G/T |
| rs34521933 | 79693343 | + | —/C |
| rs2135768 | 79693482 | + | C/T |
| rs7744604 | 79694234 | + | A/C |
| rs10755377 | 79694644 | + | C/T |
| rs5877634 | 79696377 | + | —/T |
| rs11430514 | 79697407 | + | —/T |
| rs35387172 | 79697408 | + | —/T |
| rs9350795 | 79697410 | + | A/T |
| rs12665761 | 79697747 | + | C/T |
| rs13205569 | 79697785 | + | G/T |
| rs2321897 | 79698887 | + | C/T |
| rs1911512 | 79699043 | + | C/T |
| rs9343853 | 79699300 | + | C/T |
| rs12660760 | 79699828 | + | C/T |
| rs12660770 | 79699923 | + | C/T |
| rs35416532 | 79700122 | + | —/TTT |
| rs9343854 | 79700770 | + | A/C |
| rs1044313 | 79702339 | − | A/T |
| rs35580162 | 79703022 | + | —/C |
| rs35881759 | 79703274 | + | —/C |
| rs35125759 | 79703290 | + | —/C |
| rs1044309 | 79703294 | − | C/T |
| rs34261531 | 79703338 | + | —/C |
| rs5877635 | 79704127 | + | —/T |
| rs35000895 | 79704129 | + | —/T |
| rs44464748 | 79704697 | + | C/G |
| rs10654924 | 79706512 | + | —/AA |
| rs34701016 | 79706513 | + | —/AA |
| rs13191571 | 79706985 | + | G/T |
| rs36155238 | 79706984 | + | —/T |
| rs36160851 | 79706985 | + | —/T |
| rs36170973 | 79706986 | + | —/T |
| rs36132527 | 79707051 | + | —/G |
| rs11547229 | 79707066 | + | A/G |
| rs6900790 | 79707081 | + | C/T |
| rs34609668 | 79707212 | + | G/T |
| rs2485701 | 79707264 | + | A/G |
| rs1876387 | 79707310 | + | A/G |
| rs1876388 | 79707370 | + | G/T |
| rs34463462 | 79707429 | + | G/T |
| rs10574664 | 79707958 | + | —/AC |
| rs28606484 | 79709319 | + | C/T |
| rs9350796 | 79710116 | + | C/T |
| rs6454090 | 79710425 | + | —/A/AA/AA A/T/TT |
| rs6454091 | 79710426 | + | A/T |
| rs35306286 | 79710425 | + | —/AAA |
| rs11370303 | 79710434 | + | —/A |
| rs11432700 | 79710436 | + | —/A |
| rs11447037 | 79710449 | + | —/A |
| rs9443629 | 79710479 | + | A/C |
| rs34717491 | 79710843 | + | —/C |
| rs7740307 | 79710873 | + | A/T |
| rs9688399 | 79711374 | + | A/G |
| rs5877636 | 79711409 | + | —/A |
| rs33977407 | 79711410 | + | —/A |
| rs10943605 | 79712196 | + | A/G |
| rs1135076 | 79712453 | − | A/G |
| rs1056960 | 79712497 | − | C/T |
| rs34050775 | 79713035 | + | —/A |
| rs36048894 | 79713183 | − | A/C |
| rs1056959 | 79713195 | − | A/G |
| rs1056958 | 79713223 | − | C/T |
| rs2275291 | 79713281 | − | A/T |
| rs2275290 | 79713289 | − | C/T |
| rs9361473 | 79713761 | + | C/T |
| rs1984195 | 79714110 | − | C/T |
| rs11370597 | 79714395 | + | —/C |
| rs1283320 | 79714834 | + | C/G |
| rs35766012 | 79714947 | + | —/T |
| rs35205946 | 79715066 | + | —/G |
| rs4706745 | 79715247 | + | C/T |
| rs2063123 | 79715254 | + | C/T |
| rs12529691 | 79715751 | + | A/G |
| rs2174739 | 79715889 | + | A/G |
| rs9343855 | 79716132 | + | G/T |
| rs34526870 | 79716648 | + | —/C |
| rs35018864 | 79717062 | + | —/C |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs2050661 | 79717844 | − | A/G |
| rs28623652 | 79718361 | + | C/T |
| rs9443630 | 79718517 | + | G/T |
| rs10943606 | 79718496 | + | G/T |
| rs9448600 | 79719788 | + | A/C |
| rs9443631 | 79720837 | + | C/T |
| rs9443632 | 79721159 | + | C/T |
| rs10455356 | 79721467 | + | C/T |
| rs7753358 | 79721929 | + | A/T |
| rs11316583 | 79723594 | + | —/T |
| rs5877637 | 79724015 | + | —/A |
| rs35159735 | 79724505 | + | —/C |
| rs34936739 | 79725919 | + | —/C |
| rs35865427 | 79726072 | + | —/C |
| rs12665739 | 79727563 | + | C/T |
| rs6940635 | 79727692 | + | C/T |
| rs946022 | 79728852 | + | G/T |
| rs3805746 | 79729157 | + | C/T |
| rs3805747 | 79729241 | + | A/G |
| rs34841569 | 79729665 | − | A/C |
| rs4706746 | 79730895 | + | A/G |
| rs13202531 | 79730981 | + | C/T |
| rs35504170 | 79731083 | + | —/C |
| rs10943608 | 79731648 | + | C/T |
| rs3834844 | 79731991 | + | —/CTT |
| rs3763160 | 79731994 | + | A/G |
| rs9350797 | 79732420 | + | A/G |
| rs11964204 | 79732781 | + | A/G |
| rs10943609 | 79733047 | + | A/T |
| rs1572586 | 79733060 | + | C/T |
| rs1538234 | 79733298 | + | C/T |
| rs3834845 | 79733766 | + | —/C |
| rs34920411 | 79734822 | + | —/C |
| rs9343856 | 79734930 | + | A/G |
| rs10531246 | 79735174 | + | —/TAAT |
| rs34584316 | 79736188 | + | —/T |
| rs12663267 | 79736218 | + | C/G |
| rs7742746 | 79736246 | + | G/T |
| rs7742874 | 79736287 | + | A/G |
| rs7742431 | 79736296 | + | A/G |
| rs34480532 | 79736437 | + | —/A |
| rs7768255 | 79736633 | + | A/G |
| rs7768001 | 79736672 | + | A/C |
| rs7768414 | 79736727 | + | C/G |
| rs9443633 | 79736782 | + | C/T |
| rs9448601 | 79738088 | + | C/T |
| rs9448602 | 79738107 | + | A/G |
| rs4406190 | 79738370 | + | A/G |
| rs10806154 | 79739086 | + | C/T |
| rs12190940 | 79739190 | + | A/G |
| rs7741943 | 79739286 | + | A/G |
| rs9448603 | 79739333 | + | A/G |
| rs36146106 | 79739418 | + | —/A |
| rs9352679 | 79739848 | + | A/G |
| rs9341756 | 79739909 | + | C/T |
| rs9350798 | 79739980 | + | A/C |
| rs9341757 | 79739993 | + | G/T |
| rs7766920 | 79740022 | + | C/T |
| rs7746653 | 79740031 | + | C/G |
| rs7751287 | 79740610 | + | A/G |
| rs36166556 | 79740631 | + | —/T |
| rs36128361 | 79741059 | + | C/G |
| rs10943610 | 79741136 | + | A/G |
| rs9352681 | 79741292 | + | A/G |
| rs9343857 | 79741450 | + | C/G |
| rs9343858 | 79741488 | + | C/T |
| rs12182951 | 79742891 | + | A/G |
| rs12182952 | 79742924 | + | A/C |
| rs9448604 | 79743377 | + | A/G |
| rs9448605 | 79743416 | + | G/T |
| rs36149780 | 79743416 | + | G/T |
| rs4594915 | 79743583 | + | A/C |
| rs11282710 | 79744026 | + | —/TTCAAGCACC |
| rs36124591 | 79744030 | + | —/AAGCACCTTC |
| rs34344828 | 79744037 | + | —/TTCAAGCAC |
| rs7750810 | 79744283 | + | A/T |
| rs12209235 | 79745085 | + | C/T |
| rs34362578 | 79745461 | + | —/G |
| rs4624830 | 79745780 | + | A/T |
| rs1538235 | 79746169 | + | C/T |
| rs1572584 | 79747009 | + | A/G |
| rs34246619 | 79747058 | + | —/A |
| rs1572585 | 79747295 | + | C/T |
| rs10943611 | 79747894 | + | A/G |
| rs9343859 | 79749118 | + | A/C |
| rs11547228 | 79749470 | − | C/T |
| rs10642979 | 79750856 | + | —/GT |
| rs35922935 | 79750857 | + | —/GT |
| rs35769552 | 79751527 | + | —/G |
| rs1890229 | 79751748 | + | C/T |
| rs1890230 | 79752043 | + | A/G |
| rs9352682 | 79752074 | + | C/T |
| rs35730468 | 79753387 | + | —/AAT |
| rs4623209 | 79753656 | + | G/T |
| rs35399714 | 79753801 | + | —/T |
| rs12529043 | 79754574 | + | A/G |
| rs10943612 | 79755099 | + | C/T |
| rs35529955 | 79755508 | + | —/T |
| rs4144107 | 79755536 | + | —/A/C |
| rs34495466 | 79755537 | + | —/A |
| rs3902856 | 79756556 | + | C/T |
| rs1415862 | 79756757 | + | A/G |
| rs1415863 | 79756878 | + | A/G |
| rs3818839 | 79757044 | + | C/G |
| rs34665480 | 79757153 | + | A/C |
| rs35828088 | 79757480 | + | —/A |
| rs9359359 | 79757699 | + | C/T |
| rs3841156 | 79757786 | − | —/AGA |
| rs3841155 | 79757996 | − | —/TCT |
| rs7749615 | 79758494 | + | G/T |
| rs6454092 | 79758691 | + | A/G |
| rs12208915 | 79759454 | + | A/G |
| rs9359360 | 79759515 | + | C/T |
| rs9359361 | 79762302 | + | C/G |
| rs35279139 | 79762390 | + | —/T |
| rs6940637 | 79762564 | + | C/T |
| rs6904138 | 79762733 | + | A/G |
| rs35057263 | 79763873 | − | C/T |
| rs41269341 | 79764094 | + | C/T |
| rs11752126 | 79764642 | + | C/T |
| rs7747479 | 79764719 | + | A/C |
| rs36000864 | 79767181 | + | A/G |
| rs9443636 | 79767375 | + | C/T |
| rs9361477 | 79767525 | + | C/T |
| rs13218407 | 79767680 | + | A/C |
| rs13218727 | 79767681 | + | A/G |
| rs9361478 | 79768691 | + | A/G |
| rs34042644 | 79769661 | + | G/T |
| rs2065986 | 79769884 | + | C/T |
| rs9443637 | 79771427 | + | C/T |
| rs13191068 | 79771586 | + | C/T |
| rs11965967 | 79771803 | + | C/T |
| rs9448607 | 79772339 | + | A/G |
| rs6907674 | 79773483 | + | A/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs35415106 | 79774112 | + | —/TTT |
| rs9352683 | 79775514 | + | G/T |
| rs34509958 | 79776185 | + | —/G |
| rs9443638 | 79777586 | + | A/T |
| rs9448608 | 79777881 | + | C/T |
| rs1933238 | 79778128 | + | A/C |
| rs11754374 | 79778672 | + | G/T |
| rs7766491 | 79778959 | + | C/T |
| rs4706747 | 79779358 | + | A/G |
| rs4706748 | 79779391 | + | A/G |
| rs4637600 | 79780227 | + | A/T |
| rs9350799 | 79780370 | + | A/C |
| rs9361479 | 79780474 | + | A/T |
| rs35887627 | 79780475 | + | AC/TT |
| rs9359362 | 79780475 | + | C/T |
| rs9361480 | 79781148 | + | A/G |
| rs34015061 | 79781739 | + | —/T |
| rs9361481 | 79783469 | + | A/T |
| rs36092348 | 79784000 | − | A/G |
| rs1338023 | 79785047 | + | G/T |
| rs9350800 | 79786208 | + | A/C |
| rs11754419 | 79786367 | + | A/G |
| rs9718121 | 79786606 | + | A/T |
| rs35727754 | 79786754 | + | —/A |
| rs1832396 | 79787561 | − | C/G |
| rs34244224 | 79787746 | + | A/C |
| rs34815601 | 79788716 | + | —/A |
| rs11315927 | 79789321 | + | —/T |
| rs9352685 | 79790968 | + | C/T |
| rs2050659 | 79791088 | + | A/C |
| rs2050660 | 79791445 | + | C/T |
| rs35999901 | 79791481 | + | —/G |
| rs28449859 | 79791564 | + | C/T |
| rs34111968 | 79791750 | + | —/A |
| rs9443639 | 79791873 | + | C/T |
| rs7775074 | 79792805 | + | C/G |
| rs34655287 | 79792904 | + | —/A |
| rs11326550 | 79792916 | + | —/A |
| rs7742034 | 79793825 | + | A/G |
| rs28532298 | 79795101 | + | C/T |
| rs35744497 | 79795678 | + | C/T |
| rs9448609 | 79795708 | + | A/G |
| rs3929865 | 79795727 | + | C/T |
| rs9343860 | 79795729 | + | A/G |
| rs3929866 | 79795824 | + | A/G |
| rs13218541 | 79795927 | + | C/T |
| rs3929867 | 79796069 | + | A/G |
| rs9448610 | 79796341 | + | A/G |
| rs6918296 | 79797639 | + | C/T |
| rs4565265 | 79798677 | + | A/G |
| rs2095724 | 79798820 | + | C/T |
| rs7741282 | 79799097 | + | A/G |
| rs35793703 | 79799130 | + | —/G |
| rs2105143 | 79799666 | + | A/G |
| rs1538233 | 79800454 | + | G/T |
| rs7751422 | 79800799 | + | C/T |
| rs35760468 | 79800851 | + | —/G |
| rs9343861 | 79801587 | + | A/C |
| rs10943613 | 79801826 | + | C/T |
| rs11963444 | 79802291 | + | C/G |
| rs34875528 | 79803382 | + | —/A |
| rs9359363 | 79803610 | + | C/T |
| rs9448612 | 79803872 | + | A/G |
| rs12180022 | 79803813 | + | A/G |
| rs9448613 | 79803942 | + | A/G |
| rs9448614 | 79804316 | + | C/T |
| rs4706749 | 79804772 | + | C/T |
| rs1415861 | 79805047 | + | C/T |
| rs5877639 | 79805108 | + | —/TTT |
| rs4055439 | 79805107 | − | —/AAA |
| rs35633350 | 79805108 | + | —/TTT |
| rs34124549 | 79805944 | + | —/A |
| rs11758432 | 79806313 | + | C/T |
| rs6454094 | 79806528 | + | C/T |
| rs9361482 | 79807104 | + | C/T |
| rs35197393 | 79807335 | + | —/T |
| rs34887019 | 79807963 | + | —/T |
| rs9343862 | 79808197 | + | C/G |
| rs35686657 | 79809315 | − | C/T |
| rs9343863 | 79809511 | + | C/T |
| rs2050662 | 79809792 | + | C/G |
| rs9361483 | 79810005 | + | C/T |
| rs2050663 | 79810113 | + | C/T |
| rs7739298 | 79811079 | + | A/G |
| rs35594811 | 79811779 | + | A/C |
| rs9448616 | 79813653 | + | A/G |
| rs34896515 | 79814085 | + | —/C |
| rs13204088 | 79814157 | + | A/C |
| rs34581263 | 79814707 | + | —/G |
| rs34999680 | 79814872 | + | —/C |
| rs9361484 | 79814937 | + | A/C |
| rs9352686 | 79814942 | + | G/T |
| rs34193659 | 79815383 | + | —/C |
| rs28404148 | 79815386 | + | A/C |
| rs34818907 | 79815757 | + | —/C |
| rs9361485 | 79816451 | + | C/T |
| rs35355402 | 79817319 | + | —/C |
| rs4706080 | 79817716 | + | C/T |
| rs9361486 | 79818479 | + | C/T |
| rs2152951 | 79818891 | + | A/G |
| rs35469490 | 79819211 | + | —/C |
| rs9448617 | 79819766 | + | A/G |
| rs12182597 | 79819707 | + | A/G |
| rs11968462 | 79819711 | + | C/T |
| rs9350801 | 79819985 | + | C/G |
| rs9448618 | 79820526 | + | G/T |
| rs6928507 | 79820970 | + | A/C |
| rs6928518 | 79820984 | + | A/G |
| rs6929315 | 79821334 | + | C/T |
| rs9343865 | 79821914 | + | A/T |
| rs11760038 | 79822663 | + | A/G |
| rs34192988 | 79822723 | + | —/G |
| rs9969106 | 79822922 | + | G/T |
| rs64095 | 79823093 | + | C/T |
| rs12110918 | 79823270 | + | A/G |
| rs9443640 | 79823496 | + | C/T |
| rs28393972 | 79823721 | + | C/G |
| rs28587408 | 79823722 | + | G/T |
| rs11292616 | 79823758 | + | —/A |
| rs6915558 | 79825775 | + | A/T |
| rs10528595 | 79826027 | + | —/TATATA TATATAT ATATATA |
| rs10631256 | 79826038 | + | —/ATAT |
| rs34479070 | 79826039 | + | —/ATAT |
| rs10668885 | 79826050 | + | —/ATATAT AT |
| rs10668886 | 79826051 | + | —/ATATAT AT/TATA TATATA |
| rs35594282 | 79826052 | + | —/TATATA TATA |
| rs34850134 | 79826053 | + | —/ATATAT ATATAT |
| rs10943614 | 79826062 | + | A/T |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs7753638 | 79826260 | + | C/T |
| rs6917206 | 79826433 | + | C/G |
| rs11295038 | 79826554 | + | —/A |
| rs7454519 | 79827581 | + | C/G |
| rs9343867 | 79829072 | + | G/T |
| rs6925447 | 79829270 | + | C/T |
| rs9448620 | 79829965 | + | C/G |
| rs10688271 | 79832242 | + | —/CA |
| rs1547731 | 79832823 | + | A/G |
| rs9352688 | 79832882 | + | A/G |
| rs28562383 | 79833897 | + | A/T |
| rs9448623 | 79834479 | + | C/T |
| rs9968921 | 79835098 | + | A/G |
| rs34949474 | 79835636 | + | A/C |
| rs10455120 | 79836486 | + | G/T |
| rs12529731 | 79837484 | + | A/G |
| rs9352689 | 79839533 | + | C/T |
| rs9361488 | 79839593 | + | C/T |
| rs7744876 | 79839756 | + | A/G |
| rs9352690 | 79840271 | + | A/C |
| rs3857447 | 79840542 | + | C/T |
| rs28361939 | 79840905 | + | G/T |
| rs13216433 | 79841107 | + | G/T |
| rs9343869 | 79841140 | + | C/G |
| rs34915363 | 79841523 | + | —/T |
| rs9448624 | 79841582 | + | G/T |
| rs35664126 | 79841883 | + | —/A |
| rs9443641 | 79842023 | + | A/C |
| rs9352691 | 79842326 | + | C/T |
| rs34821012 | 79843195 | + | —/A |
| rs3812161 | 79843364 | − | G/T |
| rs12526671 | 79844774 | + | C/G |
| rs1413967 | 79845731 | − | A/C |
| rs9343870 | 79846192 | + | G/T |
| rs7753531 | 79846715 | + | A/C |
| rs1413969 | 79847701 | − | C/T |
| rs1413968 | 79847761 | − | C/T |
| rs4055438 | 79848331 | + | —/CACA |
| rs1415860 | 79848500 | − | C/T |
| rs13212056 | 79849331 | + | A/C |
| rs7776432 | 79851211 | + | G/T |
| rs36017295 | 79851212 | + | GC/TT |
| rs7776138 | 79851212 | + | C/T |
| rs1415859 | 79851577 | − | C/T |
| rs35716913 | 79851705 | + | —/T |
| rs12154147 | 79852063 | + | C/T |
| rs12212124 | 79852485 | + | C/T |
| rs9359364 | 79852711 | + | A/G |
| rs9443642 | 79853322 | + | G/T |
| rs9448625 | 79853356 | + | C/T |
| rs9352693 | 79854791 | + | A/T |
| rs9443643 | 79855557 | + | A/G |
| rs12664690 | 79856551 | + | C/T |
| rs9352694 | 79857537 | + | A/G |
| rs13206256 | 79860401 | + | A/G |
| rs11963526 | 79860546 | + | A/G |
| rs4706750 | 79862281 | + | A/G |
| rs7773757 | 79862756 | + | A/G |
| rs5877640 | 79865118 | + | —/T |
| rs35313660 | 79865119 | + | —/T |
| rs12193154 | 79866583 | + | C/T |
| rs7767100 | 79867252 | + | A/C |
| rs9443644 | 79867363 | + | A/G |
| rs7767711 | 79867419 | + | A/G |
| rs12214911 | 79867844 | + | C/T |
| rs4507549 | 79868299 | + | C/T |
| rs9448627 | 79868502 | + | A/G |
| rs6899909 | 79868551 | + | A/C |
| rs12660124 | 79868563 | + | A/G |
| rs28379467 | 79868586 | + | A/C |
| rs9689135 | 79868589 | + | A/C |
| rs9689136 | 79868593 | + | A/C |
| rs6906253 | 79869724 | + | A/C |
| rs34349727 | 79870222 | + | —/T |
| rs1538232 | 79870555 | + | C/T |
| rs7749916 | 79870911 | + | A/G |
| rs12195753 | 79872084 | + | C/T |
| rs34664515 | 79872349 | + | —/C |
| rs12197385 | 79872695 | + | A/C |
| rs11968729 | 79872968 | + | A/T |
| rs9361489 | 79873504 | + | C/T |
| rs4144106 | 79873950 | + | A/C |
| rs5877641 | 79874047 | + | —/TTT |
| rs35186945 | 79874048 | + | —/TTT |
| rs5877642 | 79874056 | + | —/TTT |
| rs34582407 | 79874057 | + | —/TT |
| rs4055440 | 79874065 | + | —/T/TT/TTT |
| rs34285696 | 79874066 | + | —/TT |
| rs5877644 | 79874142 | + | —/A |
| rs5877645 | 79874154 | + | —/A |
| rs949846 | 79874315 | − | A/G |
| rs35175594 | 79874354 | + | —/T |
| rs6916081 | 79874571 | + | C/T |
| rs9341758 | 79876533 | + | C/T |
| rs9343871 | 79876838 | + | C/T |
| rs11967829 | 79876870 | + | A/T |
| rs4460185 | 79877129 | + | A/G |
| rs12203969 | 79877616 | + | G/T |
| rs35921542 | 79878727 | + | —/T |
| rs1415310 | 79879033 | + | C/T |
| rs34887350 | 79879491 | + | —/CA |
| rs9443645 | 79879643 | + | C/T |
| rs35532958 | 79879775 | + | —/G |
| rs12208017 | 79880090 | + | G/T |
| rs10943616 | 79880260 | + | A/G |
| rs6940949 | 79880754 | + | A/G |
| rs6904124 | 79881799 | + | C/G |
| rs34131532 | 79882366 | + | —/GA |
| rs34222053 | 79882584 | + | —/G |
| rs9361491 | 79882867 | + | C/T |
| rs9352696 | 79882949 | + | A/T |
| rs34096134 | 79883539 | + | —/A |
| rs13437410 | 79883867 | + | C/G |
| rs1337128 | 79884042 | + | A/G |
| rs1415311 | 79884599 | + | A/C |
| rs9352697 | 79885302 | + | G/T |
| rs6902186 | 79886779 | + | A/T |
| rs6902217 | 79886841 | + | A/G |
| rs35067617 | 79886856 | + | —/A |
| rs34297827 | 79887590 | + | —/A |
| rs7747226 | 79888212 | + | A/G |
| rs7747540 | 79888379 | + | G/T |
| rs1577793 | 79888739 | + | A/G |
| rs34004133 | 79889589 | + | —/G |
| rs9448636 | 79890158 | + | C/T |
| rs9448637 | 79890797 | + | C/G |
| rs6454096 | 79891729 | + | A/G |
| rs7768264 | 79891856 | + | C/G |
| rs7768535 | 79892231 | + | C/T |
| rs11285425 | 79892473 | + | —/T |
| rs9688601 | 79892482 | + | C/T |
| rs11361003 | 79892488 | + | —/T |
| rs11362933 | 79892493 | + | —/T |
| rs12055857 | 79892585 | + | A/G |
| rs12055858 | 79892634 | + | A/G |
| rs9294129 | 79892802 | + | A/C |
| rs9443647 | 79892908 | + | C/G |
| rs34216559 | 79893168 | + | —/A |
| rs3920791 | 79893453 | − | G/T |
| rs1361043 | 79893786 | − | A/G |

TABLE 6-continued

Polymorphic markers within the C06 region, between position 79,300,773 and 79,917,888 in NCBI Build 36. Shown is marker ID (rs-names), position in Build 36, strand and polymorphism type, where (—/N), N being any nucleotide or a plurality of nucleotides, corresponding to an insertion/deletion polymorphism (i.e. either the nucleotide(s) is present or not, as indicated).

| Marker ID | Position Build 36 | Strand | Polymorphism |
|---|---|---|---|
| rs5877646 | 79893802 | + | —/A |
| rs1577794 | 79894899 | − | A/G |
| rs7771746 | 79895912 | + | C/T |
| rs7751626 | 79895992 | + | A/C |
| rs7751628 | 79895996 | + | A/C |
| rs7751918 | 79896046 | + | A/G |
| rs11757274 | 79896170 | + | A/G |
| rs1832281 | 79896696 | − | G/T |
| rs34002011 | 79897278 | + | —/C |
| rs9448638 | 79897415 | + | A/G |
| rs9448639 | 79897548 | + | C/T |
| rs36080847 | 79897705 | + | —/C |
| rs35178487 | 79897768 | + | —/C |
| rs9448640 | 79898041 | + | A/G |
| rs6938269 | 79898250 | + | A/G |
| rs34749590 | 79898414 | + | —/C |
| rs6900032 | 79898558 | + | C/G |
| rs6899945 | 79898698 | + | C/T |
| rs1856089 | 79898889 | − | G/T |
| rs1856090 | 79899041 | − | A/G |
| rs28793115 | 79899460 | + | A/G |
| rs6906655 | 79900092 | + | A/G |
| rs6929531 | 79900136 | + | C/T |
| rs2210948 | 79900755 | − | C/T |
| rs9359366 | 79900866 | + | A/G |
| rs9343875 | 79901113 | + | C/T |
| rs9343876 | 79901219 | + | A/G |
| rs9448642 | 79901713 | + | C/T |
| rs9341760 | 79901973 | + | A/G |
| rs9361493 | 79903957 | + | C/T |
| rs34851468 | 79903998 | + | —/C |
| rs2321960 | 79904819 | + | C/T |
| rs4547969 | 79905337 | + | C/G |
| rs2321961 | 79905575 | + | C/T |
| rs9361496 | 79905887 | + | A/G |
| rs6922885 | 79906095 | + | C/T |
| rs6900076 | 79906130 | + | A/T |
| rs34635585 | 79906257 | + | —/AA |
| rs12527205 | 79906518 | + | C/T |
| rs6916942 | 79907146 | + | A/G |
| rs13192783 | 79907675 | + | G/T |
| rs35970033 | 79907754 | + | —/GTGT |
| rs13207216 | 79907776 | + | C/G |
| rs9448644 | 79909382 | + | A/C |
| rs956550 | 79909459 | − | A/G/T |
| rs11450125 | 79909773 | + | —/A |
| rs35277763 | 79909871 | + | —/C |
| rs9443648 | 79910324 | + | A/G |
| rs17785485 | 79910945 | + | C/T |
| rs17723508 | 79911083 | + | A/G |
| rs9448645 | 79911477 | + | A/G |
| rs6904674 | 79912150 | + | A/C |
| rs28369551 | 79912158 | + | A/T |
| rs6933121 | 79912963 | + | C/T |
| rs7768622 | 79913223 | + | G/T |
| rs10484946 | 79913349 | − | A/G |
| rs12196543 | 79914619 | + | A/G |
| rs9448647 | 79915916 | + | A/T |
| rs9352701 | 79916596 | + | A/G |
| rs9361497 | 79916649 | + | C/T |
| rs9448648 | 79916948 | + | A/G |
| rs9294130 | 79917888 | + | A/G |

Example 2

Further analysis of marker rs11228565, which is located within LD Block C11 and in LD with rs10896450 (D'=1, $r^2$=0.25), was performed, with results as shown in Table 7. Highly significant association of the A allele of rs11228565 to prostate cancer was revealed, with combined P-value for all cohorts genome-wide significant (P=6.7×10$^{-12}$). The odds ratio (OR) for rs11228565 after adjusting for rs10896450 was determined to be 1.16 (P value=4.9 E-04) when using results for all populations except Finland (i.e. where we have results for both markers rs11228565 and rs10896450 in: Iceland, Chicago, Netherlands, Nashville and Spain cohorts.

TABLE 7

Association of rs11228565 with prostate cancer.

| Study population | Marker | Allele | P value | OR | Cases (n) | Case Freq. | Controls (n) | Control Freq. |
|---|---|---|---|---|---|---|---|---|
| Iceland | rs11228565 | A | 7.72E−03 | 1.23 | 1784 | 0.209 | 771 | 0.176 |
| The Netherlands | rs11228565 | A | 2.15E−02 | 1.17 | 992 | 0.229 | 1781 | 0.202 |
| Spain | rs11228565 | A | 3.42E−01 | 1.09 | 394 | 0.240 | 1399 | 0.224 |
| Finland | rs11228565 | A | 3.22E−06 | 1.30 | 2643 | 0.210 | 1689 | 0.169 |
| Chicago, USA | rs11228565 | A | 8.00E−02 | 1.16 | 755 | 0.235 | 878 | 0.210 |
| Nashville, USA | rs11228565 | A | 8.49E−05 | 1.43 | 592 | 0.291 | 685 | 0.223 |
| All combined | rs11228565 | A | 6.70E−12 | 1.23 | 7160 | — | 7203 | — |

The invention claimed is:

1. A method for determining a susceptibility to prostate cancer in a human individual, the method comprising:
analyzing a nucleic acid sample obtained from the human individual to determine the presence or absence of allele G of polymorphic marker rs10896450,
detecting the presence of allele G of polymorphic marker rs10896450 in the sample, and
determining an increased susceptibility to prostate cancer in the human individual by calculating a risk score for the individual which is the product of the risk values for a plurality of factors, wherein one of the factors is a relative risk (RR) or odds ratio of at least 1.1 attributed to the presence of allele G of polymorphic marker rs10896450 in the nucleic acid sample of the individual, wherein the determining is performed using an apparatus comprising:

a computer readable memory;
a processor; and
a routine stored on the computer readable memory; wherein the routine is adapted to be executed on the processor to analyze genotype data with respect to at least polymorphic marker rs10896450, and generate an output based on the genotype data, wherein the output comprises a risk score for the human individual with respect to prostate cancer.

2. A method for determining a susceptibility to prostate cancer in a human individual, the method comprising:
analyzing a nucleic acid sample obtained from the human individual to determine the presence or absence of allele A of polymorphic marker rs11228565,
detecting the presence of allele A of polymorphic marker rs11228565 in the sample, and
determining an increased susceptibility to prostate cancer in the human individual by calculating a risk score for the individual which is the product of the risk values for a plurality of factors, wherein one of the factors is a relative risk (RR) or odds ratio of at least 1.1 attributed to the presence of allele A of polymorphic marker rs11228565 in the nucleic acid sample of the individual, wherein the determining is performed using an apparatus comprising:
a computer readable memory;
a processor; and
a routine stored on the computer readable memory; wherein the routine is adapted to be executed on the processor to analyze genotype data with respect to at least polymorphic marker rs11228565, and generate an output based on the genotype data, wherein the output comprises a risk score for the human individual with respect to prostate cancer.

3. A method for determining a susceptibility to prostate cancer in a human individual, the method comprising:
analyzing a nucleic acid sample obtained from the human individual to determine the presence or absence of allele A of polymorphic marker rs7947353,
detecting the presence of allele A of polymorphic marker rs7947353 in the sample, and
determining an increased susceptibility to prostate cancer in the human individual by calculating a risk score for the individual which is the product of the risk values for a plurality of factors, wherein one of the factors is a relative risk (RR) or odds ratio of at least 1.1 attributed to the presence of allele A of polymorphic marker rs7947353 in the nucleic acid sample of the individual, wherein the determining is performed using an apparatus comprising:
a computer readable memory;
a processor; and
a routine stored on the computer readable memory; wherein the routine is adapted to be executed on the processor to analyze genotype data with respect to at least polymorphic marker rs7947353, and generate an output based on the genotype data, wherein the output comprises a risk score for the human individual with respect to prostate cancer.

4. A method for determining a susceptibility to prostate cancer in a human individual, the method comprising:
analyzing a nucleic acid sample obtained from the human individual to determine the presence or absence of allele G of polymorphic marker rs10896450,
detecting the presence of allele G of polymorphic marker rs10896450 in the sample,
determining an increased genetic susceptibility to prostate cancer in the human individual attributed to the presence of allele G of polymorphic marker rs10896450 in the nucleic acid sample of the individual, and
performing a prostate Specific Antigen (PSA) test, a Digital Rectal Examination and/or a prostate biopsy on the individual determined to have the increased genetic susceptibility.

5. A method for determining a susceptibility to prostate cancer in a human individual, the method comprising:
analyzing a nucleic acid sample obtained from the human individual to determine the presence or absence of allele A of polymorphic marker rs11228565,
detecting the presence of allele A of polymorphic marker rs11228565 in the sample,
determining an increased genetic susceptibility to prostate cancer in the human individual attributed to the presence of allele A of polymorphic marker rs11228565 in the nucleic acid sample of the individual, and
performing a prostate Specific Antigen (PSA) test, a Digital Rectal Examination and/or a prostate biopsy on the individual determined to have the increased genetic susceptibility.

6. A method for determining a susceptibility to prostate cancer in a human individual, the method comprising:
analyzing a nucleic acid sample obtained from the human individual to determine the presence or absence of allele A of polymorphic marker rs7947353,
detecting the presence of allele A of polymorphic marker rs7947353 in the sample,
determining an increased genetic susceptibility to prostate cancer in the human individual attributed to the presence of allele A of polymorphic marker rs7947353 in the nucleic acid sample of the individual, and
performing a prostate Specific Antigen (PSA) test, a Digital Rectal Examination and/or a prostate biopsy on the individual determined to have the increased genetic susceptibility.

7. The method according to claim 4, wherein the step of determining a susceptibility includes calculating a risk score for the individual that includes a relative risk (RR) or odds ratio of at least 1.1 attributed to allele G of polymorphic marker rs10896450 being present in the nucleic acid sample of the individual.

8. The method according to claim 5, wherein the step of determining a susceptibility includes calculating a risk score for the individual that includes a relative risk (RR) or odds ratio of at least 1.1 attributed to allele A of polymorphic marker rs11228565 being present in the nucleic acid sample of the individual.

9. The method according to claim 6, wherein the step of determining a susceptibility includes calculating a risk score for the individual that includes a relative risk (RR) or odds ratio of at least 1.1 attributed to allele A of polymorphic marker rs7947353 being present in the nucleic acid sample of the individual.

10. The method according to claim 1, further comprising assessing at least one non-genetic factor to make a susceptibility assessment, and determining a susceptibility to prostate cancer for the individual from the combination of the at least one non-genetic factor and the presence of allele G of polymorphic marker rs10896450.

11. The method according to claim 10, wherein the non-genetic factor comprises a measurement of prostate specific antigen (PSA) from the individual.

12. The method according to claim 2, further comprising assessing at least one non-genetic factor to make a susceptibility assessment, and determining a susceptibility to prostate cancer for the individual from the combination of the at least one non-genetic factor and the presence of allele A of polymorphic marker rs11228565.

13. The method according to claim 12, wherein the non-genetic factor comprises a measurement of prostate specific antigen (PSA) from the individual.

14. The method according to claim 3, further comprising assessing at least one non-genetic factor to make a susceptibility assessment, and determining a susceptibility to prostate cancer for the individual from the combination of the at least one non-genetic factor and the presence of allele A of polymorphic marker rs7947353.

15. The method according to claim 14, wherein the non-genetic factor comprises a measurement of prostate specific antigen (PSA) from the individual.

16. The method according to claim 1 or 4, wherein the human individual has a Caucasian ancestry, as self-reported by the individual.

17. The method according to claim 2 or 5, wherein the human individual has a Caucasian ancestry, as self-reported by the individual.

18. The method according to claim 3 or 6, wherein the human individual has a Caucasian ancestry, as self-reported by the individual.

19. The method according to claim 1 or 4, further comprising communicating the susceptibility determination to at least one entity selected from the group consisting of the individual, a guardian for the individual, a physician or healthcare worker, a genetic counselor, or an insurer.

20. The method according to claim 19, wherein the communicating comprises making the susceptibility determination available via secure internet interface.

21. The method according to claim 2 or 5, further comprising communicating the susceptibility determination to at least one entity selected from the group consisting of the individual, a guardian for the individual, a physician or healthcare worker, a genetic counselor, or an insurer.

22. The method according to claim 21, wherein the communicating comprises making the susceptibility determination available via secure internet interface.

23. The method according to claim 3 or 6, further comprising communicating the susceptibility determination to at least one entity selected from the group consisting of the individual, a guardian for the individual, a physician or healthcare worker, a genetic counselor, or an insurer.

24. The method according to claim 23, wherein the communicating comprises making the susceptibility determination available via secure internet interface.

25. The method according to claim 1 or 4, wherein the nucleic acid sample is from a human individual who has not been diagnosed with prostate cancer.

26. The method according to claim 2 or 5, wherein the nucleic acid sample is from a human individual who has not been diagnosed with prostate cancer.

27. The method according to claim 3 or 6, wherein the nucleic acid sample is from a human individual who has not been diagnosed with prostate cancer.

28. The method according to claim 1 or 4, wherein the step of analyzing the nucleic acid sample comprises at least one nucleic acid analysis technique selected from: polymerase chain reaction, allele-specific hybridization, nucleic acid sequencing, single-stranded conformation analysis, and electrophoresis.

29. The method according to claim 2 or 5, wherein the step of analyzing the nucleic acid sample comprises at least one nucleic acid analysis technique selected from: polymerase chain reaction, allele-specific hybridization, nucleic acid sequencing, single-stranded conformation analysis, and electrophoresis.

30. The method according to claim 3 or 6, wherein the step of analyzing the nucleic acid sample comprises at least one nucleic acid analysis technique selected from: polymerase chain reaction, allele-specific hybridization, nucleic acid sequencing, single-stranded conformation analysis, and electrophoresis.

31. The method according to any one of claims 1, 2, and 3, wherein the determining of susceptibility is performed using a computer-readable medium on which is stored:
   an identifier for the at least one polymorphic marker;
   an indicator of the frequency of at least one allele of the polymorphic marker in a plurality of individuals diagnosed with prostate cancer; and
   an indicator of the frequency of the at least one allele of the polymorphic marker in a plurality of reference individuals.

32. The method according to any one of claims 4, 5, and 6, wherein the determining of increased genetic susceptibility is performed using an apparatus, the apparatus comprising:
   a computer readable memory and a processor; and
   a routine stored on the computer readable memory; wherein the routine is adapted to be executed on the processor to analyze marker information for at least one human individual with respect to the polymorphic marker, and generate an output based on the marker information, wherein the output comprises a risk measure of the polymorphic marker as a genetic indicator of susceptibility to prostate cancer for the individual.

33. The method according to claim 32, wherein the routine further comprises an indicator of the frequency of at least one allele of the at least one polymorphic marker in a plurality of individuals diagnosed with prostate cancer, and an indicator of the frequency of the at least one allele of the polymorphic marker in a plurality of reference individuals, and wherein a risk measure is based on a comparison of allelic status of the at least one marker determined for the human individual from the sample and the indicators of the frequency of the at least one allele in the pluralities of individuals.

34. The method according to claim 33, wherein the risk measure is characterized by an Odds Ratio (OR) or a Relative Risk (RR).

35. The method according to any one of claims 1-3, further comprising measuring Prostate Specific Antigen or performing Digital Rectal Examination on a subject identified as having increased genetic susceptibility to prostate cancer.

* * * * *

UNITED STATES PATENT AND TRADEMARK OFFICE
CERTIFICATE OF CORRECTION

PATENT NO.       : 8,697,360 B2  
APPLICATION NO.  : 12/315114  
DATED            : April 15, 2014  
INVENTOR(S)      : Steinunn Thorlacius et al.

It is certified that error appears in the above-identified patent and that said Letters Patent is hereby corrected as shown below:

On the Title Page:

Item (75), in Line 2, "Reyjavik (IS)" should be -- Reykjavik --.

Item (75), in Line 3, "Reyjavik (IS)" should be -- Reykjavik --.

In the Claims:

Column 316, line 13, Claim 31, "for the at least one" should be -- for the --.

Column 316, line 33, Claim 33, "of the at least one" should be -- of the --.

Signed and Sealed this  
Second Day of June, 2015

Michelle K. Lee  
*Director of the United States Patent and Trademark Office*

SEQUENCE LISTING

<160> NUMBER OF SEQ ID NOS: 201

<210> SEQ ID NO 1
<211> LENGTH: 599
<212> TYPE: DNA
<213> ORGANISM: Homo sapiens

<400> SEQUENCE: 1

| | | | | | |
|---|---|---|---|---|---|
| ctttctctcc | tctagcactt | cctgcagttg | tttatatttc | cattgttgtt | actcagcctc | 60 |
| atttaaggcc | ttctacatta | tgttttccac | taagatgaat | gaaccacttc | aagggggaat | 120 |
| aaacttgcca | tcaatggaca | tgattaaaca | taggcaagac | catctcttaa | gaattctctt | 180 |
| tcacaaaaca | atttactttg | ttataaaaga | cagaaggaaa | aatctatttt | attatcagaa | 240 |
| ttataccatt | aacacctagc | aactattatt | tcttcatttg | ttccattgtt | aacatgagaw | 300 |
| attaaagtct | tttgatgttc | tcattttttt | ctttgcctca | gtttctgaac | tctagtacag | 360 |
| gtcttgctga | cctaagatgt | tttgggagat | gtgaaaaagg | atgaatgctg | agtttgaaat | 420 |
| gctgctcaat | ataaggcaga | agttgtccaa | gaagccaaac | aggatgtaaa | cttccagatt | 480 |
| gtatagatat | taccggataa | ttgcatttgc | ctttacctac | tataatatgc | cttagcttcc | 540 |
| caaagtgcta | ggattactgg | cgtgatgtat | ttactgtcga | cagaactcca | ataaagaac | 599 |

<210> SEQ ID NO 2
<211> LENGTH: 599
<212> TYPE: DNA
<213> ORGANISM: Homo sapiens

<400> SEQUENCE: 2

| | | | | | |
|---|---|---|---|---|---|
| acatgggtca | tatatacatc | aatttgttcg | atacacatat | atcaggacca | ccttcataac | 60 |
| tattcataac | tcatcctata | acctgttaaa | tatatatgct | tagccaactt | gttcaacata | 120 |
| aaactcctac | cccaacttat | cttcactcaa | aatgcctact | aatggctttg | gccagaggca | 180 |
| tgcttcccag | tctgcaagat | agccaccta | cagtctataa | ccctttacaa | aaaataaag | 240 |
| tatccttcct | aaatttgtag | gtcctgtgat | tttttaactt | gacacactga | gtcctgttty | 300 |
| tggctggagg | tgcacttcct | agcctgccag | catggccacc | tttataagaa | atagtctctt | 360 |
| cttttcaaat | atttttttt | gtaagttacc | atatcttgtg | atgaggattt | ttcacttaaa | 420 |
| tgtgtaaaat | aatatatgga | aagtgcttag | catactgcct | gatatgtagc | aggtacttaa | 480 |
| aaactagcac | ctgtcatatt | attactgata | cattcaccta | cttcctgttt | tcttcaggcc | 540 |
| tctttcctaa | ggaatgctga | ggtgttcacc | agttactgaa | gaagaggaag | tcactaaag | 599 |

<210> SEQ ID NO 3
<211> LENGTH: 599
<212> TYPE: DNA
<213> ORGANISM: Homo sapiens

<400> SEQUENCE: 3

| | | | | | |
|---|---|---|---|---|---|
| atcttcaata | agattatcta | agattgtatt | agacaaaata | agaaaagctt | ttagcatgat | 60 |
| aacaagtaga | ttttgaatg | aatgaatccc | cagggaagtc | ctacgaaagg | tgggtggtat | 120 |
| agagaagcaa | ggaaactgag | gctcagagat | gttgagcaag | ttataaagaa | aataagcagc | 180 |
| aaagctagga | tccaaatcaa | gttcagtatg | tttgcaatgt | caaggaagtt | tctattattt | 240 |
| ctgcaagaaa | cattagtggc | attttccact | ccagagtttc | tttaaaggac | atatgctggk | 300 |
| gaactccagt | tatttgtcaa | ctctgtctcc | ctagaaatct | ctttagatta | gagttatcat | 360 |

-continued

```
catcctttgg catttcaaac cctgcacaac atgtttataa ttggatggtc tgataaatga    420
tcctgcataa accagccact aacatctttg aacttcctct gtcatttcct atgcagaatt    480
cctcttaagt gcctcataca cagtttgatg tgccctcttt taaagtagat atgcactgat    540
cctatcagtg tctaaactac cacctgactg taaagtagcc cttttaaaat ctattctttt   599
```

<210> SEQ ID NO 4
<211> LENGTH: 599
<212> TYPE: DNA
<213> ORGANISM: Homo sapiens

<400> SEQUENCE: 4

```
ataattgcat cattttagct attcatgccc tgagatttta attttcaaaa tatttttcatt    60
tatcccaat ctttatttct gttaataaga agcatactct ataaatgatc aatgaataaa    120
atccattgat gatataagca acttagttta gccaccttct cttttactaa gtctcttaac    180
acaatctgca aaaagagaaa actgttagtc tttattacat tttctattaa ccttttaata    240
gaattgcagt aagcatgagc aaaagcaaaa tttgtggtat gaaacaaaat tgttacttay    300
acttcactaa acagtgccag catatgttat aatttcagca ttaatttaac aaggttaaat    360
ttataggaca aatgttagaa attctctagg gttttctagg aaactaacat ttcatgatga    420
gaaggcttgt ttaagttatt ttattttttt gtttaagtta tttattttt aatgtttgtg    480
ggtacatagt tgtacatatt tatggcatac atgtgatatt ttgatacagg catatgtgta    540
atgaccaaat caggataatc gggatatcca ttacctcaaa catatcattt ttttgtatt    599
```

<210> SEQ ID NO 5
<211> LENGTH: 599
<212> TYPE: DNA
<213> ORGANISM: Homo sapiens

<400> SEQUENCE: 5

```
agggggattca agtcaagttc acccattact gaaaatagag aagacagtga ttttctaaga    60
gcttctctgg aaaactgaat cccatcacaa gtcttaagtc cctgggcttg agttcctgat    120
catgggtcaa aggaaccagg atttaaacaa ctgactctct gaatatacta ttactataaa    180
tcctttattt gacttctgtc tgcctaagtt tggaagcacc cttctgcttc taaaacccct    240
ttactccaat tttcaatcat aattggcagg atttctgaaa atgtacagca tttgaattay    300
ctagggcctt ttgagatatt tcctggcccc catctatcaa gtcatctctg ggggagggg   360
ctaggactct ttatttttaa caagctctta cagatgttct tatacccaca acatctgag    420
atccactgag gtgtgtaaag ctcctagcac agtgcatggc aaatttaatg ttccaaatgt    480
atatctgcag tgtcactcca gccctccaat tagagcacaa acaggaaaag ggggaaaaat    540
actgacaaat atttgctttg aaatgaactt tggtggagat ctatttaaca aacagctgc     599
```

<210> SEQ ID NO 6
<211> LENGTH: 599
<212> TYPE: DNA
<213> ORGANISM: Homo sapiens

<400> SEQUENCE: 6

```
tgctgagtaa taaaccaaag aaaatgaggg aaagagcatt tcaggccaag tgaatagcat     60
gtgggaaaga gcttgaacta aaataaaatt aaagaccagc atggctggaa aataataatg    120
ggcaagttaa agagatgcag gggctgaggt gatcaagttg gaaagggct agatcgcgta     180
ggacttctag gactttccat ttcatttgag gcacggtatg agcccttgca ggatttagg     240
```

```
aagaggagtg gcataacatg aactgcattc tttaaaggcc acatgactga acatgtggar    300
ggagccagaa tggaagcaag agacaaatat taaaggcaca taaatgtggc agatagggtg    360
atgtgataga aattgatgta agagagacag aatgctggag aaatgcaatt gaaaacgaaa    420
tctcctccaa acccaaacac ttctccacaa aggtagaaaa caattttaat gttcaataag    480
tatcaaacca gactgcaatg cacattatag gcagactgct aagagatttc aaactggaaa    540
gtaatctcac cctttatat agccaagccc attcaacctg ttacatgcct attcttaag     599
```

<210> SEQ ID NO 7
<211> LENGTH: 599
<212> TYPE: DNA
<213> ORGANISM: Homo sapiens

<400> SEQUENCE: 7

```
gaccagcatg gctggaaaat aataatgggc aagttaaaga gatgcagggg ctgaggtgat     60
caagttggaa aagggctaga tcgcgtagga cttctaggac tttccatttc atttgaggca    120
cggtatgagc ccttgcagga ttttaggaag aggagtggca taacatgaac tgcattcttt    180
aaaggccaca tgactgaaca tgtggaggga gccagaatgg aagcaagaga caaatattaa    240
aggcacataa atgtggcaga tagggtgatg tgatagaaat tgatgtaaga gagacagaay    300
gctggagaaa tgcaattgaa aacgaaatct cctccaaacc caaacacttc tccacaaagg    360
tagaaaacaa ttttaatgtt caataagtat caaaccagac tgcaatgcac attataggca    420
gactgctaag agatttcaaa ctggaaagta atctcaccct tttatatagc caagcccatt    480
caacctgtta catgcctatt cttaaggtaa gcaacaacta cagacagtcc ccaacttatg    540
agtttgtgac tttccaatgg tataatatgg atacattaga gaccatatgt caagtactc     599
```

<210> SEQ ID NO 8
<211> LENGTH: 599
<212> TYPE: DNA
<213> ORGANISM: Homo sapiens

<400> SEQUENCE: 8

```
acttaaggac tatagatgct cctcgtttta tgatccggtt atgttctgat aagctcattg     60
taagctgaaa atattatgtt aaaatgcatt taatacatct aatctaccaa acatcatagc    120
ttagtcaagc ccaccttaaa cgtgctcaga acactttat tatcttacag ttgggcagag    180
tcatctaaca taaagcataa taaagtattg aatttctaat gtaacttatt ggacactgta    240
ttgaaagtga aaaatagaat gtttatatga gtacttgaca tatggtctct aatgtatccr    300
tattatacca ttggaaagtc acaaactcat aagttgggga ctgtctgtag ttgttgctta    360
ccttaagaat aggcatgtaa caggttgaat gggcttggct atataaaagg gtgagattac    420
tttccagttt gaaatctctt agcagtctgc ctataatgtg cattgcagtc tggtttgata    480
cttattgaac attaaaattg tttttctacct ttgtggagaa gtgtttgggt ttggaggaga    540
tttcgttttc aattgcattt ctccagcatt ctgtctctct tacatcaatt tctatcaca     599
```

<210> SEQ ID NO 9
<211> LENGTH: 599
<212> TYPE: DNA
<213> ORGANISM: Homo sapiens

<400> SEQUENCE: 9

```
aggatgaact atctgtaata aatgatgctg tgaagtccac ttaaggacta tagatgctcc     60
tcgttttatg atccggttat gttctgataa gctcattgta agctgaaaat attatgttaa    120
```

```
aatgcattta atacatctaa tctaccaaac atcatagctt agtcaagccc accttaaacg    180
tgctcagaac acttttatta tcttacagtt gggcagagtc atctaacata aagcataata    240
aagtattgaa tttctaatgt aacttattgg acactgtatt gaaagtgaaa aatagaatgk    300
ttatatgagt acttgacata tggtctctaa tgtatccata ttataccatt ggaaagtcac    360
aaactcataa gttggggact gtctgtagtt gttgcttacc ttaagaatag gcatgtaaca    420
ggttgaatgg gcttggctat ataaaagggt gagattactt tccagtttga aatctcttag    480
cagtctgcct ataatgtgca ttgcagtctg gtttgatact tattgaacat taaaattgtt    540 ttctacctttt gtggagaagt gtttgggttt ggaggagatt tcgttttcaa ttgcatttc    599
```

<210> SEQ ID NO 10
<211> LENGTH: 599
<212> TYPE: DNA
<213> ORGANISM: Homo sapiens

<400> SEQUENCE: 10

```
gaacataacc ggatcataaa acgaggagca tctatagtcc ttaagtggac ttcacagcat     60
catttattac agatagttca tcctagattc acctggtaat tagggtggcc atctgtgttt    120
gctaatcagc tttatcaaaa ggagattttt aacttctcag atctttatga aaggaagtag    180
ctttgtaact cggagtaagg tactcctatc ctcccacaga gactgggaga taaagatgca    240
atctctctgg atatttacat ttcaaggaga tgatctcagg tccttgaaaa agacattcck    300
gggtcttaaa gctgataaga gactattcag cttttttaaaa ggtttacaca catttcaaag    360
agatagagaa ataacttata attacaattt tcttaagtaa ataatctaag aaagggaagg    420
gggggaatgg tctcttccct tattttcaac agggagagtt aaatctcttg ttttttaattt    480 ttatttgctc ttttttcaaga gatagataaa tggatttgag actactgtac attgggttat    540
atgtgaagat tggaggagga gaaactaaaa tgatgaccag tttgagcaat tacatcagt     599
```

<210> SEQ ID NO 11
<211> LENGTH: 599
<212> TYPE: DNA
<213> ORGANISM: Homo sapiens

<400> SEQUENCE: 11

```
agacctctga ggcggagtca ctgtcttgct gctattacct tggaagaggc tcagtgagac     60
tgtttgggaa tacggaaaag aagttgaaga ttgaaattaa ctgcccctgc caggttgaag    120
gggccttgct caggctattt gagaagaaca ggaagcaaag caaaaaggag tatttcagtt    180
cctcctccag ccttgcagtc ccctctctag tacctttatg gtggcagaac ctaacaggaa    240
gcctccttgt caaaggatca gtggaatttg gtaagccatg gccccagcat cacacagcas    300
agtgcagagg actaggtttg ttggagggag aacattgttt aatagctgga acaagtcctt    360
tgtctgcttt agcaatagac cctctgatgt gcccacatct ctgcaaatgt gtgactgctc    420
tgcttggggg ctggctgcct gcataattgc taagcttggc acttctgttt gttgacatta    480
aatgctatta gggaacaact ttgtgaaaca atattttttgg tgatgctgca ttttcttaac    540
ataattttca ttacattcac gtggacattc acgacaaacc tacaggcatg cccttatgt     599
```

<210> SEQ ID NO 12
<211> LENGTH: 599
<212> TYPE: DNA
<213> ORGANISM: Homo sapiens

<400> SEQUENCE: 12

```
aataaataac taaagcaagt ggctgccatc gctaatgttg ggggaataga gagaagggt      60
tgggttgtag gaatctagaa gcttaaaggt ggggccctag tatactggga ctcagacctc     120
tgaggcggag tcactgtctt gctgctatta ccttggaaga ggctcagtga gactgtttgg    180
gaatacggaa aagaagttga agattgaaat taactgcccc tgccaggttg aaggggcctt    240
gctcaggcta tttgagaaga acaggaagca aagcaaaaag gagtatttca gttcctccty    300
cagccttgca gtcccctctc tagtaccttt atggtggcag aacctaacag gaagcctcct    360
tgtcaaagga tcagtggaat tggtaagcc atggcccag catcacacag cacagtgcag      420
aggactaggt tgttggagg gagaacattg tttaatagct ggaacaagtc ctttgtctgc     480
tttagcaata gaccctctga tgtgcccaca tctctgcaaa tgtgtgactg ctctgcttgg    540
gggctggctg cctgcataat tgctaagctt ggcacttctg tttgttgaca ttaaatgct     599

<210> SEQ ID NO 13
<211> LENGTH: 599
<212> TYPE: DNA
<213> ORGANISM: Homo sapiens

<400> SEQUENCE: 13
ttgtgtcagt gaaacaaaac tcatactaga tattttgaca gagaaattaa ggtgggaaat     60
tggctaagtg ttggagtact gaaaaatcag agaagacact taggaaacac agataataaa    120
taactaaagc aagtggctgc catcgctaat gttgggggaa tagagagaag gggttgggtt    180
gtaggaatct agaagcttaa aggtgggggcc ctagtatact gggactcaga cctctgaggc    240
ggagtcactg tcttgctgct attaccttgg aagaggctca gtgagactgt ttgggaatay    300
ggaaaagaag ttgaagattg aaattaactg cccctgccag gttgaagggg ccttgctcag    360
gctatttgag aagaacagga agcaaagcaa aaaggagtat ttcagttcct cctccagcct    420
tgcagtcccc tctctagtac ctttatggtg gcagaaccta acaggaagcc tccttgtcaa    480
aggatcagtg gaatttggta agccatggcc ccagcatcac acagcacagt gcagaggact    540
aggtttgttg gagggagaac attgtttaat agctggaaca gtcctttgt ctgctttag     599

<210> SEQ ID NO 14
<211> LENGTH: 599
<212> TYPE: DNA
<213> ORGANISM: Homo sapiens

<400> SEQUENCE: 14 ataaatact taaatgctg agataagtaa ccatggaagc aaagttttaa agatgcataa      60
ttaattcatg cattaaatat ttattgtgtc tgctatgtgc taggtgtagt atgaggtttg    120
ggggaaaact acagtgaaca agataaaatc tctatcaata caggtttcca tcttccagga    180
gagacctgaa aatacagaga ccataactcc atggggaata tggagagcag tatctccaga    240
aatccctagg cagcaggaag cctgtctgct gaggccctga aaactaagga gcctcagacr    300
aggtctactg gcagtagact tgacttgaaa tcctggctgc atactattta agctctcaaa    360
gctttgcttt ccttgtctgt gaaatccact ccatcttcag ccacaacttt cagttttct     420
aatgcaatat agggaaaaaa cagggtggaa gaaggaagat aatgctatag ttccttttctc    480
tttttttttg cccaaattac acctatgtca atgaatgcta tgaatactta tttgattgaa    540
tcctttgagg aggaagagtt tggaataaac tgcccctcta tgagagacag ttttaacttt    599

<210> SEQ ID NO 15
<211> LENGTH: 599
<212> TYPE: DNA
```

<213> ORGANISM: Homo sapiens

<400> SEQUENCE: 15

```
catttctcct tcctggacag agaacttgaa cactagatag tcctaaatta ttcttttgaa      60
gtttgaatta gccatagttg aataatacag gggaataata aaatacttaa aatgctgaga     120
taagtaacca tggaagcaaa gttttaaaga tgcataatta attcatgcat taaatattta     180
ttgtgtctgc tatgtgctag gtgtagtatg aggtttgggg gaaaactaca gtgaacaaga     240
taaaatctct atcaatacag gtttccatct tccaggagag acctgaaaat acagagaccr     300
taactccatg gggaatatgg agagcagtat ctccagaaat ccctaggcag caggaagcct     360
gtctgctgag gccctgaaaa ctaaggagcc tcagacaagg tctactggca gtagacttga     420
cttgaaatcc tggctgcata ctatttaagc tctcaaagct ttgctttcct tgtctgtgaa     480
atccactcca tcttcagcca caactttcag ttttttctaat gcaatatagg gaaaaaacag     540
ggtggaagaa ggaagataat gctatagttc ctttctcttt ttttttgccc aaattacac     599
```

<210> SEQ ID NO 16
<211> LENGTH: 599
<212> TYPE: DNA
<213> ORGANISM: Homo sapiens

<400> SEQUENCE: 16

```
actccctctt gctgtgttta gttgccaacc aacagtgagg agtttgtaaa gtgtcttttt      60
catttctcac atccactgta ttttaaacaa tgagaatagt atgcccttac ttcatctgca     120
ctgggaaaat acctgaaagt aagctaatga tgagatttct ccagatgaaa catgccaggt     180
gatatcttaa acacaatttt taagtctgt ttagtttcat gcagtgcatt tctccttcct     240
ggacagagaa cttgaacact agatagtcct aaattattct tttgaagttt gaattagccr     300
tagttgaata atacaggga ataataaaat acttaaaatg ctgagataag taaccatgga     360
agcaaagttt taaagatgca taattaattc atgcattaaa tatttattgt gtctgctatg     420
tgctaggtgt agtatgaggt ttgggggaaa actacagtga acaagataaa atctctatca     480
atacaggttt ccatcttcca ggagagacct gaaaatacag agaccataac tccatgggga     540
atatggagag cagtatctcc agaaatccct aggcagcagg aagcctgtct gctgaggcc     599
```

<210> SEQ ID NO 17
<211> LENGTH: 599
<212> TYPE: DNA
<213> ORGANISM: Homo sapiens

<400> SEQUENCE: 17

```
ggttggggta tgaaaagggg caatttcccc atctctggct actggcaaat ttattttgca      60
atgagccctg caaacgatgt gtagtggccc tgattggaac ctgttctccc aaggtcacca     120
taactttcat tccactgtgt gttgactgca actgccctgt ccaatcccca tcttcagctc     180
agacctgagt ttcagccatg tctatgccac tgtatccagt gaccgcatct tacctttcct     240
cctattctca caggttccca catgttcttc tcagctagct gaaaagctca tctttgctar     300
taatagctgc tgcttattca gcacctccta aaaactaggc ttggggttta tatgccttat     360
ttctgtgact cacaatgatg cttcaaggta aatatgatca tctacatttt ttttgagacg     420
gggtctcact tgttgccag gctggagtgc agtggagatt tcaaatgttg gttaatttcc     480
aaaacatatc tcttttact tcagtcacaa agtgtctaaa tgattttgta gtagatacta     540
atgaactatt ttgttacctc ttctagatag aaatagtaag cactgggtat gtgccagat     599
```

<210> SEQ ID NO 18
<211> LENGTH: 599
<212> TYPE: DNA
<213> ORGANISM: Homo sapiens

<400> SEQUENCE: 18

```
atgtacatat atacatacaa catgatgtat gtgtatgagg gtatatatat ttttatattg      60
aatatatata cacatatgta gtgctaaaat gagaatatag ttaggttcag agagtaaata     120
atgttcatta ttgccataaa gtgactctat aatgattaat aaagatataa aatcaaatgc     180
atttaagagg aaaggcatta attgaattaa gtactattat tatattggca tctcctttat     240
gcctgtgcta tgttactggt gtgggaaata tatatgcact taaactattt tgcaacgtay     300
acccaaaatc acactgctgt ttttgaaaag cccataaaaa gcctgaattc tccacacata     360
ttccatacat gagagcagaa aagaagaatt tgccaacttg taaagtttct atgcatgtac     420
ttaatttctt cccaaaggtc caattcacta gttattcaga ctcaacattg ggaaatggac     480
ataaggaagt acagttggag caaaacatgg ctacactttg ccagcaaaaa tcttcctcac     540
cagcaatatg gatactacag acagcaaaat tatcaatcag cactggaaaa agaaaatga     599
```

<210> SEQ ID NO 19
<211> LENGTH: 599
<212> TYPE: DNA
<213> ORGANISM: Homo sapiens

<400> SEQUENCE: 19

```
tgttctacat tatatgaatt tctcaaaagc agatggctga ataacttaca gaattgaatt      60
tcagctccat tagattccat tcttacctaa aatgtgtgta ccacattata tctgctagtc     120
agaacagtct tttggcaata atataaactg tgagcactca gaccagatca gaatatattt     180
attgttttgt tagaaagcac ctagttcatg ttaactttca atggaagtta tattgtttag     240
caacttgagg aaaaaaattt taaagatgtg aataggatac tttaggtagt atctctttty     300
cagatagtag agataaatta taaatggcag ggataaaaac aaagatgaaa ttttggcctt     360
aaattgtcat atgcaaaaac atccccaatt tatttaaacc tgtttaaatt taatttccaa     420
ttatttaagc ttttattgca ggttcagcat tcctaatcta aaaatccaaa atgctccaaa     480
atcaaacttt tgagtactg acatgatagc acaagtgaaa acttccacac ctgacatcgt     540
tgctttctca tttcattgca cacgaacttt ttcatttact aaattattaa aaatagtgt     599
```

<210> SEQ ID NO 20
<211> LENGTH: 599
<212> TYPE: DNA
<213> ORGANISM: Homo sapiens

<400> SEQUENCE: 20

```
agaattctca ctctgtcaac agagtgtctt gtccagcctt tggattttg cagatacagg      60
aggtgagaaa tggtatctga gtgaaggatt aatttgtgct tcttattatg aagtcaggca     120
tcttttactt tacttaaggg ccatatctac ttcttttgtc aattgcttgt tcatgttgtt     180
tgcctatttt tgtctgtttt tgtgactttt tctttctctt cttccttttc atattcactt     240
aatatttcaa tttttaaagt acttttcatg ttgtgaatag ttttgtataa acccacgaar     300
tatatttgag tagtgttgtt tgaactctaa cctgataaag tttcacttcc tcaacctgcc     360
ctcaaaatat ggccagggtg gacatgttcc aaattgaatt actccataaa aacagtcaga     420
atctcagata aacagtgact tccaaatatt aaaaataaat atgtgaataa ttttaattaa     480
```

```
tgtaacatag tttggcagat tttatatgag ctggccacag ctttttaata ggtatgtaac    540
tcccttttaa acaaaggatt tcatagacaa aatgttctac attatatgaa tttctcaaa     599
```

<210> SEQ ID NO 21
<211> LENGTH: 599
<212> TYPE: DNA
<213> ORGANISM: Homo sapiens

<400> SEQUENCE: 21

```
tcttgaatgg gattgtgtct gtgttgttat aaatatttta tattcagaac aagagcttga     60
atctagtcta ttgtgaagga tgaaagagaa gtattttatc agggaagcca cttatcagat    120
ttatgttttc taaaaatcaa tgtggttgtt ttgtttaaag caccacagat tctttcacat    180
ttctcctact aatgggtggg atctatgttc cttcctcttg aatctgggca ggcttgtaac    240
tgcttcaacc aatatggatt gacagaagtg atactatttc actttcaaag cccaaggtcr    300
tatatcttct acctggttct cttttggaggc tcactctgga ataagccaaa ttccacttaa   360
ggattccaat tacaccattc tggagaagtc tgtaggtaca tctgtcagca gttcaaacct    420
tctagtcatc tctgccaaga caccagacag gtgagttaag gagcttctag aggatttcag    480
tctccagcca tttgtcaccc ccagctgttt aaatatcccc aaatgaaacc tcacacactg    540
aggagtagag acaagccatc cctactatac cccatcccag tttctgactc ctagaatcc     599
```

<210> SEQ ID NO 22
<211> LENGTH: 599
<212> TYPE: DNA
<213> ORGANISM: Homo sapiens

<400> SEQUENCE: 22

```
aacaatctgt ttgccaagga gcttcctgag agcttcaaaa gcagtggtag ttaaggcctg     60
cctcttgaag atagtcctga tccaggtgta ccaaccacat aaaaaagaca gtccacaaag    120
gtctcagtga tttatgctca gtcccttca ttaatattgc caatcatgta atccattctt     180
taccccttga aaagaaggga gggtagaagt gggggtagtg tagaagaaat agtgggagct    240
ctgttcccag ttcttctgaa ggagctgttc ttgttttgtg agtctaagtg aaaacattay    300
gtcaaaaaga atatagcttt ttctttgctc tctgctctgt ggagccaggc agggtaggaa    360
aaggagattc cagggagcta agaatttaaa gccagagtga ctgtcaacat cccatagtg     420 aaacgcagct ccccttcact agtcctaaat ggtgccctat agaaccctgg aagaccttcc    480
cgggggcacg tcacaacctc actgacgcaa aatgtcctct ttgggactac cagaagacac    540
catgtagtaa cctttgtagg tagatggctg ctgagtcact ataatgaaca tctaaaatt     599
```

<210> SEQ ID NO 23
<211> LENGTH: 599
<212> TYPE: DNA
<213> ORGANISM: Homo sapiens

<400> SEQUENCE: 23

```
cagctcccct tcactagtcc taaatggtgc cctatagaac cctggaagac cttcccgggg     60
gcacgtcaca acctcactga cgcaaaatgt cctctttggg actaccagaa gacaccatgt    120
agtaaccttt gtaggtagat ggctgctgag tcactataat gaacatctaa aatttaacat    180
cttctccttt tactttgtat taccaatgat ttattttta ttcttttta aaagaataca     240 atataacttg gaaagaatt ggctagatac agctcagtgg acttaaaaca atgtgctatr    300
tttgaacaac atcaaattat ttttgaaaac cttgccaagt gacttcaata agatgagaac    360
```

```
tattaacatg aacttttaaa acagcaaatt tcaaacattt tttagatgtt ttctgcactg    420
gatgttgtag agtactattt agatcctccc tgaagaccaa ggcattcttt tcctcaggtg    480
ctaagaatct tgcctactga tgactcacag ctgagtccac ctacaggcat ttcccttcac    540
tgaaaaaagt tgtttccccc aatcctgcac aaactatgtc ccatcctgga aggcagcca     599

<210> SEQ ID NO 24
<211> LENGTH: 599
<212> TYPE: DNA
<213> ORGANISM: Homo sapiens

<400> SEQUENCE: 24
ctgccaacag tcgtgttatt aaaacaataa cttgcgaatt tcaagctcaa aattcttaca     60
tgatttctca ttcaatacaa aataaaatac aatctcatca acccagaatt caaagtcctc    120
taccatatga aatagtcttc ttaacaacta tttgctgctg acacacacac aacatccaca    180
caccatactc ctcttaattc cttcagtcta cacttttaga actctgtgtg gcttttgtta    240
agctattgtt taagctaaaa gctcttcttc caagccatct cttccttaac agttcaaatr    300
ccactttttc ttacatccat tagttgattt ttttcttgaa tttttattgt acttttaattc   360 ttcctttatt ttgatgctga acactgcttt ttctataaca tacgtgagtg catacatatg    420
tattatatat gcatttttta gctccttaaa agttaagaac tatgtcttag taatcttgac    480
atagaagatt ctaaaaatag tatttattaa tttctattgc aagttggtaa taaggcaatg    540
atattttcca taaagaaaaa tgagagtaga acttttatttt agtttgttga tattttgac    599

<210> SEQ ID NO 25
<211> LENGTH: 599
<212> TYPE: DNA
<213> ORGANISM: Homo sapiens

<400> SEQUENCE: 25
aatggtagag ttagaaaaca agggcatggg atgcatccca agtctttcat cctttttaata    60 ttcatagaca accaagagcc aactacatac atcaattcaa gattaaaaac atgaaagttg    120
aaaggaaaag aaatctataa gcaattacca ccttccaagt cttatgttga tattacagag    180
tatcttggga gttggtttga ttaaggaaat acgtggtgct ccattaaaat ttcttactta    240
tttttattac actctcactt gccctaatga aaataatttt cttctgtttt caggcctgts    300
catcttttgt taaagttaaa tacgccatta gtaatataaa atcaaataac cagatagatg    360
ataaagccat aaagagacag acagagagat aacagtttca aatgctttta gagtctacta    420
acattggtga atttctaaga tttagttaat acatcaggaa actgagaaat tagaccacct    480
cttcattttc tttgaaacct agttggcata ttgatctgtg ttgggttgca ggtttaaaaa    540
ggagccatac gccaattagg actgtgacag tggaataact cttcctgtat acccccatta    599

<210> SEQ ID NO 26
<211> LENGTH: 599
<212> TYPE: DNA
<213> ORGANISM: Homo sapiens

<400> SEQUENCE: 26
tctaatatac cactggaatt aaataaaatag tgtcatatag aaggaattac attggtgtag    60
aggcctaggt tcttgcccca atctacagtt gccatctaac tacattgtac acattaccat    120
catgaaactc gataaataac tactcagatt gataataagt aaaagccatt agactttcct    180
tcaaaaatac attgagtact ctttttcaca ctcttcaatc ttcaatgttc tcaccagttg    240
```

```
ctctgtgtct tgcagatgaa tctttgtttg ttttagttct ttttagttct tttcttctty    300
ctaggatgtt tgtccatatt aacaattcct tccttttata acagctccct aaagaaactc    360
tttggtcttt tctcccattg caccctcttc acattggaat caaattgcct ggttttccat    420
ctgcataaaa ttatctctga aatctgaatt ctacatatca cccaggaccc gttcctatgc    480
tatatttttc atgagatttt tactggtcct cccagctagt gcttcctcca ctcatggaac    540
ttccatagca ttcaatccat gcctctttta agataattac aattttctgt gaatatgca    599
```

<210> SEQ ID NO 27
<211> LENGTH: 599
<212> TYPE: DNA
<213> ORGANISM: Homo sapiens

<400> SEQUENCE: 27

```
gcagaatttt aaaaaataaa agatggccaa taaactagac caaaggacaa aaagataatc     60
ggtgaaacct cacctcaaag atggcagagg acaggagttt aagaaaacaa agggacagtt    120
gaatggacac taaggagaaa gagaggttcc caaagaaggg atataaacac ttcctgagaa    180
atccagagat gttcaacccc tagaaataag aagaaagaca cattgggaat aggtgtttaa    240
gatgtagatg aggcaagatc aataaaatag aggcacatat gtgccacgaa gggacactcy    300
atgtgaatta ataggcaa cttatggctc acctcaagaa cagttatgtc cattgttctg    360
aactttgaca tatgcaccca cattattgaa cttacaaagc ttaaggagtg aaagagatc    420 aaatgcattt ggaactgatg ataaacgtat gtgacagaat gtgcctgtac tttgggtgat    480
atcattgagt gaatacacat atagaagaaa gctttaattt tcatttttg ccaaaactca    540 tgtcaacttt aaaatatgct catatttcat taacaagaaa acaaaatatc ctgtcataa    599
```

<210> SEQ ID NO 28
<211> LENGTH: 599
<212> TYPE: DNA
<213> ORGANISM: Homo sapiens

<400> SEQUENCE: 28

```
cagtctaatt caaccccaag gcaggtgaat gttaagagat tgaaggctgc tgccaacact     60
tacagctgag aaatccttgt atctgcctcc tgtgggaaaa gagaaatgga cccagagtga    120
ttctatttct ccttccaaat cttgagcaag ggcttcctat tggcagaact ctaaatgcat    180
ttagaatact gagagcaggg gagttcagga gttgcagttc cttggcttct agcctctgtg    240
atacagagaa gagcctaaaa gagattgtca gtgtgatggt tgtggtggtg ggggaggar    300 gaaaatgcga cttgccaaaa gaacccaata tttagcaaaa ccttcccttt cattctgata    360
agtgtgttta accaaagatg aatacgtctt tttctaggaa ctagaaagag ggaatagttt    420
ggcatattga atatgcttga tttaagttgg cattaatatt agatagcaac tctctggctt    480
aagtgatgaa aatactgaga tatacattaa aaacacaccc aaagctaagt taaggcatag    540
attgcttttt cataaagagg aattgtacaa ttttataagc tattacattg ttatgctta    599
```

<210> SEQ ID NO 29
<211> LENGTH: 599
<212> TYPE: DNA
<213> ORGANISM: Homo sapiens

<400> SEQUENCE: 29

```
cttagattat agaattatat gtgaatatgc ttttggctct tacaccatta atgttacatg     60
taatcaaaag taattaaatt ttcaaaatta gtaaaaccac tcagttaagc aatgtaagca    120
```

```
tacattagct gataatcatt tacaatgcca attgcatcct gaggctgtta ttgacatgtc      180
agcagagcat atgatagagt tgttttctg ccagtactaa tccagaaaca atgtaaggtt      240
gccaatgcag atgggattgt atttgtagaa tggagcaatt cccataagag attttttgccr    300 tactaacagt cgctaggact tcctcagttt tctcctgtgc caggtggcag tagccaccaa      360
cagcatttgg gcactctgcc ccaccacctc cctcctctcc tgtggggaca tccaataaag      420
atgagaaaga cgtgctttgg gcaccaataa attagggaca caaaatgtg atattctgga      480 agaaatgtca agtcaaaaaa tactgggaaa tctcagcatt tcttcacatt tatttgtatg      540
gtctattaat taatataagt atcataccat ttggctgtgc tttgatgttt gtcagtgac      599

<210> SEQ ID NO 30
<211> LENGTH: 599
<212> TYPE: DNA
<213> ORGANISM: Homo sapiens

<400> SEQUENCE: 30
cccagagaca tgcacctcca gaatactcag agccaatgat tggcccaact gaagacaatt       60
ttgaggggcc actgggcttc cattgtagtt aaaaatctgc agaattctac ttagttctcc      120
tgctttccac atgcattcca tgggcacttt tcaaataatt ccctgaacac taaactctgt      180
cccagagact gctcctaggg aatccaactg gcaatgcttt tcatgcaact ccatccattg      240
ttttcttcat ttttctctta ttgggcccaa aaatatgcct cttgcatttc cacttaccar      300
tccttcttct gtcctcagaa ccaacacaaa taggaatatt ctgatgttaa tttgaaaatt      360
cctttaaata tttgtttatt ggaatttctt gaaacatacc tgatcaatgc aatgacaaca      420
gttaactagg tcaatattta taccaacata taacttgcaa ttctttctcc aagaattaaa      480
atacaaattc attgaaaact gctaaaaaac taatcgatac tttccaacat atttatactg      540
ttataagacc tatttcatca cttggaccct ccttttctaa catagctgtc aaaagaatg      599

<210> SEQ ID NO 31
<211> LENGTH: 599
<212> TYPE: DNA
<213> ORGANISM: Homo sapiens

<400> SEQUENCE: 31
ttataggtgt caatagattg agtgatgtgc cttaggcaca tgaaaaccag gctttccaga       60
tgcagctctg aggttaatgt ttcactgttg tatagcaact ttccatccga gggttcctaa      120
gagctttata actttacaaa caatctaatg tctttgaagt caatactctt cctttcctaa      180
atgaacataa attcttctcg aattcaccag ggaaaaaaag cacaatgact gctccattgc      240
ttcatcagtt ttagctgtgc ctgacactgg actccagctg cacttttta tataactgty      300 atagctctta tcacattatg gcaaaattat taatttatac atctgtctcc ccaaatagcc      360
agcaggcaac ttgatggcaa agactgtgtc ttattccct tggtacagtt tcagttcaac      420
aaccatttaa tgagcacgta ctctgtgcca ggattcaagc tagatggtgt caggttataa      480
agacaaatga aacacagcac aggcccttga ggatgctgtg acaagtgga ggagacaggt      540 acattaattg ttcatttcag cagagtgtgg aagaaactac aatggatatt taaagccct      599

<210> SEQ ID NO 32
<211> LENGTH: 599
<212> TYPE: DNA
<213> ORGANISM: Homo sapiens

<400> SEQUENCE: 32
```

| | | |
|---|---|---|
| aagcacaatg actgctccat tgcttcatca gtgttagctg tgcctgacac tggactccag | 60 | |
| ctgcactttt ttatataact gttatagctc ttatcacatt atggcaaaat tattaattta | 120 | |
| tacatctgtc tccccaaata gccagcaggc aacttgatgg caaagactgt gtcttattca | 180 | |
| ccttggtaca gtttcagttc aacaaccatt taatgagcac gtactctgtg ccaggattca | 240 | |
| agctagatgg tgtcaggtta taaagacaaa tgaaacacag cacaggccct gaggatgcy | 300 | |
| gtggacaagt ggaggagaca ggtacattaa ttgttcattt cagcagagtg tggaagaaac | 360 | |
| tacaatggat atttaaagcc ctgcatagac tttcttctgc ctctaatact ctaccccat | 420 | |
| cttctaatac tctccccatt gcttactgga ctgtaggtac attggttttc ttgctgtttt | 480 | |
| tttgaacata accagcatgt catcacatca aaatatttga actttccttt atggaatagt | 540 | |
| gttctcctac atattcacgt ggcttacccc tgcacatctt tgagtgtttt taattctgc | 599 | |

<210> SEQ ID NO 33
<211> LENGTH: 599
<212> TYPE: DNA
<213> ORGANISM: Homo sapiens

<400> SEQUENCE: 33

| | | |
|---|---|---|
| tatgtatatt gggtttgagc caagtaacta gtatgctgcc cagataatag acccttcagt | 60 | |
| ctcactctca agggcagcag ttgggggaag gagttgtttc tagggcagct ggagcgctga | 120 | |
| tgtgatgggc attggaatac actgagctag agcatgggct ttgcagtcag gaaaatatgg | 180 | |
| ctctgctagt ttaaatgcta tgtaatctca gttaggcaag ttagcatctc taaatatttc | 240 | |
| aattcccttc ctgtgggaaa aaaatgaat actttcattg tgtcataccc attaaatagy | 300 | |
| gttagatctg tgaaaggctt agcagagttt cagactcata gcaggtgcct aaggagagag | 360 | |
| aattagctaa ttaaaagtat tataagcata ttacaattat aatacactaa tgaagtataa | 420 | |
| aagtaatcta gtcgttcata tattctttga ctttttgcca cgtaaaacta aagacagat | 480 | |
| ctgagaattg ccctgagaga taactcagca tgctgtgaaa atgaaacaaa ttggtatagg | 540 | |
| ttgataatct ccctgaaaaa aaggattccc aagcaccata ggtgagaagg gcagtgtaa | 599 | |

<210> SEQ ID NO 34
<211> LENGTH: 599
<212> TYPE: DNA
<213> ORGANISM: Homo sapiens

<400> SEQUENCE: 34

| | | |
|---|---|---|
| aaatatgaca cattatttga aagatcctaa tgtgttagtc aaaatctttt tatgacagca | 60 | |
| aggattttaa ttagccatac attggtaatt tcagttagtc atacattttg taaataaaaa | 120 | |
| cggaagtgag gatggccaaa taggaacagc tccagtctat ggctcccagt gtgagtgaca | 180 | |
| cagaaggcaa atgatttcta catttccaac agaggtacca ggttcatctc actggggatt | 240 | |
| gtccgacagt gggtgcagga cagtgggtgc agtgcaccga gcatgagctg aagcagggck | 300 | |
| gtgagctgaa gcaggcaagg aatcgcctca cctgggaagt gcaggggtc agggaatacg | 360 | |
| cttttcctagc caaggaaagg ggtgacagac agcacctgga aaattgggtc actcccaccc | 420 | |
| taatactgca cttttctcat ggtcttagca aacggtatgc caggagatta tatcccacgc | 480 | |
| ctggctcgga gggtcctacg cccagggatc ctcactcatt gcaagcacag cagtctgaga | 540 | |
| tcaaactgca aggtggcagc gagggtgggg gtggggcgcc gaccattgct gaggcttca | 599 | |

<210> SEQ ID NO 35
<211> LENGTH: 599
<212> TYPE: DNA

<213> ORGANISM: Homo sapiens

<400> SEQUENCE: 35

| tgatgaaaac acctaactca ccttagaaga aagtatttgg catgaggaag cactcaaaac | 60 |
| ccatcactaa ttgctctaaa atcatatgtt caataggcta tgaattaagc taacttgtca | 120 |
| caattcctcc tatcatcact tccacatttc tcttgatgat attaacaact tcatagaatc | 180 |
| attcctctgt aatagtttgg tggaagaatc tgctatataa ataaatgcat gttatagaga | 240 |
| cactttgaaa agctcatgtc gcctttatct gacagcacct ctgttcagaa aagtggaaam | 300 |
| ctggctctat gagtatatgc attcatgagc tcttgattga aaggggtcag tttcagaaat | 360 |
| ctctgagttg gaggtcttgg gcctgagcct attaagataa ataactcccc cagggtaact | 420 |
| catcaatgag gagacttcag cagttaaatt ccctagacta agtctcatgt tctcactcag | 480 |
| cacactaacc catgcacagc taaattatct catccacaat ttcaattttt gattcaacta | 540 |
| aaaaatacat gcctataaag ataagtcttc aagtaagcca gacacacggt agtaggaag | 599 |

<210> SEQ ID NO 36
<211> LENGTH: 599
<212> TYPE: DNA
<213> ORGANISM: Homo sapiens

<400> SEQUENCE: 36

| tcatctgaaa cttctgtaaa tgctgtgaga agagcttggg gaagaagaga cattgaactc | 60 |
| tcttcaaaca taaccatgaa atgtgaagtc accctaccaa aaggagcctc tcatctatat | 120 |
| aaaaatgaaa acaaccagg caaaaagaa aaaaaaaaca ttttgctctt caagttaaaa | 180 |
| taataagaat caaaggtaa ggctgagtcc tgggaagtat gttatataaa tatcaacac | 240 |
| aagagagacc attatgttaa gaaggctcca gcaagaatta tagctgcttt cctgtttacr | 300 |
| tgacaatcta cctatgacaa aagttttcca ccctttctct tattgtagac ttttaacaaa | 360 |
| atctcatgct catactcttc tccatcattt aaaactcaac tcactggcat cctcactaca | 420 |
| atgccttacc tttgaaatgt acatcatgta aacttacagc caaaacgttg tggaataagg | 480 |
| agtgcagatt agaaaacttc ttaatttcaa tgcttgtcct aatactgtta ctaaaatgaa | 540 |
| tgaaaagtat attcctgggc aggcacaggt gggcagatca tttgagtcca ggggtttga | 599 |

<210> SEQ ID NO 37
<211> LENGTH: 599
<212> TYPE: DNA
<213> ORGANISM: Homo sapiens

<400> SEQUENCE: 37

| gagcccactt cctcattcat agacagctgt cttttccctg tgtcctccca tgatggaagg | 60 |
| aacaagacag aaccccgctg tctctttttat aagagcacta atcccattca tgagggctcc | 120 |
| acctttatca gttaatcagc tcccaaaggc cccacttcca aataccgtca cactggggat | 180 |
| tagatttcaa catatgaata tggagcaggg aggggacaca acatttagt atattgcaag | 240 |
| aactattttt cttgctgttt catgatgtaa ggtaagttct cttccgctgc tcctgtggas | 300 |
| agtacctcct actggtggtg tcatggtggc tgaggatgtc tgttatgaag caaaacagag | 360 |
| aagagaagag gcctcttttt tggctgtatt cagttaaagg agtcctacaa cagtgttgct | 420 |
| catactacaa ggtgttaaag aagttaatta aatagtcctc tcagcattca ctcataatct | 480 |
| tctctggaac cagaacttag acaagcatcc tgagtgatgg aaacattttc atggaggaag | 540 |
| gaccagacat tttgagaaca ttttatgtct atagtaaaag agaagagaaa acaggaata | 599 |

<210> SEQ ID NO 38
<211> LENGTH: 599
<212> TYPE: DNA
<213> ORGANISM: Homo sapiens

<400> SEQUENCE: 38

```
aaacactgac aaaaaaaaaa aaaaaagagc ctggcttcct tggctctgca tgtagataat     60
ctccctcagc taattacagt aaatgccaaa gatctaacat ctttcctgca gacccacaag    120
gaagatatat gagaaaatac tgtaggatgc ttgcaagact gaatttccaa agcagcttta    180
aagggaatta taaggaagat gttagaacat taggggaaaa tcagtgctgt attgcaaagg    240
aaatgtttaa ttgtaaagag ataactgttt ttttgtacat gtgttccaac aggagattcr    300
tgaaaactta actgaactta acatggttat atgagacagc aagtgacatg aaggagcaga    360
ccaccaagat tttggtagta tatcccagtg ttcctttgtc attggcaact tgttctcagt    420
aaaatatata tatatatata tatatatata tatatatata tgtttattcc    480
tcctccctca taattattaa gtgaaactcc cagttaccaa agttagttat tattttgatt    540
aatttggcat taaaccatta ggagtgatat acttaactct tcccatggga attttttcct    599
```

<210> SEQ ID NO 39
<211> LENGTH: 599
<212> TYPE: DNA
<213> ORGANISM: Homo sapiens

<400> SEQUENCE: 39

```
cattttgccc ctgccctaga gatctgtgga actttgaact tgagagtgat aatttagggt     60
atctggcaga agaaacttct aagaagcaac gcgttcaaga ggtgacagag cataaaagtt    120
tagaaaattt gcagcttgac aatgcagtag aaaagaagaa cccatttcct ggggagaaat    180
tggaaattgt gtttttattaa tagacttcgg agtatgtatg gaaatgcctg gatgtccagg    240
gagaagtctg ctgcaggagc agacctctca tggagagcct ctgctagggc agtatggaar    300
ggaaatgcgg gattggaacc ccaacacaga gtccccactg gggcactgcc tagtagagct    360
gtgagaacag ggccaccatt ctctaggccc cagaatggta gatccaccaa tggcttgcac    420
catgcacctg gaaagctgc aggcactcaa caccagccca tgaaagcagc caggttgagg    480
gctgtacccc gcaaagccac agaggcagag ttgcccaagg tgtaggagcc tacctcttgc    540
atcaacgtga cctggatgtg agacatggag tcaaacgaca tcattttgga acttaaagg    599
```

<210> SEQ ID NO 40
<211> LENGTH: 599
<212> TYPE: DNA
<213> ORGANISM: Homo sapiens

<400> SEQUENCE: 40

```
agatgagttt gaagggttaa aatgtcagac attatttgga aatcaaaaaa tcattatttt     60
cttgataatt agaaaataga ggcagggtta ataatgact tatttatatc taagataact    120
taggctcatt ttctccttta ttgaaataat acctgcagtg atagatattt ccagaagtga    180
gagatatatg tgtatttgta tatatttttc ccagagctta ttattttgca tattaccact    240
acatagagat gttgtaaaag aactaagagc aaactatggc aaaggcagat aatgaaggr    300
taaaattaat gtttaaaata gaatcctcaa caatcggtga caataaaggt aaatgataag    360
tgaaattgta tatttcagta atgtaagcat ataaaagaag atagcttttg aaagattgaa    420
ttaccctcat tcattctgaa gaaaaaaaat aaagttttat tatacataga tgctatggag    480
```

```
tggaactcaa ttgtgggtga tcataaaagt atctttact tgctgtccca agcatttgga      540
agtgtaacaa attccaagat tgggctgcag agcctcttta aaagggtat ccacatagt       599

<210> SEQ ID NO 41
<211> LENGTH: 599
<212> TYPE: DNA
<213> ORGANISM: Homo sapiens

<400> SEQUENCE: 41
aagagtttat ttgggacaag attgaggact gtggcctggg acacacttcc aaagtgcctt      60
gggaagtgct ctggcaaaca aaggagagac tcaagttttt aatgaaaaac gaggcaaatc     120
agcagaaggg gaaactataa aagtagttca tcaggaattc tcactggttt acagaagtaa     180
ctttgattag caattggcta tacattgtta aattacaggg taagagttat ggtggtaaga     240
gtatgttatt ttatggctac ttggtattag ttagtagcca caaatgctc acacagcaas      300 tggtttcaag aggtaatggt actcagttca atggggagtg aaatttgtta cattttaaat     360
gcctctttgg gactgaaaat gtaaaggagc tctcattgct cagataattt ttttctttct     420
cacattcaat atttattcaa caaatgccta ttgaatgaac ggatggatag atggtgaaag     480
ataaaatgaa aaaaattcaa tggtgtgcaa tatcaaagaa acatcagctt ggagccagac     540
atacagggat tcaaatttcc tatctgccac taactagctg tgtaatcttg ggaaataac      599

<210> SEQ ID NO 42
<211> LENGTH: 599
<212> TYPE: DNA
<213> ORGANISM: Homo sapiens

<400> SEQUENCE: 42
gagatgtatt aatggtgttg gttttatagg acccttagc tttgattctg ggtgcatatg       60
gcaatgtagc ctctatatgg tttctttggc tgtaaacagt atgagtaaca tctgtggttt     120
cctaggtggt ttaggctcta attattagtg gaggctatgg tgaagttttt ctgggggcag     180
ggatggcagg tgggtccata tctggtcccc attggtggaa gcagtgggct gagcatgctt     240
actcttgggc ccaagcatag cagatgctgg cacttgtgtt agtgggataa agtaggccar     300
ttcttgagcc tgtagtggct gcagtgggct gggtgggtaa atgggttccc atgtccccga     360
gaagtcaacg tggtatcagt gaagccagta gcagtggtgg gatgactctc tgggtcctga     420
gcactgcaca ttggtattgg tggtggttgt atgcaaggtt gccagtcaca gccccagaca     480
tacagttctc aaatgttcct gctctccaca gcagcagcac cacagcatca cacagaagca     540
ggtaggaacc acacatttca tgtgctagcc tgtgtatata ggctatgcta ccaaaatat      599

<210> SEQ ID NO 43
<211> LENGTH: 599
<212> TYPE: DNA
<213> ORGANISM: Homo sapiens

<400> SEQUENCE: 43
tgctctccac agcagcagca ccacagcatc acacagaagc aggtaggaac cacacatttc      60
atgtgctagc ctgtgtatat aggctatgct accaaaatat gtcatatgat aacaagtatt     120
agtgaaggta tgaggaaatt ggaagtattg tatatcatca gtgtaaatgt aaaatgacac     180
aactgctata gaaaacagta tggtggttct gtaaaaaatt aaaaatagaa cagcatatga     240
tccagcagtc ctagttttag atatttatcc aaaagaattg aatacaggat ctcaaaaagw     300
tgtttgcatt ctcacgttca ttgcagcact attcacaata gccaatatgt ggagacaacc     360
```

| | | |
|---|---|---|
| taaatgccca tcaacagatg aatggataat gaatatgtag tatatacaga aaatcctgtc | 420 |
| atatctacaa catggatgaa ccttaaggtt atgctaagtg agacagctca tcgtattagg | 480 |
| acaaatactg catgcttcca tttatatgag gtatctaaag gagtcaaact catagaagca | 540 |
| gaaagtagaa tgacagttgc caggggttat ggggagggga aaatgaagag ttgctatttt | 599 |

<210> SEQ ID NO 44
<211> LENGTH: 599
<212> TYPE: DNA
<213> ORGANISM: Homo sapiens

<400> SEQUENCE: 44

| | |
|---|---|
| atagaaaaag aaagtagatt agttgccatg ggatctggag aaggtgagat tgagactaac | 60 |
| tgctaataat taccaggttt ctttttttgac atgatgaaaa tgtctggaat gaaatagtgg | 120 |
| tgatgtttgt acaacatata agtaaactaa aaatcactat attgtgcatt ttacaataat | 180 |
| gaatgttgtg tgaattgtgt ctcaattta aaacttttg aggtatattg tttaatttgc | 240 |
| aaaaacagat ggtctctggc ttatggtagt ttaacataca attttttgac cttatgatas | 300 |
| gtttattaag gtattaagta cattttttgac ttatgagttt atcaggatgt actccatcat | 360 |
| aagtcaagga acatcgatat gtggtgatgt ttgtattatt gtttgaaatt tattttcata | 420 |
| ttaattctct tataatcaaa gaaactgtgt attatttaaa tcttttgaca tttgttgaaa | 480 |
| tttaattat atactagtat atgatccatt tggtcgatag tttataatta taaaaatgtg | 540 |
| cattcagttg tagttcatta tagtgatcta tatatgtcat ttaagtcaag tgtcttaat | 599 |

<210> SEQ ID NO 45
<211> LENGTH: 599
<212> TYPE: DNA
<213> ORGANISM: Homo sapiens

<400> SEQUENCE: 45

| | |
|---|---|
| gaaagtagat tagttgccat gggatctgga gaaggtgaga ttgagactaa ctgctaataa | 60 |
| ttaccaggtt tctttttttga catgatgaaa atgtctggaa tgaaatagtg gtgatgtttg | 120 |
| tacaacatat aagtaaacta aaaatcacta tattgtgcat tttacaataa tgaatgttgt | 180 |
| gtgaattgtg tctcaattta aaacttttt gaggtatatt gtttaatttg caaaaacaga | 240 |
| tggtctctgg cttatggtag tttaacatac aattttttga ccttatgata cgtttattar | 300 |
| ggtattaagt cattttttga cttatgagtt tatcaggatg tactccatca taagtcaagg | 360 |
| aacatcgata tgtggtgatg tttgtattat tgtttgaaat ttattttcat attaattctc | 420 |
| ttataatcaa agaaactgtg tattatttaa atcttttgac atttgttgaa atttaattta | 480 |
| tatactagta tatgatccat tggtcgata gtttataatt ataaaaatgt gcattcagtt | 540 |
| gtagttcatt atagtgatct atatatgtca tttaagtcaa gtgtcttaat cacgttaat | 599 |

<210> SEQ ID NO 46
<211> LENGTH: 599
<212> TYPE: DNA
<213> ORGANISM: Homo sapiens

<400> SEQUENCE: 46

| | |
|---|---|
| cagttgtagt tcattatagt gatctatata tgtcatttaa gtcaagtgtc ttaatcacgt | 60 |
| taatcagaac atttataacc tgatttttg tgtccatgct ttactaatta ctgaaaatta | 120 |
| gaatttccca caatttgtat attgccatta gatatgtcat ttttgtttta ttggtttga | 180 |
| tgctacgtta ttttagtcac atacaaactt agaagtgttc tatctttcta tttgaccatt | 240 |

```
ttatcattag aaaacattct acccttattc ctgataatat tttttgccat aaaatctacm    300
ttgtcagaca ttagctttct tttgctaaat tttacatgct gtttattgtt ccattttcta    360
cattcaaatt ttgtctttat gtttagagtc agccttttaa aagcagcata tagttgattt    420
tctaaaaata tgagcctgac aatcattgcc tttcacttga aaattttaga ccatttatgt    480
ttaatatacc actaatatat ctcaacttaa acatatcatc ttattatttg tcccaccttg    540
tctattttct ctcttttctc accttctttt gaattaatca actattttat tatttcatt     599

<210> SEQ ID NO 47
<211> LENGTH: 599
<212> TYPE: DNA
<213> ORGANISM: Homo sapiens

<400> SEQUENCE: 47
cttataagtc catgtctgat tcactcaata tttgtttgtt tttatgtgtt ttttctcgtg     60
tgtgtgtgtg tgtgtgtgtg tgtgtgtgtg tgtacatgtg tgcctggtct tttctttgat    120
atgggtaagt ttttattca aaaatgagtg ttttgaaaga aaagttgcat aaataaattg     180
aagccttaga gaatgttatc tgcttccaaa gagtatttag tcatacttct gttagaaaga    240
gtagaagctg attgccttaa tccaacagga ttaatcactt ttaaaagaga gtttccaacy    300
ttgtgatggt ttatttctag tttcccatga ctcatagaat atagtccctc ccatatgaaa    360
gcctgggagg tttaccaagg cttctgctca ttttttaat gtaaatgtat tacaatagaa    420
ataattcaaa gttctgctcc acttcctagt ctcttaacca caattttctg ctcagtctca    480
gcttctaaac tgctggttcc aaataagcaa atctctcaag gaaaaggcat tgcagaatat    540
tgggattatc tcaatgcatt tcccatctca ggaatcttgg ccttcaagcc ccattgcct    599

<210> SEQ ID NO 48
<211> LENGTH: 599
<212> TYPE: DNA
<213> ORGANISM: Homo sapiens

<400> SEQUENCE: 48
aaatttgcca tatgtgtatt atcttttgta aaatttttc tgttggtaat tatctatgtc      60
ttttgctcat ttaaagaatt atatttataa aataaattca taggatggta aattctgttg    120
ctgtgcatgt atgaaaagta gttactatgg aaaattcctt tacaaacaat gctgggaaat    180
ttgcttcata aatgaatcct taattagctg caaaacttat ttgttaacaa tactggatac    240
tgtattacta gcattgagaa ttaccattat tctttagttg caaaatttct tatggtctgr    300
caacataata aattattcat tgccatggtt tgatgaattc tgattattta tacttgaata    360
tatatgttat gttactgcaa tgaaaaggcc atttattcag tactatctca tcatcttctc    420
tttctaggga ttcatcatga atatccataa tatggtttct aaaaatgcat gaaggaatca    480
gaggagacct gctaaccatg aaaagaagag catagcaata gagaaccaaa gtggcacaag    540
aatgatcatc tttgaataat ttagaatcaa ataacatcaa atcaacaaac acttattga    599

<210> SEQ ID NO 49
<211> LENGTH: 599
<212> TYPE: DNA
<213> ORGANISM: Homo sapiens

<400> SEQUENCE: 49
caaacaatgc tgggaaattt gcttcataaa tgaatcctta attagctgca aaacttattt     60
gttaacaata ctggatactg tattactagc attgagaatt accattattc tttagttgca    120
```

-continued

```
aaatttctta tggtctggca acataataaa ttattcattg ccatggtttg atgaattctg    180
attatttata cttgaatata tatgttatgt tactgcaatg aaaaggccat ttattcagta    240
ctatctcatc atcttctctt tctagggatt catcatgaat atccataata tggtttctam    300
aaatgcatga aggaatcaga ggagacctgc taaccatgaa agaagagca tagcaataga     360 gaaccaaagt ggcacaagaa tgatcatctt tgaataattt agaatcaaat aacatcaaat    420
caacaaacac ttattgaagc ctccatctt tccatccttg attcctgtgt tattcagcat     480
ttttggtagg tttccagcag gcagccttct ctcaaaagta ctgttaggtt gtaatgtttg    540
caagtgctgt cttcaggctc tcttactgct gatgagtatc aatcacataa aattgtgta    599
```

<210> SEQ ID NO 50
<211> LENGTH: 599
<212> TYPE: DNA
<213> ORGANISM: Homo sapiens

<400> SEQUENCE: 50

```
taaaaaagtc tgaattttt tactcctaaa gcaccctatt tcttatttac ttctaacata     60
acctacaagt cactaaagca gttaggttag aaagaaaatg tctgcagtgt ctcatagagc    120 aaagaccct ccaaagactc cagactctgg gtgaagatta agagcaggcc agcaatatta    180
cactgtaata aatgacaact gtcaataaga agtaaaagta aagggtagt aatggcatct    240 taaaaaggca actacatttt gctttcttgc tttctttata tgttatatcc tgccttttaw    300
cttttcctat cgaccctggg tttatccgta tgccaacctc acatattaaa agcactctaa    360
tgtctccaca aagaagtact tgtgtgcatt tatttatcta tgtatattaa acgaaactgg    420
ttttctttga cttcttaatc cttctcgtta ggtccttaat tctcaataaa gaatatcctt    480
taaaacaaaa ttggtctaca caaacataca ggcagtgcca cctaatggca gctaccattc    540 atttttaaggc attcaaaccg gagagactgc tgtagtattt agatgtcttt gtgaacaaa    599
```

<210> SEQ ID NO 51
<211> LENGTH: 599
<212> TYPE: DNA
<213> ORGANISM: Homo sapiens

<400> SEQUENCE: 51

```
tagcataaaa tgaaagcaca ggacctcttg tttaaaatgc tgggaaaaaa acagtgctgt    60
tgaagtccta aaatataaag ctgtttcctt tcttccatga tctctctctt gacttcttgt    120
ggtgtctttt atttgttact tgtgacaatc taagttttaa aaactctgtt tttttatttt    180
ttaaattaaa aaaatagatt caggggccca tgtgcaggtt tattacatgg gtatattttg    240
tagtagtggg gtttggactt ctagtgtacc catcacctga atagtgaaca ttgtagcaaw    300
aggtactgtt tcactcctca ctccgttccc actttcctcc ctcttggagt ccccagtgtc    360
cattatttcc ctctgtagct ccatgtgtac ccattgttta tctcccactt ataagggaga    420
acatgcagtc ttgggttttc tgtttctgag ttattccact taggataata gcctccagct    480
ccatccatgt tactgcaaaa tacatgtttc attcttttgt gtggccatag caattttaaa    540
atataaggac atttaactag tatacaggat agtcaaaatt acacaatttc tcagacata    599
```

<210> SEQ ID NO 52
<211> LENGTH: 599
<212> TYPE: DNA
<213> ORGANISM: Homo sapiens

<400> SEQUENCE: 52

```
cctgtgtgac tgcacaggtt gtgaacctag ccctgtttgt gaaatgtagt aggacaaaaa      60
aaatcactct tctttaatca gggataaaaa caagacttac atttattact tcccacatgc     120
tgaatggtag gttaagtcct tcacatacac tatctcattt aaccatcaaa taacagtttg     180
gggtaggtat tattaccttc atttacagag aaggaaatag gagattttag aaactaagtg     240
atttacccaa tatctattga ctaaaaggta gtggagtagg gattttaacc cgggtttgas     300
tgaccccaaa gcccagttaa tctactactt ccataaaacc atttagtgca gattttaaat     360
tacaaaatat ttttaaactg ttagtattag atatacacat ataataaata cctacatgct     420
aataagacca agtatgaatt aatgaaatag catgattcac agattaattt tttaaaatct     480
cttctggcct tctaatgtaa tatgacaagt ggaacacata tgtttatctc ctttacctcc     540
tgaggcttca ttaaaatgat gatagtgctt ttttaaggta taagccatca actacaaat      599
```

<210> SEQ ID NO 53
<211> LENGTH: 599
<212> TYPE: DNA
<213> ORGANISM: Homo sapiens

<400> SEQUENCE: 53

```
agcccagtta atctactact tccataaaac catttagtgc agattttaaa ttacaaaata      60
tttttaaact gttagtatta gatatacaca tataataaat acctacatgc taataagacc     120
aagtatgaat taatgaaata gcatgattca cagattaatt ttttaaaatc tcttctggcc     180
ttctaatgta atatgacaag tggaacacat atgtttatct cctttacctc ctgaggcttc     240
attaaaatga tgatagtgct tttttaaggt ataagccatc aactacaaat atcacaggay     300
agaggctatt agtaaatgag caatttcaat aaatcaaatg agcaattcac taaaaaatgc     360
attacaaatc tatttataaa gtttaaaagc aggcaaaact aaataataat tgtttagtaa     420
tacatacata ggtggtaaaa ctattttttaa taacaaagga atgattatca caaccttcag     480
tgtagatgtt acctctggag gggaggggca catgatgaag agggagaaca caggaacttt     540
tatgctgttt aaccaaggca agaggtgcat gggtattcat tttgttatac atttattgt      599
```

<210> SEQ ID NO 54
<211> LENGTH: 599
<212> TYPE: DNA
<213> ORGANISM: Homo sapiens

<400> SEQUENCE: 54

```
tacagaaaaa acgaagaggg aaagagattat cacagaaatg ctaatagata atttccctaa      60
gatggatcca gtcttcagac taaagaact cattctgtat ccaggactta aatgtgtcct     120
ggaaaaaaat gttatatatc taaggataaa gagaagaccc aaataactgc caaggagaaa     180
atacagctca catgcaaagg aataagagtc aaagacgtta gctttctcat cagaacacag     240
aatgtggaaa gtcaatgaag aaaggtcgtc aaagttccca ggaaaaaatt attttcaacm     300
catatttcta taactaacct tataaccact gaaaagaaca tcataaaaat gttttttaac     360
atgcaaggac tcagaagttt actcaaatgc accatttctt agaaataaaa atgtatctca     420
agaaaatagg caagtattcc atcaaaacaa aggaagaaag cataatggcc tcagaaacag     480
tgatacccaa actaagagag gaatgaagca aaattccagg atgacatcca cactgctgtt     540
ctagagagtg ctagtaaaga ttggggccag agaacagaat gttttgcatg ggaagttca      599
```

<210> SEQ ID NO 55
<211> LENGTH: 599
<212> TYPE: DNA

<213> ORGANISM: Homo sapiens

<400> SEQUENCE: 55

```
aaaacaattt tgaaaaacaa caaagttgta ggatttacac tccctgattt caagatttac    60
tataaagcta tagcggtttt tacaatgtga tctttggcca agaatagaga agtaaatcaa   120
tggaacaaga tgaggtccag ccataagccc acctatacat ggtcaattgg ttttcaacaa   180
aaatactaag gcaatttaag aaagaaagat aatgttaata aatggtctgg aacaactgaa   240
tctccataag aaaaaaagaa gaatcttgac cactacctct taccatgcta aaaaaaaaar   300
gggggaggcg ggtgaatatc ttcatgagtg tggagtaaag atttgtttac actaggccaa   360
aatatgtgtg tgtgtgtata tatatatata aactttaata aattttactt catcaaaatt   420
aaaaactata actattcaaa aacaccatta tgaaaatgaa aaggtgatcc acagattggg   480
aggtaaatct ttccaaaaca tgtatctgac tagtattaaa gatatacaaa gagttctgta   540
tcaatcaggg cttgattaat gaaacagaac cactaagagt cccatacata tgtgtatgt    599
```

<210> SEQ ID NO 56
<211> LENGTH: 599
<212> TYPE: DNA
<213> ORGANISM: Homo sapiens

<400> SEQUENCE: 56

```
tctcttccta ttcagatgcc cttttctct ctctctcttg cctggttgtg ctggctagga    60
cttccaattc tatattgaat aggagtggtg agaggagtca tccttgtctt gtgcttgttt   120
tcaaggggaa tgattccagc tttccccagc taattaattt tttttttctc agagattagg   180
tctaattatg tttcccaggc tggtctccaa ctcctggcct caagtgatcc tcctaacttg   240
gccttccaaa gtgctgggat tacaggtgtg agccactgtg ccctgctcaa atccatgaas   300
ttttgagagt ggagatgtac gtgactttct tatcagaaag ctaagacctg ttccatgtct   360
gagtctcact gctcataatt tctttgagtc atttgctgac atgatcctgc tcacacccag   420
agaaagctgg gtggcactgt ggaaggaatc atggagtgag agcccagaaa cataaggtgt   480
agactgtctg ggcccgtgtga gcaactggtg atagcccaga tgctggactt ccctgcttta   540
ttttatctgt aaaacaatct taatagtatc tacttgtgtt aacttccaat ggctgatgt    599
```

<210> SEQ ID NO 57
<211> LENGTH: 599
<212> TYPE: DNA
<213> ORGANISM: Homo sapiens

<400> SEQUENCE: 57

```
caatattgtt aaaatagcca taccgcccca agcaatttat aaattgaatg ctattcctat    60
taaactacca acgacattct tcacagaacc agagaaaacg atcttaaaat tcatatgaaa   120
ccaaaaaaga gcccaaatag ccaaggcatt cctcaacaaa aaggacaaag ctggaggcat   180
cacactatct gacttcaaac tactgtaccg ggctacagtc acaaaagcag cacgatactg   240
gtacaaaaac agacacatag acaaatggaa cagaatagag aacccagaaa taagaccatr   300
caccaactat tatctgatct ttgacaaatc ttacaaaaac aagcaatggg gaaaggattc   360
cctactcaat aaatggtgtt gggaaaactg gctagccata gcagaggtt gaaactggtc   420
cccttcctaa cacctatatg aaaattaact caagatgaat taaagactta aatgtaaaac   480
ccaaaagtat aaaaactctg gaagataacc taggcaataa cattcaggat ataggcacag   540
agaaagattt catgtcaaag atgccaaaac aattgcaaca aaaacaaaaa ttgacacat    599
```

<210> SEQ ID NO 58
<211> LENGTH: 599
<212> TYPE: DNA
<213> ORGANISM: Homo sapiens

<400> SEQUENCE: 58

```
caatgtgaga gtacacttat cttgctttgc ccaaagatgt gtcagcaaca taaccttcag      60
actaaaacca aaaatttcaa tttagagtat ttatcccagg acctaaaaga cactaaggcc     120
taccacacac atcaatcatt ttaaacaatt ttataggagg actatgtgaa tttatgttat     180
tgagcctctt gtggcttggt accaggagtc tccttttgta agaaatcaaa taaatgaccc     240
tgaccttctt caagaattga aaagtggttc agagaagtac tttgttttat ccgggtagcr     300
ggttaagtat caaagtatca tcccttagag aaactgattt aacacattaa attatgaagc     360
aatctagagt gtccccaggg ctgctgctta ttattgacaa cataagtagg tggtctagaa     420
gtaaatgaat atatgggaag agcacagcag ctacacgttt cccaactcca tgggggcatc     480
attcacataa aagacatgtg agcagtgacc tctagaattg tacattaccc tcagtccctg     540
agggtttgag attttttgag actgtatact cttcagcctg tcacactcat aaactgcct      599
```

<210> SEQ ID NO 59
<211> LENGTH: 599
<212> TYPE: DNA
<213> ORGANISM: Homo sapiens

<400> SEQUENCE: 59

```
tgcctacctg tttaatacag tgacacagaa actcccattc gtctctaaat atttccacca      60
ccaacctgct aaaagagttt aaaaatccaa tctctagagt catcctttgt attaataatt     120
attactgaaa tgattatttt aaagtgtaat ggatacttgg aagaggcaat acaatctata     180
taatactgag cagaaaataa ttaaatacta acatctcttc cattcttctt agagcttctg     240
taagatatgc agaagaagtc aatgatgtca gagatgttat cttcttgcta caaattgagk     300
gatcacatac tcaacgtata cactaagcag gaaggaaccc attccaccag gaagaactta     360
gtcaatcttc ctactgatat agcccatgca ggtcctaagt gtagcaaaca atgcaaatca     420
tggtagagaa cagaaaatgc aaccagtagt gagagaaaga agaatcaaga caaacagaac     480
ttgggctaca gagaaaacac aatggccaag gaatccataa aacctatttc ttttacaggg     540
aatttggctg cctgaactcc tcagactata taaaaaagga gcaaaccctt ttttaagca      599
```

<210> SEQ ID NO 60
<211> LENGTH: 599
<212> TYPE: DNA
<213> ORGANISM: Homo sapiens

<400> SEQUENCE: 60

```
cactccagcc tgggtgacag agcaagactc tgtctttttt ttttctttat tactatactt      60
taagttttag ggtacatgtg cacaacatgc aggtttgtta catatgtata catgtgccat     120
gttggtgtgc tgcacccatt aacttgtcgt ttagcattag gtatatctcc taatgctatc     180
cctcccccct cccccaccc tacaacagtc cccgctgtgt gatgttcccc ttcctgtgtc     240
catgtgttct cattgttcaa ttccttaaaa aagaaagaa agaaagaaag aaagccttay     300
cttatcttat gggaaatcaa tggataacat gggtgaaaat actacaagaa atggctgaaa     360
taaataaaaa tgattgcctc tgggaggact gggaatttgg aggggcaaga caaaggacag     420
cagttttca ttattatgct attttatatt tcacatttat gaaatacttt gagatacaag     480
```

```
tgagaataaa tgaaacagtc aaactctgta tgttcaagaa gtatttgtgc cctttactct      540
gcttgaaaaa tctaaaattt tgatttagta aaaattgagg atgaatatat tctacaaat      599
```

<210> SEQ ID NO 61
<211> LENGTH: 599
<212> TYPE: DNA
<213> ORGANISM: Homo sapiens

<400> SEQUENCE: 61

```
gctaaatttc cttaactaca aaaggtaaa atacagtctt acatcaggca aatgaaaaac       60
aagcagagga acactatac aaagggaagc actataaaga ccatgcaagt atcacagaaa      120
ttagcacttt ataactttat aaaacatgat ctctccttta agtgtctaaa ttgtgactaa      180
ataatttaat acttacctga aaattatatg tttaatctgt gcaatcattt tttggcatac      240
aactttctgg actgttttg ttttttcatt tgattagttg gctgggctgt tgttttattk      300
tgtgtgtgca atgaaaaatc tcatgtattt tagtgagttc atctgtacgc caagtactcc      360
aaccatctct caacttttca aacaaatccc caatggcctc cctgagttaa atcagcagaa      420
caataatatt tcatggctca ttagtgcatg caatcaagca acagatcctg atccagtagt      480
ggaaagggag aagcaatagt tggtttcaat tttgttaata ccacaatatg cccataggcc      540
tcagccaaaa ggtgtaaatt aaggattgaa cataaccacg aagcaattgg ctgacaaca       599
```

<210> SEQ ID NO 62
<211> LENGTH: 599
<212> TYPE: DNA
<213> ORGANISM: Homo sapiens

<400> SEQUENCE: 62

```
tgactaaata atttaatact tacctgaaaa ttatatgttt aatctgtgca atcattttt       60 ggcatacaac tttctggact gtttttgttt tttcatttga ttagttggct gggctgttgt      120
tttattgtgt gtgtgcaatg aaaaatctca tgtatttag tgagttcatc tgtacgccaa      180
gtactccaac catctctcaa cttttcaaac aaatccccaa tggcctccct gagttaaatc      240
agcagaacaa taatatttca tggctcatta gtgcatgcaa tcaagcaaca gatcctgatm      300
cagtagtgga aagggagaag caatagttgg tttcaattt gttaatacca caatatgccc      360
ataggcctca gccaaaaggt gtaaattaag gattgaacat aaccacgaag caattggctg      420
acaacaaaaa agggggaaa aagacttta acagaaagag ctactgcaac ttaaattgtt       480
ctcacatttt aaatgtgtta acaatatcta ttttatttg taagccaact ttgtgttgca      540
actctgctga gtttcatctt ttaagcctct tttgcctctc tgagccagtt ttatcttcg       599
```

<210> SEQ ID NO 63
<211> LENGTH: 599
<212> TYPE: DNA
<213> ORGANISM: Homo sapiens

<400> SEQUENCE: 63

```
atccccaatg gcctccctga gttaaatcag cagaacaata tatttcatg gctcattagt       60 gcatgcaatc aagcaacaga tcctgatcca gtagtggaaa gggagaagca atagttggtt      120
tcaattttgt taataccaca atatgcccat aggcctcagc caaaaggtgt aaattaagga      180
ttgaacataa ccacgaagca attggctgac aacaaaaag ggggaaaaa gacttttaac       240 agaaagagct actgcaactt aaattgttct cacattttaa atgtgttaac aatatctaty      300
tttatttgta agccaacttt gtgttgcaac tctgctgagt ttcatctttt aagcctcttt      360
```

```
tgcctctctg agccagtttt atcttcgtat ttgaggcttt acattcaggt gacttctttc    420
attgcatttc aagggttctc taacccaaaa aaaagatgga agcagcacac gacaatcctt    480
tggggtgagt aaagaaaaat attagaattt ctatttccat tttctctaaa tataatatga    540
gtctacattt gatatatgga ttttcacagg cattcttgtt cagtaactat atcagagga     599
```

<210> SEQ ID NO 64
<211> LENGTH: 599
<212> TYPE: DNA
<213> ORGANISM: Homo sapiens

<400> SEQUENCE: 64

```
tggaattaca ggcatgagcc aacatacctg gccaatctct tcttattacg agtaactgtt    60
agccaagacc atcacttatg gccaaagtta ccacaataat tcagttaaca gctgcacaga    120
actgacaaga agaatgcatt gtgaaggcaa atcacagcaa aagcacacac agttgagaag    180
agctttgagt gggaggtagc ttttgcttga cattttttgtt ccagagatct agaagcttat    240 cttttctttta ctggcctccc tccaaggttc agccccagt gttagcaaca aaccagactr    300
tttgccattg ttcaatcaca gaatgttctt tcaaatctcc aaactgttct tgctttctgt    360
gcctgaaaac agctcctcat cctccttcaa ggcaaagttc ccaaatacgg catttgaatt    420
taattacaat ctattgatta tattggcttt ttcctttggc aaaacttagt gatcctactg    480
aaatagggat tatagtgtag caaagtaatt aggagttaaa tagaaaacct tcttctaagg    540
actgatgttc ccagaaagga ctcttgtgat ctcagtacaa atggtcccta aatgaatgc     599
```

<210> SEQ ID NO 65
<211> LENGTH: 599
<212> TYPE: DNA
<213> ORGANISM: Homo sapiens

<400> SEQUENCE: 65

```
tatacttcta tgtgtacaaa atcaggaaga acctcttatt ttccctagag cagatcttgg    60
ggatgttgca taccagttca catttattga gcacttgtag gtgctatacc aagtgttgaa    120
tggatactct ctcatttaat cctctcaaga gtcctcagac acaaccatta ttatcacact    180
tctgaagttg tagaaacagg catggagaac gaactcactt gtgcaaagtt acacagcatc    240
agtcaggatt cagattgttt tctgttgact ctgaagttca taccattaac tgctatactm    300
caaaaggtgc ttgcctaaag atggtcctat acttttgact tgtagtctc tgaagcttaa     360 gtacctctgg gttttgcagc agctatggac atagaagcat gtatggtaat aataatgata    420
aagctatcaa ttgtaataat tataatggtt aataatataa atgatagcat ttataacaat    480
ataattagat aatatagtaa ttaatatttt tataatgtgt tatatgttag taatattata    540
aaatagctat cttcaataac ccttacaata tgctagacaa tgttctgtgt gttaaacca    599
```

<210> SEQ ID NO 66
<211> LENGTH: 599
<212> TYPE: DNA
<213> ORGANISM: Homo sapiens

<400> SEQUENCE: 66

```
caaagataga taaaattaga tttaacaata ggaaacatat tttcaagaag tatagttcag    60
ttttactctt gggaaacata ttttttataga gctaaaagta aataatgtcc taatctgaga    120
ggcctgaaat aacactgctg aaatttacat gctttgttga atgcgacttt tagaaatgtt    180
tactcccaag aagtctaggt tcaagatgta tataaaatga tattgataat tcacatgtat    240
```

```
taattgttta ttatttgcta agcattgtgc tagatgcctt cctcttacag tcttatgagr    300
taggcacagt atttgcatcc ttgttttaaa gatgagaaaa ctgaagctta gggatgttaa    360
gtgacatgcc atactcatac ctcggcagga tttgagtgaa agtctgactc tcaaatttaa    420
gcttttaatt agtatcctat acagatttta taggacaaat tgttaagtc agagatacaa     480 gccctctgtt gttgtcacct tttaacaatc tttcttcctt cagagaactc ccttacccct    540
caagtacaca gcttcttcct gatttctagg gatccttctt tattgagaaa tttcatgct    599

<210> SEQ ID NO 67
<211> LENGTH: 599
<212> TYPE: DNA
<213> ORGANISM: Homo sapiens

<400> SEQUENCE: 67
cacctaagtt tcctttttt cattcaacaa gagctgcaat tacagtctga gaagtcagct     60
tttccaagtt tctgctgtgg taaaaatcaa cccccaaatc ctgttgtttt acaaaaaagg    120
tttatttcca gcctatgttc catattgact gcaggtgggc tgtgactctg ttccacgttt    180
tcttcattcc aggatccagg ctgaaggaac attctctatg acacaccatt cttgtgccac    240
agggaaaaaa gcaatggtga aatgactgat ggcaagtaaa gtttatggtt agacaacatr    300
taagtcactc atgttcccat tagtcaaaga aaagcacatg gccaaccctg gggctgggaa    360
gtacaatcct cctatgggga actcagtgaa taattgggga aaataataac aacctagcac    420
atggaccctg gggaagcaag ttctttaata cacatctaca atcatgtgaa gaaccatgac    480
atttaaagaa tataacttag aaagtaacta ttttgggaac tactgcttaa gaatgtttgt    540
ttaaggtctc ttaagtcacc agataatctg aagaagtttc tggtcagcag gaaaaggta    599

<210> SEQ ID NO 68
<211> LENGTH: 599
<212> TYPE: DNA
<213> ORGANISM: Homo sapiens

<400> SEQUENCE: 68
caagcctagg ggaggtgtca catcaagtag tatctgaaaa attgcaaaag tgaatcagta    60
tttttttttt aaggtggagt ctcactctct gttgccaggc tggagtgcag tggtgcgatc    120
ttggctcact gcaacctccg actccctggt tcaagcaatt ctcccgcctc agcctcccga    180
gtagctggga ttacaggcat gcaccaccat gcccagctaa tttttttgtat ttttagtaga    240 gacggggttc accatgttgg ccaggatggt ctcgatcagt tataatgagc ttttttttcay    300 atacctgttg gccacacgtg tcttcttttc aaaagtgtct gttcatgttc tttgcccact    360
ttttaatggg gttgtttttc tcttgtaaat tggtttaagt tccttataga tgttggatat    420
tagacctttg tcagatgcat agtgtgcaaa tactttctcc cagaatgtag gctatctgtt    480
tattccattg ataattttctt ttgctgtgca gatgctctta agtttaatta ggtcccactt    540
gtcaattttt gcttttgctg tactttattt tggtgtcttt gtcattaaat ctgcccatt     599

<210> SEQ ID NO 69
<211> LENGTH: 599
<212> TYPE: DNA
<213> ORGANISM: Homo sapiens

<400> SEQUENCE: 69
gtcactattc aagagctagg agagagagat gagatcaatg atgttcaaca gaaatctgat    60
ccaagccaca tacttgattt aaaattttct aatagtcaca ttaaaaacgg taagaaaaaa    120
```

```
accaggtaaa atgaattttt tttaaatttt attattatta tactttaagt tgtagggtac    180
atgtgtgcaa tgtgtaggtt tgttacatat gtatacatgt gccagaattt taatagtata    240
ttatttaacc taagatttct aaaatattat ttcaacatgt aataaatatt atttgtatts    300 tttttggtg ctgattcgga aatcagtatg tgttttaaac tgacagcaca tctcaattgg     360
actagcctaa tttcaagtgc tcaatagtaa catttatata gtggctacca tattggacag    420
ttcaacaata gataattcag aaaagagcta ttactacagc tgaaagaaac aagaaatgtc    480
aaagtcacgt gccaccaata ctgggttcgc cacattttct ttgtacatga aggatagctt    540
atttttattg ttctggggaa acagatgagg atcacatcac caggatgctc atccaggag     599
```

<210> SEQ ID NO 70
<211> LENGTH: 599
<212> TYPE: DNA
<213> ORGANISM: Homo sapiens

<400> SEQUENCE: 70

```
ctggctcctt gcttctagcc ctcctaggct cctagatcaa ttgtattccc attatctgag     60
gtagcagaac atattccata taaatgctaa accatcacag ctgtagatca tgtgcctgcc    120
cttttgaacc ccacattctc accaactgtt tctttgttag attaccaata aatagcatgg    180
gctcccagag ttcagggcct ttgcagcctc cacgatcgtg atggcccct ggtcccactt     240 tacttctcaa actgtctttt tctcaatcct ttgactccac tagactttat cgcccccacr    300
acgtggtgtt gggtctgatc accccaacat tcctggctgc ccaatgtgga gcaacaaaga    360
cctggtgaag aaatgctaga gcgtgtgaaa gcggacgatg cattgtcaaa ggatacccaa    420
gtacgtctaa aagaagctcg gtgggaaagc tgagcactcc ggaagaacca gggtaacaat    480
gggacaaagt gaaagcagac attctgcttg tttaaatttc tgaaggcatt tactacaaag    540
agatgaagtg aaagttagca ctcagaattt gttatcactc tttattgcag taaagcagt     599
```

<210> SEQ ID NO 71
<211> LENGTH: 599
<212> TYPE: DNA
<213> ORGANISM: Homo sapiens

<400> SEQUENCE: 71

```
tacatgttac aggggaaaaa tatccttctt tcagttctgt ctgacaagga cctaaagaat     60
cctattgatt ttattgctcg gctccaggag gctgtgtata aaaccataac tgataaaata    120
gctcaagatt tgtaatgcag cttcttgcat acaataatgc taatgcagac tgtcaaactg    180
ctattagacc cctgagaggg aaggctcatt tagctggata tactaaggct tgcgatggca    240
ttggaggtaa cttacataag gctactcttt tagctcaggc tatggctgga ttaagagtcr    300
gaaataatat gccccatttc tcaggctctt gctttaattg tgggcaattt ggacacagaa    360
aaaaggaatg tagaaaagga aatcaaaagg caagagctac catcaaacaa cagaaaagtc    420
ccagtgtatg tccccgttgt gaaaaaagcc atcactgggc aagtcaatgt cattctaaaa    480
gtagcaaaga tggacaacct ctctcaggaa acaggaatag gggcccgcct tgagcccctc    540
aacaaaccaa ggcatacctg gcacagccag tgcccttaca aatgtacaat tgtcccctg     599
```

<210> SEQ ID NO 72
<211> LENGTH: 599
<212> TYPE: DNA
<213> ORGANISM: Homo sapiens

<400> SEQUENCE: 72

```
aaaaaagcca tcactgggca agtcaatgtc attctaaaag tagcaaagat ggacaacctc      60
tctcaggaaa caggaatagg ggcccgcctt gagcccctca acaaaccaag gcatacctgg     120
cacagccagt gcccttacaa atgtacaatt gtcccctgcc acagcaggca gtgttgtcgt     180
agacctctgc agcacaattc ccctctcctt acttcctggg gagccacacc aaaaaaggtc     240
cctatgggag ttaggggacc cttaccagca ggaacagttg gtctattact tggaaagtck     300
agttaaattt gaaaggtgtc actgtgcata tgggaataat tgattctgat tataccggag     360
aaattcaatt agttactagt tcctcaactc cgagatctgc ttccccagga gaaagaattg     420
ctcagttgtt gctgttacct tacataaaac taggaagcag cacagtgaag agaacaggag     480
gctttggtag tactaatcca acaggaaagg ctgtatactg ggttaatcaa atgtctgaca     540
aaagacctat ttgcacagta actattcagg gaaaagatta tgaaggacta ctagatact      599
```

<210> SEQ ID NO 73
<211> LENGTH: 599
<212> TYPE: DNA
<213> ORGANISM: Homo sapiens

<400> SEQUENCE: 73

```
gttagctttg acactattaa aatttggaat taaatacttt tgggaggtta aaatatctgt      60
gggcaaagct acctctaatc cactgctttc aaggagagac atcaagaaga agcagtcttt     120
atcaaagtga gagtttcaca gcttaaatct gaaagaact gtcaaacatt tcttagtctc     180
ttggatacga tgtaaattag ttaagatata attacaacta atacttgtta ctattactac     240
catagcttca tttataaaat attacttctc cactaattaa atgaagcatt cagtgcttcs     300
cataaccaat taaatgttta agtagttaca ttatgcagct agatatgtga aaaccaagaa     360
taataagcca gataatacaa agaaaaaca gtgatgtgaa atgagttaca gcgaaaatga     420
gcaaagtgaa aacacattta aaccataaac ttttctgaaa atttgagtg tccaagagga     480 cagtcaagca tgtacacaga atcaggtggt atgaaatcta acagcaaaat atagggtagc     540
ccagtctaac aacaaaatga tatagtggat tggctgattc aggtttattt tcactcaga      599
```

<210> SEQ ID NO 74
<211> LENGTH: 599
<212> TYPE: DNA
<213> ORGANISM: Homo sapiens

<400> SEQUENCE: 74

```
cagtctttat caaagtgaga gtttcacagc ttaaatctga aaagaactgt caaacatttc      60
ttagtctctt ggatacgatg taaattagtt aagatataat tacaactaat acttgttact     120
attactacca tagcttcatt tataaaatat tacttctcca ctaattaaat gaagcattca     180
gtgcttccca taaccaatta aatgttaag tagttacatt atgcagctag atatgtgaaa     240
accaagaata ataagccaga ataacaaaa gaaaacagt gatgtgaaat gagttacagy     300
gaaaatgagc aaagtgaaaa cacatttaaa ccataaactt ttctgaaaat ttgaggtgtc     360
caagaggaca gtcaagcatg tacacagaat caggtggtat gaaatctaac agcaaaatat     420
agggtagccc agtctaacaa caaaatgata tagtggattg gctgattcag gtttattttc     480
actcagatat caagatacac ttgagagcac ttttcctgga ctaaattgta acttcaagg     540 tgaagatgta atcatgagac tagaaccctg tgtaaggggg cagcagagac aagtaaaca      599
```

<210> SEQ ID NO 75
<211> LENGTH: 599
<212> TYPE: DNA

<213> ORGANISM: Homo sapiens

<400> SEQUENCE: 75

```
cacagaatca ggtggtatga aatctaacag caaaatatag ggtagcccag tctaacaaca      60
aaatgatata gtggattggc tgattcaggt ttatttcac tcagatatca agatacactt     120
gagagcactt ttcctggact aaattgtaac tttcaaggtg aagatgtaat catgagacta     180
gaaccctgtg taaggggca gcagagacaa gtaaacaaag ctgactggca aaatccccca     240
tggtccacac agcatcctat tctacctgta tcatttaagg tgccagaaga taaacaaccr     300
caacctatta agaaagcaag aaacaaacct ggaaataaaa taaaagccta dacggaaagc     360
tatacccagt gtctgggtta tttgtgagat aaaataggat aatacctcac ttcatttctg     420
gaaagtctaa atccaattac ttaaaaaaaa aaactcacta tagagaacat taacaaatat     480
ttatctcttt ctacttttcc caatcacttt tccttaaccc tttgctatct ggttaacagt     540
aaaacatttc tttgaatggt cactaaaaat ctgctaaata ttacatgcaa taggcatgt      599
```

<210> SEQ ID NO 76
<211> LENGTH: 599
<212> TYPE: DNA
<213> ORGANISM: Homo sapiens

<400> SEQUENCE: 76

```
agagcacttt tcctggacta aattgtaact ttcaaggtga agatgtaatc atgagactag      60
aaccctgtgt aaggggcag cagagacaag taaacaaagc tgactggcaa aatccccat     120
ggtccacaca gcatcctatt ctacctgtat catttaaggt gccagaagat aaacaaccgc     180
aacctattaa gaaagcaaga aacaaacctg gaaataaaat aaaagcctag acggaaagct     240
atacccagtg tctgggttat ttgtgagata aaataggata atacctcact tcatttctgk     300
aaagtctaaa tccaattact taaaaaaaaa aactcactat agagaacatt aacaaatatt     360
tatctctttc tacttttccc aatcactttt ccttaaccct ttgctatctg gttaacagta     420
aaacatttct ttgaatggtc actaaaaatc tgctaaatat tacatgcaat aggcatgtct     480
tcatcttcaa gttttgacc tgtaccatga cattatggat cacctctttt tgacaattat     540
acaaactttg gttccacaac attgtactat cttaatcttt cccttacccc tttgagcct      599
```

<210> SEQ ID NO 77
<211> LENGTH: 599
<212> TYPE: DNA
<213> ORGANISM: Homo sapiens

<400> SEQUENCE: 77

```
ccacacagca tcctattcta cctgtatcat ttaaggtgcc agaagataaa caaccgcaac      60
ctattaagaa agcaagaaac aaacctggaa ataaaataaa agcctagacg aaagctata     120
cccagtgtct gggttatttg tgagataaaa taggataata cctcacttca tttctggaaa     180
gtctaaatcc aattacttaa aaaaaaaac tcactataga gaacattaac aaatatttat     240
ctctttctac ttttcccaat cacttttcct taaccctttg ctatctggtt aacagtaaar     300
catttctttg aatggtcact aaaaatctgc taaatattac atgcaatagg catgtcttca     360
tcttcaagtt tttgacctgt accatgacat tatggatcac ctcttttga caattataca     420
aactttggtt ccacaacatt gtactatctt aatctttccc ttaccctttt gagcctttt     480
tctgttcctt ttggcttctt catttaccaa tatattttcc ataagtattt aattataaag     540
tgtaacaaag tctaaagtga ttttagtaca tctgacatct ttttgaacaa ggcaaggac      599
```

<210> SEQ ID NO 78
<211> LENGTH: 599
<212> TYPE: DNA
<213> ORGANISM: Homo sapiens

<400> SEQUENCE: 78

| | | | | | |
|---|---|---|---|---|---|
| gcaggtggtg | gtgcgagtga | gcagcaccaa | ggaggcggca | gccgaggcca | aaaagagcgt | 60 |
| ttgtcgccgt | ctagattaca | tcacgcagag | cctccagcag | cagggcgtgc | aggtgagatc | 120 |
| tccgcggggg | aggaaataag | agccggaaga | cacaaaaggg | ttggcagatg | gtcgggcccc | 180 |
| acaggccccc | ctagcgggaa | gggagatgtg | gagggtctgg | agcgtttagg | acgcgtttgt | 240 |
| tgcaaaggta | ctccgggacg | ccaggacctg | gcagagtgaa | tatttgaccc | attcttctcy | 300 |
| tagacgaagg | taattattgg | cctcaggcaa | attaaaaata | aaagaatgca | aattgggtag | 360 |
| gtttttatct | ggggatattt | gcttcagtga | ttttgttttt | aaatttaaag | tgatgaaatg | 420 |
| ttaaaacttg | aaatgttagt | tgtaaatact | tgcccacgtg | gagtgctgga | cactaaatat | 480 |
| tttgttttgt | tttgtttta | ttccgcacca | tggaattggc | aagtgaagag | cacgacctgc | 540 |
| ttccttccga | tcatgtaaaa | ctttgcatgg | aatggttctt | gagtatgttc | cgcaaacag | 599 |

<210> SEQ ID NO 79
<211> LENGTH: 599
<212> TYPE: DNA
<213> ORGANISM: Homo sapiens

<400> SEQUENCE: 79

| | | | | | |
|---|---|---|---|---|---|
| aatagtcttt | gtttcctgca | accatattta | ttttaaaaaa | tcctacagtt | cactctaaat | 60 |
| agacaaccta | aacttatttt | tgtggccaga | gaaatgccag | accaattagc | ttagatatgg | 120 |
| atttctgtcc | atcttttaac | ctaatcctat | agcaaatcag | atgtgatcat | cctaagtagt | 180 |
| ttaaacctat | tacggcttac | cctgaatcac | atagttactg | ctcagaggta | gtaggggaag | 240 |
| agtgtatgac | atgaggattc | tgtatttctt | gttttaccta | ctgctttgaa | atgttactgk | 300 |
| ttattgctat | ttgtaatctt | cagatgttct | tgaattagtt | acagaattaa | ttagttcatt | 360 |
| tgatccttgt | tacggtcctg | tgccagtact | atcctgttta | aattattatc | ttcataaagc | 420 |
| atttgtaggg | caagttctcc | cctcattact | cttctgaaaa | aaattccctg | tctgcaagga | 480 |
| acagagggac | attttaagtg | acaacatgaa | attatagtca | gaaattccag | agggtggaaa | 540 |
| atttctatac | aaaaaatttc | tatttatatt | ttgcattcag | tttacaaatt | aatttcagg | 599 |

<210> SEQ ID NO 80
<211> LENGTH: 599
<212> TYPE: DNA
<213> ORGANISM: Homo sapiens

<400> SEQUENCE: 80

| | | | | | |
|---|---|---|---|---|---|
| cactatagaa | tgggagaaaa | tatttgcaaa | ctatgcatct | gacaaaggtc | taatgtccag | 60 |
| aatcctataa | ggaataagca | ggaaaaaaaa | caatctcgtg | aaaaagtggg | caaggaaat | 120 |
| gagtagacac | ttctcaaaag | aaaccataca | agcagccagc | aaacacatgg | aaaagtgctc | 180 |
| agcatcacca | gtcattggaa | agatgcaaat | caaaaccaca | gtgaaatacc | gtctcacact | 240 |
| agtaagaatg | gcttttatta | aaagtcaaa | aataacaga | tattggcaag | attgtagagm | 300 |
| aagaggagtg | cttatactct | tggtggaaat | gtaaattagt | tctgccactg | tgaacagcag | 360 |
| tttggagatt | tctcaaagaa | ctagaaataa | aattaccatt | tgacctggca | atctctttgc | 420 |
| cgggcctata | cccaaaggta | aataaatcgt | tctaccaaaa | agacacattc | acttgtatgt | 480 |

| | | | | |
|---|---|---|---|---|
| ttattgcagc | actattcaca | atagcaaata | catggaatca | acccaggtgc ccatcaacaa | 540 |
| tggattagat | aaagaaaatg | tgatgcttat | acacaatgaa | atactgtgta gccataaaa | 599 |

<210> SEQ ID NO 81
<211> LENGTH: 599
<212> TYPE: DNA
<213> ORGANISM: Homo sapiens

<400> SEQUENCE: 81

| | | | | |
|---|---|---|---|---|
| ctgcctttttg | tatttagaaa | taaacagtag | cttaatcaag | aaaacttagc agagtaggct | 60 |
| gatatatttc | aatattttc | agttttgtgc | cccttatagc | aggctttctc aatcttggca | 120 |
| gtattaacat | tatggattgg | ataactcgtt | gttgttgggg | gctgtcctgt gcattgtagg | 180 |
| atatttaaca | gcattcctgg | ccctaccca | tggggtgacc | agcatgtcct cctttacctg | 240 |
| aaactgttca | agttttaaaa | ctggcaggtc | catgtctgag | gaacctcctc agtttgaggw | 300 |
| tcacagggac | acttgatcat | cttgtgtatc | cacttagtag | tgtattcctc ttccccagct | 360 |
| gtgacaataa | aaaatgtctc | caggcattgg | cagatgtccc | ctagggcaaa atcatctggt | 420 |
| ggagaaccac | tgccctatag | ataaacaaaa | aatctcatac | tctgtgttgg aacccaccag | 480 |
| ccagactatc | agaaacgtat | ctatagtgaa | acaaagttag | gtttatttag catgatgcaa | 540 |
| caaagaataa | tgcatcccaa | aggaccttag | gagtgtttca | gaaacaggta ttcaggagg | 599 |

<210> SEQ ID NO 82
<211> LENGTH: 599
<212> TYPE: DNA
<213> ORGANISM: Homo sapiens

<400> SEQUENCE: 82

| | | | | |
|---|---|---|---|---|
| agaggattac | agttaggcta | ggtgtgcctt | tagtaaaggc | acagcaatca agcagaaaaa | 60 |
| gaatgttaat | tatttcttgt | ggttgcaggt | ctgttagttt | ctgttagaaa ctttggctct | 120 |
| gttaaaaact | ttcttagatt | ctatgtcctc | tggaaacatt | gtttatgttc tgcttagacc | 180 |
| ttctccatct | gattgtcaac | aggcaatttt | tatttctcca | ttccctgtaa tattatttag | 240 |
| aatttcaaaa | tatatcagat | attttactat | atagagaagc | aagataactg tcttcttatr | 300 |
| tgggttgttt | tcagactgca | cacacttccc | tttaaaaact | actgggctgg cataggttcc | 360 |
| aagatggcca | aataggaaca | gctccagtct | acagctccca | gcgtgagcga tgcagaagac | 420 |
| gggtgatttc | tgcatttcca | actgaggtac | tgggttcatc | tcactagggc ttgtcagaca | 480 |
| gtgggtgcgg | gacagtgggt | gcagcccatg | gagcgtgagc | cgaagcaggg cgaggcatca | 540 |
| ccttacccgg | gaagtgcaag | gggtcgggga | attccctttc | ctagccaagg gaacccgtg | 599 |

<210> SEQ ID NO 83
<211> LENGTH: 599
<212> TYPE: DNA
<213> ORGANISM: Homo sapiens

<400> SEQUENCE: 83

| | | | | |
|---|---|---|---|---|
| gaagcaattc | gataaagaaa | ggagtctttt | caacaaatgt | tgctgcaaca gtcaaatgtc | 60 |
| tgtatgcaaa | aaaatgaacc | tccacactca | cctcacacct | tatacaaaac tttgttcaaa | 120 |
| attggtcaat | attgagcatg | tagcatctgt | tgcctgttac | caggatagaa gtccaagcac | 180 |
| ttctgcccac | tgcattttgg | tatgagagtc | accaagaaaa | cacaatgcag tcaagcactg | 240 |
| gatggaacaa | accttactta | tgtagagaaa | agacaagagt | gacatcagag tcagtagtas | 300 |
| atgtcagtcc | cccatggcca | gcaactgctt | cccagcagct | aatgcagggg cagttgacct | 360 |

-continued

| | |
|---|---|
| acatgcacat ctcttgtgct gcaacagaag gactcagtcc ccttcctgca gggtacagat | 420 |
| atagtagtga ggttggtcag gtgtcatatg acatacaacc tttaagtaga agcaaaaagt | 480 |
| acatattgag tctgaaatgg ggaaggtatt cccatacaag gaaacaagcc cagcacaagc | 540 |
| tctgaaagat actttatctc ttagtaagca agtgttccag ggccacagcc cattcctgg | 599 |

<210> SEQ ID NO 84
<211> LENGTH: 599
<212> TYPE: DNA
<213> ORGANISM: Homo sapiens

<400> SEQUENCE: 84

| | |
|---|---|
| tttgagctttt tcgaattttg gattttcaca tttaggatgc tcaacctgtg ttaccaaaaa | 60 |
| gcacagtcca tgaaacaaac aaaaagataa attgtatttt atgacaatta aaaactcact | 120 |
| ttgtgaaaaa cattgttaag aaaatgaaaa gtcaatctat agactgggag aaaatatttg | 180 |
| taaattacat agctgataaa ggacttgtat ctgttaagaa aatgaaaagt cagtctatag | 240 |
| actgggagaa atatttgta aattacatag ctgatgaagg acttgtatca agaacatatr | 300 |
| tagacctcaa ttcagcagta acaaacagct caataaaaat gcacaaaaga tcttaacaga | 360 |
| cacttcgcca aggaacttat acagatggca aataggcaca tgaaaagata ctcaacatta | 420 |
| cttgtcaata gggaaatgga aaataaaacc acaatgaaat actgctatgt acctattaga | 480 |
| atggcttaaa tacagtaaca ctgataccaa atgctgggaa ggatacagag caacaggaat | 540 |
| tctcgttcat tgctggtgag attgcaaaat tatatggcca ctttggaagg tagtcttat | 599 |

<210> SEQ ID NO 85
<211> LENGTH: 599
<212> TYPE: DNA
<213> ORGANISM: Homo sapiens

<400> SEQUENCE: 85

| | |
|---|---|
| ttggaagcat gtcactaagt gcagcccaca ctcactcaat aaatactact ttatttcttt | 60 |
| tgttgctcaa ttgttctagc tttggccatt gggacttctt tcaggttggc tcctttatct | 120 |
| gtttgacata cccctttcct ttacttttg agcactttct tactttctgt tgcaagatat | 180 |
| tataggctta tgcagtttcc ttgccccagt cctagaataa gcccttctc caagaagcat | 240 |
| agtaccttt ctttgagatt tatgtagaac caagatctga atgctgagac tgctcactgy | 300 |
| tattggggtg tcattccttc taggctctct cagtggacag agctaggtta catatatata | 360 |
| tgcatagaca tatatatacg cacacagata ctaacttaca tgtaaaattt tctgtatttt | 420 |
| tccacctgta caatatacaa aggtaaacat gagttcacac tgatgttttc aactctaatc | 480 |
| ctgaatcaca gaattcattt taaccttcca tttttatctg taacttccct ctctgatagt | 540 |
| gagaaacctg gctcccacca tccactatcc acttatttat ttgtttaacc ccagtatat | 599 |

<210> SEQ ID NO 86
<211> LENGTH: 599
<212> TYPE: DNA
<213> ORGANISM: Homo sapiens

<400> SEQUENCE: 86

| | |
|---|---|
| tttaccgtat tgtgataaat attgtttaaa aatgaaaacc attcaacctt tatacaaatt | 60 |
| gaaaagaata aaactatttt caaattataa aaggagtgac atttatgaaa ttttaagcaa | 120 |
| aatcaatttc tgaattcatt ttatgtcact tttaggaaag ttttaaaaca tcaggcaaag | 180 |
| ttcttttgc atattttatg ttttttctgat tttaattagt gtaggtttct aatttatgtt | 240 |

```
ttagagtaat tgcatcaaat atttagtaat catactcttg gactttttct gtttcaggcr      300
gaaaatataa ctgtgacaaa ggattttagg agagtggaaa atgcttatca catggaagca      360
gaggtatgta cttaacaaat aattggaagc agcatgattt tgtggagaca gtcattttta      420
ttcttgaact gaaatgaatg gtgaaaaatg cttctcatga tattaataga agattatttt      480
tctcaaaatc atcttggtgt tatatatcta tttcggcttt taaataaact tgagatttaa      540
aagaaagttt aaaatggaat aaaaacagca agtgggaaat agcagttaat tgccactaa       599

<210> SEQ ID NO 87
<211> LENGTH: 599
<212> TYPE: DNA
<213> ORGANISM: Homo sapiens

<400> SEQUENCE: 87
aaatgcaaga tttgaatttc catattcagt ggacccagtg ggtgcccagc gcaatgaaca       60
acaacaacaa caaactcatc aaagcatatt ggaaatgtta aaccccagg aataaaagga      120 ctccaaaagt tctagagaaa gaaaatagt tcacaaacca agggtcagaa atctgaacag      180
caattggacc tctcagtgtc aacactggaa gctagaaact gaaaagcaag acagcaacat      240
cttccaattc tgagagaaaa caatgtctaa tctagaaatc cttacctggc caaaaaacar      300
tgaaggagac ggtaatacaa ggacaagcag acagggctga ccagaagtgt cacactgttc      360
tttatttggc caggatctga tggattaatg ccctctgaaa gatgttaaaa atgtgaaaca      420
tcactcctgc atacaaggtc tcaaaacatt tccctaccat acgtgaggaa gcaaaccaag      480
aaagagaaaa acaggagttc ccaggtaatg gcaaggaat gtccccagat tcaggggaca      540
ggaggactaa gggcttcagt aaaatgcctc caagaaaaaa ataaaggaac tcatagatt       599

<210> SEQ ID NO 88
<211> LENGTH: 599
<212> TYPE: DNA
<213> ORGANISM: Homo sapiens

<400> SEQUENCE: 88
ataaaattta aaatttagtt cctcagtcac actagccata tttcaagtac ttgaaggcca       60
caaatggctt gagactacct tgctgaacag accaaggtca aacactgaga taataatgat      120
tcttaaggcc atttgaaagt taacagcaag tatgtattac tgctatctac agtaagaatt      180
acattttatc tacaggcaat cataagccat gtctgttatg cagcataggc tttccattct      240
ctatacatct aggtcataga gttttttccat tgataaatct ggatgtttat ataccaacak      300
tactttctta caacatattc cagtatatag tgtccagctt cacccacttt ttaaagtggc      360
cctgaaacaa ttttattcat cttattggag tgttgctgta ggggaagagt agaagctaag      420
aagagtttga gttcaacacc attatatcca aatcctgacc ttactactgg aatgtaagct      480
ccttgaaagt ggagatcttg tctgtcttgt tcacagttgt gttcccagcc ccagaggtag      540
tctcagggcc aatatcaagt atgctctcaa atatttgctg ggaaaattta ctagctgga       599

<210> SEQ ID NO 89
<211> LENGTH: 599
<212> TYPE: DNA
<213> ORGANISM: Homo sapiens

<400> SEQUENCE: 89
atacatacat acatacatac atacatacat acatacataa aatgcccagt atcttacaag       60
actgtagttc acagtgggta attcaaatca gacactgctc ttcaagagag gtaatattaa      120
```

```
tagaaatctt tcaagaagga ttgttttcta ctattaaaac aataaaactc ttataaacct    180
gtttatcaga aggatatttc tgtttcagca actcctggaa tccttcttca acatcccaac    240
caacaattac tcccagatag ccatgtcacc tgtgaattat catgaatccc acatcaaatr    300
aacaaatact gcctctggac tctgaatgta agttggttca ttataagagt gagaaaaga    360 agactaagaa aaagcatact gtattctttg ctacataggg tttaaacttt attaggaggc    420
caggcatggt ggctcacatg tgtaatccca cacttcggg aggccgaggc aggtggatca    480
cttgagacca agagtttgaa accagcctgg acaacatggc aaaacccgt ctctactaaa    540 aatacaaaaa aaaaaaaatt agctgggtgt ggtggcacac gcctgtaatc ccagctact    599

<210> SEQ ID NO 90
<211> LENGTH: 599
<212> TYPE: DNA
<213> ORGANISM: Homo sapiens

<400> SEQUENCE: 90 ccattttca gaataagaca ctttttcagt gtctttcaaa aataaagatt ctgtctccta    60
tcctgctcct tttttcaaag aacaattttg ggcaaagagt aaaatacaga catatagttt    120
cagtgcttca tatggacatc agttttacgc tggtcacatt aattatgccc taattatttt    180
ttatcttccc cttcacaaga ctgtgaactc ctcaagagta gggctatgct tgaaacagtt    240
tttttcccaa ggtttgggta ataaaaggct aaggaggaaa aaagttggct gtgaggtaty    300
gtgctttatt ctcaaataag acagatactg tttatggcaa agttacctga acattggtac    360
acctggaagc agggatggga aatgcaggac acatattcaa actgtgtttg cacattttgc    420
agtccaataa gcatgctttt atttctccag gcttagctt tctcaaaaag tagttttgtgg    480 ctatgcaaca acatacattc tgttgtgtaa acaagcctct taaatcattt cagaacctat    540
gttcatttca gcttattgg atcagctata agtgtgtatc tttgccctt acctcctat    599

<210> SEQ ID NO 91
<211> LENGTH: 599
<212> TYPE: DNA
<213> ORGANISM: Homo sapiens

<400> SEQUENCE: 91
aaatacaacg ctttagaagt gttttctcta aagattaga cacttcattg accaatatta    60
attaatgata tttcatattg tttggtgata actctggaaa cataacactg caacagccac    120
ctaaataact atgagaatac atgaagctct gagttttgga cagatttcag ccctcagttg    180
atcactgtag ccctgatgac aggaaaagtt gaaacatcag caatgttcaa agagccatgc    240
aattactgct tctctatgtg tgaattagaa tattcagaaa gggacagaga catgcagttr    300
aagaaacagt aaattccttg aaaaatagtg tggcatgata gggcctataa tattacttcc    360
agaatatatg gaggtaatac tttgaatgct aagttttcag tctgctactt gttagaaatg    420
ttttttttga gattgaatct tgctctgttg cccaggctgg agtgcagtgg tgcgatctcg    480
gctcactgca acctccgcct cctgggttca agtgattctc ctgcctcagc ctctcgagta    540
gctgggacta caggcacatg ctaccatgcc tggctaatgt tttgtatttt tagtagaga    599

<210> SEQ ID NO 92
<211> LENGTH: 599
<212> TYPE: DNA
<213> ORGANISM: Homo sapiens

<400> SEQUENCE: 92
```

```
acaaaaatac aggaaaaggg tggaagggaa acaatgaaaa agttcaggtg ggtcacaaac    60
atggacacaa ggagtctgaa aggcaggcct tgacatttgt ctgaataata ctaacgatga   120
cccttcggag tttcacggga gaggagggtt gccagactgt aatggagaga aactggactt   180
agttgctaat taggatgatg gtgcaaggtc catgacaggg gatgagggaa tgcctgctcg   240
gggaggggaa aagggactg gacggagggc acggcaggat ggcctaggga ggacgggcgr   300
gggcctatca gttacaagag gaaggagaaa gaggatactg gttttcctct gcataaaaaa   360
cgcgatggat tctcaagaat ttattgaaag tctgtgtgtc caccatagtc caggatattt   420
tggaatattc aagggaaata caaatccaag aatttagctc aggaatcagc atcagaacag   480
aatccccgaa gagtaaacta ttcatggaaa acagtagact gataacattt gaaaaactga   540
tttcccatag aaacaatagt tactgtttga cgaattatac aacgtagacc taggtcgtg    599
```

<210> SEQ ID NO 93
<211> LENGTH: 599
<212> TYPE: DNA
<213> ORGANISM: Homo sapiens

<400> SEQUENCE: 93

```
ggtggcatgc acctgtagtc ccagctactc gggaggctga ggcaggagaa tcccttgaac    60
cctggaggct gaagttgtgg tgagctgaga tcacaccact gcactccagc ctgggcaaca   120
gagcaagact ctgtttcaaa aaaaaaaag tacaagtcat tactgggcc gggcgcagtg   180 gctcacgcct gtaatcccaa catttggga ggccgaggca ggtggatcac ttgaggtcag   240
gagttcaaaa ccagactggc caatgcggtg aaaccccatc tgtactaaaa atataaaaaw   300
tagctgcgca tagtggcaca cacctgtaat cccagctact tgggtggctg aggcacaata   360
atcacctgaa cccaggagcc agaggttgca gtgagccaag attacacact gtactccagc   420
ctaggtgata gagcgagact ctgtctcaaa aaaaaagtca ttgctgagaa gatgactgca   480
tctttaaaat acagtttaga ctaaaagtg atgagagtga actaattaat ggctatttac   540
agtgaaacct ctactttttt cactccagga gtatttcaac tatttatatc aaaggaata    599
```

<210> SEQ ID NO 94
<211> LENGTH: 599
<212> TYPE: DNA
<213> ORGANISM: Homo sapiens

<400> SEQUENCE: 94

```
tcagcagaaa gctaacagca ggagatattg ggtgcctatt ttcagcattc ttaaagaaaa    60
gaaattctaa ccaagaattt catatcctgc caaactaagc ttcataagtg aaggagaaat   120
aaaatctttt ccagacaagc aagtgctagg ggaatttgtt accactaggt cagccttaca   180
agagatcctc acaggagttc taaacatgaa aatgaaagaa tgataactgc taccacaaaa   240
cacacttaag tacatagccc acaaccacac ctaagtacat aggccacaca gtagaaactw   300
caaagcagct agctaataac ttcatgatag gatcaaaacc tcacatatct tgcttgagcc   360
caggtatttg ttaccagcct agccaacata gagggatccc atctctataa aaatacaaa    420 attagctggg tatggtggca cacaccggtg gtcccagcca cttgggaggc tgaggtagaa   480
ggattgcatg agcctagaag tttgaggctg cagtgagcca tgattatgcc actgcactcc   540
atcctgagtg acagagtaag accctgtctc aaaaaaaaat tatttttaaa atatcaata   599
```

<210> SEQ ID NO 95
<211> LENGTH: 599
<212> TYPE: DNA

<213> ORGANISM: Homo sapiens

<400> SEQUENCE: 95

```
gcacacacca agcctggcta attttttgtat ttttagtaga acgggggttt caccacgttg    60
gccaggctgg tcttgaactc ctgacctcag gtgatccacc caccttggac tcctaaagtg   120
ctgggattac aggcgtgagc cactgtgctt ggcctacaac atgtatttct taaataacaa   180
gacttgaaaa tcaaaattac tccttgatct gtgaggtgca gaacgatgt tgtgttagca   240
ggcatgaaag caacactaat caccttgtac attgccatca gagttcttgg gtgaccaggy   300
tgtcaatgag cagtagtgtt ttcaaaggta tcttttttat tttttatttt ttttctgga    360
aagcaggtct taacaatgga cttaaaatat tcagtaaacc atgctataaa cagatgggct   420
gtcatgcagg ctttgttgtt ccattgacag agcatggtag ggtagattta atataattct   480
taagggccct agaattttg gaatggtaaa gaagcactgg cttcatctta acaccagctg    540
cattagcccc caatgagagc ctgtcctttg aagctaggca ttgacttctc tctagctat    599
```

<210> SEQ ID NO 96
<211> LENGTH: 599
<212> TYPE: DNA
<213> ORGANISM: Homo sapiens

<400> SEQUENCE: 96

```
ggagaaaaga acaaagactc aggaacttct aagtgtttag gatgactggg atacaaaaga    60
gagaagaag gtaaagaac ctggaatgtt aggcaagagc caagtaataa agagtcttgt    120
gtaacaggca aaaaatttaa aatgtttcca tatatgattt gaaggcaagg aagtgttttc   180
tctgtgtgta cgtacacaca tccacatgtg ctagagagaa ataaaaagat cgctttggct   240
gcaatatgag agagggactg gttaagaaag agttgagaac tgaggcagga agaccagttw   300
ggaaactagg aaaatagtcc aagcaagaaa ttatgtaggc cttgaaataa tgtcatggag    360
gtgagaatgg agaggagaga atagatttaa gagatgttat ggagggagaa acaacaaaaa   420
caaaaagctg ttgaacagat tcagttgctg aagagaaggc taggatgact ccctgatttt   480
aagtttacac gggtagatcc caatgccatt aacaaaaata agatttcagt agagaaatta   540
aattttgaga gaggtttctg aagacaacaa tgaagaaatg tcttagacac actttgaaa    599
```

<210> SEQ ID NO 97
<211> LENGTH: 599
<212> TYPE: DNA
<213> ORGANISM: Homo sapiens

<400> SEQUENCE: 97

```
ttcaaagctt tggaatgttt cacagaattc tctagtacta aaacatacaa acaaaattta    60
aaaattaaga gttattgaac ctaaagataa gaaaaaaggt taacctgaat tatttgaatt   120
agccaagaca acaaaacctg aaggatgctt aaagctttct taggaaagct actttctaat   180
aggaaaaagg cgtatccaac tagaaactct taatagtttc agccctttta gaagctgtcc   240
catcatttca aaatttcgaa ggcaagtctt ggcaaattgc tagctagtgt gggtactgtr   300
atttaaattc aggtagttta gatcagagtt gccattttta agcattagtc tataatgacc    360
taaacctcaa tttaattctt cttattaaaa acttttttt aaaataggaa attaataaag    420
aaggcaaaaa caacagtgtc tgctaggaat tactaaaact cagtatattg catttggcaa   480
agtaaaagct taaattaaga aaatcatcat atacatttca atttagaaag tgagtcttac   540
ttgttttccc tggtattgca gatgcattag cttttgtaat aaaagtcttt gcagctgaa    599
```

<210> SEQ ID NO 98
<211> LENGTH: 599
<212> TYPE: DNA
<213> ORGANISM: Homo sapiens

<400> SEQUENCE: 98

```
gttttgtctg tatgagccat ttgaatttag agtcggactt ttctttaaga atctcaaaac      60
ttggaagatt tctgttctaa acacaaaaat acataattgt taaaatgctt cagtttacct     120
tttcatcaaa agattaggaa aaagggatgt aaaaaacaat aattaaattc taaatatttt     180
ttactggaaa aatatttaca ttacagtatt tactgaacaa aggtattttc ctccaaggaa     240
tggttgaaca cttttttttt tccctcacag atttacagca tgagtttgcg cctgtctgcw     300
ttctttgaag aacacattag ttcagttttta tcagattata aatctgctct tcgttttcat     360
aaaagaaata ccataaccaa aggaggaag aaaagaaaca gaagcagctc tgtttccagt     420
agtgctgcat caaggtatttt aatttctttt aaataccact agctgatcta taactttcat     480
ctaaatgata gaacttggtg ttttttaata cttcctttac tattccctat attgcagaat     540
gataatttga catgcaagtt cctatgatgt ggaggatttt taatcttttta actaaagct      599
```

<210> SEQ ID NO 99
<211> LENGTH: 599
<212> TYPE: DNA
<213> ORGANISM: Homo sapiens

<400> SEQUENCE: 99

```
gacaataagt tttgtctgta tgagccattt gaatttagag tcggactttt ctttaagaat      60
ctcaaaactt ggaagatttc tgttctaaac acaaaatac ataattgtta aaatgcttca     120
gtttaccttt tcatcaaaag attaggaaaa agggatgtaa aaacaataa ttaaattcta     180
aatatttttt actggaaaaa tatttacatt acagtattta ctgaacaaag gtattttcct     240
ccaaggaatg gttgaacact tttttttttc cctcacagat ttacagcatg agtttgcgcy     300
tgtctgcttt ctttgaagaa cacattagtt cagttttatc agattataaa tctgctcttc     360
gttttcataa aagaaatacc ataaccaaaa ggaggaagaa agaaacaga agcagctctg     420
tttccagtag tgctgcatca aggtattttaa tttcttttaa ataccactag ctgatctata     480
actttcatct aaatgataga acttggtgtt ttttaatact tcctttacta ttccctatat     540
tgcagaatga taatttgaca tgcaagttcc tatgatgtgg aggattttta atcttttaa      599
```

<210> SEQ ID NO 100
<211> LENGTH: 599
<212> TYPE: DNA
<213> ORGANISM: Homo sapiens

<400> SEQUENCE: 100

```
tgattgcagt ataagggggg ggagtatgaa ataaataaga attattagaa aaaagggact      60
cttgataagg ggaacaggag tgattattaa gagttctagg acttgcagtc atcataaaaa     120
tcctgtgcga atccctgcac tgagaagtga tgctttgtgt agtaataatc ataacaccac     180
ctgttttccc tctcctagga ctacagagac atcattgaca ctccaatgga ttttgctacc     240
gttagagaaa ctttagaggc tgggaattat gagtcaccaa tggagttatg taagatgty     300
agacttattt tcagtaattc caaagcatat acaccaagca aagatcaag ggtatataat     360
tacattattt tcttttatga ctagattaag ttagaggagt gtgttaaatg actaaatgtt     420
gctttactta aaatttaggt caaagttaac tttctgttac attcttaatg ttgtcctact     480
```

```
ggaaaaagaa attataccttt tctactcagc tccttgtatg aaataacatt gatgttatct      540
ttgatgtctg ggaatggtta cttttcttga agtagtgcgg ttgatgcaaa ttgtcctgg       599

<210> SEQ ID NO 101
<211> LENGTH: 599
<212> TYPE: DNA
<213> ORGANISM: Homo sapiens

<400> SEQUENCE: 101
ggaagttttc ctttgttccc ggttttctta ggggttttat aatgaattaa tgtctcactt      60
cttcagattc tgcatttgtc tatttgccat ctattcacag gccaatgatg atctggtacc     120 tgggggggcct tacagacctg ggaaaagatt gccccttcct gggcagtctt agtgaggggt    180
tccactgaga acatgtcttt catatacata ccaatgaatc ccaagtataa agccacaatc     240
agctcctttt ctcactctca cacactaagc cagtatttcc ctgttttaaa tcatctcagr    300
gctgggacca gacaactaga tacctgtgcc ccagggccca ctggaattat caaactagc    360 caataataag ctgttaactg tgacctgcct tgcatttcct gcagaaaccc aataaagga    420 tttctaagct tttccctggt tttggtctct cctacccaac caaaacctag cacttcccct    480
gtggccctgt gtggcatgtg gtaagccccg acttttctgg gactcttttt tacttttttt    540
tttttgttgt taatgagata gggtctcact ctattgccag gctagagttc agtggtatc     599

<210> SEQ ID NO 102
<211> LENGTH: 599
<212> TYPE: DNA
<213> ORGANISM: Homo sapiens

<400> SEQUENCE: 102
aaatcattag ttcattcagt taaggattaa catttttttcc ataatggatt tctacacaag      60
ggtggtgcaa atttggattc taagtccatg tatagtgtaa gtttaggaaa atttctcctc      120
tctgacacta gaaccactgg gggaaacatt ctttgttgtg aaaggaatta ttcaattctt    180
cttttcattc agggtacagt tcttcaatat ttctggttta gggttgggtt tcagctccaa    240
attccttttt caccactgcc caaggactca attatctctg tatagtgtta atacttgtgm    300
ctctagaata aaaacattgt cttatttcta tctcttcttt tctgtgcaaa gcccagaata    360
caaacgctta aaacaatgaa taaactgcaa cttatttttc aaaagaatac atagctgagc    420
ttgcaagaac caaagcgaaa tccataagtt gtgaaaacac agagagaaat gaaagccaga   480
acattatagc atcagctcag tcccaggttt tttgaaaggt gaggttctaa ttagctcaat     540
ttatcacgcc gctggaatta aagatttctc ttccacattt aacattctat gtttctggc    599

<210> SEQ ID NO 103
<211> LENGTH: 599
<212> TYPE: DNA
<213> ORGANISM: Homo sapiens

<400> SEQUENCE: 103
ataaggctat tcctataaag tgttggcatt ttataaaata cttcagattt gaatattcct      60
caatctccgt gtccatccag ctcttcttac tcatgttaat ttctctctag actctttgca     120
gctgattctt tattgagaga gtgggttgct acaaaccacc acataatcta gttacttcag    180
aagcccagaa tttagataat caagttttgt ggtcactgtt ttcttttaac aaggcagagc    240
aattaatata ccctctcctc tccccttaag aagatcctct tttgtgtgtg tatattaagy    300
tgggggagac cagtacaagc tacccatata attataactc agctttcaat cctcctcctc    360
```

```
caattcatat catgtcagcc tgaatatgtc aagtgtttta aattgggttg tggaggaccc    420
agttttttca gagatgcctc tggcacttct aggaggccct tattctaaaa ttcagctaac    480
ataacctaat ttataactgt tttaaatagt taagtcctgt gttaagacca cattcaaaaa    540
gagattccac ttaaaatgtc tgaaaccact gacttaggat attgtgaaaa aaaattttt     599

<210> SEQ ID NO 104
<211> LENGTH: 599
<212> TYPE: DNA
<213> ORGANISM: Homo sapiens

<400> SEQUENCE: 104
tcttactcat gttaatttct ctctagactc tttgcagctg attctttatt gagagagtgg     60
gttgctacaa accaccacat aatctagtta cttcagaagc ccagaattta gataatcaag    120
ttttgtggtc actgttttct tttaacaagg cagagcaatt aatatacccct ctcctctccc   180 cttaagaaga tcctctttg tgtgtgtata ttaagttggg ggagaccagt acaagctacc     240
catataatta taactcagct ttcaatcctc ctcctccaat tcatatcatg tcagcctgar    300
tatgtcaagt gttttaaatt gggttgtgga ggaccagtt ttttcagaga tgcctctggc    360
acttctagga ggcccttatt ctaaaattca gctaacataa cctaatttat aactgtttta    420
aatagttaag tcctgtgtta agaccacatt caaaagaga ttccacttaa aatgtctgaa     480
accactgact taggatattg tgaaaaaaaa ttttgttgg agaataacag tattttttca     540
ttactttgtg ttctgccagt ttttctata ctcgcgtgtt gctttactta cctagtgtc     599

<210> SEQ ID NO 105
<211> LENGTH: 599
<212> TYPE: DNA
<213> ORGANISM: Homo sapiens

<400> SEQUENCE: 105
tttttggctt atgcaattgt gcatgtgtgt tgtatttttt acaaacaaac aaaaatgggc     60
aatgaagtgg aaagaaaata taatctccag gctttggtcc caacgtcctt ttctcagtgc    120
aaggaagatg tcatactcac tgcctaaggc taattattaa atcctgaatg tgtcaggcca    180
tatgcataat gacagttata ttatcattat taattacaac tatatcttca ttgagctctt    240
atatgtgtca ggctctacaa taagcacttt acacacatga tgctatttaa tcttcaaagy    300
agccctataa ggaaggtatt agctttgacg gtttctaagg ccgagtacta aaaagttggg    360
gtgtgaggct ttatggaact tgccaagatc acataaaaaa tgacaagtca ggatatgaac    420
tgatgtccgt ctcactcaaa agcatgacct cttaactatt atgttacact ttaaacactc    480
tgctaaagtt acaaaagtgt ctctgcctcc caaatgcaca ctttcttggg tgaatagtaa    540
ttaataaaac aatttcatgt tttgctgtaa taaattaatt tcaatcaatt ccaagtagg    599

<210> SEQ ID NO 106
<211> LENGTH: 599
<212> TYPE: DNA
<213> ORGANISM: Homo sapiens

<400> SEQUENCE: 106
agcctaacac acacttacca ttattaggta taagctccat atcccaagga ctcatctttt     60
ctgtatctcc attgtcccag cttaaagaaa gaaaaatcat tatattaaaa aatctaaatt    120
attgtatcac aattttaata aaatcaatta tcaaaataat tgcttctgtg tttaaaagaa    180
gtctctttat ctcttaatag atggaaaaaa aaattcaaag caagcctagg tgaactaaaa    240
```

| | |
|---|---|
| tacaacaaat atttccttac caaacattgt agcattgaaa cagactatca gggtactcar | 300 |
| gttgaagagg ttcctggctt tcgattgttc caaaccacca ggcatcatct atgacagacc | 360 |
| tgaagcggtc acctggccaa gaacaaaaac taactcatca ttctgaaatg catggctgct | 420 |
| gtcactgctt tttcctaacg ttaaccttta agtacctaaa ctgcctgtat gatttcagaa | 480 |
| gacaaaagt gaaccacaaa ctccaaaaat aagtaagtac aatcagcaat accaagagaa | 540 |
| aaaaggaatt tagtaagcat acttgaagtg tgacttaaca gttttcaatt ctattttt | 599 |

<210> SEQ ID NO 107
<211> LENGTH: 599
<212> TYPE: DNA
<213> ORGANISM: Homo sapiens

<400> SEQUENCE: 107

| | |
|---|---|
| gaagcggtca cctggccaag aacaaaaact aactcatcat tctgaaatgc atggctgctg | 60 |
| tcactgcttt ttcctaacgt taaccttta gtacctaaac tgcctgtatg atttcagaag | 120 |
| acaaaaagtg aaccacaaac tccaaaaata agtaagtaca atcagcaata ccaagagaaa | 180 |
| aaggaattt agtaagcata cttgaagtgt gacttaacag ttttcaattc tatttttat | 240 |
| atttcattaa ggtatacaga aattcacttg ttttaggcat ttttaccaat ctagcatttr | 300 |
| aaattcatca ttaacactat acccaaactt ttcactgaaa taaaattata attgcggcaa | 360 |
| gttccactca acaattactt agtcttttaa tttcttactt tctgtaagca gtttcccca | 420 |
| accaacaatc aatcaagact ccacgctaaa acaacaaac aacataaaat ccaacctgtc | 480 |
| ttccttcatc tcaatcaccc ttaatactca ctcactctcc ctttcctgta aaggaaaca | 540 |
| aaaaagaaac aaaaataaaa caactattct ttttaaaaca gaggacactc cttgtgtct | 599 |

<210> SEQ ID NO 108
<211> LENGTH: 599
<212> TYPE: DNA
<213> ORGANISM: Homo sapiens

<400> SEQUENCE: 108

| | |
|---|---|
| cagatgtacc aaaggctgat agccaaaacc aagaaaaatg ttttcatcta ttttacctac | 60 |
| tacttcttga cttacagatt tcttcactca tcaattttg acagtaagta tcagagttga | 120 |
| ttcttgaaga catgggtttt aactgaccag gtctacttat acacagattt ttccaataaa | 180 |
| cagatttggc cctctgtatt ggcagattct gcatcagcaa ccaaatgcag attgaaaata | 240 |
| cagtattagt gggatgtgaa atccatgaat atggaagggc caacttttca catcgggggr | 300 |
| ttccgtagga tcaattctgg aacctatgta tgcaaagatt ttggtatcca tggaggtcct | 360 |
| ggaagtaatt ccctgtggat actaagggac aactataact tcaatacaac tgtgcataaa | 420 |
| aagtatgtgt attatattta atccatattc aatttttaat catgactgtg taaatactgc | 480 |
| ttgctcctaa gcaaacagc atataattcc ttccttatat aattttgttt tccctaaaat | 540 |
| taataattgc ttcattttt taatgcttgg ttttcagtga atttacaatt aaatcttcc | 599 |

<210> SEQ ID NO 109
<211> LENGTH: 599
<212> TYPE: DNA
<213> ORGANISM: Homo sapiens

<400> SEQUENCE: 109

| | |
|---|---|
| tttaatccta gttatagtaa gttacaacta aataaggtat tctcatagga gttgagtagt | 60 |
| gcaacatgta gaaagctaat tatttccata agctggacat tacacttcta cacagcatga | 120 |

```
gaaactatgc ctctgagaaa gttccttaac tttgctggtc acccacaagt ggccacaatg    180
gtcttgatgt tgttaccta  gactcaggaa aaaatgaac  tttctaagaa catttgaaac    240
ctaatatttt tacaagtaaa aaaagttatg caattgatta aagtcttttg tgaatcacay    300
gtaaaacatt aaaaatgatt gtacactaag actgctacat tttacttgtt tttttaaaaa    360
caaggtagtg taattatcag tataaaataa tacttgttta ctaaaagaag caatgccata    420
acatgatatc agagaacact acttgcaata ggtaatacta ctacttccca actgtagtag    480
ttgtcatttt cctctttttc ctattagcca cagccacact gagtgtttct cagtcaaaca    540
tatcaagagc attaccctgg agagttaggg taaaggtctt tggaatttac tgtacgtga     599
```

<210> SEQ ID NO 110
<211> LENGTH: 599
<212> TYPE: DNA
<213> ORGANISM: Homo sapiens

<400> SEQUENCE: 110

```
ttaaagaata gaccctaggg agaaacaagg agaaacagga agacacatga gatgctacca    60
cagtaatata aatgagagtt cagggtgatt cacaccaatg tgatggcagt ggagtggtga   120
aaaacagtaa agtgctgaat atacttataa tccattagat aattaattcc ctgatggact   180
ggatgtggaa tatgagagaa aaagaggaat caaagatatc tccagggttt ctggtataaa   240
caactaagag agtcgtcata ttactgagat aaagagggct ggggtacagc gggtttgagr   300
aaaaagcttg gtaaataagt tttgtaggtg ttggatgtga ggagtaaaat gatatccaaa   360
cagtaatttg atatatacac agttatcaaa taaagtagcc attatgttat gcactgagta   420
tatcacagag atcccacaac ccaggaactt ccactgtgct ttattcagag cagctgctat   480
cagttttgta tactgaggag ctaaaagttt gtttgaaaaa ggtttccttt gactaataaa   540
aaggaaaaga aagacagaaa agtttgaaaa tcataattct agcctcaata tggactatt    599
```

<210> SEQ ID NO 111
<211> LENGTH: 599
<212> TYPE: DNA
<213> ORGANISM: Homo sapiens

<400> SEQUENCE: 111

```
cagcgggttt gaggaaaaag cttggtaaat aagttttgta ggtgttggat gtgaggagta    60
aaatgatatc caaacagtaa tttgatatat acacagttat caaataaagt agccattatg   120
ttatgcactg agtatatcac agagatccca caacccagga acttccactg tgctttattc   180
agagcagctg ctatcagttt tgtatactga ggagctaaaa gtttgtttga aaaaggtttc   240
ctttgactaa taaaaggaa  aagaaagaca gaaaagtttg aaaatcataa ttctagccty   300
aatatggact attaattgct aggcaaggat ttctccccat aaggaattta tctatgttca   360
atggggaagc taacaacttt tacatcaaga caggtaagtt gtatattaaa taagaataat   420
catatgtatg actgaaagac tttgggcatc accaaaaatc attatgagga catatcttat   480
tccccaataa ttcctgagga acttagaatg tttggttgag gaagatttct gtcacttatt   540
aattataacc attaagggg taagaatgca ttgagtattc tttaacattt ctagctcca    599
```

<210> SEQ ID NO 112
<211> LENGTH: 599
<212> TYPE: DNA
<213> ORGANISM: Homo sapiens

<400> SEQUENCE: 112

```
agatagttaa ctcaggaggc ttgcattgct ttcttaactt catactttc aaaaccagta      60 atgaaactgg tttgcaattc aacattataa cggtattcag aagaaacaat actaagatga    120
taaagttaaa agcatcattt tgcagatcta gttgcaatca ccaaaaaatt attttctata    180
gagaacatat atcagaaaat ctacatttca tacaacttca aaaactctct gaagaacttt    240
gaacttacag agactttgaa acgtgttgct ggttaaaaaa aaaaacacct ttctaaagay    300
tttatataac atttggaaaa ataaaaagca ttcatttacc tagaactgcc atcactgtgc    360
catgctctct cttcttcttc ggatgttcca ccactgacag caactacttc gccttcctaa    420
gatatgttga atacatgtct tattgcataa ttttataaaa taacatttta tgattacaga    480
aaatatcagt gatatcttat aatatcagtc atattgggat atttaaaatt tgatttaaat    540
tagttgcaaa gggtgttgtg gctcacgcct gtaatcccaa cactttgaga ggtcaaggt     599

<210> SEQ ID NO 113
<211> LENGTH: 599
<212> TYPE: DNA
<213> ORGANISM: Homo sapiens

<400> SEQUENCE: 113
ctcaggaagt acgtatctct ctcaattagg ccatgaccaa ttgaaatcta ctgggtgcaa     60 cagttttttcc agagtaggat gacagaaaag ccaataagtc aaaactatta gggacaatct   120
acctctctta atgaagaaaa tgagaaatat tatctatagc agcattagct gacttgatta    180
tctagaataa tgaatagatg caagacacca caaaaacaca tagaaaaaca taacaaaatg    240
ctatttttag actgtacaaa gatggcacac aagattatga agagctaaag aaagttcttS    300
atgaggcttc agtgtaattt attagaattt catgagtatg taagaattgg cactttggga    360
aagggtatgc tacaaagcag aaatggaatt aaaaatttta aatagtaaac aatagataat    420
ccagagataa ccaagattta ctatgttaat ttttatcatt aacctgttta taataccatg    480
ttaaattaca aaatggagcc ttaaaatggt cactatactt aagaagcaaa tattaaacat    540
caaaataatt aatatgtacc tttgagacag tgggtatttt attctctttt ggaacagtt    599

<210> SEQ ID NO 114
<211> LENGTH: 599
<212> TYPE: DNA
<213> ORGANISM: Homo sapiens

<400> SEQUENCE: 114
ctctcctcag gcctcactat tccctgagac agaacaatat taaagttagg ccaattaaaa     60
accctaactg atccagtgaa aacatctctc actttaaatc aaaggtagca acgattaaac    120
tctgtgataa aggcatgtca aaatctgaga caggctgaaa gctatgcctc ttgtgcccaa    180
caaccacgtt ttcaatgaaa aggaaaagct cttgaaggaa gttaaatatg ctactccagt    240
gaacacagga atgatatgaa agtgaagcag gcttgttgcc gatacagaaa tagttttgy    300 ggtctggata aagattaaa ccagctacaa cattcccta agccaaagcc taatccagag     360
caaggctcta actctattct cttctatgaa ggttggaaga gggaaaaag ctgcagaaga     420 aaagttggaa gctagcagag gttggttcat gaggcctaag aactacctgt gtaacataaa    480
agtgtagggt gaagcagcaa gtgctgatga agtagctgca gcaatttatc cagaataact    540
agctaagatc actgaagaca gtagctacat taaacaacag actttcaatg tagtaacag    599

<210> SEQ ID NO 115
<211> LENGTH: 599
<212> TYPE: DNA
```

<213> ORGANISM: Homo sapiens

<400> SEQUENCE: 115

| | | | | | |
|---|---|---|---|---|---|
| gaagaatgca | gtgatatttc | actgtggttt | caacttgtat | ttccctagtg | gttaatgaca | 60 |
| ttgattatct | tttcatgtgc | ttatttgtca | tctatagatc | ctctttggta | aatgtctgtt | 120 |
| catgtctttt | gcccattctc | cggttggatt | ctgttgttta | ctattgagtt | atgagaatta | 180 |
| tttctatgtt | acttagcccc | ctgttgggta | tgtcattgga | ttccattta | attaatggat | 240 |
| gaggctgacc | catttcagag | agccttttta | aaaggaaact | ttagactacc | cactggagas | 300 |
| attcttagga | agattcccat | aggatgagta | caaagtttta | gagacaaagc | tccaggaagc | 360 |
| ccaaagaaag | aatatctgtt | aaagttatgg | ccacagtctt | gcttgaccat | aggccaatga | 420 |
| atagttaagc | ccaatgataa | aggaataaaa | ggatgaagaa | tatttgaaga | gaaataaatc | 480 |
| ttcctcactc | ctcaggttcc | cttccatgtg | caggagcctc | aacctacaac | tagcaacctt | 540 |
| atctcctgac | tcattcctct | ccagaggagg | agtaaattag | tcaactgata | tgctctgga | 599 |

<210> SEQ ID NO 116
<211> LENGTH: 599
<212> TYPE: DNA
<213> ORGANISM: Homo sapiens

<400> SEQUENCE: 116

| | | | | | |
|---|---|---|---|---|---|
| cgtactgaga | cacattaatc | tcacaaactc | cagataagtc | cactggactg | cactactcta | 60 |
| ggagtagcag | caggaatgat | tcctctaatg | cttcttctca | ccctccattc | taagtggacg | 120 |
| tgtctaattc | caagaggagc | cccttctatc | cagtatgtcc | atctttattg | caacttcatg | 180 |
| ctaaatcctt | taagaaaaat | aagatgcacg | tttgaggttg | atttttttctg | tgctccttac | 240 |
| agaatctaat | ttcattattt | aaaagtcact | caacacaaaa | gctacttaga | agcttttgty | 300 |
| gattgaagtc | tagaacttaa | aatattttca | taaatatttt | tctagtctaa | aaatatagta | 360 |
| gaagtattca | taatgacaaa | actggtttaa | ccttctttac | agaacctttc | cttattttta | 420 |
| cttaatacac | tagtgctgca | tttcttgtca | aaagagggaa | agcagtttgt | agactttgac | 480 |
| tccattttaa | ctctcattta | attcttcaac | actccattat | acttcactaa | aacagctctc | 540 |
| aacactttcc | atgtcaatcc | tcttataaac | ctttaaaagt | tggtaacttt | ttaaaacat | 599 |

<210> SEQ ID NO 117
<211> LENGTH: 599
<212> TYPE: DNA
<213> ORGANISM: Homo sapiens

<400> SEQUENCE: 117

| | | | | | |
|---|---|---|---|---|---|
| agaagccaag | agagagaaca | aaaaagcaac | tactttataa | atctactcta | ataaatgttt | 60 |
| ccagaagtat | aattacaagt | ctaagattac | aatttgaagt | agagtggaga | cttgaaagta | 120 |
| gtccaattta | gcaatttcaa | aggaaatctg | ataaatgttc | ctaagcatgg | tatccttcat | 180 |
| gtgttgttta | aacaaacatt | ttttctttt | ggggtgagg | gttgcggggc | aagtaggact | 240 |
| gatcaaccct | tgaccctatt | atttatcaat | gttgccacat | ttacagttag | tagatctctr | 300 |
| aaataatctt | ggggacagtt | gaagcttata | aagctctaaa | agagcaaaga | aaaaatagca | 360 |
| atcatattta | agatgcctgt | gtgtcctata | taacacattt | cattgtgaat | atggcaagac | 420 |
| agtattaatt | ttcttggtat | aaggcatctg | tttaactcca | aagtgacttt | tatatggaga | 480 |
| aaatgaaagt | atatttcaat | catatcagaa | aaaagaaaag | gatattattt | ggattaacca | 540 |
| tttgtttact | aaaggaggca | ttaaaagaat | ctgctttact | catgaaccag | ttagaaaag | 599 |

<210> SEQ ID NO 118
<211> LENGTH: 599
<212> TYPE: DNA
<213> ORGANISM: Homo sapiens

<400> SEQUENCE: 118

| | | | | | |
|---|---|---|---|---|---|
| tccacatagg | tagttcaacg | caataaacat | tattacaaat | gaactgaata | aagaagtcag | 60 |
| ttctccctta | tgtctttcat | atttccacta | ataaaaccat | tgttctcaag | gtcacccggg | 120 |
| cttaacactc | tataaaccca | tttattaaat | ctttcctccc | tgtcatccta | tagcccaaat | 180 |
| cctaatatag | tcacaaaaca | ccaagtcatt | tatgtatttt | tttctttaca | aatttcctac | 240 |
| caactacccc | tataatattt | catgactaat | taaagtagtt | gtcctcacac | ttattcaatk | 300 |
| tcatacctga | aattgtacta | ctggcaacca | aactatttt | ctcttagctt | ctcgaccatc | 360 |
| ctataaaata | atttactaaa | gcccccacaa | ggttcatagg | tatttatgcc | tatgagatca | 420 |
| tttgaagtca | ctgacagttc | atctcaattt | gttttcgtc | attatttcca | aaatctactg | 480 |
| caatcaagct | tcctaaatat | ctaaatttct | atgaacatgt | cttgacactt | agctttttat | 540 |
| aatgttcctc | ttgtttataa | aattcattct | ctttcttact | gactcgattc | ctatttatc | 599 |

<210> SEQ ID NO 119
<211> LENGTH: 599
<212> TYPE: DNA
<213> ORGANISM: Homo sapiens

<400> SEQUENCE: 119

| | | | | | |
|---|---|---|---|---|---|
| tagttaaact | cgtagttaaa | acttagctgt | ccggtgctaa | tttaatgggg | aataaaagac | 60 |
| cataaaacaa | tttatattta | ggaacattta | aggttataat | taacttctaa | acctggcgac | 120 |
| ctctttcaca | gaaggccctc | agcttcagtc | ctgagagttg | cacacatttt | caagctattt | 180 |
| ctgggaatta | tttatctgcc | ttttagcatt | taatgggagt | atagagcctt | tagagtttag | 240 |
| aacaactctc | atcaaaacaa | agctattctg | atgtttacct | cctgccaatg | ccaaacaaaw | 300 |
| gtgggcttac | taagttatac | ccaactatta | tagtttggaa | tattcttaat | atacactact | 360 |
| tgcttcagta | aaatatccaa | atatatacta | catttcctct | gaatactcaa | gttatgtaag | 420 |
| gactgttcag | ttgattcgta | aagaaataaa | agtactgaag | gcctagaatg | tagtttgttt | 480 |
| gttttttaaag | aataaagttg | tctcataata | ttttctacaa | aattctcttt | ggtttcttct | 540 |
| cctgttcact | taaaaagaa | aaacaacaac | aacaaaaaga | accacaaagg | ctttcccaa | 599 |

<210> SEQ ID NO 120
<211> LENGTH: 599
<212> TYPE: DNA
<213> ORGANISM: Homo sapiens

<400> SEQUENCE: 120

| | | | | | |
|---|---|---|---|---|---|
| attttagtaa | ctgaaaaact | tattgattag | ctacagagag | ccaaatagct | ataattatag | 60 |
| ccaaaactca | acattcatga | tagcaagcag | tgagaacgca | ggccctccct | cgaattgttt | 120 |
| ctctttattt | tcttaatagc | aatgctggat | gctttatctt | ccatttgccc | ataaataaaa | 180 |
| caagcaatga | aaagaacaaa | agagtgaaga | gcaaaaagaa | ttagggcaat | tagataactc | 240 |
| ataaaagaca | gacaggaaaa | aaaatcaagt | taaagagtaa | gatgtcaaaa | gatccactcr | 300 |
| gatttattac | cattatgaaa | acatttcttc | atagacatat | cactaactga | gtattgttaa | 360 |
| aagttagcta | tgcagtaaca | ttgacaaaag | ctcaaaaagc | caaccatgac | aagatttgag | 420 |
| tacaaccaga | gtcatgggtt | tatgctccaa | gtgcccgcat | aatagctgtg | tgaactcagt | 480 |

```
aaattggggc aaagcacttt atctctgtaa tgtacagttt ctccattcct aagaccaaga      540
ataataaaat ctatcttgat catcttacaa ggttttcatg agacccaaag gaggtaaaa      599
```

<210> SEQ ID NO 121
<211> LENGTH: 599
<212> TYPE: DNA
<213> ORGANISM: Homo sapiens

<400> SEQUENCE: 121

```
aggtatctct aatatacaga aagtagacat ttaaaaaata tgactacaca aactgcagta       60
gttgaggaga ccttaatact tcatacagta aatagaaaca ctgctcggta agttgtatgt      120
gatatattaa acattgtaa ttcaaatact tggccaatta tgttaacatc taagaaacaa      180
aatgtgaaga gaagagtata aactcaaata tttaatatac taccaattga ttaaaagcaa      240
gaaatgcttg attctttggc cttaatttta aaatcagtgt acttgagtaa aattctattr      300
tgctagaaga ctattaaaca agtacaataa tacgagtatt tatttataat ttcttcacat      360
ggttttccaa gtatttttc ttctctatat tgtatcttca tacttgtgaa tttccaaagt      420
ttcactgcta aaactgataa aactgtatca gttatcacaa tgtacaggca ctgtaatatg      480
cacaattaat tttcttttaa attcagcatg tcaataaaag tgtggaataa atcattcttt      540
attgatggga atttaaagtc aaaataatga accattttt aaatggattt cctttgtga       599
```

<210> SEQ ID NO 122
<211> LENGTH: 599
<212> TYPE: DNA
<213> ORGANISM: Homo sapiens

<400> SEQUENCE: 122

```
aacatctaga agttagaaaa tgaacatgtt tggatattag tatggcaaag acagactcac       60
ttcattagtt tgctatccct tatctcaggt aatactccta tccacaatta taaaatgagc      120
ggaaaaagta aaactgaaaa taaaggtagg aggaacaggt attagacact atttggatct      180
actcatgttt catttaattt tcttatcaat ttactacaaa taaccagatt tttttttataa      240 cttgtttaaa ataccctaa catccattca aaatgctgct gcataaacac aaatctgaak      300
tggaatctta gcactgctat acaatcactt tttaaagtgc aaataagaac aatatgtagc      360
gaattaactg ataagatgt acaaatatga atcaaattta ttttacttaa ctatagaata      420
ccttcaaaat ccatgaaaac ataaaccaga tttaaaatac cattcttaca atgaaacaac      480
tatttaaaca ttcattcttt aacagggtcg attttgaaac tatttattct ctcctactag      540
aacattatag tcttcttaaa gaaaaacagt catgtgatta tataaactaa actcttgca      599
```

<210> SEQ ID NO 123
<211> LENGTH: 599
<212> TYPE: DNA
<213> ORGANISM: Homo sapiens

<400> SEQUENCE: 123

```
caggagaatg gtgtgaaccc gggaggcaga gcttgcagtg agctgagatc gcgacactgc       60
aatccagcct gggcgacaca gtgagactcc gtctcaaaaa taaataaata aataaataaa      120
taaaagatat ggtatagaaa gcatcaaagg gcagagaagt gctctagtcc tggccttgcc      180 aattttttaaa catagtttta actatgggaa agtcatttaa ccatttcagt gcccttaatc      240
caaagataat actatccagc caacttgttt tgataaaccg aagtattaat atgggcgacy      300
gcacaaatgc aaaatgttat tatggggagg gaggggaata catctatcta ccttgatgca      360
```

| | |
|---|---|
| gtttagtgaa acttcaatga ttctgtctcc ctacattttc ctagatctaa aataaaatct | 420 |
| aaagtttata gattcagtag catcaataat taaaattatt ctaaagaaca gcattagaaa | 480 |
| ttcttaagat taagttctga gcatcaaaag cagctattaa aactatgcag cacatagaaa | 540 |
| ggagtggtaa taaaacaggt aaatgctgaa ggaaagagct aggattagga taaagagaa | 599 |

<210> SEQ ID NO 124
<211> LENGTH: 599
<212> TYPE: DNA
<213> ORGANISM: Homo sapiens

<400> SEQUENCE: 124

| | |
|---|---|
| tgtgacctcc acctcccagg ttcaagtggt tctcatgcct cagcctcctg agtagctggg | 60 |
| attacagatg tgcaccacta cacccagtta atttctgtat ctttactaga gatgggtttt | 120 |
| cgccctggtg accaggctgg tctcgaactc ctggcctcaa gtaatccacc caccttggcc | 180 |
| tcccaacgtg ctgggattac aggctataaa tgtgttttaa ataaatgagg aagaatgaat | 240 |
| taaaaatcga taaatatgat tatttttaaaa aagaccaaaa tgtctaacat aatttgaacr | 300 |
| gatacactct cttttccata agcctacctc tagttccacg aatgttacta agatcaataa | 360 |
| gccaaagagt aagatattat agtcttttga ccaaagaaaa ataaaatgtt aaaaccaagt | 420 |
| tatggatatt aaaaataatg ttacgtaaat ggtgaaaagg ggcaatgaca taagatatac | 480 |
| ctcttctaag gtgtatgaaa gaaaggaag tagggagaga tcatgtaacc tcagcaaaaa | 540 |
| caaaacaaaa caaaatctga ggattaaaag tgagagggag agaacaacaa gcgaatgaa | 599 |

<210> SEQ ID NO 125
<211> LENGTH: 599
<212> TYPE: DNA
<213> ORGANISM: Homo sapiens

<400> SEQUENCE: 125

| | |
|---|---|
| catttgtgtg ctcactggag tagcacgttt aatttccttc aagaactttt gctttacatt | 60 |
| cacaacttgg ctaactcttt taacatgcat tcctcactcg ccttaatctt ttctaacttt | 120 |
| tgaattaaag tgagagacct gagactcttc ctctcacttg aacactaaga ggccattgta | 180 |
| gggttattaa ttggattaat ttcaataggc aggcccaagg agagaaaaat ggggaagggc | 240 |
| cagttggtgg agcaatcaga acacatgcaa cattcattaa gttcgccata agggtgcagk | 300 |
| tcatggcacc ctaaaaagac ttacaatagg aacatcagag attatagatc accataacag | 360 |
| ttataataat aatgaaaaag cttgaaatat tgtgagaagt atcgaaatgt gaaagagaca | 420 |
| agacttgagc atatgttgtt agaaaaatga tgctgacaga cttgctttac tcagggtttt | 480 |
| cacaaatata caatttgtaa aaaatacagt atttgcaaaa tgcaataaag gcacaatgaa | 540 |
| acagggtacg tctgtattag cattttttcat aaagcctagg cagtgtctag taacacatt | 599 |

<210> SEQ ID NO 126
<211> LENGTH: 599
<212> TYPE: DNA
<213> ORGANISM: Homo sapiens

<400> SEQUENCE: 126

| | |
|---|---|
| ttaaagaaat caacgactaa cattgattaa cactgaatga ctaatattct ttgagtgtgc | 60 |
| gggatggcaa ctaagaaaca acttgtccaa acactgaaac tccctctact tatgagatag | 120 |
| aactggctga atcagttgg aaccaagatg gccaactgga gtctgacag aacaagcttg | 180 |
| ctgacatcat agcctgacta tctaccacat ttcatactaa ctaccctaga atttgcacat | 240 |

| | | | | |
|---|---|---|---|---|
| gtgacccatg | aggtatcata | atgagttaac | tgtgcatgcc | cagggacatt | ccagacctcm | 300 |
| cctttccttc | caccaaacac | ctactaatct | cagaattcac | ccctactgaa | cctgtaataa | 360 |
| aaatactgcc | ttgaaaccag | catgaggaga | cagatttgag | cttgacccct | gagtcttctt | 420 |
| gggagttgac | tttcaatata | aagcttttct | tttctcaaaa | acccagtgtc | atagtattgg | 480 |
| cttctagtac | actgggcagc | aagccccctc | tgctcaataa | cacaagcaga | aaactgtaca | 540 |
| cattgggaaa | cagtttactt | ctgttcagat | aacttgagaa | accttaaaat | taaaatatt | 599 |

<210> SEQ ID NO 127
<211> LENGTH: 599
<212> TYPE: DNA
<213> ORGANISM: Homo sapiens

<400> SEQUENCE: 127

| | | | | | |
|---|---|---|---|---|---|
| tgtgacccat | gaggtatcat | aatgagttaa | ctgtgcatgc | cagggacat | tccagacctc | 60 |
| cccttccctt | ccaccaaaca | cctactaatc | tcagaattca | ccctactga | acctgtaata | 120 |
| aaatactgc | cttgaaacca | gcatgaggag | acagatttga | gcttgacccc | tgagtcttct | 180 |
| tgggagttga | ctttcaatat | aaagcttttc | ttttctcaaa | acccagtgt | catagtattg | 240 |
| gcttctagta | cactgggcag | caagccccct | ctgctcaata | acacaagcag | aaaactgtay | 300 |
| acattgggaa | acagtttact | tctgttcaga | taacttgaga | aaccttaaaa | ttaaaatatt | 360 |
| gacctatgta | cctaaaagag | aggcataaat | tatacaaaga | ttactacttt | gacatgaaaa | 420 |
| taaaagaaat | tatgtgattt | tttaactaaa | aatatcttag | agaatttggc | attccttgaa | 480 |
| aacctactgt | tatctggcag | agtcaacaag | gagaatttta | atttctcttg | aggctacttt | 540 |
| acagcttttg | agtcagagat | ctcatctctt | attgccatta | gaataagcag | tagaaatga | 599 |

<210> SEQ ID NO 128
<211> LENGTH: 599
<212> TYPE: DNA
<213> ORGANISM: Homo sapiens

<400> SEQUENCE: 128

| | | | | | |
|---|---|---|---|---|---|
| actgcttaaa | acagtggctg | gttcataaaa | ctctgaagtt | cattaaagga | atgcataaac | 60 |
| tcatttcctt | tattataccaa | tattaattag | aatcagagag | acaatttatg | tttctgaaaa | 120 |
| gggggaaaa | ctctgctttt | tatatggcgt | tccatgtact | tttgagtgcc | ttagttgtga | 180 |
| aaattcatta | actctgcttt | tctccgttaa | atgtcactta | aggaaatgat | tttaaaacca | 240 |
| agtaaaaaac | attaaaaggc | taaaagagaa | ttagtgaaca | aaatctgact | tggcaattay | 300 |
| gctatttccc | tccttgggtt | tttctcatta | aaataattgg | gaaagcaccc | attcttaaaa | 360 |
| tactgtcata | caaaataatg | atacattttc | ctaatacaga | atttcattat | caattacaat | 420 |
| gatttccttt | ttaattcttg | tataccattt | ataataaga | ttttatttgg | ataaaaaata | 480 |
| aaagataaaa | tttacttaaa | tctataagta | gcagtaggaa | aaacctaatg | actgctttct | 540 |
| attttgttca | gtactaatta | tatgcattat | ttcatgtaat | cccacaaaaa | tcctatgtg | 599 |

<210> SEQ ID NO 129
<211> LENGTH: 599
<212> TYPE: DNA
<213> ORGANISM: Homo sapiens

<400> SEQUENCE: 129

| | | | | | |
|---|---|---|---|---|---|
| caagagaatc | ccttggaaaa | agctttcaaa | tatatataca | caaatatctt | agaaataaat | 60 |
| ctgcaaggtc | ttaaaatacc | aattatataa | aaaggaaata | ctggttgatc | cattaccaaa | 120 |

```
ttgttacctc caaaataat aacagtatgt tctctcacag gagtgtttca ctggtcaatc      180
atgatctact atcttaaagg ctgattctat ctattttcaa gactgatttc cataggacta      240
gttagcgtct agtctgtgcc tagtgaaatg caaaaaacac tcagcaccca ctttattaay      300
gagcaatatg aatagtgaac atatgtgtac cctaccacca cttgaagtga aaataataaa      360
aatacaagaa ttttcaaaa aaatagtgcc ctcatatctt cgttatttct tattgtaagg      420
taacattctg aaatctgtaa ctccaaacca ccagtaaaaa attacaaatg agactgaatt      480
tagcaaaaca aattctatca cattcttaaa aaataaacat ctttagactt tggtaagacc      540
atataaaata gtacagtgct acttttcttc tcttaattga tgtgctttca actaaagaa       599
```

<210> SEQ ID NO 130
<211> LENGTH: 599
<212> TYPE: DNA
<213> ORGANISM: Homo sapiens

<400> SEQUENCE: 130

```
ttcacctata agcaatattt cctcaattac atatatgaat ataaataata ctttagcaat       60
tacttacagt aaatatccgt ctgccagttc gatcaaaagt tacacagtac acagatgaca      120
agtgtccaag aattcgttta tgcattttca tgtgctgata cactgcagtt ggaacaagtc      180
gctcaagtct gtatttccca ttcagcttcc ttgaaaacag agtatccgct accaagaaaa      240
agaaggaaaa taaatgtaat ctggaaatta attttcttac atgatcacct tttaagaaty      300
cacatactcc aatttgtcat gtgcaggtaa aaataaagaa gctttctgat atatatggct      360
tctagttaaa agtcttttaaa gtaatgaata aaaacattgt ttcacctgaa ataagtcagg      420
cactatcatt ctcactttat aacttaattt gtaagttaaa tgacctgtcc aaaaatcaca      480
aagtaaggca tgaagctagg attaaagctc agatttattt actctctggc tagtgctctt      540
taaaaaccta agcatttat atgttatttc cttaaaagct gtctatgaaa tagttttttc       599
```

<210> SEQ ID NO 131
<211> LENGTH: 599
<212> TYPE: DNA
<213> ORGANISM: Homo sapiens

<400> SEQUENCE: 131

```
caaaggcact taaaactgga acccagtgta cttttcataa atcagtaaca cttgaacact       60
cgaaatctga catgcagaat gatatttaaa acatctttta taacaagtga agataaagga      120
atacgtcatt tgcattatta aaaataata attaaactgg gaatcttgcc aaacacctgt      180
ataatgattc cttctctgga atctattagc tctcccttag ttctcccttt caactcattc      240
attctaatca ttattcaaga tctgactgaa gtttatcttc tgtcccaaag cttgatacay      300
tgactccagc tgaaaatgtc ctcttccatc taaattacta ctgtacttat tttctatact      360
ggtaacttat ggacaaagaa ggtgctcaat aaatatatgt tgactgatct gcaggcacat      420
tattaaccta cagatgatct tctaatacag gcttttttt tttttctaa cagtgactgc       480 catctacatt gggtaattag cactagggtt tctcggtcga atttagccct aaagaaaact      540
aaatatatat acaaaatact acttagccaa ggtacagagc ccagtaatta tgccctaaa       599
```

<210> SEQ ID NO 132
<211> LENGTH: 599
<212> TYPE: DNA
<213> ORGANISM: Homo sapiens

<400> SEQUENCE: 132

```
aaaggaagat ttatctcaca gattaaaata ttcaaaatat ctctaaatag tgcttcattt     60
taactgccct gctaaatgaa tttaattggg aaataagggg agaacgtatt cacttaattt    120
tctgaatata gaggataaat gaataaaaaa ttccagaaat cactgttatc catttgaata    180
aagtctgaag taaaaaagga gcaaaatact gaagcatgtc atttgcagca aatcattcag    240
aacagccttt gaaataaagt atatgtgctc aagtctacaa agccaattag tagagatcar    300
caaaaggccc acaacttctt aaacattaga tgtgactatg cgcatattca gcccttgggt    360
tctcatccat tacttcttta ggtgctagga taataagtca aattccccca taagtcactt    420
cttacttcac acctagttat ttttcgagaa ctgatttact tatccaatca taatactaat    480
gcatattcaa tttagaaaag aacataaatg aaagaaaaac ccataattct attgtctata    540
gcaatcactt ttaaaatttc gcaaaggttt acctcaaaaa cagcatttta acagctatg     599
```

<210> SEQ ID NO 133
<211> LENGTH: 599
<212> TYPE: DNA
<213> ORGANISM: Homo sapiens

<400> SEQUENCE: 133

```
tttaacttta ctaccaaact gacatctttc tatctagaac atggtgcttt cttcctgttg     60
ttgggcccaa attttcaatg cagatgattt tttaaaaaga taaacataat aaagttacct    120
cattttctct cactacatca tttgaaccaa gttcacaaag aaagaaaaag gtagctgcca    180
taaaagagta tctgtaataa ccttagtaaa tacatttttg aaggcactag aaaaatacat    240
gataaaaaaa accctgcaaa taagtactat agcagaaata ccattacctc cctacaaaak    300
gtttagactt ttttctcctt ttgcaaagat ctttgtaaaa tgaacaagca cacatgataa    360
agctgcaata aattacccaa gatcaaaatt aaccatggtt aaaaagatg acttggaaaa     420 aaatgaaaat gactatgaat taacaaaata caaaggttag tgttttttgt tattattgtt    480
ttctaactgt taataacaat ataatatgct atataatacc tactccagtg taggaaagct    540
gttccctctt aatcagaaat ggaggaccac aaaaacagtg cttacaactt ctgccaact     599
```

<210> SEQ ID NO 134
<211> LENGTH: 599
<212> TYPE: DNA
<213> ORGANISM: Homo sapiens

<400> SEQUENCE: 134

```
ggttctaaac acgttggggc tgaggggtgg atatctggga gtctgggaaa acttctctga     60
aaaactgaca tttaaactaa gacctgaaaa atgaacagcc acagaatgct gatgtgagcg    120
cagcatattc caggttgagg aaacagcatg tgcaatagcc tgaggctgga aagagcatag    180
cattcaagca acatgaagaa gtcaagattg acttgcacac agagtagaga aagggcaagt    240
gtcaagagaa gagactgaga aggtaggggga gcggactata tagagtgctt tctaagctar    300
gttaggtatt ttggactaaa ttccagtaat aacgggttga agttttgggg gagaaaagaa    360
tggagtaata tacatagtaa gatttacttt gggataactc attgcagttt tctcttgacc    420
acaatgagaa tgaattggaa aggatataag taaaagcaaa agctaacttt gcaaaaaaat    480
caaagggttc tgaaaacaaa atttcatttt agaaaaaatt taatcagctt gacaccaaaa    540
ttatcaacac tttcccaagg aattaaatac ctgatctcat aagtatctgg cactatata     599
```

<210> SEQ ID NO 135
<211> LENGTH: 599
<212> TYPE: DNA

<213> ORGANISM: Homo sapiens

<400> SEQUENCE: 135

```
cctagagata aaaagtttac tttgctaaca tgtcaaatgt aagaaaaatg caaacaaagc      60
aatcagcaga aattgcttta atttaatgta ttacaatctt tttcacaaga taaacatgca     120
ttaaaccaac ttccaaattt aatcttaaaa accccttaa tgtatttagg tctcttcttt      180
cctatctccc cttactcatg cacatttatt actgaagtat aagcaaatat agaataaact     240
atatctgaaa acaggcataa tgtgggtatg gaggtaagag aaaggacaat actaaagatw     300
cgctaatacc tttggaagta aatgctgcta tgccaagtac acactcacat ctctcttcca     360
caataaaaga atcacaagct agtaataaca acagatcagt gggatctttt gtctttgctt     420
ttgaaaacag tattaaagga ggttctagag cactggaagg caggtgaacc actttgggtc     480
tcttgctgag actgagttct agttcaattt tcacaactta catcaaagac caaaaggttc     540
aaagtagttg ggaattctaa gcacataata aaataaaaca ggataagaaa acactgaga     599
```

<210> SEQ ID NO 136
<211> LENGTH: 599
<212> TYPE: DNA
<213> ORGANISM: Homo sapiens

<400> SEQUENCE: 136

```
gcatttaaaa gaaaacttac caaaatgagt ttttaaaatc gtatactttt ctttaatctt      60
ccccaaaata atttactcaa aaataaaatt tagaagtcta gaatacttgt aaggttgctt     120
ccagttctaa gcttgcaaat gattatttta atgtgactta attgatcaaa attccttta      180
aaaattttac tttaaagaag atggaagttc attacttatt aacttcagat gtgtgatgat     240
cctgttttag tatcctctgg caaaatatat tttcaggtag tgaaactgaa aatccttack     300
gtaatattct atctttcaat aaaatattat gaatccactc tgactcaagc tttcttggt      360
gatttagaat gtttgaattt ttcaaaatca actttcattt taaagttaga agagatactt     420
ccagttctta aattccttgt gctttctctg cttttgaga ctttatacaa gctgatgcct      480
ctgctggcaa tcttgtctta cctgctcacc tctacacctc attctccttc atgtctcagt     540
ctatgtctca ctcactgcct tccatgacct atttacacca cctgtgcccc tttttggac     599
```

<210> SEQ ID NO 137
<211> LENGTH: 599
<212> TYPE: DNA
<213> ORGANISM: Homo sapiens

<400> SEQUENCE: 137

```
tttctcagta atctgccata caatattatt tcaggggaaa ataacccct caagatcccc       60
aatttctgat atacgagtta ctttctgtga ccctaagtgc tttcaaattc ttaacattca     120
agacataaaa agtatgacca gattataaag tcagtgtgat aaattatact aatatagcta     180
acacatattg gctgcacact gaatgccagg ccctatggta agtgtggtaa gttttacatg     240
gaactactca taactctgag aggtatatac tatcattatt cccattctat aaaaaaattr     300
tagaatttat ttaaaaagat attgagacct tcccaagttc aaacacagca cataagagag     360
tcaaaccata gcaatctaac tctggaccct acaattcata ctatcacaca aatgacctat     420
tacctcaaat atgtgtatat atcaatgtgc aagatataag caagtcatac aacagacatt     480
ttgaatagtt ttcaacagac attaaactga gccagaaaaa gagaaacatt tcacagttca     540
cttgcactac taaggaaact agcataaaag cataaattcc tataggtaaa agggaacac     599
```

<210> SEQ ID NO 138
<211> LENGTH: 599
<212> TYPE: DNA
<213> ORGANISM: Homo sapiens

<400> SEQUENCE: 138

```
caatttctga tatacgagtt actttctgtg accctaagtg ctttcaaatt cttaacattc      60
aagacataaa aagtatgacc agattataaa gtcagtgtga taaattatac taatatagct     120
aacacatatt ggctgcacac tgaatgccag ccctatggt aagtgtggta agttttacat      180
ggaactactc ataactctga gaggtatata ctatcattat tcccattcta taaaaaaatt     240
atagaattta tttaaaaaga tattgagacc ttcccaagtt caaacacagc acataagagr     300
gtcaaaccat agcaatctaa ctctggaccc tacaattcat actatcacac aaatgaccta     360
ttacctcaaa tatgtgtata tatcaatgtg caagatataa gcaagtcata caacagacat     420
tttgaatagt tttcaacaga cattaaactg agccagaaaa agagaaacat ttcacagttc     480
acttgcacta ctaaggaaac tagcataaaa gcataaattc ctataggtaa aagggaacac     540
tttaaaaaat tctaagggta aaagtagaag ataaaactac aatatttata agattatac     599
```

<210> SEQ ID NO 139
<211> LENGTH: 599
<212> TYPE: DNA
<213> ORGANISM: Homo sapiens

<400> SEQUENCE: 139

```
gcctattatt tctttataat tataataaaa ttaatataga accttattaa gtgtaaaaat      60
cttgatggtc tatttgctca agtaattgtg aataaacaag cttcaaagaa tatgtcatat     120
tcagaattta cttaactgtt aagaattcat ttagataata attcagttta cattatcaat     180
acaaatacca acacaaattt gtcatttaaa gaaaatgcaa tactataaga aaaacaaaca     240
aaaaagaaa atgcaatact acgcttccaa attttattca tcataaacca attacatctk     300
gctaaaaaaa agagactcta ttcagaattg aggtttccat aaaccaaagt agggatgctc     360
cataaaaaat aatttaaaat acaacaaaat gacaacattt aactgcttaa aataacaaat     420
tttcaagttt tgatgtttaa gtcgtcatat gtgctaattt gtgtaatttt aaaattctct     480
ttaaagcatt attagtaaaa cgttaaactc aaatctagga atctgatgaa aagttactgt     540
gtattaattt aaggacgaaa catcctttaa ctgcttatac taaggccaat gtaaataat      599
```

<210> SEQ ID NO 140
<211> LENGTH: 599
<212> TYPE: DNA
<213> ORGANISM: Homo sapiens

<400> SEQUENCE: 140

```
ctagattcac tattcaaact aagaaataaa caaatgacaa agctttcctt tcgtccaaaa      60
aaagttttt attctacagt ttaagaattc tgatacttgg aaaaagtgcc ccttttcttt      120
aaaataaatc tcatatttta aaaaatgtaa aatctaatta aacgtatacc atagtaccaa     180
aaacaacttt tagcttccta tccaattcca tttactttgt taaaaatgtt ttaaatctta     240
aggtagatgg tgataatcag tcatgttta taccagagac agaaacaacc ataagatacs      300
accatttcct ttctcaatca cacttgaaat gaacgcatca attttaacct gcaaacttt      360
aaaactgctc ttaaaattct actttcctct tgattaaaat tcaaccattg cgattgtaac     420
tagactaact acagatgatc agtgactatt tttaaattca catctacaaa tattcacccc     480
```

```
cattttaagc agcaataatt tgaggtttcc tagaaatttc aatgcgatgt gatatatgag      540
ttctcccatt taaaatattg ctcagtttat tagttaatac aacaaatcat ttccaggta       599

<210> SEQ ID NO 141
<211> LENGTH: 599
<212> TYPE: DNA
<213> ORGANISM: Homo sapiens

<400> SEQUENCE: 141
aattaaatta actcaaaatc aaaattgata gctcattttt actgaaaaaa aaaacaaaaa       60
aacaaaatga tattcctacg aggattagcc attaccataa tttagccaga taacattaag      120
ctgcttcatt taaaaaatgt aacattacca aaagattaag aaaatgcagc attcctcagt      180
gacttaaggt ttgtgggttt ttaagagatg cacagatgta aaagcagatg caaagacgag      240
ttttgtaaaa cctgccccat cttaaaaatg gagtattata atctttgcga taattttttty      300 aaatatcaag gaagacatgt aaattcactg aagacttcta tcaagtattt gtaaacctaa      360
aaattaattt caaattagta aatcttggag tttacttcca gctccattca ctttggccaa      420
gaattgaatg aaagtaaccc aaatcactcc ttgaaaatta acacacgttc agtgtgaaaa      480
tgaatacact aatacactgt taaatctcca ttagatgtat taaacctcag tacccttgct      540
tatttcaaca gccttgagcg ttatcaaca tcttatatta aaccacaaga gatttatac       599

<210> SEQ ID NO 142
<211> LENGTH: 599
<212> TYPE: DNA
<213> ORGANISM: Homo sapiens

<400> SEQUENCE: 142
gccctatact aaaacatcca gaaatcatca tacatatgag gaagaagaaa taaagcctca       60
aaccctttgg aataatagga tataaaattg cctttttgtaa ctgaatctta aaaatggaag     120
gttaccatga cttgtcctat tgcaacctgg ttatcagaat aacttatttt ttttaagata      180
gctattctca aatactgaac atatttgcat ctttaaagac actttattct attcaattat      240
aggtaaagta gcctatttct aggtggttag gcttgaaaag atagactgaa aagataggam     300
attttgtatg cctttttgca aattgtattt acttctaaga ccgatgctgt tttagcttaa      360
cttttaaaaa agtgttcttc aaataattgt aatattttac acgatcttga agttcttcaa      420
ataaacagag tttagaaact aaaaattata gtgggatttt ctggttttga aggcttggaa      480
tgtatgattc ttactaatag atgttttatt cttgtgattg aaaataaacc aaattatgac      540
atggaatata atattactct gggtaaagtt tgtgatatat atcttctgtg tgttttgta      599

<210> SEQ ID NO 143
<211> LENGTH: 599
<212> TYPE: DNA
<213> ORGANISM: Homo sapiens

<400> SEQUENCE: 143
gttaatcacc caactttttt cctgttatta ttttatgatc ttttccattt ttactactca       60
taatatttta atagaaattt tttaatgtt aaaaagatg aaaaaaataa gaacttctgt        120
cacaagttct ggtgttctgc attgctgtga agctgtgttt ttttttttcct gggcaaaatt     180 atttaagatg acataaaaac ccaaagtcaa cctctaacat ctgtccttgg cccttatatg      240
tcattcctac tactatagta ttctcattgc agcgttattc ctttctctct gtgtgtcagy      300
tgaagaacca tcatttaaac acttgcagtt tgaccctcat tatgtacttt gtttcaacac     360
```

| | | |
|---|---|---|
| atggagatgc ccagcttact agaggctgat aatctgaagc agcagtgacc cctctaacca | 420 | |
| caacatctgg aaaacaaagg ttgcataatc tggctagtct ccagaaattt tcagttatta | 480 | |
| aaatctgact ttgtttaaca gcaataactc aatttattga atggattgca agagatatga | 540 | |
| atcaatggct atatatacca ttcaaattta actgcaaaga attcacattt ttgaaacaa | 599 | |

<210> SEQ ID NO 144
<211> LENGTH: 599
<212> TYPE: DNA
<213> ORGANISM: Homo sapiens

<400> SEQUENCE: 144

| | | |
|---|---|---|
| aaactgctaa caaatatcat tcaactgctt aaacccatc catgatgctt catgagtcct | 60 | |
| ggacagtcct tagtatgata tgtgagatcc ttcatgatct gccctccctc gaactctcca | 120 | |
| cactcagttt tatccaccag agcataatca ttctaaattc tttctgtatg gaaatattta | 180 | |
| gttttccaga tatgtctcct ttatttttt gcacatactg gcctctctat aatcttcatc | 240 | |
| tccaaaccag gccaattcca atgtggtttt caagagacag cccattcttt gcctctttgr | 300 | |
| gaaaccttac cctgtgtctt tcctcccagc aaacaaacaa ctaggtgttc atcctttgtg | 360 | |
| cttccagaga atcttctgta tatctctaca gtggtatagc attcagatag tttattgttt | 420 | |
| tatagtgctc ttcctcacta actaaactaa gaggtttttt ttagaatagt tcctgaacgt | 480 | |
| tagatttctg tattatgtgg cacaattcag aacatacaat gggtatttaa taaattcagt | 540 | |
| gggttttttt ccttggaatg tgttggttaa ataaataaac tatggtcatt tctggagat | 599 | |

<210> SEQ ID NO 145
<211> LENGTH: 599
<212> TYPE: DNA
<213> ORGANISM: Homo sapiens

<400> SEQUENCE: 145

| | | |
|---|---|---|
| gctaacacat atcaaatatt tagtatgata catagtacca tgggatatgc cagacactgt | 60 | |
| taactactta ataaatatta cctaatttaa tcttcataag gcctgtataa ggaaggcaat | 120 | |
| gttacctccc ccactttaaa gatcaaagag actgaggcaa agaatgataa acatcttgt | 180 | |
| cctaagtcat gaattagtga ttaataaagt caggaataaa acctaggaag gttgctccag | 240 | |
| agccttcact cttagccagt caatctcctg actcctatgc tattaatatg cataaacccw | 300 | |
| tttccatgca cagaactagg tacataataa gggcttaata aatgttggat aatactattt | 360 | |
| ttatactttc tcatgtggac aaagaaaggg atgcctaata ttgactaaag gtttactcta | 420 | |
| agcataaggt attctctta caactaacct ggaaggcaca cagaggccca gggaggttcc | 480 | |
| atggctcaac cacagtcaga agccagtaag gacacaacca ggattcagaa gacattggtc | 540 | |
| ttggtccaaa gcccatggtc ttattactac attccaacat gaactcttat ttggatcaa | 599 | |

<210> SEQ ID NO 146
<211> LENGTH: 599
<212> TYPE: DNA
<213> ORGANISM: Homo sapiens

<400> SEQUENCE: 146

| | | |
|---|---|---|
| tttttcttgg ctgaataata ttccattgtg tatgtggtgt gtatgtatgt gtatatactt | 60 | |
| acatacatat gtatacatat acacacacac atacatacac accacatttt cttttctatt | 120 | |
| catctgttga caggcactta ggctgtttcc atatcttgtc tatagagaat aatgctgaag | 180 | |
| caaatattgg agtgcagata tctctttgac acacaaattt cattccttt ggatatatac | 240 | |

```
ctagacgtgg gattgctgga tcatatggta gttctatttt aattttttga ggaaacctcm    300 tactctttc tacaatgtct gtagcaattt acattcccac caacaatata aagagaatgg    360
gtttcttttc tccactttct caccaacact tattatcttt tgacttttg ataataatct    420 tcctatcagg agtaagatga tatctcattt tggttttgat ttatatgccc ctgatgatta    480
gggtattagt cagggttctc tagagggaca gaactaacag gatagatgca tatataaagg    540
agagtctatt aaggtgtatt gacccacatg atcataaaag ttccacaatc tgctgtctg    599
```

<210> SEQ ID NO 147
<211> LENGTH: 599
<212> TYPE: DNA
<213> ORGANISM: Homo sapiens

<400> SEQUENCE: 147

```
ttttctattc atctgttgac aggcacttag gctgtttcca tatcttgtct atagagaata     60
atgctgaagc aaatattgga gtgcagatat ctctttgaca cacaaatttc attccttttg    120
gatatatacc tagacgtggg attgctggat catatggtag ttctatttta attttttgag    180
gaaacctcat actctttct acaatgtctg tagcaattta cattcccacc aacaatataa    240
agagaatggg tttcttttct ccactttctc accaacactt attatctttt gacttttgr    300 taataatctt cctatcagga gtaagatgat atctcatttt ggttttgatt tatatgcccc    360
tgatgattag ggtattagtc agggttctct agagggacag aactaacagg atagatgcat    420
atataaagga gagtctatta aggtgtattg acccacatga tcataaaagt tccacaatct    480
gctgtctgca agctgaggag caaggaagcc agtctgaatc ccaaaacctc aaaagcaggg    540
aagccaacag tgcagccttc agtttgtggt cgaaggtcca agagtccaaa agctgaaga    599
```

<210> SEQ ID NO 148
<211> LENGTH: 599
<212> TYPE: DNA
<213> ORGANISM: Homo sapiens

<400> SEQUENCE: 148

```
gtgaggactt tctggcactt cagataggaa aatagggggta caaatactat gattatattc     60
aataaacaaa atggtttatt tcaatggtgg gtccctgaca cattctgaaa ttttgctctc    120
caatactaac ttttgaaggt ttaaaaagtc actaaatatg acaaaattat gttgatttaa    180
aatatttctt ctttgattct ggggtcattt gctccatttt ctacagcttc aaaaccacaa    240
atataagtga gtagaaatat ttaatgcttt ttagtttttt gtctattttc tataaatatm    300
ttgagactgg cctgattata cagtctaagg aaggaaaacg gtgtcagagc aaatcttcat    360
tttattaata aaaatctaag aaataagagg aagtaagaaa tgttgcttca agtaaaacag    420
aaataaaaac caagcaacta aaacaacaa aaagaacat attttcatga aaaatataact    480 ggtgatgtgg gagcagaaaa gagaaggaaa ataatcttga aataacctt taagtcaga    540 tgtattcaac tcatcagaac aaggaaaaga tgacaataaa agtttagaga gttgattac    599
```

<210> SEQ ID NO 149
<211> LENGTH: 599
<212> TYPE: DNA
<213> ORGANISM: Homo sapiens

<400> SEQUENCE: 149

```
gcaagttatg ggaacctctt tgcactttac attactcatc tgtgcagaga attatggcat     60 cttttcctgtt gttattgagt tgttggaaga aaaaatatga cagtgctttg taataataaa    120
```

| | | |
|---|---|---|
| acttatacat ataaggggat tgtaataatt aaaattcata agaaaatgg ttgatgagat | 180 | |
| cgcccagcca ctgttatctt tgaggactca tgaaagcaat agttggaaat aatttctctc | 240 | |
| tcttgattag acacactgtg gagttagtgt tgcacccagt ttttgtctcc ttaccttaay | 300 | |
| aaggatgctg tgaagttaag gagtttggag tagattaata atatgattaa agtgttgaat | 360 | |
| aaataagacc catgagaaaa ggagtttgaa ttaattagtc tggaaataat aactgccttc | 420 | |
| taatacatga agcattatta caagaaaaat atagaccatt tctcttctct gagaaatgac | 480 | |
| ttgaaagtaa ctgtggacat ataacacaga cataagaagg aattcactga tagggttgag | 540 | |
| agttaaatat taaacagga tataagaaga atatttggca tctcctttgc tgctaacta | 599 | |

<210> SEQ ID NO 150
<211> LENGTH: 599
<212> TYPE: DNA
<213> ORGANISM: Homo sapiens

<400> SEQUENCE: 150

| | | |
|---|---|---|
| ggcttctgcc atttttgaaga aaatctggc aaagtcattg tgcatatatc atatgattat | 60 | |
| ctgatctcac tcttaaagag aaaggggag ataaaaattt tataaaagaa tgtaagataa | 120 | |
| tatgttttttt cacaacattg tttatgaagg cagggaactg gaagcaacat tgttgtccat | 180 | |
| tattagagga ctatactaaa ataaggttgt ggaggcatac tactgaatac cacatggtag | 240 | |
| ttagaaacaa catagatctt aaagtgtaa tgctttgtga aaacagaag aaaatgaatr | 300 | |
| ggttccattt atgtaaattt aaagtatac acaaaaaaat gacactacat gtttctaaag | 360 | |
| atacatataa atttgagaat gtatatcaaa cacattagag cagttacctg tttgggaggg | 420 | |
| agtagaatat gataacaaga agaaatcagt ttaaaattgc ttttttttttt tttgctttgc | 480 | |
| tcaaatcaat gatgataatg tgccatgaac cagagtctgc atctatctca ctctcctctc | 540 | |
| ttttttcttta aaaaaaaaaa aaaaaagga agaaagcta catacattgt aaaatagta | 599 | |

<210> SEQ ID NO 151
<211> LENGTH: 599
<212> TYPE: DNA
<213> ORGANISM: Homo sapiens

<400> SEQUENCE: 151

| | | |
|---|---|---|
| gtcattttt tgtgtatact tttaaattta cataaatgga acccattcat tttcttctgt | 60 | |
| ttttcacaaa gcattacact tttaagatct atgttgtttc taactaccat gtggtattca | 120 | |
| gtagtatgcc tccacaacct tatttttagta tagtcctcta ataatggaca acaatgttgc | 180 | |
| ttccagttcc ctgccttcat aaacaatgtt gtgaaaaaac atattatctt acattctttt | 240 | |
| ataaaattt tatctccccc tttctcttta agagtgagat cagataatca tatgatatay | 300 | |
| gcacaatgac tttgccagat ttttcttcaa aatggcagaa gccaaatatg aagaaatact | 360 | |
| catttatcca ttaacaatta atattatcaa aatcagcaat ttttttcccat atgatggatg | 420 | |
| taaagtagta tctcattgtt aaatttattt tctatttact gagataatat actaattatc | 480 | |
| catatatttt ccatctttct aggttttttag tcttgctgat tctaggagtt tcttccatag | 540 | |
| taccttatc attcctttgt ctgtttctta tgtctgttca attcatctat ttgtctatt | 599 | |

<210> SEQ ID NO 152
<211> LENGTH: 599
<212> TYPE: DNA
<213> ORGANISM: Homo sapiens

<400> SEQUENCE: 152

```
aaaaaccttg gaatatgctt ggcttttcta ttgtcttgtc catcagtaaa atctaacttg      60
tctattgcca caattctagt tcaagtcatc attatctttt gcctatactc tcctaattgg    120
tgtccctggt tctgcttttg tctctctaca ggatacttta tagcagccca ggtgatttat    180
ctaaaacata attttaataa tatctgcttt aagttttcca agggcttcct acttcactct    240
caataaaaat aaaaatcctt gccttgactt ccaataaatg atctggtccc acgccaccty    300
tcttacctcc ttttctaaca ggcttccctt cccatcctac ctctcaactc cacttcagta    360
gcactaggct tcttgttcct tgaacagaga aagcatactt ctaatttagg ggctttatca    420
cctgcagctc cctccatctg gaatgctctt atttcagatt tttgtacggc ttagttcctc    480
acttttttca gggttctgct tgaatatcat cttatcttga ggacattccc ttaacactct    540
ttaactcaca ggcaaagatg gagaatcaaa catgtgcatt tcccttagca ccctcttca    599

<210> SEQ ID NO 153
<211> LENGTH: 599
<212> TYPE: DNA
<213> ORGANISM: Homo sapiens

<400> SEQUENCE: 153
atggcagtta atgattgtat tttaagccta taaactcaca aagacaaaaa gaacaaagaa      60
gactctaatg acaaaatttt ggaaggtgga gagaagagat aacaaaacac acacacatac    120
acaacacaca cacacacaca cacacacacc atgactatcc attcctctta cctagcttta    180
tttttcttaa tagcacttca cctagataaa tgtaagtaaa tataaacaca agatatatat    240 tgattttac atttgtttgt tgtcgcttcc ttttgcttc cagaacataa gctgcatgay    300
agcaatcttt tcagttttgt tttggtgttg cattctcaag ctttggaatc atagcagaat    360
caaattcagt ataatttttt gactgaataa ctgaggtgga ctggatgagt gtagtttgtg    420
tgaggtgtgg ggttgtggga atcaagtgtt caattttgaa tgttaacttg aggtgtctat    480
tagacatcta agtgatgata tcaagtgaaa tccgcatatc tgaggctaag tcatggctaa    540
aattataaat tttagagtca tcaacattgg ctctaaagaa gatcacctgg ggggactat    599

<210> SEQ ID NO 154
<211> LENGTH: 599
<212> TYPE: DNA
<213> ORGANISM: Homo sapiens

<400> SEQUENCE: 154
agccaagctc caagccttgg aggacaacac catttagaga tcaggcagag cagaggtctt      60
tgaaccttat aattatacac tacaatttgt aagaagaaga aaactaatt taaactaagc    120 aatgtgatat gtagatattt atctataaat aatatatatg tatctttgca caaatatatt    180
atgtacatta caaaatacac agacacagat attaaaaaag aatgagctga caacttcca    240 gttaaagagg aagtattgaa cacatgcatt tttcagctcc ctgctaaagg cccactacar    300
tgatagtaaa tggattttaa aaaataaggt ataaacccac aaggacaaag agaacagcag    360
acaaacaata ccaccaaaat ataggaagct gtaagaagaa aagacaaata acaactgact    420
cacagactca ggaaagctga ggctgcagtg gagaaaaagc agagatacaa cctgatttac    480
aatacagaat cagccatgcc cctgccccct gcaaaggct cagaaattgt ttctggcact    540
tctgctagtg gaggttaatg ttgggcaata atagacttag ctgaatgtct gtttgagaa    599

<210> SEQ ID NO 155
<211> LENGTH: 599
<212> TYPE: DNA
```

<213> ORGANISM: Homo sapiens

<400> SEQUENCE: 155

| catgcccctg | ccccttgca | aaggctcaga | aattgtttct | ggcacttctg | ctagtggagg | 60 |
| ttaatgttgg | gcaataatag | acttagctga | atgtctgttt | gagaagcaga | tacatccaca | 120 |
| gacaccccca | ccactctaca | ctaccaagtg | actaacctct | accaggcagc | aacagcctgg | 180 |
| agacttattt | tctgaagagg | gttaagaggg | gatcttgctt | gcagacaac | aggcacacgt | 240 |
| gaatgggaat | tccaagtgga | aagcaggag | attaagtcaa | agttaatatc | agaatgcttr | 300 |
| aaaccaaaat | attaagaata | atttctattt | gttactaagg | gatgtggagg | caaataaaaa | 360 |
| gaacactatt | ttgttgtgta | gcaatgattg | ccaatggaat | tcacctacat | aaaaagaatt | 420 |
| ttaaaataat | gaactgctat | ataacatttt | ctttatttct | tagagctatt | tcaaatattt | 480 |
| atttctattt | cttttaaagt | gcatggattg | tttgaacatt | atcttggtac | atgaatgcag | 540 |
| gcatttaaa | gtaattgcat | ttgttgtatc | ctggattaga | agcaggcata | aatattgat | 599 |

<210> SEQ ID NO 156
<211> LENGTH: 599
<212> TYPE: DNA
<213> ORGANISM: Homo sapiens

<400> SEQUENCE: 156

| atgccatgaa | tgtgattgtg | gttacactct | atgcccaatt | gtccaaattc | agtgaagtat | 60 |
| gcacttaagc | ttgatgaatt | ttatttatgt | aaattatact | ataataaaac | tcacaaaaat | 120 |
| gtttaacaga | gagaaaacaa | acagtgggag | aaaaaatcct | ttcagtacca | ctacatttct | 180 |
| catagtaaag | ttggctaagt | catatcagtc | atatgtgtgt | gggcaagagg | agggttgtcc | 240 |
| caaggcaatg | ggtgttgaac | agaggaaata | gggactttc | tgaaatgtcc | atagaggagy | 300 |
| gacaaaagga | gtaacctggt | tcagggagta | gaggaagggt | aactaaggaa | cagctgaggg | 360 |
| tgtgggcca | tttcgaacaa | aactctttca | ttatttacat | ggtccttcat | gatctgggcc | 420 |
| ttgcctgtgt | ctccaactca | cttgcctacc | ctctctctca | gtctgttttt | actctgactt | 480 |
| cttgtttagc | tctttcttaa | gtttctttgt | gcactcctca | tagctctatg | ctgggccctg | 540 |
| cttttttttt | tttttttttt | ttccacttac | acccttgtt | ctctttaggt | caattatcc | 599 |

<210> SEQ ID NO 157
<211> LENGTH: 599
<212> TYPE: DNA
<213> ORGANISM: Homo sapiens

<400> SEQUENCE: 157

| tgagaagtaa | gtaacaaaaa | aactataatc | cttaaaaaaa | tcagttgaat | taacaaaggc | 60 |
| acttgcttca | cacaagatta | aattaggcca | tatgaaaagt | tactttgcat | aatctcttca | 120 |
| tgactttgca | tctagttatt | tccaagctaa | tatatctagc | ctctaattca | aaagaattg | 180 |
| tagacatgac | tttattatct | tccttatgga | aaatttcttg | ataaaaatta | ggttgcttca | 240 |
| ctattgattt | gaatctaatt | ttagcagtgg | ttagaagttc | caacacagct | ttctacaagk | 300 |
| atttgagatt | tgacatccat | cttagtaggt | gttgatttac | tttctgtttt | aagcagtttc | 360 |
| cacattaggg | atttggggct | cattctaccc | acaaaccta | ataattgcct | aggtataatg | 420 |
| ctactctgca | tatatcacat | gactggtgga | aaaataaatc | attcatttaa | caaatattga | 480 |
| tcaaagttct | gctgtgtgcc | aactattatg | gcagtgtgg | aagaatcaga | attaactaag | 540 |
| aagaaaaac | agacatggaa | acatttcaag | gaagaactag | ctagaaggga | aggatacag | 599 |

<210> SEQ ID NO 158
<211> LENGTH: 599
<212> TYPE: DNA
<213> ORGANISM: Homo sapiens

<400> SEQUENCE: 158

```
ctcctttaaa aaaattggaa ctgtattttc atcagtgaaa ccctctgctt taaaatctca      60
gtgtcattgc caaagactaa atacattgac cttggactca attttgagct acacattcat     120
ttctctagaa tgttggtaaa agttgcagaa gtagagtcat ctgtatattt ctcttcaagt     180
ccttaaactt ttagtaaacc attatttatg gatctaacac acttgtaaac aatgccagca     240
acatattatt tgtcctgcat gcttataaaa ttctttttt ttttttggt catggttagr       300
tgattcccgg taactacatt ttaattctaa ttctgagaag taagtaacaa aaaaactata     360
atccttaaaa aaatcagttg aattaacaaa ggcacttgct tcacacaaga ttaaattagg     420
ccatatgaaa agttactttg cataatctct tcatgacttt gcatctagtt atttccaagc     480
taatatatct agcctctaat tcaaaagaa ttgtagacat gactttatta tcttccttat      540
ggaaaatttc ttgataaaaa ttaggttgct tcactattga tttgaatcta attttagca     599
```

<210> SEQ ID NO 159
<211> LENGTH: 599
<212> TYPE: DNA
<213> ORGANISM: Homo sapiens

<400> SEQUENCE: 159

```
ttttctggtt tcttctcatt tgctaaagga aggcctaggg ctcaaggcta ttgtttagat      60
tcttttgtcc catgggttgt tcccttgagg tagtagtctc tcccttttcc tagggaggtg    120
gcttcctgag agccaagctg tagtgattgt tatctctctt ctggacctag ccacccagca    180
agtgtacaag gctccaggct ggtcctgggg gttgtctgca cagagtcctg tgatatgaac    240
tgtctgtggg tctctcagcc gtggatacca gcacttgctt cagtgaaggt ggcaggggggr    300
tgaaatggac tctgtgagaa tccttatatt tggttggtta atgcactatt tttgtgctat    360
ttggcctcct gccaggaggt ggcggtttca agagagggtc agctatggta gtatggggag    420
gaacaggtgg tgggcagggc cctagaactc tcaagagtat atgtccttg tcttcagtta     480
ccagggtggg taaaaggacc attaagtggg ggcaggtcta ggcatgtctg agctcagact    540
ctacttggac aggtcttgct gcagctgctg tgggggatga aggtgaggtt cccaggtca     599
```

<210> SEQ ID NO 160
<211> LENGTH: 599
<212> TYPE: DNA
<213> ORGANISM: Homo sapiens

<400> SEQUENCE: 160

```
gtaagttatg ccactgtcct ctgagtgaag gaaacacagt agtgcctttc catcatgtat      60
ccaagaagaa ttatgaacaa attcttgggg taggctgagc atcttaacag tggcaacagc    120
agaggtgtac agggtgtccc cacactcact tccagaactt ggtcatctca atttaccagc    180
ggttcttatt taggttctca tagcccagaa aattctgcca gggtactaca catagtgggc    240
tatttttagc actgggcctg cctcaggaaa ctggagaact tgaacactca ttgacaaggr    300
agtagaagac agcaaagact taagagagaa agatgagatg ctttatattt tcctcctgtg    360
atttttatttg gcagctcatc atccagttag gaaggtctaa gagataacga agatataaag    420
tgctgagtag agagatacac acttgggaac aggaaagata gctggcagtg ggaaggagtg    480
```

```
tgaaacattt tttacatgga gaggaggaaa agctgtggaa ttgggttact taaacataga    540
gagggagtta agagcaaaga ggctctttct ggagaagttg atcaagacct gaagtgaaa     599
```

<210> SEQ ID NO 161
<211> LENGTH: 599
<212> TYPE: DNA
<213> ORGANISM: Homo sapiens

<400> SEQUENCE: 161

```
catgtatcca agaagaatta tgaacaaatt cttggggtag gctgagcatc ttaacagtgg    60
caacagcaga ggtgtacagg gtgtccccac actcacttcc agaacttggt catctcaatt   120
taccagcggt tcttatttag gttctcatag cccagaaaat tctgccaggg tactacacat   180
agtgggctat ttttagcact gggcctgcct caggaaactg agaacttga acactcattg    240 acaaggaagt agaagacagc aaagacttaa gagagaaaga tgagatgctt tatattttcy   300
tcctgtgatt ttatttggca gctcatcatc cagttaggaa ggtctaagag ataacgaaga   360
tataaagtgc tgagtagaga gatacacact tgggaacagg aaagatagct ggcagtggga   420
aggagtgtga acattttttt acatggagag gaggaaaagc tgtggaattg ggttacttaa   480
acatagagag ggagttaaga gcaaagaggc tctttctgga gaagttgatc aagacctgaa   540
gtgaaaatct ttaaaagttc tgaaagagtg gctaaaaaat aattgtaaat tacttacga    599
```

<210> SEQ ID NO 162
<211> LENGTH: 599
<212> TYPE: DNA
<213> ORGANISM: Homo sapiens

<400> SEQUENCE: 162

```
tagtgcataa ggcctccagt tgatatgtag caagaattat taattaaact tcaaaacaag    60
aacatgtaaa attaatatta gaaagataat tgtgtgttct aagcaaaaga aaataactca   120
caggaggtac tgctgcactg tccacaattt tagactacat gacttctaaa atcctttaa    180 ctctcagtaa aaaaaagtag cattatcatt cctttgtatc aaaaaacacc atagatgtta   240
tctcttttaa tgttgccttt tcttcaactt gatttttttt tcatttggtt ttccagtgar   300
aagcaattga tactggaagt cttggaatat ggcatttcat aatttgcata acaaatatca   360
gctctgctct tcaagaagac tgaagttttt ttggttttat agtatttat aaaatttat    420 aatttgtact taaaaaattg tcagcaactt tcatttaaac atcttatttt aaattcttcc   480
agttatctac agcacacacac acacacacac tccttctcaa tgcaatctag aaaggagcaa   540
atgtacaaga tttttttgtct ccactatttt ttctttttcc ttgcaacaat atccccatt    599
```

<210> SEQ ID NO 163
<211> LENGTH: 599
<212> TYPE: DNA
<213> ORGANISM: Homo sapiens

<400> SEQUENCE: 163

```
aatcatgaac gaaactgttt taatccacca ataataatga atttcaatta cccatgtttt    60
ggagtaaaat cgaattatct ttctattctc tttacaggaa aaaattataa ttataaaagt    120
attgtcatgt taggaggtgg taaaacagta tgtaacccaa aacagagaaa atggtatta    180 tagaaatggg tcaggtagtt aagaaataaa aacatcagca ctttcctgtg ttttgtggtg   240
tttgcaatat ttgtgagctt tgtaacattc gacttgtgat ttttttcctt ctcattctar   300
taaatattca ggttggtgtc tagttttgta gttgcaattt tgtcttcttt ttcttttct    360
```

```
tttcttttct ttttcttttt ctttcttctt tttttttttt ttttgagaga gagtctcgct    420
ctgttaccca ggctggagtg cagtggcgcg atctcggctc actgcaacct ccgcctcccg    480
ggttcaagta attctcctgc ctcagtctcc taagtagctg ggattacagg cgtgtgccgc    540
cacgtctggc taattgtttt tgtatgttta gtagggacag ggtttcacct tgttggtca     599
```

<210> SEQ ID NO 164
<211> LENGTH: 599
<212> TYPE: DNA
<213> ORGANISM: Homo sapiens

<400> SEQUENCE: 164

```
tcccttgggg ctttccccat agtgagcatg tgatgctttc aggggaacac tgccttttaa    60
tttttatccc aagattcaag cagcacagat cctctcttgc ttcacagccc ctgtccaatc   120
ctgcctttca ttaactaact ttagtaactt tcctcgctgt gtttaattaa gattcatacg   180
agcaagactt gaaggaacac aagcatctca gtgcggctgg gccggccttt agtcttgggc   240
tttttacctc ttgcccgtgg tggtgctggc tgcagaggac cccctgagct gggagtagam   300
ataactcacc ttggtttttt tcttgctgcc agacttttag gatggctctg aaacaccaga   360
ctaagtctgt gtccaaaagc ctcaagcatt ggcctgggat tatgtaggtg gatatcattt   420
gaggactatg gaggccaaat tatttccttg attgtctaat ctccttgtta acaacatttg   480
tgaaaaaatg aagggttttt tttttttttg tttttgttt tttttggctg caatggaagt    540
ttcaagactt acaaggaaac agcttttgct gttcccctct tagggccttc cagcctgac    599
```

<210> SEQ ID NO 165
<211> LENGTH: 599
<212> TYPE: DNA
<213> ORGANISM: Homo sapiens

<400> SEQUENCE: 165

```
tgggattatg taggtggata tcatttgagg actatggagg ccaaattatt tccttgattg    60
tctaatctcc ttgttaacaa catttgtgaa aaaatgaagg gttttttttt ttttgttt    120 ttgttttttt tggctgcaat ggaagtttca agacttacaa ggaaacagct tttgctgttc   180
ccctcttagg gccttccagc ctgacaaaag aaatcagcag cttgcccgtg ggcaatctgg   240
agaggcagga aggtgggtga gggaagcatg acatcatatc aggtgggaat aaaaaggcgy   300
gtcctgcagt gtccctgttc aaacatattt tggtgcttgg atgcccgctt tggaagctgg   360
aagaccctca gcaggaactg cgaagggctc cagagacccg gactcaagtt ttcaaacttt   420
aaaaatgagt atggcaaggg aggagtgagg ggtgaagggc agcagccccc tggtggggag   480
caggggcgcc gggagtcaga tctgacagag ggctcccggc tgtgtgctgc atgcgtggtt   540
cccctttttc ttggagaaaa tggggaggca ggagtgaggc agattgctct gggacaatg     599
```

<210> SEQ ID NO 166
<211> LENGTH: 599
<212> TYPE: DNA
<213> ORGANISM: Homo sapiens

<400> SEQUENCE: 166

```
gggcgcccag tggccaacac ggaggggagt tttcagatgg aaatcggaca aaacaatgca    60
atcatctgtc tcgcaatctg ttttgaaggg gaaagaaaga gcgggcagag aggagagagt   120
cgttttctac taggggaggc ttcattcaga gagtttttata ggagaagaca gatgtcatga   180
atactgatgt ggagagcctg ggtctggcag agttttttta attttctgag ttgtaaagac   240
```

```
aaagtgtttt aataacacag ggaaacacat gttgatgggt gggtctttag ctcattctgr    300
tttctctaac tccctctctt tctcctcctt tctttccgtc tttctgcctg cctgcctgcc    360
tgcctgcctg cctgcctgcc ttccttcctt ccttccttcc ttccttcctt ccttccttcc    420
ttccttcctt ccttccttcc ttcctccctc cctccctccc tccctccctc ccttccttcc    480 ttttttttgag acagggtctc gctctgtggt ccaggctgga gtgcaggggt gcaatctctg    540
ttcactgcaa cctctgcctc ctgggttcca gcgattctct gccacagcc tcctgagta      599
```

<210> SEQ ID NO 167
<211> LENGTH: 599
<212> TYPE: DNA
<213> ORGANISM: Homo sapiens

<400> SEQUENCE: 167

```
gctctctggg cagtggggca cgtgtgccca taaggcaggt gctgtccctg gtcttggaac     60
ttcttatgaa accagcctgc ccggcacctc ctgccatccc tgtgaggtga tgggacaggt    120
gctaagcctg cccttggaca gataagaaaa ctgcagcccc aggcacagag cacaagctg     180 agaggtgacg tcaggactga actgtgagcc tgggagtcca aatctaggct cacccagtct    240
ttctggctcc agtgagggcc cgccactgtc atccgacgga tggcatgtgt gattttggy    300 acacgcctgt gcaggtgact cccacaggtg ccccggaggg aggcgctgct gtgatgttca    360
tgctacatgc aggaaacaga gaggttgagt gacttgccca cagccccaca gctcctacct    420
agtgaagcct ggtttgaggc cacacctgcc ttactagttt tattatttat ttatttttg     480 agactgagtt tcactctgct gcccaggctg gagtgcagtg gcgcagtctc ggctcactgc    540
agcctccgcc tccggggttc aagagattct gctgcctcag cctccagagt agctgggac     599
```

<210> SEQ ID NO 168
<211> LENGTH: 599
<212> TYPE: DNA
<213> ORGANISM: Homo sapiens

<400> SEQUENCE: 168

```
gtctgtggat tgacttctc tgggcacctc atgtgagcgg aattgtacgg catgtgtgtc     60
ttcatgtctg gcttatctca cccagcaaat gtcgtctagc ttcatctgtg ttgtagtgtg    120
tgtctgagct tccttccttc ttaaggctca atactattcc aatgtgtgaa gagaccacat    180
ttcgtttatc tgttcatctg tttggtgact gagctccctc catgctctcc aacaataatc    240
atgctcctcc acagacaggt gtcttggctg atggtgtcag agaccccctg gcaagccgcy    300
gctatgggag gggtcttctc cctctcatgc cacccaagga gactctgtgg ggtccctgca    360
gaccccgcag catggtcagg ggctctgact ggaggctgtt ccctccaaca ggactcagca    420
gtcagggtct cccagggaac ccctgtatgc agactctggg aagacaggtg gatcaggtgt    480
ggggactgtc tgtccctcag gagctgctgg ttgaatgaat gcgactgtct cctgctggga    540
cacgcctctg cctcaggctc tgggcagtgg gggacgtgtg cccctaaaga aggtacaac     599
```

<210> SEQ ID NO 169
<211> LENGTH: 599
<212> TYPE: DNA
<213> ORGANISM: Homo sapiens

<400> SEQUENCE: 169

```
cccatcgtcc tctgccgtag gaggtatcag agagcaagta ccttccttag tcacacccat    60
cacgtacata gtggatgtgc ctcttttttcg gggcagggggg taatcttaat caccaagcaa   120
```

| | | | |
|---|---|---|---|
| ttactaaatg ccgaccatgt | tctcaggctt | ggcagaggtg ggtgcttgtt | accccaaggg | 180 |
| acaaccactt ccctccatgc | tccccacccc | acccaagacc cttctccact | ccactcctga | 240 |
| ctgccgcctc ccacctctgc | cctgggtcgc | tgtctttatt gtcttcctca | acatcttccr | 300 |
| tgggaaaggc caatggcttg | aaacaggatt | gacgagacac ccggggcctg | ctccacaccc | 360 |
| gtgggctcct gggcgtgcac | ccaagagcct | ccacccctga atggctggca | tccaggtggg | 420 |
| cttcccataa ggagccccct | tctgcgggcc | tgggaggggtg gggagcctgt | ggcgaggtgg | 480 |
| cggggaagag aaagggcaca | ggtgccccct | cactccgagc ctatcggatc | ccggagactt | 540 |
| gcaggctata gacctagagg | tccagccagg | agggctggca gggaccatga | agcaggaga  | 599 |

<210> SEQ ID NO 170
<211> LENGTH: 599
<212> TYPE: DNA
<213> ORGANISM: Homo sapiens

<400> SEQUENCE: 170

| | | | |
|---|---|---|---|
| cccctcactc cgagcctatc | ggatcccgga | gacttgcagg ctatagacct | agaggtccag | 60 |
| ccaggagggc tggcagggac | catgaagcag | gagacgtcag gcagagaga | atgccttta  | 120 |
| gagccagata aattcttact | tcccctttcc | cagctgcgtg accctgggaa | acttcaacac | 180 |
| tccgtgtctc agtcctctca | tctgtaaaat | gaatctgatg agaactgtgt | aagaatagag | 240 |
| gtgtgtggag agctctctgg | tgccaggctc | atggcaagac tgtggtgaca | ccagccatcr | 300 |
| gaaggcaggg aggctcctct | gtggacagct | ggatgcacag gtgcgtagca | ggagctcagg | 360 |
| agggtgtgcc cgcggagtcg | caggtaaggg | agccactcca gattgcagag | cttggcttgg | 420 |
| aggtgtcgcc tcaggagggt | cttccattgc | ctggagaccc cacataggcc | ctcttcttcc | 480 |
| ttcaaacaca gcccccaacc | tctctgcagg | gaagtcctcc ctgaccttcc | aaaccagggc | 540 |
| agacccttgt ctgggctccg | tcggcctgga | catggtgcca tttcccacta | gtggggcag  | 599 |

<210> SEQ ID NO 171
<211> LENGTH: 599
<212> TYPE: DNA
<213> ORGANISM: Homo sapiens

<400> SEQUENCE: 171

| | | | |
|---|---|---|---|
| ttgctctcca aggttcctgg | actttcctcc | agacccgagt gcaagctccc | tgtggcttcc | 60 |
| acccaccgct cacaggagtc | tctgcagcca | ccagacccag agcccagaca | ccatccactg | 120 |
| tcggggagag gcacgtgtcc | acagcttcct | ggaatgcaag gctgcatgtg | gccagggctg | 180 |
| ctgcccgctg aggggcaagt | gcatgcctgg | agaccacagt aaggagccag | tctcatgctc | 240 |
| tgggagttta gataaggctt | catgcccctt | ggagccaaac ctctgaattc | catggagttr | 300 |
| ttgggtcaaa gagcttgcct | aggtctgagt | tgtggatacc tgttgtcaat | gagctctcca | 360 |
| caaagggggtt accatgatag | gtcccaccac | ctgtacctct cctctccaaa | tttcaccact | 420 |
| gttctttcac acctttgcca | atttggtaag | tgcaaaatga tattttagtt | gtctatgctt | 480 |
| acactgattg gaggaatgct | ttaagtttga | ttattggtaa gtgaaacatt | ttgttacctg | 540 |
| tatttactga tcccactttc | cttttatgaa | tgtcccagtt acatcttttg | tccattttt  | 599 |

<210> SEQ ID NO 172
<211> LENGTH: 599
<212> TYPE: DNA
<213> ORGANISM: Homo sapiens

<400> SEQUENCE: 172

```
ctggtgacat ctctgctctc atctcccttc ctctccctgg tgtggacact gcacccacca      60
ccagctctga gcacatggcc cattggtctc gcaggggccc tcctctctgt ctgcagtggc     120
caccttgcca ccaggcccac ctgaaggaac cgtgcctctc tttacggact gaccccaagg     180
tttgcccatg cttggaggtc tgtctgactt tgcttcctg atgcctggca gtggaccacc      240
atgcccactt gtcggtggct gtgtagctca tactcactcc atctggcagt ttccacccam     300
cgaggaccac tcaagtttgc cccactccat gtctgctgtt gggaggggat ggtgcatccc     360
acaagcaaca ggagccacgg agctgggggc tggggctgtc agcctggatg ggccaggagg     420
ggaccttgct gtgcctagtg gaagagtagg tggtcccta ctggctccag gccgctgggt      480
gggtcacttg cccatccctg cctgggtgtc tatagtgggt gttcccgcca aaattcatgt     540 cccctggaa cctcagaatg taaccttatt tgaaaatagg gtctttgcag atatagtta      599

<210> SEQ ID NO 173
<211> LENGTH: 599
<212> TYPE: DNA
<213> ORGANISM: Homo sapiens

<400> SEQUENCE: 173
cgaggaccac tcaagtttgc cccactccat gtctgctgtt gggaggggat ggtgcatccc      60
acaagcaaca ggagccacgg agctgggggc tggggctgtc agcctggatg ggccaggagg     120
ggaccttgct gtgcctagtg gaagagtagg tggtcccta ctggctccag gccgctgggt      180
gggtcacttg cccatccctg cctgggtgtc tatagtgggt gttcccgcca aaattcatgt     240 cccctggaa cctcagaatg taaccttatt tgaaaatagg gtctttgcag atatagttar     300
gtaaggatct tgagatgtgg tcatcctata ttggggagg ggacagtaaa tacaataaat      360
gtccttggga aagacaaaag aaaagaccca gccacaaaga agaaggccat gtggagacag     420
aggcagggat ggggtgatg tggctacaag gcgtggaact cagagccccc agaagctgaa      480
ggaggcggga agtttcctcc caagagctgc caggggtggg gcggggcaga ggtggcatgc     540
ggaatgctct gcccacactg gatgtatgaa tctgttctca tgctgctagt aaagacata     599

<210> SEQ ID NO 174
<211> LENGTH: 599
<212> TYPE: DNA
<213> ORGANISM: Homo sapiens

<400> SEQUENCE: 174
tcccctactg gctccaggcc gctgggtggg tcacttgccc atccctgcct gggtgtctat      60
agtgggtgtt cccgccaaaa ttcatgtccc cctggaacct cagaatgtaa ccttatttga     120
aaatagggtc tttgcagata tagttaagta aggatcttga gatgtggtca tcctatattg     180
ggggagggga cagtaaatac aataaatgtc cttgggaaag acaaagaaa agacccagcc     240 acaaagaaga aggccatgtg gagacagagg caggatgggg gtgatgtgg ctacaaggcr      300 tggaactcag agccccaga agctgaagga ggcgggaagt tcctcccaa gagctgccag      360 gggtggggcg gggcagaggt ggcatgcgga atgctctgcc cacactggat gtatgaatct     420
gttctcatgc tgctagtaaa gacatacctg agactgggta atttataaag aaaagaggt      480 ttaatggact cactgtccca cggggctgga gaggccttat aatcatggtg aaggcaaag     540 gagatgcaaa gtcgtgtctt acgtggcggc aggcaagtga gagagagcat gtgcagggg     599

<210> SEQ ID NO 175
<211> LENGTH: 599
<212> TYPE: DNA
```

<213> ORGANISM: Homo sapiens

<400> SEQUENCE: 175

```
aatagaatac agatgaatcc agacttggag caggccatgg ggtattctta aagactccat     60
gtgtgtcttg gagtagccca tgtcatattc agaatcacag ctggggctcc aaatcccact    120
ggcctaccca ttaatctatc actgtagact agtggtagaa ttggtgacca gatattctag    180
tctgggatat gatcttggga tcttaagaga actttctgca cttcaaggtc cagtttcttc    240
acccagagaa ggggctgcca ggtataccac gagatgagag ttcctccaca gggggacacr    300
attgcagcag agatggccaa gggcaggaac tcctactatc ctcatttata tatgaggcaa    360
acaagacttg gagaattcaa gtgacttgct caaggtaatg cagccagcct caaagaaagg    420
gagccgagat taaaaccctg cccacatgc tccagagctg ggaggcttt ctgtaggccc     480
atcaggagat aagttatgtc tcctggctga aggccacctt ccacctccca gcccccaagc    540
caattgcatc agacataaag atttgtttca gggtgtcttg ttggttttcc agctccaac     599
```

<210> SEQ ID NO 176
<211> LENGTH: 599
<212> TYPE: DNA
<213> ORGANISM: Homo sapiens

<400> SEQUENCE: 176

```
tcatctccac cttccttact gcagcccttc tgctgacagc tggctgcatg ggggcaaaaa     60
tctgacaaca cccactcctg ctgccacagt ctgtcctttc tgctctgggg ttctctgctg    120
cagtgccttt gggagcttct cagccatctg actcatgctg gcgaggtgtg cactctgcag    180
cagcgccagc tgtaagacac accctcagat gggcttgtcc tcttgccctg tttcatgcct    240
cctggtccct gtttctgggc cttatcccca aaacgtgaca cttgagtaag ccctttttctm    300
aggctcaggc agatccaaaa gcacatttaa atattttcag gattctgccg atttagagca    360
actaggattc caaagaagga aaacttactc aatcagttta ttgtcagagg ctccacatca    420
ttcatttgtt tattcatttt ttcgcttatt cattcagtca ggccacaagt ttcttcagga    480
ctgggatcat gcttgtcccc attctgttcc taatggaggc tatccatgta gtagtcgctg    540
gcaaataact cttagtgact taagttcagg aggcagaagc atggtgaagg gggcagata     599
```

<210> SEQ ID NO 177
<211> LENGTH: 599
<212> TYPE: DNA
<213> ORGANISM: Homo sapiens

<400> SEQUENCE: 177

```
tgaggctctc attcctggag agagagccca gggagggaag gtggtggggg aacctcgggg     60
ttggaggcgt gggcccccaa gcatgtcccg tcctgcagac actccctgct gcccgggctg    120
accatggggg catcctgcct ggtgccagcc agcccagcct tgtctagcct gcctctgcca    180
agtggcccat ttgactgtcc ccatctgttt gcccatggag tccggagggt gtgccctggc    240
ccagagccca gctgcagcct gggaaacacc agactccatc catggctctt tgttttatay    300
tttatccaat aggcagtaag gacctcagag agcatcaggt ccagacctct tgccctgcac    360
aaatggagaa actgaggcag agagagggaa ggggcaggtc agaggcagta tggggttgag    420
tcctgcgctc tttcaagatt ctgttggcta aatccattgt ccccagaagc ccttgtgcat    480
gtagttttcc atgccgtgat gggggctggg gagtcccttg gcatcaaatg ggtggtttgg    540
attctgctga ggggtccacc tgcctggtga gcaagagacc aggagccagg agccaggag     599
```

<210> SEQ ID NO 178
<211> LENGTH: 599
<212> TYPE: DNA
<213> ORGANISM: Homo sapiens

<400> SEQUENCE: 178

```
gtgaacataa gtcttcattt atttaggagt aactgcccag gaattcaatt gttgggtcac      60
atggttcttg ctatatgaaa ctgccaaact ttttcagagt ggctgtacca ttttacagtc     120
tcaccagcaa tgtaggagtg acccagtttc ttcacatcct caccagcact tgataccatt     180
attttttatt ttagccattc tgataggtgt ctagtgatac ctcattgtag tttgaatgtg     240
tagttgccta atggttaatg atgtcgaaca tctttttatg tacatatttg catctaggtr     300
tcttcttcag ggaaatgtct ctttatatct tctgctcatg ttctaattgg gttgtttgct     360
cttttcactgt tgagttttaa gggttctttc tatagcctgg atacttctct tttgtaggat    420
ttgtggattg caaatatttt ctcccagtct ataccttgtc tttccatcct cttagcaggg     480
tctttggcag agcagaattt ttatttggat taagtccagt ttatcaagtt ttccttttat     540
ggatcggctc tgagagtcaa gtctaaggac tctttgtcta cttctagatg ctgaagatt      599
```

<210> SEQ ID NO 179
<211> LENGTH: 599
<212> TYPE: DNA
<213> ORGANISM: Homo sapiens

<400> SEQUENCE: 179

```
gtacataatt cattatgagt tacttttttgt aaaaggtgtg aaatttaggt tggagttcat     60
tttattgcaa atggatatcc agttgcttca gcaccatttt ctataaatgc tattttttctc    120
catcgaattg attttatacc tttgttaaaa attagtgggg tgtattcttg tgaatctatt     180
tctgggttct ctgtactgtt ccattgttct gtatgtttat ttgtctgcca ataccatgaa     240
cttttgatta ttgtattatt atttgattat ataagcctat atattaagct taaaatcaas     300
tagactaaat gctctcactt tattcttatt tttcaaaatt gttttagcta ttctaaaacc     360
ttttcttttc tatatacatt ttagaataat cttgtgtata tctacaaaaa aatcttactg     420
aaactttgac aggaattgct gtatatcaac catacctaaa cactgattta gggaggattg     480
tcatctttac tatgttgggt cttctaatct atgaacatgg tatgtctctt catttattta     540
gattttcttt gatgtctttc atagtggttg tgtagttttc agcatgcaag ttctgtata      599
```

<210> SEQ ID NO 180
<211> LENGTH: 599
<212> TYPE: DNA
<213> ORGANISM: Homo sapiens

<400> SEQUENCE: 180

```
tttagatttt ctttgatgtc tttcatagtg gttgtgtagt tttcagcatg caagttctgt      60
atatcaaaaa aatttacatc tagttatttta attttttgagt gatttcaata gcattgtatt    120
tttaatttttt atgttcacat gtttactact aatacataga aatacaatca gttttgtata    180
tttatcttgt ctgtcacctt gctgaactaa cttattagtt tctgggaggt attgtttatg     240
tagattcatt gggattttcc acagcgataa tcatgttatc tattttatttt ctcctttctm    300
atatgtatgg cttttgaatt catgttaatt attctgcaaa gaattggtac aattgtccag     360
taaaatcatc caggcttgga gatttctgaa atgatgtctt taatttcctt aatagttata     420
aggctatgca aattatctat ttcatattgg gtgagttgtg gttaagaagt tgatttatct     480
```

| | |
|---|---|
| aagttgtcaa atttatgtgt gtagagtggc tcatagtatt ctatttatc tttttgatgt | 540 |
| ctgcagggtc tgtaatgata ttcccggttt cattcttcat gttggcaatt tgcatcttc | 599 |

<210> SEQ ID NO 181
<211> LENGTH: 599
<212> TYPE: DNA
<213> ORGANISM: Homo sapiens

<400> SEQUENCE: 181

| | |
|---|---|
| ccagccatta tttctgtaag catttttttca ctatcatgct ctttctcctt ccttctgga | 60 |
| actccagaaa cttaaatatt agatttttg ttgtgtttct tgactcttgg ttccttttgt | 120 |
| tgtgtccctg aggctctgtt atttttatt tcagtctctt ttctctgtgt tgttcagatt | 180 |
| cagtaatttc tgttattctg tctcccactt cactctttcc tctgtccttt ccattcttct | 240 |
| gttcaaggtg tcagtgaatt tttcatttct catactgtat ttttcagttc taaaattty | 300 |
| catttggttc ttcttatctt ctatttcatt gcaaaggctt tctattttt atttgcttca | 360 |
| agtgtattca taattgatcc tggaagcatt ctgtcatggc tactttaatt attttcaggt | 420 |
| aactctaaca tctctgtcat cttggtgttg gcacctattg attgtgttt tcatgcagc | 480 |
| ttgagatctt catgattctt ggtatgatgt gtgatttcca gttgaaactg ggatgtttct | 540 |
| gtattattta gatcctgtgg ttcatctgga ttgttttct tttgacattg ctttggcaa | 599 |

<210> SEQ ID NO 182
<211> LENGTH: 599
<212> TYPE: DNA
<213> ORGANISM: Homo sapiens

<400> SEQUENCE: 182

| | |
|---|---|
| ctcctttcct tctggaactc cagaaactta aatattagat tttttgttgt gtttcttgac | 60 |
| tcttggttcc ttttgttgtg tccctgaggc tctgttattt tttatttcag tctcttttct | 120 |
| ctgtgttgtt cagattcagt aatttctgtt attctgtctc ccacttcact ctttcctctg | 180 |
| tcctttccat tcttctgttc aaggtgtcag tgaattttc atttctcata ctgtattttt | 240 |
| cagttctaaa attttccatt tggttcttct tatcttctat ttcattgcaa aggctttctr | 300 |
| ttttttattt gcttcaagtg tattcataat tgatcctgga agcattctgt catggctact | 360 |
| ttaattattt tcaggtaact ctaacatctc tgtcatcttg gtgttggcac ctattgattg | 420 |
| ttgttttca tgcagcttga gatcttcatg attcttggta tgatgtgtga tttccagttg | 480 |
| aaactgggat gtttctgtat tatttagatc ctgtggttca tctggattgt ttttcttttg | 540 |
| acattgcttt ggcaagagaa gggggtctgc tgcctcatta ttgataggtg gaggtaaaa | 599 |

<210> SEQ ID NO 183
<211> LENGTH: 599
<212> TYPE: DNA
<213> ORGANISM: Homo sapiens

<400> SEQUENCE: 183

| | |
|---|---|
| cccagcatta tttactgaaa agatcaccct tcctttccct tgattacagt tgtccttatg | 60 |
| tcttaaatca gaagactgtg taggtgaggg tcagctctag actcattgct tcattgctag | 120 |
| tgtcaactat gggccaggat ccagggcttg gaaccaagaa cctcttttgga ttaatgccta | 180 |
| ttaagataat attgaaaatg aagtaagtgc aatggagact catcattgca ttacagagac | 240 |
| agaaggggcc cccaaactaa tctggagtgg tgtacaggat cagggaagtt gccctgaagk | 300 |
| tgataagcag aatgtggaag gatgggcagg agttgtctaa gagaagagtg tggcaataga | 360 |

```
agggcaccct gggccacagg gaacaaacca tagctgaaag atgaggagtc aagaaatatt      420
ctggcaccca tggggtacta ttagcagttt aactttacag gagctgaaaa tttaagaagg      480
ggaatgtcaa gagatgaggc tgaaccttgg cagggatgga tccttggacc acatcatgta      540
gttgaccctg tcacatagct tggacttcac cttgtgggtg acaggaggcc accagggct       599

<210> SEQ ID NO 184
<211> LENGTH: 599
<212> TYPE: DNA
<213> ORGANISM: Homo sapiens

<400> SEQUENCE: 184
ttaatgccta ttaagataat attgaaaatg aagtaagtgc aatggagact catcattgca      60
ttacagagac agaaggggcc cccaaactaa tctggagtgg tgtacaggat cagggaagtt      120
gccctgaagt tgataagcag aatgtggaag gatgggcagg agttgtctaa gagaagagtg      180
tggcaataga agggcaccct gggccacagg gaacaaacca tagctgaaag atgaggagtc      240
aagaaatatt ctggcaccca tggggtacta ttagcagttt aactttacag gagctgaaar      300
tttaagaagg ggaatgtcaa gagatgaggc tgaaccttgg cagggatgga tccttggacc      360
acatcatgta gttgaccctg tcacatagct tggacttcac cttgtgggtg acaggaggcc      420
accagggctg acagtagagg aagaacatgg ccatggaatc cttgggagaa gtggtgtggg      480
ttcattgaaa aggccagggc agaggctgaa agactcatca ggggaatgta gcagtgatcc      540
gcaggggttg tttagggacc agtcatgact gtggcatggg gctgggaaaa tggggccat       599

<210> SEQ ID NO 185
<211> LENGTH: 599
<212> TYPE: DNA
<213> ORGANISM: Homo sapiens

<400> SEQUENCE: 185
ggaaccatga tgggattat cctcttcaac atgaataat gatgatgagg atggagacag        60
taatgatatt attgtatgat cactacacaa catgtctggt tcaggcactt tatgtgtatt      120
aaactatgaa ttccttcaac aaccttataa ggcagatatc actcttagcc ccactttaca     180
gatgaggaaa ccatggccca gagagagcca gtaacttgct ggggaacttg gttttttgagt   240 ggcagagctg ggattcagac ctagaaagtc tggctccaga acccatacac tgatagagtr    300
tatttctgtt caatatttat taaactcctg catgtgtttg acactctgct aggcaccagg     360
gatttaggat ggaaaggaca gtcatttcct tgcctgccct catggagctt ctgatttgtg    420
gatggaaggc atgaacatag gtgtggtggt catggtgcct cccacccatc atgaacttga     480
accaaaacag gaattctttt gtcagttttt tctatcggtt tttggggaag ttttattgga     540
aaaaaaactt ctaaacaaaa gcttaaaaag tatgctttat tgtcttttac ccttattat     599

<210> SEQ ID NO 186
<211> LENGTH: 599
<212> TYPE: DNA
<213> ORGANISM: Homo sapiens

<400> SEQUENCE: 186
aacttgctgg ggaacttggt ttttgagtgg cagagctggg attcagacct agaaagtctg     60
gctccagaac ccatacactg atagagtata tttctgttca atatttatta aactcctgca    120
tgtgtttgac actctgctag gcaccaggga tttaggatgg aaaggacagt catttccttg     180
cctgccctca tggagcttct gatttgtgga tggaaggcat gaacataggt gtggtggtca    240
```

-continued

```
tggtgcctcc cacccatcat gaacttgaac caaaacagga attcttttgt cagtttttts      300
tatcggtttt tggggaagtt ttattggaaa aaaaacttct aaacaaaagc ttaaaaagta      360
tgctttattg tcttttaccc ttattatcga accagtggaa aatcagaaaa atacaagtgc      420
ttacaccagc aataaaaaaa tatggttctc atcaacacca ccctttgccc cgagccctag      480
agtgtctttc tccaagttgt ctaaatttcc cttcagttcc tgggaccagc tgagaggaca      540
gggagcccac acttggcccc acatgagacc tggttccatt tctctccttg gggcactct       599
```

<210> SEQ ID NO 187
<211> LENGTH: 599
<212> TYPE: DNA
<213> ORGANISM: Homo sapiens

<400> SEQUENCE: 187

```
taaacaaaag cttaaaaagt atgctttatt gtcttttacc cttattatcg aaccagtgga       60
aaatcagaaa atacaagtgc ttacaccagc aataaaaaaa atatggttct catcaacacc      120
accctttgcc ccgagcccta gagtgtcttt ctccaagttg tctaaatttc ccttcagttc      180 ctggaccag ctgagaggac agggagccca cacttggccc cacatgagac ctggttccat       240
ttctctcctt ggggcactct acaacttccc actctgcccg ggtcatgtgt ggagctgacy      300
agatacttaa aaacaacaac aacaacaaca caacaacaa caacaaacaa tgttattttg       360
taagagcagt tttaagttca cagcaaaaat gagtggaaag tagagcattc ccacaggtcc      420
tctctcccca cgtgcgcagc cccggttatc aacacgccca ccagactggt gcatttgtta      480
caactgacgc agctacactg acacgtcatt tccagtgaag tccagagtct gcattagggt      540
tccctattgg ggctgcgcca ttttctcac cagcagtgaa tgagagttct gctgctcca        599
```

<210> SEQ ID NO 188
<211> LENGTH: 599
<212> TYPE: DNA
<213> ORGANISM: Homo sapiens

<400> SEQUENCE: 188

```
ctgcccgggt catgtgtgga gctgactaga tacttaaaaa caacaacaac aacaacaaca       60
acaacaacaa caaacaatgt tattttgtaa gagcagtttt aagttcacag caaaatgag       120 tggaaagtag agcattccca caggtcctct ctccccacgt gcgcagcccc ggttatcaac      180
acgcccacca gactggtgca tttgttacaa ctgacgcagc tacactgaca cgtcatttcc      240
agtgaagtcc agagtctgca ttagggttcc ctattgggc tgcgccattt ttctcaccar       300
cagtgaatga gagttctgct gctccacatg ctcagcagcc tttggtgcca tcagtgttct      360
ggattggacc attccctaac gacatacgat gtggggcacc ttttcaaatg cttacttgca      420
tctgtacatc ttctctggcg aagtgtctgt tcaggtcttt tgcccattgt ttaactgagt      480
tgtgctgacc aggtactttg aggaactcca gacttgtggc tatggcatca tcctgggcc       540 ccataggcca gttcaggagg gtggctggtg agcgatcctg cttgctggcc tgtgcaaaa       599
```

<210> SEQ ID NO 189
<211> LENGTH: 599
<212> TYPE: DNA
<213> ORGANISM: Homo sapiens

<400> SEQUENCE: 189

```
agccaggatg acacctgac cccacctgtg ttggttgggt tatttctgag ctggtttctt        60
gaccacgaga attgaaatgg ccacttccca actgccaagt gctccaagaa gcagagaaca      120
```

| | | |
|---|---|---|
| caggagtaaa aagaagcaca gaagggacag aggttccagt tcttcttgag gcctgctgtc | 180 | |
| ccatccttgg gttttgagag acacctctgt gtccttgcag agaattcacc actttgttca | 240 | |
| aaccagtctg agaaagcttc tttattgtgg tccccaagtg cagctgctgc aatgaccacy | 300 | |
| gttaacttcc ccgccttggc aaaataactg atactccaaa ctgctaagag tcccaggact | 360 | |
| gcaccagtta gctattactg tgtaacaaat tgtcccccga tacagcagct tcaaacagcc | 420 | |
| ataaatattt attacctccc aggttctgag ggccaggcat ctgggagtgg cttgaggggg | 480 | |
| tgtttctggc tcagggtctc atgaggctgc agtcatactg tccctgaggc tgcatcgtct | 540 | |
| gaaggcttgg ctggggctga aggatccact tccaagctcc catgcatgct tgtggacac | 599 | |

<210> SEQ ID NO 190
<211> LENGTH: 599
<212> TYPE: DNA
<213> ORGANISM: Homo sapiens

<400> SEQUENCE: 190

| | | |
|---|---|---|
| gtgcttcccc cagagtcaga gatgagagag ggagggaggg agtggggtta gagagagaga | 60 | |
| cggggtgtgg ggcaggagat tgaagctgca atctttcata acctaagctt ggaagtgcta | 120 | |
| ttccatcact tctgccacgg gctgctggtc acttggacca tccctgggga aaggaaacta | 180 | |
| cacagggtgt gaaaaccagg aggcggggct cactgggggt ctctgagaat ctggctacca | 240 | |
| gcaagatctt gcaggaagtg atggacagcc ccaggtggac gcgtggcata ggggtctgcy | 300 | |
| gcctcctcct cgtattatct tatcttctga gagctgctcc tgggtgaaca ggtgctcact | 360 | |
| gcctcttttt ctgggttcac atggacctgg gttagaaagc tgcctctaac atttactagc | 420 | |
| aagtgacttc tctatgcctc tattttctta tctgcaaaat cgggagaaaa atattgtcct | 480 | |
| catcgagttt ttctgaacct taaatgcaga gatcttatca gaaagttctt ggccgttgtc | 540 | |
| tcagaaactc agagtctctc ctgctttagg ggcaacgaaa gttcattcac ctacctgta | 599 | |

<210> SEQ ID NO 191
<211> LENGTH: 599
<212> TYPE: DNA
<213> ORGANISM: Homo sapiens

<400> SEQUENCE: 191

| | | |
|---|---|---|
| cagcccaccc atcgccctgg acctctggcc tctaggtatc tgggattctc ctttgtgaga | 60 | |
| ggcaaaaaaa aaaaaaaaaa cccaaccaaa aaaaaccccc aaaaaaaccc caacttgaag | 120 | |
| tggattcagc cacaatgtat tggatggtga acacgaaggg caggaggaag ggggggggt | 180 | |
| gggggtggta gggagggggcc tggttcaggc cccacaggcc ctaggacgct ggtgccctct | 240 | |
| cccccctctgg ccacaccctc cagggctctg ctgaccccct cccagcttcc ccctgcaty | 300 | |
| cgtaccatgg cgggagcagt gcaagcctca cgtctagtag aagcagcag gagtctttcc | 360 | |
| cagcattccc caacaagagt ctcattggct gtggttgggg cacatgacag tccctgacca | 420 | |
| atcactgagg cctgggtctg attggctagg cttgggtcac atggcccact tttggcccag | 480 | |
| tgggtgaagc cactcttgaa atggatcctg gccaggagga gtcctcctta taggaaagtt | 540 | |
| gggttacggt tcccagaaga ggtgggaagg gatgctgggt agccagaact gacactggc | 599 | |

<210> SEQ ID NO 192
<211> LENGTH: 599
<212> TYPE: DNA
<213> ORGANISM: Homo sapiens

<400> SEQUENCE: 192

```
taaccaaggg cattgcgttt gtcccacatt ccgaaattca cagtggcagg tggtggctca      60
gaggctggaa cctggccctg agagacccat tgcctttctc tgttctgtaa cctcttccca     120
tagagatttt tatcctgtaa ccctgtggtc atcaccatgc ctcccattta tgtgcagttc     180
ctatgggctc ctgatgcttt cctggatttc tcccaggaga ggctgttggg tgttggggtg     240
ttggggaaga gaattagtgt tctgcagtct ggagttcact ggtctgcaga ctgctaaaar     300
tctgggggct gcgtctgcca gggatagtgg ctctggctgg tatggggacc aagggcaaaa     360
ggatcagtga tttcagcaga tgcctttgag ccccgagtct ctggctgtgg actagtccag     420
tagaaagagt gtcttggagt gtggcagagt cccagtcccc tgtctttctt actgtcaaaa     480
ccaaggtttg ggcaatcgat gatctagcta aaaaaacgat gttttcagc ctgtcctttc     540 tgggctcctc ctgtcccaaa cacagatgtg aagcaatgtg cgagaattcc tattctaca     599

<210> SEQ ID NO 193
<211> LENGTH: 599
<212> TYPE: DNA
<213> ORGANISM: Homo sapiens

<400> SEQUENCE: 193
gtatcctttg accatggttt taaaatttgt agacattttt aatatattct aatacaaatc      60
ctttgtcaat tataagtatt gcatatatct tcttctttgt gcctgttctc ttcatttttc     120
ccacagtatc tttggtcata ctaaagtttt ttttgttgtg tgttttttt ttttacatt     180 tgatacagtt aaattaaatc ttgttttgat tgtactttt gtgttagttt aatacataat     240
ttcttatctt ggtgtcagaa aggcattcta tcagaattta ttttcaaatt gtatagatty     300
tccgtgtaca gtttggtctt tggctcaact gaaatttatt tcttttgta ggtgtaagga     360 aaggatatat tttatcttg ttttcctttg taaagccatt tgtccccaat ccatgtattg     420 aattctttt ctttttttc tacagatata ttcttatata ttgttccat aaaattcctc     480 tctattttgt cccatcaatc tatttattca tgcactaata ccacacaatt ttaattatga     540
tagttttact gttaatcttt atctttggta tgactctttc tcactcgttc cttccttcc     599

<210> SEQ ID NO 194
<211> LENGTH: 599
<212> TYPE: DNA
<213> ORGANISM: Homo sapiens

<400> SEQUENCE: 194
gaatttattt tcaaattgta tagatttttcc gtgtacagtt tggtctttgg ctcaactgaa      60 atttattttct ttttgtaggt gtaaggaaag gatatatttt tatcttgttt tcctttgtaa     120
agccatttgt ccccaatcca tgtattgaat tcttttttctt tttttctac agatatattc     180 ttatatattg tttccataaa attcctctct attttgtccc atcaatctat ttattcatgc     240
actaatacca cacaatttta attatgatag ttttactgtt aatctttatc tttggtatgw     300
ctctttctca ctcgttcctt ccttccctac cttcttttcc tcgtcttcct ttttcaagac     360
cttcttcctg tttttagcac cttaatcatt cacataaatt ttaggattac cttgttaagt     420
tttatgaaat aatctgttgg aattttggtt agacttgcct taattcatac attaactgga     480
gtagaattgt catctttacc atactgagtt ctactcagga gcatgacata tctcttaatt     540
tatttaatgc ttcctttgtg tctttccatg aagatttaga attttctcca taggtcttg     599

<210> SEQ ID NO 195
<211> LENGTH: 599
<212> TYPE: DNA
```

<213> ORGANISM: Homo sapiens

<400> SEQUENCE: 195

```
tgtacagttt ggtctttggc tcaactgaaa tttatttctt tttgtaggtg taaggaaagg    60
atatatttt atcttgtttt cctttgtaaa gccattgtc cccaatccat gtattgaatt    120
cttttctttt tttttctaca gatatattct tatatattgt ttccataaaa ttcctctcta   180
ttttgtccca tcaatctatt tattcatgca ctaataccac acaattttaa ttatgatagt   240
tttactgtta atctttatct ttggtatgac tctttctcac tcgttccttc cttccctacy   300
ttcttttcct cgtcttcctt tttcaagacc ttcttcctgt ttttagcacc ttaatcattc   360
acataaattt taggattacc ttgttaagtt ttatgaaata atctgttgga attttggtta   420
gacttgcctt aattcataca ttaactggag tagaattgtc atctttacca tactgagttc   480
tactcaggag catgacatat ctcttaattt atttaatgct tcctttgtgt ctttccatga   540
agatttagaa ttttctccat aggtcttgca tgtcttttgt tagacttctt cctaggtgc    599
```

<210> SEQ ID NO 196
<211> LENGTH: 599
<212> TYPE: DNA
<213> ORGANISM: Homo sapiens

<400> SEQUENCE: 196

```
atagattgaa agtaaatagg tggaaaatga tataccatac aaacgataag cataagaagg    60
ttggttgaag gggttatatt aaatcagata aaataaactt ctaggcaagg tgcaataact   120
ggtataaaga ggaacatttc ataaaaaaca taataacaca tgtaataaat tacttaatag   180
caaagggaca ttcataagga agatacaata ggctatatat atatatctgt taatggatct   240
tcaacatgaa tgaagcaaaa tttgacaaaa ttgcaggggtg aaaaaatatc cacaaatatr   300
attggaaatt ttagtaccta tctgtcagca attgatagaa caactagaca gaaactgaga   360
gaagacatgg aaaagctaag cataagtatc ctattaactg cctttgttga attgatactt   420
ataaaaatca acatccccaa ggagagaata cacactttt tcatattcat tatgatggac   480
tatatgctgc accatacatg aaaattgtta ctgttcttgt ctttttccct ctgtgtataa   540
tgtgtctttt tctctggctg ctttcaagat tttctcttta tcacttgttt gattacaat    599
```

<210> SEQ ID NO 197
<211> LENGTH: 599
<212> TYPE: DNA
<213> ORGANISM: Homo sapiens

<400> SEQUENCE: 197

```
ccagttcttc caaatgtccc cattttacag cagaggaaac tgagggtcag gatctctttg    60
ggcacggttg caaagaaagg cctcctagag aaaggggcct gtgtgcaagc ccagggggat   120
gggggggtgag gctagagca tttcccgtgg gtggaaacag tgaacaggcc tctggaatca   180
agctagccca taacctgccc ggggcacagc aagtggtatg gcgagaacag accaagtttt   240
gggtgccgaa taaggatgag gtaaaccagg ggcagagttt tggaatctca gcccaaaggr   300
gtggcctgag tccaaggctg ggggagcatg cacctgctgg ttgctgacac aggtgatcct   360
ggctgtgttt ttgttaagac tggctttgtc gtagctccat ggatctgggc acaatccaga   420
gatgttgtct tcttgcacac tcattttaca gatgaagaaa tcaaggcttg gggtagtaga   480
gaactttcca gaagtacagg gcaagttgt gtctaagcaa agctgagccc tctgcccct    540
tgtggtgatc tcctcagccc cgttctcatc cttccagggc aatagtcttt ccttgggag    599
```

<210> SEQ ID NO 198
<211> LENGTH: 599
<212> TYPE: DNA
<213> ORGANISM: Homo sapiens

<400> SEQUENCE: 198

```
ggcatggcca caaccctcac ctggatgcct gtcctctgtt caccctctgt tctctttcca      60
gcagaacatt cagcccagcc ttgggtgtca ggcatgtgcc tgcctctctg acctcatctg     120
gtggccaggc tgtgggaagg gaaaactgga ggagtctttg ggggctgagc ctctgggcat     180
ttgtaggagg caccaccagg gtgtcaatga agataatgac gctgaagctc caggcccttc     240
atttgcatgg gcccatccca cagttcagcg tgggcttccc tgcccctacg ctgaaggatk     300
ctccttgact gtgagtggga ctgtgggctg tggcaacctg gtaggtggac ctcatggatc     360
actgactctc tctcttggct ccaaggagga agatgaagca gtcgctgctg cgcttcctgc     420
tcagggccat ggtgcccagg ctttatggcc atctcttccc tccaggacca gagggaatga     480
gggcctggct cagttggctt ggttgcccaa ctgtggtcat caggagggtg aatgatgtca     540
aagaactggt gtctcttaca gatacccctgc ccaggcaaga aattgtagag gacatttca     599
```

<210> SEQ ID NO 199
<211> LENGTH: 599
<212> TYPE: DNA
<213> ORGANISM: Homo sapiens

<400> SEQUENCE: 199

```
ggggcatgtg agcatccttg tggtgtgtcc ccatgtgcac acatgcatgt gtgcccacat      60
gtgagaagga ggtgggggca ttgctgccag gagatggatc atggggagag aaagaaactc     120
tttttaccaa ctcttggaat caggcctgtt catacatgat ggcattgctg gatctgggga     180
tgtgtctgta gatgaatttc aaggtctctc ttggcttaaa atttctaaga atcccaagca     240
attaccttgc aggagaaata tgggaaaagc ccttttttag tctgtccatt catgcatctk     300
tttattcaat cacctatccg ttcactgact taggcatcca tctacccact cacacattca     360
cccattcact catccatcca accattcatc tactcatcca accattcatc tacccatcca     420
ttcagtcatc cattcacttg cccattgacc cacccatcca tccatccacc catccatcca     480
accatccatc cacccaccca tccatccatc catccaccca tccatccatc catccatcca     540
tccacccacc cacccatcca tccatccatc catccaccca tccatccatc catcccccc      599
```

<210> SEQ ID NO 200
<211> LENGTH: 599
<212> TYPE: DNA
<213> ORGANISM: Homo sapiens

<400> SEQUENCE: 200

```
ggagttcccc agttccggct ttgaagccct gcctggtttg gaagttaagg ctatcctgaa      60
gacttgagcc ccaggacatt ggaaagagct tttgttctca tgcaaatcac aggggggccag    120
ttctcctggg gtttgcatgc taatagctgt ctttttttgtt ttgttttgtt tctaattcac    180
agcagataaa cagtgaatgc caggaacaga caagtgtgca gggtcagcag atacaagccc    240
cttgtgggaa gggggttttt ctctaagtat cagattcgtc aattactggg taaatttctm    300
atctcttagg acttccccctt tcaataaata cttttcccaga aagtctcacg aaatcaaccc    360
tgggtctaaa aataaggctc tactcccatc ccctgggcat gagtggtccc catgagccca    420
ggtgcatggc ttgaggaagg cactgggcgg tcacaggagt gctttgtgga caaggtgcca    480
```

| | | |
|---|---|---|
| atggtgtggg cagagatctg gcagacagta gtccctactc tcttcctgtc ttgatgagga | 540 |
| ggatccgagc tggcccagag aagggggcaag ccttccaggt agagggaata acatgggca | 599 |

<210> SEQ ID NO 201
<211> LENGTH: 73344
<212> TYPE: DNA
<213> ORGANISM: Homo sapiens

<400> SEQUENCE: 201

| | | |
|---|---|---|
| aatcatgaac gaaactgttt taatccacca ataataatga atttcaatta cccatgtttt | 60 |
| ggagtaaaat cgaattatct ttctattctc tttacaggaa aaaattataa ttataaaagt | 120 |
| attgtcatgt taggaggtgg taaaacagta tgtaacccaa aacagagaaa aatggtatta | 180 |
| tagaaatggg tcaggtagtt aagaaataaa aacatcagca ctttcctgtg ttttgtggtg | 240 |
| tttgcaatat ttgtgagctt tgtaacattc gacttgtgat ttttttcctt ctcattctag | 300 |
| taaatattca ggttggtgtc tagttttgta gttgcaattt tgtcttcttt ttcttttttct | 360 |
| tttcttttct ttttcttttt ctttcttctt tttttttttt ttttgagaga gagtctcgct | 420 |
| ctgttaccca ggctggagtg cagtggcgcg atctcggctc actgcaacct ccgcctcccg | 480 |
| ggttcaagta attctcctgc ctcagtctcc taagtagctg ggattacagg cgtgtgccgc | 540 |
| cacgtctggc taattgtttt tgtatgttta gtagggacag ggtttcacct tgttggtcag | 600 |
| gctagtctcg aactcctgac ctcatgatcc acctgcatca gcctcccaaa gtgctgggat | 660 |
| tacaggcatg agccactaca cccggcctta ttttttcttaa agagccctg tccagttgtg | 720 |
| taagctccag gctccttggc gcctggcttc accccaccct ctcagcatcc cctgcccagg | 780 |
| gaatccactt tactggagtt gggggtagat tccaaccagg acgctttgcc tccctcccat | 840 |
| agggtggggt ggaccctgtc ctcctaacct tcgtgaccat gcagaacagc tgcccccatc | 900 |
| cttcaaggac tggcacccac ttttcacatg cctcccctca tttaatcccc ttaatttcac | 960 |
| atcgcttctg tatattttca gaattattgg ttaagccaaa attggattat tgatcattcc | 1020 |
| aatatttcag aataatgaac accacccagg ttgccataga gagatttgag gcaggagagg | 1080 |
| tgaacacacc ccagcttccc agccagtaag tggtcgtgct gggatgtgaa cccagggcta | 1140 |
| tggctcccct gctggcagcc ctagtgccat tgtattctcc actcttggtc accagcgatc | 1200 |
| acagcagcct tgtcaatagg aacagaaacc ttttatgtgc accctcccct gtgccctgtg | 1260 |
| ccttgcgttg gaccacattt cagtctcaca gcagtgtttg aagatggcta cactgattat | 1320 |
| cctgtgttac agataagcaa attgaggcta agagtggcta agcaatacat tcacgatggc | 1380 |
| acagctgata tgtagtgaga gttcagtttt gaactcaggt ctgagagccc cattttcatg | 1440 |
| accctggcat ccccagggaa gtcatccctg ccacccctgg attggtgcta tcagccttcc | 1500 |
| tgcgcagaat gttccagaat gtcatccect gcccgggaaa actggcccctt tgagtggctg | 1560 |
| accagcccccc actcccaacc actctccttg gctctatttg taaagtgaat tactgcatta | 1620 |
| tgggaggaac aagaaggttc tttatctcca cttgggcaaa tccattagga ttagaggccc | 1680 |
| ctctgaagcc cctctgaggg ggtgacgtaa gcctgtcttt ggtgatttgc agagtgacag | 1740 |
| catgataagg agtccgggcc cgttttagtg gtgacaggac atcctccccc tgcagcaccc | 1800 |
| aagaattagc gggcctatct ctccatttat caaagccctt tggggatga ggcaatcggg | 1860 |
| cggaggagta ttgcagcctc tctgtctcgg agtctgtgga gctgtcgctt cccgccagct | 1920 |
| tgcccaggtc atacagctgc ccaggatctg cggggtcttc gtgacttccc acagtgagaa | 1980 |
| ccaacagaag ggtctccaac tgccaggctt cgtggcccag gtccctccag tgtctgacct | 2040 |

```
gcatggcctg ccaccctcta gacaatgccc agacttttgc cctgaaatac catgaggatg    2100
gggatgccat tatctagcaa ggggaccgcc atgtctgggg aaaaattcaa gggttctgcc    2160
tggctcaggc tcagtctgag gtgctaggga agatggcagg tcccaaagat gatgcccct    2220 gtatatctcc cattccacct gctcttctta caaagtaagg tcgacactct ccctttgaga    2280
ggaagagtga ccctgtccct gagcttgtgc agacctgtac gctgacagag tatatggcag    2340
gagtgacgcc ctgtggctcc tgagttgagg gctgaaaagg caatatggct ttcatttgac    2400
tctctctttc ttggaattca tcctccatgt tgtgaggaag cccaagccac atggagaggc    2460
catgtgtggt tctggccagc agccttgcc aggcccgcag ctgacatcag cctcaactgg    2520
cagacatgaa ggtgaatgag ccttcaggtg gttctgtctc tagcctctga gccacccag    2580 ctgaggcccc agatgtcact gggtggagag aaaccatccc cgctgtgcct gcttgaccgg    2640
cagaagccat gagagataac aaatgatgat tgttgttttg agtgactcca tcttggggca    2700
gtgttattca aacagaataa ccagaacaca tgctgctaat aaagacgtat ctgagactga    2760
gtgatttatg aaggaaagag gtttaattgg ctcacagtcc cacatggctg gggaggcctc    2820
acaatcatgg ctgaaggtga acaaggagca aaatcacgtc ttacatggca gtaggcaaga    2880
cagcatgtgt aggggaactc ccctttataa aaccatcaga tctcaggaga cttattcaca    2940
gtcacgagaa cagcatggga aagacccacc cgtatgattc aattacctcc caccagatcc    3000
ctcccatgat aagtgggaat tatggaagct acaggaatta tgggaattac aattcaagat    3060
gagatttggg tggacataca gtcaaaccat atcaccgttt gtgtgtggaa ggcagaatag    3120
tggcccccaa aaatgtcttc atcctaatcc ctgaaatttg tgaacatgtt aggttacagg    3180
acaaagggga attaaagtca cagatggaat taaggctaat aatcagcagg cctcaagata    3240
gggagaccat cctgaatcat ccagcttggc ccagtgtcat cacagggtcc ttaaaagtgg    3300
aagagaggga gtaagaggag aatcagaggg agttgtgatg gtggaggcaa ggcacagaaa    3360
gatgcagtgt tgctggcttg aacatggag aaggggcacg agccaggaaa tgctggtggc    3420
ctccagaagc tggaaaaggc aaggaaatga tttgcacccg caggctccag aaggaacctg    3480
gattcaagcc ctgtgagacc tgtcctgacc tctgggactg tagagtgata agtgtctgtt    3540
actttacgct accaagtttg tggtgttttg ttgtagcagc aataacaact gacacagcct    3600
ctatgtgctc ttgggaatga gagaaggaga taatatcaaa gaaaagagg gcctagctgc    3660 aggagaaagg tcttgcatag gtgagaggga atgggggcca ggaccccagt catagccatt    3720
taatagtaat gccatcagca tcattgttat cagcatcatc accaccattg tcatcatcat    3780
tgtcaccatc attaccacca tcatcatcat caccatcatc atcataatca ccatcatcat    3840
cattgtcgtc ataatcacca ttatcatcat tgtcatcatc accattatca tcgtcatcat    3900
catcatcacc accaccacca ccaccaccat caccaccatc atcatcattg tcatcataat    3960
caccattatc attatcatca ttaccaccac caccactacc atcatcatca ttatcatcat    4020
catcaccacc accatcatcg tcatcactgt cattattatc attgtcattg tcaccattgt    4080
tgtcatcttc attgtcatca tcattatgaa gactgttcag caaagacccc aggaggtagg    4140
gccccatcag gagacagcat tttccctgca gggataggtg gcctctagca cttagttcaa    4200
ctctttcctt ttctggggat gggggtgcag gagggaaaac ctaggatccc atccaaaccc    4260
tccacatttt atctcttgct tcatttgcct cttttctctcc tgccttattt gagagctgat    4320
gtccctccga cctcttttgg aacactgttg acagacagca cagggctgta ggaacccact    4380
ggccctggag ccgactgcct gtgcttgaat cctgtctcta gcaccaatat ttgggtaacc    4440
```

-continued

```
ttgggttatt taacctctct gtccctcagt gttcccacct ctagaaggag atgaatgctt    4500
ctgcctcata ggggagttgt gacttatacc tggaatgaac tttggcctat aatgggtgtg    4560
tgacaagtct cctcagcatt ggacagcttc actgctctgc gcccaagact gccctcgtca    4620
gtgctggatg aatgaggcca ggaggcgggg gaaagaatgg aggcaggtgc ccaagcttgg    4680
gtttggggca acatcgagct aaagagccag aaggcagggc tgcatgatcc caaactctac    4740
cagaggcttc ctctccctga ctccaaagtc ctttagccct gggcaggtag aaagaaggcg    4800
ggggccggag atggagattc ccggtggaca gtaatggtgc ctggccgcta ccatggctga    4860
agtttgcccc tctggccttg cctggggact ggcagtctca agacagtgga gagaggctaa    4920
actccatcct gccctggta gaacctgaca ctggacatca gaggcatctt ggaaggtggt    4980
gtcttcccgg cctgttccag gcaggcatg tgagacaact tgcccaaga atgcaagcac    5040 cttcctgggt ccctaccatg agggctcatg ttgtttacca tagtagtttg cagacataaa    5100
caaaataata ataaaattga tgtattaaag aaacttttca ttgaatggag ttttaatag    5160 aaaacttagt ttgaaaaaaa cagacaggct gagtgtggtg gctcacacct gtaatcccag    5220
caatttggga ggctgagatg ggaggattgc ttgaggccag gagttcaaga cctgcctgga    5280
caacatagca agacttcatc tctacaaaaa aattaaaaat taacctggta tggtggcata    5340
cgcctgtggt cccagctact cgagaggctg aggtgggagg attgcttgag cctggcagtt    5400
cgaggctgca gtgagctatg atcgcactgc tgccctccag cctgggagac tgagtgagac    5460
cctgtctcta aataaataag taaataaata aatggtcctc ccagtggaca cagccctggc    5520
tggaaggtgg gttcttggct gagtttcaac cccgttcaac cacgtgatgt tgggaagatg    5580
gtgagatctt tctgaatctc agtgtctcca tctgcagaga cagaggcgca aaatggcacc    5640
actacacagc actgctccct gggccgtcag gggcagggtt cctgggtggc gccagccatg    5700
tgggctcatg tcccctggca atcttgtgac gtcgtctccc atttccacct ggacattgcc    5760
catcggtccc tccatgggtg gaagcttccc tgtgatgctg ggggtgcaga gcgctcctcc    5820
atggttctgc ctgtgcctgt gggtgatgcc cttgctcggc tgggctggaa gtggccactt    5880
ggccgtacaa agcactctcc atctgtgata ggatgacttc acagccgcag ctgggtctcc    5940
tgggcctctc ggaccctttcc tcagaaggct ctcagggctc tgcagctggg cagagcctgc    6000
atgattcgtg gcactgtccc tttctccctt gatttctctg cacctcagtc ttcccatctg    6060
taaagtgggg atgctgacag cccatgcggt agggtgttag gaaaagcagg cagagaatgc    6120
ccggggaaga cctggctggc ggttgacctg cagtgagtag tggtgagggg cagtgttgcc    6180
acttgaggaa tagcgctgag agagaccagg cagaggtgag gttttgagac cagggagatg    6240
ttcagggtga ctggggtggt gggtagtgag aaggggagac tacagcgttg ttaggggctt    6300
ggaagtctga gctaaagagc ttagacttca tgttgtagca tggaagagct ggttgtaggg    6360
ctgaagagac agaaacagag aaggcaagca acgtagccaa tgtcacatgg cccattttt    6420 ttttttttga gatggagttt agctcttgtt gccgagactg gagtgcaatg gcatgatctc    6480
ggctagctgc aacctccgcg tcctgggttc aagcaattct cctgtctcag cctcccgagt    6540
agctgggatt acaggcatgc gctatcacgg ctggctaatt ttgtatttct agtagagacg    6600
gggtttctcc atgttggtca ggctggtctc aaactcctga tctcaagtga tcctcccacc    6660
tcggcctccc aaagtgctgg gattacaggc atgagccacc atgcccagcc cacactgcac    6720
tttagtggca aactgggatg aggatgggca tcctgtttct ctacctctca acagtgtctg    6780
agccttgggt gcagccttgc aggtgaaacc ctgggctgag agtagaggct gtagcgccct    6840
```

```
tgaccttgag tgcaggtgac atttccaagc tgtctttaat ttgccttgaa atcaggcaca   6900
aatcctttgc aaaacaggaa actctctctt tgggactgac atgaaatagt attgctattg   6960
aattaaagag ttagagctgt ctcaaaggag tggcatattg aaatagccgg tggggtcagc   7020
ccagcctggc taagcctttg atagcacagc tgataataga ccccggccta taaataccgg   7080
gaatcaatca cgggctggag ctgctgacag cctgcatgtt cacatatcat ggcagatggg   7140
cgggaggcag gggcggcgat ttgtcttgcc tttcagatgg atttcctgtt ttctagggag   7200
tgggaaagga cccatctggt aatcagatcg tggccaagat cacctcctct gggtcactgg   7260
cccctgctcc atgtgtcccc tcggccacgt ggccccagca ttgcggcggt caggcggccg   7320
ggcctctgaa aatgagagcc acaccaggag gcctctcgcc ccgtggaagc ttccggaggc   7380
tggggaggcg gggactcctg cctttcatct tcctttctgc ttcttttctt ggcacctggc   7440
tttgctcata ggcatttcgt tattatttt tcttcaaag gctcgtctca acttgcacat   7500
gtatgtgcaa acttccacaa acacatgcac atgtgtgtgt gcacacatgg ggtccacagc   7560
ctcctttgca ggccctcctg ggcttccctg tcaacccaca gctcctccta gatgcgtcct   7620
gatgccttag ccaggtagag ttctctgtaa tattatttgt tctgatcatt gcattttcac   7680
tgctcctgac tctcagtttta caacatagcc caaggccagc tacggctctg agccaccttt   7740
ttgtcttggg caaggtgtcc cagagctgaa gggtccacac tctccttggc tccgccagga   7800
gtctctgtcc ctcctcccct cttacttccc ccaatcccca ggcattcaca gagtgggtcc   7860
tttgtgtgag accttgggct ggtggacaca tggggctctt tcttcctgag gagctggtcg   7920
ggggatgcgt ctatcctgat catatctcag gtgtcttctc tcccctggct catgaaatct   7980
cctgtctccc aaattatgtc cagacagggg tggtagcagg catctctctc ttccagccca   8040
gaggcccacc caccagccaa atgggcatt taattggaaa gggaggctgg caggctgcct   8100
ggaaatcctg cagaaaggat cggagtggcc tgctttgaaa actttgccac atacctt ccc   8160
cgcagatttc tgtttcaaat atttgaaggg gttcttggga ccatttgaga attacacccg   8220
gagccatgca atgacagatc cctccaaacc ctggtgggc ctgtgtggtg gtgccgccca   8280
atcacttggt ataaatggga aacggaggca gatcagaggg ggagaaagaa ttgaattcaa   8340
tttggttcag cactccaaat gttggttgaa ggctctttct gtgagagaca cacaaaatac   8400
ttacctgaaa gcccctcccc gccaaatcct gaagtcacag cttccttagg gacttcagcc   8460
agaactctcc ccaatatttc agtcctgctg gatgattcct gagcctgcag attcctgttg   8520
gtgtgagtca gcagggtgga gggatgggtg aaggaaggag tgagggtcgg tgagggagat   8580
tcatcctaga ggcctcatgg gtttatctgc caagcagata aagcccctcc tttcagagcc   8640
aaaatcaggg ttcatcaggg ctggagtgag gccatggaag gcaggatcag ctgtgtgtgc   8700
aagacagact gagagcaaga gaagaactgg ggtgtggagg ggtggctggg ggcagctgtc   8760
agaaggtcca ggccctgaag cccggggtgg tcagctgctc ctcttcacag agaccacggt   8820
gctggcatct catcatcagg gggcatgtgg ccagtggaag ccatgcaact tggtaaccat   8880
gggtgagtag ctggacctcc tctagcctgg tttcttcctt ggcagagcag gaatgaccag   8940
agttgctttg ccaggtacct tgagatgaaa tgaggtgtga gggcagaggg ccgccctgtg   9000
ctgctcagag ctggtccatc agtccacagg ctgtttccag ggccatattc cagctctggc   9060
cttttttgagt catggtgctc taggaaagtt tctaagccta gagccccatg ggatactaat   9120
gggatagtaa cagtcctacc tcacagggct ggggcatgaa attggttaat ccatatagat   9180
aacctggaat agtccctgac tggtacacaa aggggggttaa attgaactgg tgctgtgatg   9240
```

```
gtggtggtgg tagtgataat gatgatgatg gtatgaggag aatggtggtg ttgatggtga    9300
tagtgttgat ggtggtgata atgatggtgg taaacgtggt gatgatgatg atgatggtca    9360
tgatgatgat gatgatggtg atggtgatgg tgatgatggt agtggtggca gtggtgatga    9420
tgatggtgat actggtgatg gtgatggtgg tgatggtgat gatgatggtg gtggccagtg    9480
gtgatgatga tggtgatact ggtgatggtg atggtggtga tggtgatgat gattatggta    9540
ggcggcagtg gtggtgatga cagtgatact ggtgatggtg atgatggtga tgatgatggt    9600
gatactggtg atggtgatgg tgatggtgat gatgatgatg atggtggtgg tggcagtggt    9660
ggtgatgatg gcgatactgc tcatgatgat gatggtgatg atgatccgtg atggtgatga    9720
tgatgctatc ggcagtcgtg atgatgatgg tgatggtgat ggtggtgatg gtgatgatgg    9780
tgatgatgat gatggtgatg gtggtgatgg tgatgatggt ggtggcagtg gtgatgatga    9840
tggtgatgat gatgatgatg gggtagtggt ggtggtagtg attgtgatga cgatggtgat    9900
gatgatgata tggcaatagt ggtgatgtg atggtggtga taatgatgaa taaatcgtca    9960
tcatttagca cttgttatat gcttagatct gtcccagcca tggggatacc acaatgaaca   10020
agacaagtat ggttcctgct ctcctgagaa tcagtactac tgatggcaat agccagtggg   10080
taagttaacc gacccatgag caaagtaaca tttcagaggg aggagctgga gagttgtgtg   10140
aagtgtgggg cagcccagta ggctccttgg aggaggtgac atgtggatga agagacgggg   10200
ggagccacca tcatgagggg cagagaattt atattggctc agataactag gacatctggg   10260
gttgcatcta gcattgggaa caggcgttaa agatgccctc tcgctccccc tctctcctct   10320
ctgcctctcc tgactacctt ttgacttcca tggtaccccg aatcaatgcc actcttacgg   10380
cttccaagat ccgttgtccc gggctagttg tgtcccctcc ctggaactca gtggtcccat   10440
ctggaaagtg tgatggggaa cgctagccag acacccctgt ggtccttcc atctctgggg    10500 tcccgagtgc ctggccctgt gctggcgccc ttgttgggcc atggagtaac tgacagtaag   10560
cagtgggcat gaggagcact tcctgcttca gggcctgcgg gagggtgaac agttcacttc   10620
acagtaggtc tctgtggctt acctgggatg gagctggctc caggagcaat ttcccctgga   10680
tgaaacaatc tttggaatcc accgtatatc actcgccatg acgtcttctg tttaaacagc   10740
ggcagccggc agagggtgag cgaggaggcc gtgctgggag gagggcccat gtcccagccc   10800
ccaaccccgg ccccggtgga aggccccgct atggggaaa gcaggcatat ggaacccatt    10860
tgggaaattc tttctgcata aaccactttt tccaggtaag acacatgccc atattgactg   10920
ggaaagatgc aatacctctt acactttgcc ggctacattt ttatggacct taattaaacc   10980
cacggtctgc cggggttggga aattggacac tctttgtgcg gcgccttctt aagaagtact  11040 gttgcccag gggaggccaa ttataacctc gcgtcctccc cacctcccag gacctcacag    11100
accctccaag cgcttggaaa atgtgcgctc gacagagggc ctttgattct gcttgcctgg   11160
acagcgttag gcctgtttcc aggcctgagg caagtggtgg tcagggtccc aggcggccgg   11220 cggagggcc acagagaccg gagttttcaa acttcattga gcaccagcgc tttccttttca   11280 tgcccaatcg catggagacc tcggataaaa accagatgag cctgctgggg ctgaaggggg   11340
aggttggtgg ggggtgcacg tggcccctttg ctcacccca gctcctgttc gccatgaggt    11400
gacagcgagg acagccgcct gggtgttcag tgagttgtta acgcctggat ggttgtgctc   11460
gttatcctgt ttaacaggca caggccaagt gaggtaggtg ctgttaccat tgccatttca   11520
cacctgaggg aacctaggcg cagagcagca gagggacggg cccagggtgg cccggccgga   11580
gcaggaggag tggtggggtt tgggtcctgg aagcccgtgt gcgtggccgc ctctccagaa   11640
```

```
ggctgctggg gagctactga ttgggcccaa gcctctcttt tgacggtgct ccgggctcag   11700
tgctgtgcct tccactcccg gtggccctg cctgtgcgtg atctccacag cacagccccc    11760
ttcttgtgtc gggtagtggc ctaggcccct cctatgcttg ggttcatgga tccagcaggc   11820
cgggggggtc ctctcaccgc tggaggggct actctgccag cctctctggt tgggtggaac   11880
ctgcccttga ctagcataca tggtccgggg caccccagga cttttcaagg atgccttttgg  11940 ttggaggaga aggtgtcttt gctttggtcc tttttgtgct ctgggcttcc acgaatattt   12000 cattttttagg gaagagattc gttaatcaag aaaagtgtcc cctggatgag cttttcctgg  12060
gattggctct tcctgggatg ctcaggtcat ggcccagaa accccaacct agccaaggga    12120
gcatgttagg aagccaggcc aatggaggga taatttacat gcggtaacat ccatcctttc   12180
aaggtgtatg ctttggtgaa ttttgacaaa tgcaagtagt cacagacacc ctcgtaatca   12240
agatacggaa gatttctatc acctccaaag ctccctcgtg cgtcctccca ccccagcccc   12300
ccagtggtgg atccgttttt ggtcctcata gctctgcctt ttctagaatc gcatcaatag   12360
acccatgcag ttggcagtct cttcagtgtg gcttctttca ctttgtatta tgcctttaac   12420
atccagccat agttacaggg acatcgctgg cacctcgcag gctgggtggc ctcagggaag   12480
atggagctgg gctcaccccg gtaccctgg agcagtcgag ctctctggca ggtagagcag    12540
ggtgggtcca gaagcttctg ctagtctttg tttcctcatt aactcaggaa tgttaatcag   12600
tgctgacttc ttggggttga tgggaaatga tgggccattt ggatacttgc tcagggactg   12660
tgcacagtgg ctcatgcctg tgatcccaag gttttgggag gctgaggtga gagaagcact   12720
tgaggccaag aatttgagac cagcctgggc aacatagtga gaccccatca ctagatatgt   12780
gctcctgacc tcatagcaca gaaacccaac cagaaaggat tcaataagtc tggatgagga   12840
tggctccagg gcagcttcat ccaagcactc atgacatcag tgatctgggt gactcctcag   12900
ctgcaagatg gtggcagctt cttctagcat cacgtcccta cgggacaaca tccaagtggg   12960 aagggggcact tccctgtggt gttcccctct gttagcaaga aacccttttc cgggagcagc   13020
ccccagtttc agcagtcttc cctgtgcctt actggtcagg gtgtgtccca tgcgtcatgt   13080
ctacaccaat ctccagcaac agacgggagc tgccaggaga gggtgaagcc tgagcagcct   13140
ttgctctggg ctggagaggg gctggtgaag cacagagcag ataatgcctg gataagacgg   13200
gggctctccg ggcaagggaa ggaggacgtg cccagaggtg gggaactggc cgtctgctag   13260
atgctgtgtg tgagtctgat tgcaaggagg ttctctgtct acaaaagacc agaacaggag   13320
ggagccatta gggaagaagg ccaccaacat ggccggctga ctgtggttgg ccttcctcag   13380
ggctgaggct tagataggg gagcctatct tgtagatgtt cctcaaagga gaggacacaa    13440
atgagcaatt tgtgacccttt gtgtgcttgc tgtccatacc ttcatccttc catctctcca   13500
tctatccatc cgtctctcca tcccttccta atccattcat cccttcatcc atcccttca    13560 tccatccatc atccatcaat ctctctatcc ctccattcat ccatcaatct cttcatcctt   13620
ccatccacct attatccatc cacttctcca tccatccatt catctatcct ttattcattt   13680
atccatttat ccatccatcc atctctctat ctcttcatcc atccatccac tcatctatcc   13740
atctctccac ccctccatac atccattcat cagttgtcct tccattaatt cgtccatgtt   13800
tccatccctc cagcagtctc tccatcccctc catctctcca ttcatgtatc atccctccac   13860
ccatcatcca tccatatctc catccatcca ctcattgatc ctccatttat tcatccatcc   13920
acccacccat ccatccatcc atccatccat ccatccatcc atctcctatc tctccatgca   13980
tccgtctctc atttctccat ccctccatct caccattgct ctatcactgc atccttctat   14040
```

```
ccctccatgt ctccatccct tcttccaagt aacaaccaag cacttgctct gggtgggccc    14100
tgtgctgggt cctggagaga aggggagaaa ctgggctctg tcgttcagga ctttggcaag    14160
ggcccctcac ggttggggtg tggaggcgtg gtttcccttg gggctttccc catagtgagc    14220
atgtgatgct ttcaggggaa cactgccttt taattttat cccaagattc aagcagcaca    14280
gatcctctct tgcttcacag cccctgtcca atcctgcctt tcattaacta actttagtaa    14340 cttttcctcgc tgtgtttaat taagattcat acgagcaaga cttgaaggaa cacaagcatc    14400
tcagtgcggc tgggccggcc tttagtcttg ggcttttac ctcttgcccg tggtggtgct    14460
ggctgcagag gacccctga gctgggagta gaaataactc accttggttt ttttcttgct    14520
gccagacttt taggatggct ctgaaacacc agactaagtc tgtgtccaaa agcctcaagc    14580
attggcctgg gattatgtag gtggatatca tttgaggact atggaggcca aattatttcc    14640
ttgattgtct aatctccttg ttaacaacat ttgtgaaaaa atgaagggtt tttttttttt    14700
ttgttttttg ttttttttgg ctgcaatgga agtttcaaga cttacaagga aacagctttt    14760
gctgttcccc tcttagggcc ttccagcctg acaaaagaaa tcagcagctt gcccgtgggc    14820
aatctggaga ggcaggaagg tgggtgaggg aagcatgaca tcatatcagg tgggaataaa    14880
aaggcgtgtc ctgcagtgtc cctgttcaaa catattttgg tgcttggatg cccgctttgg    14940
aagctggaag accctcagca ggaactgcga agggctccag agacccggac tcaagttttc    15000
aaactttaaa aatgagtatg gcaagggagg agtgaggggt gaagggcagc agcccctgg    15060 tggggagcag gggcgccggg agtcagatct gacagagggc tcccggctgt gtgctgcatg    15120
cgtggttccc cttttcttg gagaaaatgg ggaggcagga gtgaggcaga ttgctctggg    15180
acaatgggcc cctctcccgt cgggtgggag cggctctggg cccaaacaat aggcctgggc    15240
cggcccctct cctgctgccc accgtctgag acagatgccg gggagccgcc gggagtgccc    15300
cagaggtgac cttcggggc tgccctgtca ctttgtggag gagtcctgga gagggaggga    15360
ggcaaacaat ggtggcctca tgccaggcgc ccggcctccg gcacgggcca gggctcccca    15420
gggagagcac ggcctggcag gtgctgctat tgtctcaggg cgcaggggcc ttccgcggag    15480
gtctcccggc agggaggcag ggcaccggtc agcacgcggc aggagaggct tgggctggag    15540
gccctcttgt tgttctccag ggaggacgca aggagctgat tctgctggct ccattcaggc    15600
ctgacagccc cagcccagtt ctgccctcag cccctaaaag cgtcattcag aaaagcaatt    15660
aacgtctctg gcctccaatg gcaccgggac tctgagtgtc agattttaca gccggacctg    15720
ccctaggaaa tgcccaaatc tgagctgaca tcctcgcttg agctggggc acaggcgag    15780 ttttctggag gaagggcatc agctcaggag gacaagggt gagccctgga tttgtctttt    15840
ctctgcaaag agacttgccc tgggagaacc cccacaccat aagctgaaag cagtggatga    15900
gcgcagcaag ggctctctca tcctggggag gagcagtagc taatgggtgt gcgtgtgtcc    15960
gtgtgtgtgt gtgtgcatat gtgtgtgtgc atatgtgcat gtgtgttttt gtaggcatgt    16020
atatgtgcac atgtgtgtgg ctatacatgc gtgcacacac acatacactg caaatgtgtt    16080
catgttgtgt gtgcgtttgt gtgcacacac gtgtgtctgg gcaggtgtac atacctgcat    16140
gtgtacacaa gtgtatttgt gtgtgcatgc ccatgtctgt cccatgtctg tgcacatgtg    16200
tgcatacgtg tttggcgggg tgcatacttg tgccaggcac tttgctgggg attttttgcaa    16260 acgtcattca tgtgacttat gatctgctgg gaacaggcat tgctatcttg accacagatg    16320
aggacacaga cccctgaaag gcacatgact tgactatacc tcctcaaact cctcagaccc    16380
caaggtgggt ctgcaagacc tcacaacttg ggccttttct actgtccact catctgcagg    16440
```

```
ctgtgtcctt cctcagcctg ctggctctgg gatctgggaa tgtgccttgg tcggctgggt    16500 cttttgagact gttctaggcc ctaggggaga agcagacaca gtctctgccc ttgtcctgca    16560
aaggggaagg gaacatggag ggcagaagtg gctcctctag gtggcaggga aggtggtagg    16620
ggagtccaga ggaggcccat gtcctgctct caggggccag ggaatgcttc ccgggagaat    16680
gatgtccaaa gccaggctgc aggttgagcc agcgtgaggc aggtgagaga ggcctggaga    16740
agtccctagc tgtagagaag gtgcccgcag ccctgaggga gccaggggtt acctgggggg    16800
aggtctgagg ctcaccaagg ttgggtgctt gctgtcacct gcttcattgc ggagccatac    16860
atggagctgc ggagttcaag gttggcttct cagacaccta aggcagcctc acagctgagc    16920
cagtctgggg aggaggacca cctaggggcc tggcaggtgg tccaagtggc tcctcaactg    16980
gaactatgcc ctgccttgcc ctggttccct gtgctgggt gactctgtgc tcaagcctat    17040
gataatcgtc tctctgcctg cctctggtgt ccctggtcct ccttgtactg caggagcttg    17100
tgcagggcag ggtgagtggc ggggacttga ctctcacagt ccctagctct actggctctg    17160
agatttcagc caacctcccc tccatgagct gcgctgtcct catctgtaaa gtgggggat    17220 tggcagaaag ccacggacag tttcccacag tgccctgccc atcaagcagg ccatattcag    17280
acagtgctgt catttcaccg aatggaggac tccctctcac cccctctggc tggcatttca    17340
ccaaaccgag ggttccctct cacccctctc ggctggcatt tcactgagca gggggccccc    17400 tctcacccctc aggcagacct gtcattgcac ccagcctttc tctctcctga tgtgcaacac    17460
caggctgggc cggcgctgac caccctggac atggcagtgt ggacggtaac agagccggtg    17520
acccgccctc cgtcggggcg ccttccctgg cggctcttgc tcctgccgtc ttgagttcaa    17580
cctcccaaga ggggctctgg tgggtccagg tagttcttct ccccgctgtg tgtggctttt    17640
gctcctgatg gtttcaggct gtcggtgccc cgggggttgg tgttttcccc ccagctcctg    17700
gtctctaagc tgaactaggt ccaggctctg tgaacactgc ccagtccctg tggcagctcc    17760
atcaggggcc tctgagcgtg gcaggcaccc atgcactgtg ggcgttttct ttgagatgct    17820
gcctgcccgt tgcgagctgc tggcctaagc tcctcactga gactgcctgg cattcggagg    17880
acgaccacag gggtgtgagc tgccccgggg tgcattcgcg tcaaagaggt tgaggtggaa    17940
ccagctgcga ccctcagcag cagcaagtgg ccactttggg gaccctgtgg gttttgagtc    18000
agaggaaaac agagtttaag ccttttccca tttgtcctga gagtactcac caggggcttg    18060
cgactgcagt gtttaccccg agataactcc gccacgaaat agctcgattt tattattatt    18120
tttgcatcgc tctagtatat tgactttgga aacaaaagac gtcatatcct actcatagca    18180
ttctgtttct agtagcggca tttccattta caaatagag tcattctcga tcgctgaaaa    18240
tgtcacatcc tagaaaacac agaattccta cgcgtggttg ttctcggatg tttgttggcc    18300
aaagattgat ttgacgaatc cgttttttcc aaaatagacg attctgatga ttcacgcgag    18360
tctgatgtta gttctgttta gaaatgactc caagaacagt ttttatgttt tattttctca    18420
ttgaaaagca gtcagatttg cttcagcctc aagaagtgtg tttatgtaaa attaaatgag    18480
tgctggcttc gagccgcact ttttttttccc cctaaacaag aaaagggtta aaactggaag    18540
aaccttagaa atgacccctc aatgcacaga tgctgacaca gaggcccaga agaagggtg    18600 tttttgtggt ccctggaag ctgggctct gctgccctca ggacatggag cgggaatact    18660
cagcccaggg caccctggcc ttttctctct gggctcccgg gtgagtgttc aggacagcag    18720
ccaggtcatg actgatgatt ttctagggac ctctactttg ctcatttaga atcactgtga    18780
ccctatgggg tgggggggcac cggagatgtt tgttccgttt tacagtcagt aaaactgagg    18840
```

```
cccagaagga gccaggatgt gctcgaggtt gcacctgagg ccagggcaca gcagtgtcca   18900
gggttctttt agaaacgttg cccttggtct gagtcctagg cgcgtgggtc caaagggatc   18960
tcaggtggga ggatggtgct ggggggtggg gcccacccag cacctctcag ggaggcccgg   19020
actcatggct gcccggggct gggtggagga gctctgttcc tctgggtctg tgcaggcagg   19080
agcagaggtc atctcctccc tgagtgaaca ggccttgacg gttgtgtcat ggggccccgt   19140 tgggggaca ctgtttaatc tgactggcat gagtagattt caacgggtcc aagtctgact   19200 gctgtgggt gcctgggagc ggggctgggt gtgcacggcg gaggcccag ataccatcct   19260 gcctggagat gcaaggtggg aaggtgtggc agagtcctca tggccttggc gggctcgggt   19320
ggcagggggg acctccatct ccaccctgct ctgtttgacc tgggctgctt actggagggt   19380
ggagggagag cagcagggcc ttggagggac ttagtgaatg accagcagaa ggagtggctt   19440
ccgatggcac aggcgtccag ggcagatggt tccggcccgc ttacggtggg tgagacacgc   19500
agaggaaata ccctcagagc taaaccctgg ctcctgggtc agccacggag tttcttcaag   19560
ccccagcttc tgtatctgga aaggggtga ggagatgacc tttcttgagt aagtcagtgc   19620
tggagaagct gttcgtgttc gctgagggtc agcttttgtc ggcgcaagaa tcagacctgg   19680
ccatgttgcg gggcactcac tcagccagtc tggttgggaa acctgccttg accttggctg   19740
gagcgaaccc ctctcccaga cagtgattca tcggggatg tggtgttgag gaagggtgg   19800 tgaacacgtg ctattgaagg gacgctgttt ttctcccccc gcccccgggg tttcgtcact   19860
ggcctgggaa aaggctgaat ttggagcccct gtgggccgtg cacttggtga ggactggtgg   19920
gtggggtgtg tcccggctgc caagggagga aggcacaccg tcctcttttc ctctttttcct   19980 gaggcctcgt ggtggtcatg acagtagcag ggccgatgac agctcacacg ccagcagtg   20040 tgggctcctc actcaaagct caaacatgag gcacaggcga gcttggtcac ctggcaactt   20100
gctcagggtc acatgtctgc tcagccatgg ccgggactcc aatctgcctc gcgtcctctc   20160
ctgctccttc tgggccacgc tgcgcaggga aaggacccc ggctggtgg aagcccttgg   20220 actccctgcc tcagtttacc catcatgtct tttgacctaa ccatagcgac ctttggcgct   20280
tatgtataaa gctcgctctc ttggctgcgt caccaggcct gggttccaga gagccctccc   20340
tccccatggg cccaaggaag ggcctggagt gaggtggcca gccgcagctt ggctgggatg   20400
gtatggtggt ccataaggcc tcgtgggctg tccagctcca gccagccagc ctcggtgaag   20460
ccagccgact tggcggcagt ctccagcact ttgagacgtt tgtccccctc ctgcccccgt   20520
ccagctatga caagtgggct ttcagtagat atgcagcct ctggtgggg gtccctggcc   20580 cctgtccatg tctctacact tgacttgctc ggagttcact ggcccgaaat aatgttccca   20640
atgcaagtcg gcggacggaa cattcggagt ggacggtttg cttcccccc acttttttaat   20700 acattaaaca tgcgttactg gagttctacc cgattcctct gacagctgtg aaaaaataaa   20760
gaaaattcag tttgaactta aaagctcgg gcttaattta tgtcccgcac ctttgtctgc   20820
tgggtccttt ttcctcttcc gatggaaagg ccccagggag cgggcgacag aggctcggcc   20880
accccacgtg gcccctcagt gcccgggcct aatagggc gcccagtggc caacacggag   20940
gggagttttc agatggaaat cggacaaaac aatgcaatca tctgtctcgc aatctgtttt   21000
gaaggggaaa gaaagagcgg gcagagagga gagagtcgtt ttctactagg ggaggcttca   21060
ttcagagagt tttataggag aagacagatg tcatgaatac tgatgtggag agcctgggtc   21120
tggcagagtt tttttaattt tctgagttgt aaagacaaag tgttttaata acacagggaa   21180
acacatgttg atgggtgggt ctttagctca ttctgatttc tctaactccc tctctttctc   21240
```

```
ctcctttctt tccgtctttc tgcctgcctg cctgcctgcc tgcctgcctg cctgccttcc   21300
ttccttcctt ccttccttcc ttccttcctt ccttcctttcc ttccttcctt ccttccttcc   21360
tccctccctc cctccctccc tccctccctt ccttcctttt tttgagacag ggtctcgctc   21420
tgtggtccag gctggagtgc aggggtgcaa tctctgttca ctgcaacctc tgcctcctgg   21480
gttccagcga ttctcttgcc acagcctcct gagtagctgg gaccacaggc gcccatcgtc   21540
acgcccagct aattttttg tagttttagt agagatggag ttttgccatt ttgcccaggc   21600
cggtaacaaa ctcctggcct caagtgatcc acacacctcg gcctcccaaa gtgttgagat   21660
tacaggtgtg agtcaccatg cccggcctct cctttttct tcttctttct ttcctttctc   21720
ctccttttcc ttttatcacc ctgtctccct ctgtctgtct ctttctccct gtttcttctc   21780
ttggcctgtt atggggttcg ggagccacac aaaacatttc cttctgtgcc ctttcacggc   21840
ccaccttcct ggttgagaga aggaatctgc tcttctgaag cactgtgctt ccatctgaat   21900
ggcacagcat ttccgagttt ggggacagaa tgtattgagc taaaagaggt gtttgctcat   21960
gcactcactc tacaatgggg gcgggaaaaa caggtgaatc aagtgtgggg cctgcctgtc   22020
cgtcaggagc tgctggtcag acaaatatga acgtggacac aacctgctgg gaggcgtctc   22080
tgcttttggc tctctgggca gtggggcacg tgtgcccata aggcaggtgc tgtccctggt   22140
cttggaactt cttatgaaac cagcctgccc ggcacctcct gccatccctg tgaggtgatg   22200
ggacaggtgc taagcctgcc cttggacaga taagaaaact gcagcccag gcacagaggc   22260
acaagctgag aggtgacgtc aggactgaac tgtgagcctg ggagtccaaa tctaggctca   22320
cccagtcttt ctggctccag tgagggcccg ccactgtcat ccgacggatg gcatgtgtga   22380
tttttggcac acgcctgtgc aggtgactcc cacaggtgcc ccggagggag gcgctgctgt   22440
gatgttcatg ctacatgcag gaaacagaga ggttgagtga cttgcccaca gccccacagc   22500
tcctacctag tgaagcctgg tttgaggcca cacctgcctt actagtttta ttatttattt   22560
attttttgag actgagtttc actctgctgc ccaggctgga gtgcagtggc gcagtctcgg   22620
ctcactgcag cctccgcctc cggggttcaa gagattctgc tgcctcagcc tccagagtag   22680
ctgggactac aggcgccagc caccacaccc agctaatttt ttgtgttttt aatagagacg   22740
gggtttcacc atgttgacca ggctggtctt gaactcctga cctctggtga tctgcctgcc   22800
ttggcctccc aaagtgctaa gattaccgt gtgggccatc atgaccagcc actattattt   22860
tttaaattgt ggtaaaatat aacataatat ttatcattct agccagttgt gagtgtacaa   22920
ctctgtggca tttcatccat tcatgatgag gtatagccac tgctgctccc tatacccaaa   22980
catttccaga gtcctcagca aaacctgggt acccattaaa cagcaactcc tcccagcccc   23040
tggtaacctc tgttcttctt tctgtgtctg tggatttgac ttctctgggc acctcatgtg   23100
agcggaattg tacggcatgt gtgtcttcat gtctggctta tctcacccag caaatgtcgt   23160
ctagcttcat ctgtgttgta gtgtgtgtct gagcttcctt ccttcttaag gctcaatact   23220
attccaatgt gtgaagagac cacatttcgt ttatctgttc atctgtttgg tgactgagct   23280
ccctccatgc tctccaacaa taatcatgct cctccacaga caggtgtctt ggctgatggt   23340
gtcagagacc ccctggcaag ccgctgctat gggaggggtc ttctccctct catgccaccc   23400
aaggagactc tgtggggtcc ctgcagaccc cgcagcatgg tcaggggctc tgactggagg   23460
ctgttccctc caacaggact cagcagtcag ggtctcccag ggaacccctg tatgcagact   23520
ctgggaagac aggtggatca ggtgtgggga ctgtctgtcc ctcaggagct gctggttgaa   23580
tgaatgcgac tgtctcctgc tgggacacgc ctctgcctca ggctctgggc agtgggggac   23640
```

```
gtgtgcccct aaagaaggta caaccccgg tcttggtgcc tggagtcata agatccatag   23700
acacagggca agaggggctt cctgggcacc cgccgtgtgc aggctctgcg tgaggcacag   23760
ggttcgggac tcagtggtga ataaactgcc atccccttgt ggggaagaag ggcaggtgca   23820
cctagcttac gcgttcactt gacaagcaag tattgagtgc cttctgtata caggtctgca   23880
gctggtgctg ggggccggcc tttggatctg gtgtccaccc cctgacctgg gcccaggccc   23940

tccccatcgt cctctgccgt aggaggtatc agagagcaag taccttcctt agtcacaccc   24000
atcacgtaca tagtggatgt gcctcttttt cggggcaggg ggtaatctta atcaccaagc   24060
aattactaaa tgccgaccat gttctcaggc ttggcagagg tgggtgcttg ttaccccaag   24120
ggacaaccac ttccctccat gctccccacc ccacccaaga cccttctcca ctccactcct   24180
gactgccgcc tccacctct gccctgggtc gctgtcttta ttgtcttcct caacatcttc   24240
catgggaaag gccaatggct tgaaacagga ttgacgagac acccgggccc tgctccacac   24300
ccgtgggctc ctgggcgtgc acccaagagc ctccacccct gaatggctgg catccaggtg   24360
ggcttcccat aaggagcccc cttctgcggg cctgggaggg tggggagcct gtggcgaggt   24420
ggcggggaag agaaagggca caggtgcccc ctcactccga gcctatcgga tcccggagac   24480

ttgcaggcta tagacctaga ggtccagcca ggagggctgg cagggaccat gaagcaggag   24540
acgtcagggc agagagaatg ccttttagag ccagataaat tcttacttcc cctttcccag   24600
ctgcgtgacc ctgggaaact tcaacactcc gtgtctcagt cctctcatct gtaaaatgaa   24660

tctgatgaga actgtgtaag aatagaggtg tgtggagagc tctctggtgc caggctcatg   24720
gcaagactgt ggtgacacca gccatcggaa ggcaggga gg ctcctctgtg gacagctgga   24780

tgcacaggtg cgtagcagga gctcaggagg gtgtgcccgc ggagtcgcag gtaagggagc   24840
cactccagat tgcagagctt ggcttggagg tgtcgcctca ggagggtctt ccattgcctg   24900
gagaccccac ataggccctc ttcttccttc aaacacagcc cccaacctct ctgcagggaa   24960
gtcctccctg accttccaaa ccagggcaga cccttgtctg ggctccgtcg gcctggacat   25020
ggtgccattt cccactagtg gggcagaagc ctgtctactt cagtctccct tgtgtcccca   25080
agcaatgggg acttgagcat aaacgttcat gagtgacaca tttatattga taggcagggc   25140
cacactgtgg gaggagctgg tggcctgaga acccctgtga acagcagggt gacacgtggc   25200
ctctggtgat cccttttggg aaacgtctga gagtctgagg ctgtcaggcc cctgacgctg   25260
actcatggct gggacaacct tgagagagtc actgctctat ttccccatct gtcagccagg   25320
ggcttggcat gggtgttctc tgtgggtcct tccagcactg aggttctgag gtcattgttg   25380
caggggtaga cgactctggg gtggcaggtg gggctgccgt aatcttgggg gaatgagctt   25440

tgctttaggt gaggctgtgc agaggcatct gtgtcgaagg agaccaaggc ctgctctgct   25500

tgcctccctg cagctggctg ggctccttgc tctccaaggt tcctggactt cctccagac   25560 ccgagtgcaa gctccctgtg gcttccaccc accgctcaca ggagtctctg cagccaccag   25620
acccagagcc cagacaccat ccactgtcgg ggagaggcac gtgtccacag cttcctggaa   25680

tgcaaggctg catgtggcca gggctgctgc ccgctgaggg gcaagtgcat gcctggagac   25740
cacagtaagg agccagtctc atgctctggg agtttagata aggcttcatg ccccttggag   25800
ccaaacctct gaattccatg gagttgttgg gtcaaagagc ttgcctaggt ctgagttgtg   25860
gatacctgtt gtcaatgagc tctccacaaa ggggttacca tgataggtcc caccacctgt   25920
acctctcctc tccaaatttc accactgttc tttcacacct tgccaattt ggtaagtgca   25980 aaatgatatt ttagttgtct atgcttacac tgattggagg aatgctttaa gtttgattat   26040
```

```
tggtaagtga acacatttgt tacctgtatt tactgatccc actttccttt tatgaatgtc    26100
ccagttacat cttttgtcca tttttctatt attgtgtttc ttgttcttac tgatttgtaa    26160
gagctctttg tatattcagg ttatgaagag ggtcaaggtt tattcatgaa tgacatttct    26220
cttttctgaa gggggcaaat ggagcattta ctcctttctc aaagtgagct gatatttgaa    26280
tttattattg tctattttc catactctgt tttacactt tctttgcact ttgtagctgt      26340
ctgggcacag atgccaccga gagagctaga aaaagtcaca aggagatctt ggtctcagag    26400
caaagggccc gcatgtaacg gctttgtagg tcccagtgtg caggagagga tgtctgagtt    26460
catgctctgg gtgctttccc tggccggcag atgacaggga aggagcaagc cccagtccct    26520
ccccaacaca cacagcccct gcccccgacc aaacacgaag tcacttcttt ggggacaagc    26580
agatttttca aacaaagttt gccaaatatg cacattttt ttttttctcc agggcagatg     26640
caaacggtct tttcaaatca gtttggagga aaataaatga gcccacgctg aggcttcaat    26700
aaatctttgc gtagccacaa gggtgagttt gggcccgat gaagggccca gtgtgtggct     26760
tatgaatgat gcccagtgac ggctctgctg ccccgcctt cccctcttcc cctcctccgt     26820
cccccaaccc aatttaaact tggacattaa tgttttaaga caaagggacc tttgggcatt    26880
tctccccctt gtggaggaag tctctccggt gaattatttg tcgtggctgt gctcggcgtg    26940
tgatgggggc tcgtgtctcc gagccagggc ctgtctccag gagatgatcc atgtgccgcc    27000
ctcctgccct gggggctcca ggaccccag ccccagatgc agacaggact gtggtccccc    27060
gaggggatta ttcctccctg cctgccatcc ctgctggatc ctggatcgtg ctggcagcaa    27120
cccagtgtgg ctcacatagaa catcgcctct tgatgggtct ccctgcctta gtccccatcc    27180
attctccaaa gtggggtgg ccgaaggatg gcgtgagagg ctctgagcct gccttcccc     27240 tgaatatccc tggatcaagc ccaaagcctt agcttagcat cctggtgaca tctctgctct    27300 catctcccctt cctctccctg gtgtggacac tgcacccacc accagctctg agcacatggc    27360
ccattggctc tgcaggggcc ctcctctctg tctgcagtgg ccaccttgcc accaggccca    27420
cctgaaggaa ccgtgcctct ctttacggac tgaccccaag gtttgcccat gcttggaggt    27480
ctgtctgact ttgctttcct gatgcctggc agtggaccac catgcccact tgtcggtggc    27540
tgtgtagctc atactcactc catctggcag tttccaccca ccgaggacca ctcaagtttg    27600
ccccactcca tgtctgctgt tgggagggga tggtgcatcc cacaagcaac aggagccacg    27660
gagctggggg ctgggctgt cagcctggat gggccaggag gggaccttgc tgtgcctagt     27720
ggaagagtag gtggtcccct actggctcca ggccgctggg tgggtcactt gcccatccct    27780
gcctgggtgt ctatagtggg tgttcccgcc aaaattcatg tccccctgga acctcagaat    27840
gtaaccttat ttgaaaatag ggtctttgca gatatagtta agtaaggatc ttgagatgtg    27900
gtcatcctat attgggggag gggacagtaa atacaataaa tgtccttggg aaagacaaaa    27960
gaaaagaccc agccacaaag aagaaggcca tgtggagaca gaggcaggga tggggtgat     28020 gtggctacaa ggcgtggaac tcagagcccc cagaagctga aggaggcggg aagtttcctc    28080
ccaagagctg ccaggggtgg ggcggggcag aggtggcatg cggaatgctc tgcccacact    28140
ggatgtatga atctgttctc atgctgctag taaagacata cctgagactg ggtaatttat    28200
aaagaaaaag aggtttaatg gactcactgt cccacggggc tggagaggcc ttataatcat    28260
ggtggaaggc aaaggagatg caaagtcgtg tcttacgtgg cggcaggcaa gtgagagaga    28320
gcatgtgcag gggaattccc ctgtataaaa ccatcaggtc tcgtgaaact tactcaccaa    28380
cacaagagca caggaaagac ccatcctcat gattcagtta cctcccacta ggtctctccc    28440
```

```
aggacatgtg gggattatgg gagctacaat tcaagatttg ggtggggata cagccaaact   28500
gtatcacttg atttcaggat cctggcctcc aggagtgtga gagggcaaat ttctgttgtt   28560
ttaagccacc tggtttgtgg caatctcttc cagcagcccc aggaaatgaa cacagggtcc   28620
attgccaaca gtcctaaaat cattttgaa ggaagcattt ctcaatttcc aggtttcctt   28680
caagtagagc aggtcctttc cactgctgcc acccagagca ctcgtctgtg agcccagaga   28740
gcttcaggca ccatctcctc tgcccttaca gctgccctgg aagagagagg cccatgttgc   28800
cccctcttca tggaccaaaa aattgagccc agagagata ggcacatgat caaggcttca   28860
gagcttgacc acttgggctg actccctgtg acttgggcca ggccacaggg ggaagcagca   28920
gacaggctgt ctatattcac agaatctggt tttgtggctc cacacactgc ttgtacctgg   28980
gtgggagctg gtagacttca ctgctaccag aatgttcacc caggaggcag tcagaatgca   29040
ttgaatgaat gactgcctga ctatgaagga atgaattgat gatgcagcca gtctggcaaa   29100
ctccagggat gacgatcact tttaccattt ggaccaacca accatcggt taaattacca   29160 ttcagccaac caaccaacca accaactaac caaccaacca accaatcaat cggttaaata   29220
accaaccaac caaccaacca accaaccaac caaccaacca accaaccaac caatcaacca   29280
accaaccaac caatcaacta accaatcagc caaccaattc aataagcaac taactaaaca   29340
acctaacaac caactaacta attaaccaat taaataacca actaaccaac caaccaatta   29400
aataaccaac taaccaattc aatagccaat caattgatca attaacaaac tcatctctcc   29460
ctccctacct ttctgcctta atgggagtgg ctcttgttcc ccttgcaggg ctcccagtcc   29520
ataagtgcct ttggcatact ccatttggga agtggacagc tcatctcatt ttctaagaac   29580
acctctggat tatgcccctt ggtgatgtag ccaccttcca ctcagtgatg gtcaacatct   29640
ggaggtgtaa atagaataca gatgaatcca gacttggagc aggccatggg gtattcttaa   29700
agactccatg tgtgtcttgg agtagcccat gtcatattca gaatcacagc tggggctcca   29760
aatcccactg gcctacccat taatctatca ctgtagacta gtggtagaat tggtgaccag   29820
atattctagt ctgggatatg atcttgggat cttaagagaa cttctgcac ttcaaggtcc   29880 agtttcttca cccagagaag gggctgccag gtataccacg agatgagagt tcctccacag   29940
ggggacacaa ttgcagcaga gatggccaag ggcaggaact cctactatcc tcatttatat   30000
atgaggcaaa caagacttgg agaattcaag tgacttgctc aaggtaatgc agccagcctc   30060
aaagaaaggg agccgagatt aaaaccctgg cccacatgct ccagagctgg gaggcttttc   30120
tgtaggccca tcaggagata agttatgtct cctggctgaa ggccaccttc cacctcccag   30180
cccccaagcc aattgcatca gacataaaga tttgtttcag ggtgtcttgt tggttttcca   30240
gctccaacct ggctcaggat ctccttttgt tttttggact cattcccagt gcagaggtgc   30300
ctgggctatt aatagcagag gaatctgggc tccatcacca gcctttccat ccatccatcc   30360
atccatccat ccatccatcc atccatccat ccatcagtcc atctcatatc tatttgtctc   30420
caacatctgg tttagtataa acatcgatag aatgaacaaa tgcaccagtg ggccttgtgt   30480
tggacacttt ctgtgtcctg cctcaaatca tctccacctt ccttactgca gcccttctgc   30540
tgacagctgg ctgcatgggg gcaaaaatct gacaacaccc actcctgctg ccacagtctg   30600
tcctttctgc tctggggttc tctgctgcag tgccttggg agcttctcag ccatctgact   30660
catgctggcg aggtgtgcac tctgcagcag cgccagctgt aagacacacc ctcagatggg   30720
cttgtcctct tgcccgtttt catgcctcct ggtccctgtt tctgggcctt atccccaaaa   30780
cgtgacactt gagtaagccc ttttctaagg ctcaggcaga tccaaaagca catttaaata   30840
```

```
ttttcaggat tctgccgatt tagagcaact aggattccaa agaaggaaaa cttactcaat   30900
cagtttattg tcagaggctc cacatcattc atttgtttat tcattttttc gcttattcat   30960
tcagtcaggc cacaagtttc ttcaggactg ggatcatgct tgtccccatt ctgttcctaa   31020
tggaggctat ccatgtagta gtcgctggca ataactctt agtgacttaa gttcaggagg    31080
cagaagcatg gtgaaggggg cagatactgg gccagaaaga catgcattcc aatcccagct   31140
ctaccacttt gtagaagtgg ggtcttgggc atgtcatttc acctctctga gcttcagttt   31200
tcccatatgc aaaatgggca taaagatagc aatttgaggg gttcctgtgg ggctgcaatg   31260
agacctcatg catcaggccc ttcacacaga gcctggcgag ggctcatggt gagggatggg   31320
ctgtcactaa tgtgactggg agcaagcagc cttgggcagt tgggctggat gtctggggcc   31380
tggcacccga actcttttgg cctgcctcag tacccgaggc tgcccgacac atttcttggc   31440
cttagaaaca gccaagaaaa tcagcagccc ctggctcatc ggtagaaacc caagaaaaca   31500
aacaccttgg tggccaggag gggatgggca ccttgccctc ccagcgggac agctgacagc   31560
aggcctgatg cagtgatcac aggcatctgt gggggtgact agccttgccc tggctgtgtg   31620
agacatttcc ttgggaaaag tcttgctcct ttatgtgcat gtcagctggc tgtgaaatga   31680
gaacttctga gaggcttaaa gaaacccacc caatctttgg agatctctgc cgccctcttc   31740
aagtctcaat agcattttc tgccgacggc tcgtgactca cagaggctac atttgtgact    31800
ttcgtaccct cagaattgga tttaaagata ataaaaattt ccaataggaa aaaaaatgt    31860
ctgggttctg acattatgct aagtctccac ctttttgggc tgagtgccca gtggggcaaa   31920
tgcgggtcac tttcttgaca ggcccaagga agggtctcct tccagcagga accttggatt   31980
ctcgaatcag tatctttcct gatgcccagt gtgaggtgca attcttgaaa gaacagacca   32040
gatcagtttt ttttctgttc ttttcttatc atcagtttgt tttagctgtc tttcagcaaa   32100
agtttcatgc atttcatttc cttatgtagt cctgacatca tctcttaaga gcaagacact   32160
gggatcatgc ccatttcaca gatggagaaa gtgaggctca ggaagaggaa atagcttgtt   32220
caaaatagtg cagctggaaa gcagagtgtc tgggacctga acccagggca gccaccctgc   32280
accagccatg tgtcagagcc tttctcagct cccacctggg caggtcatcc cacaacccctt  32340
cgtttcctgg ccccagccag tggcatctga gctgaagacg gagggctgag gatgaggctg   32400
atggcttgtg gctggttgga gtctccacag acctgtaccc cactgcgagc ttccatgagc   32460
tgctggcgcc tcacagcccct gggcctgagc ctaggtgggg tcactcaggg acatgggcct   32520
gcctgctgct gaggctctca ttcctggaga gagagcccag ggagggaagg tggtggggga   32580
acctcggggt tggaggcgtg ggccccaag catgtcccgt cctgcagaca ctccctgctg    32640
cccgggctga ccatggggc atcctgcctg gtgccagcca gcccagcctt gtctagcctg    32700
cctctgccaa gtgcccatt tgactgtccc catctgtttg cccatggagt ccggagggtg    32760
tgccctggcc cagagcccag ctgcagcctg gaaacacca gactccatcc atggctcttt    32820
gttttatact ttatccaata ggcagtaagg acctcagaga gcatcaggtc cagacctctt   32880
gccctgcaca aatggagaaa ctgaggcaga gagaggaag gggcaggtca gaggcagtat    32940
ggggttgagt cctgcgctct ttcaagattc tgttggctaa atccattgtc cccagaagcc   33000
cttgtgcatg tagttttcca tgccgtgatg ggggctgggg agtcccttgg catcaaatgg   33060
gtggtttgga ttctgctgag ggtccacct gcctggtgag caagagacca ggagccagga    33120
gccaggagaa tggggaggct cagggccagc cgcccacctc ccttgggcac cttaatatac   33180
gcagcttgtg tatatacata cacttgtgca aggagcttta cgtcctgcct ttgtccattc   33240
```

```
aggctgctgt aacaaaacac catagatggg tgggcggctc gtaaataaca gatgtttatt    33300
ctggaggctg gaagtccaag atcaaggcgt cagcagattc agggtctggt gagggcaggc    33360
tggttcgtaa accacacttt ctcacagggt ggaaggggtg aggtgtctct ctatggggtc    33420
tcttttataa gggcactcat ccctttcatg agagctctgt cccctaagc taatcacctc     33480 cgaaaggccc catttcctaa caccatcacc ttgggggttt gcattttggg ggaacataaa    33540
caatcagacc atagcagtcc tccactcaat acccatgcct ggctagtggg tacccgtgtc    33600
tggctagtgg gtacctgtgt ctggctggtg atacctgtgt ttggctagtg gatacctgtg    33660
cctggctagt ggatacccct gtctgactag tgggtacccg catctggcta gtggatatcc    33720
ctgtctggct agtgggtacc aatgtctggc tagtgatacc tcgtgtctgg ctagtgatac    33780
ctgtgtctag ccagtgatac ctgtgcctgg ctagtggata ccatgtctg gctagtgagt     33840 acccgcatct ggctagtgat accggtgtct ggctagtggg tacccatgtc tggctagtga    33900
tacctgtgcc tggctagtgg atacccgtgt ctggccagtg gtacttgtg tctggctagt     33960 gatacccgt gtctggctag tgatacctgt gtctggccag tgatacctgt gcctggctag     34020
tggatacccg catctggcta gtgataccta tgtctggctg gtgggtaccc atgtctagct    34080
agtggccaat acccagaggc acccaattca cattttgtct cctttggcag aagatgacct    34140
gtttgctgaa atgaaacctc ttttctgggg cacccctctg accaccagaa atcgggctgc    34200
tcttatgcag ggggtgagtt ttgatgagat gggaacaatt tcaggattga gcttctcctg    34260
gaggaaacaa agtgcctcac gtagggagaa gcaaggggct taaaagttgg gagagagaga    34320
gagtgtcaaa gacaaaactc aggggcaggg tgtcggacag aaatccaagg tgaacctcaa    34380
aggcatgatg tcacgttttc ttgtagtcac attaaaaaaa aaaagaacaa ataggcaaaa    34440 tgtatttaa taatatattt catttaattc aatcgatcca aaatgcaatt gtctcagcac      34500
ataactacta taaagcattc ttttttgata ttttttattga tatagttgta tgcatttggg    34560
agtcgtgaca ttttgatcaa tgtacacaat gtggaataat taagttaggg taattgggat    34620
atgcaccact gcaaatattt atcttttctt tttcctttct ttctttttttt ttttttttg    34680 agacggagtc tcgctccgtc acccaggctg gagtgcagtg gcgcgatttc agctcactgc    34740
aagctccgcc tcccgggttt ataccattct cctgccacgg cctcccgaca tttatctttt    34800
ctttgtgtgg gaacattaca cgttttctct tctagttaac ataaagcatt attaatgaga    34860
tattttacac cttttttttt tttttttttt tttttggaa aaagccttca gaattcgaca     34920
cctctctatt tggaccagcc acatgtgaag tgcctgagg ctgtgacggg gcagtggctg     34980
tcatggtgaa ctgctatgta gtgattctag agtcagatag agatgggttt gagacctgcg    35040
tgtgccacta actgcctgtg tgacttacgg gtgccaagta ctattctaag agctttacac    35100
atatgaattc acccagtctt aggaagtagg gtgctgttat catccctcct ttttttttaag    35160 ttgaagacat gagggcacag agaggttaag tgatttgccc acagctacac agctattgag    35220
aggtagggcc gagatctgaa ccccgagttt gatttgtcag aagtgctttg taaactgttt    35280
cacaaagcct gatcattaat caatcagcga ggcaactcat agagtagctc cctgggaatg    35340
gagccattga gtgtcgccat gccctgggaa ttcaccgcag ctcagcagac atttattaga    35400
tgcttgctcc ttgccagcta taggggagcc tgggcagac ctgagttttt ctgccaggga     35460
ctgttttttc ccggccttcc cacggagccc ctcctgcttg ctgggtgtcc acccagagcc    35520
ctcgtgggct gggctccccc accctggcct ccaccctgcc tcagcctcgc ccagagagctc   35580 acatgttcag gccgagacct gcgccagcct gggcattcct gcaagtgggg gaaagctggg    35640
```

```
cccacatcca cggacagtct tgtggcccag cccgccctgt ggccgggcag gattttttgcc    35700 cagggaatctg cagggtgctc ccttgtctct ggggcctcct gggtccctgg aaacaggtgc   35760
tggttttaat agccgagtca gtttctggtc tgggtttgat tctcctgacc cacggagctc   35820 agccccctccc tccttctctt ccctgtgtc tcatttatcc acctaaaagc cattgaacac    35880
tattttctac agttgagttt taacgtatat aagtagcatg cacacatttt aggtggacag   35940
ccaggggata ttaacttacg tttacaccca tgcaactacc gcctggctca aggtagtaag   36000
gatttccagc ccagcaaggt tgccctgtgc ccattcccag ccaatagccc ccactgcagg   36060
tcaccactca tctgagtttt gtctctgtag atgagttctg cctgcccttg aacttcataa   36120
cagtggaatc ctccagtatg tggtcttttc tatttgtttc ttttgagcaa catgaacttt   36180
ttgagattca ttcattttgt tgtgtgtatc catgattttt tatttttattt ttaaaaattc   36240 ctgagtagtc tctctttgta ggaatttacc atgggtttgt tcattgtttt tggcattggg   36300 ctgtttttcat tttgttttgt tttgttttttg tttttagaca ggatcttgct ctgtcaccca   36360
ggctggaggg cagtgacgtg atcttggctc actgcagcct ggacctccaa gggctcaaac   36420
gatcctccca cctcagcttc ccaggtagct gggaccacag gcacgcgcca ccacacccag   36480
ctaatttttg tatttttttgt agagatgggg ttttgccata ttgcccaggc tggccttgaa   36540
ctcctgggct caagccatct gcccgcctca gtctcccaaa gtgctgggat tacaagtgtg   36600
agccacaacg tgcctggccc ttgggctgtc attactaaaa cgtgtatagc attccagtac   36660
gcatcctggg tggacacata catgcactgt tctctaggac tgaaaatgct ggcctgagca   36720
ctgtagttgt ttaactttag tagatcccac cactcagttt gccaaaatgg cctatttcct   36780
ttcctgcttc caatgacaag gcaggaaggt tctggttgtt ccacatcctc gcctacattt   36840
ggtatggtcg tttttttttt ttaattttag ccattctgtt gggtgtgcta taattatggt   36900
tttaactgca tttccctgat gactaacgat attgagcacc ttctcatatt cccagtggct   36960
atctaaacat cttttgtgaa ctgcctgttc aagccttttcc ctcactttaa aaacatttgg   37020
ggctgggtgc ggtggctcat gcctgtaatc ccagcacttt gggaggccaa gcaggtgga    37080 tcacctgagg tcgggagttt gagaccagcc tgaccaacat ggagaaaacc cgtttctact   37140
aaaaatacaa aaattagcca ggcgtagtgg cacatgcctg taatcccagc tacttgggag   37200
gctgaggcag aagaaccact tgaaccaggg aggcggaggt tgcagtgagc cgagatggcg   37260
ccattgcact ccagcctgga cgacaagagt gaaactccat ctcaaacaac aacaacaaca   37320
acaacaaaac agcaacaaca cattcggttt tgtctgtctt tttctaactc atctttagca   37380
actgtttgta tactctgatg acaagtcttt ggttggatct atgtatcatg aatatcttct   37440
ttcactctgt gacttgcttt ttcactctgt ctttagacgg agtgtctttt gacagctttt   37500 ctcttttttga tttcttaaac ttttttggctt tttaaaaaaa ttaagctttt tattttgaga   37560
taattgtcaa ttcacatgca gttgtgagaa ataatacaaa gatatcccgt gtactctttc   37620
atcagtctcc ccccaatggc aacgtctttc aaaactatag tacaacctcg caaccaggct   37680
actgacattg atccagtgaa ctaactgaac gtttccatca cctcgaggat tcctcatgtt   37740
gcatttttat acacacacct actctcctcg tgtcccccac cctccttaac ctttggcaac   37800
cactaatctg ttctccatct ccataaaatt gtcattccaa caatgttata taagtggatt   37860
aataaatttg ttttttttccct cagcataatt cttttggagat tcatccaggt tgttgtgtct   37920
gtcaataggt tcttccttttt attgccaagt aatcttagtt tgtttaataa ctcacttgtt   37980
aagaacattt ggattgctct ccagtttctt gctattacaa taaggcagct ataaacattt   38040
```

```
atgtccaagt ttttgtgtga acataagtct tcatttattt aggagtaact gcccaggaat    38100
tcaattgttg ggtcacatgg ttcttgctat atgaaactgc caaacttttt cagagtggct    38160
gtaccatttt acagtctcac cagcaatgta ggagtgaccc agtttcttca catcctcacc    38220
agcacttgat accattattt tttattttag ccattctgat aggtgtctag tgatacctca    38280
ttgtagtttg aatgtgtagt tgcctaatgg ttaatgatgt cgaacatctt tttatgtaca    38340
tatttgcatc taggtatctt cttcagggaa atgtctcttt atatcttctg ctcatgttct    38400
aattgggttg tttgctcttt cactgttgag ttttaagggt tctttctata gcctggatac    38460
ttctcttttg taggatttgt ggattgcaaa tattttctcc cagtctatac cttgtctttc    38520
catcctctta gcagggtctt tggcagagca gaatttttat ttggattaag tccagtttat    38580
caagttttcc ttttatggat cggctctgag agtcaagtct aaggactctt tgtctacttc    38640
tagatgctga agatttttc ctctgttttt ttctaaaagt attatagttt cacatgtaca    38700
taattcatta tgagttactt tttgtaaaag gtgtgaaatt taggttggag ttcattttat    38760
tgcaaatgga tatccagttg cttcagcacc attttctata aatgctattt ttctccatcg    38820
aattgatttt atacctttgt taaaaattag tggggtgtat tcttgtgaat ctatttctgg    38880
gttctctgta ctgttccatt gttctgtatg tttatttgtc tgccaatacc atgaactttt    38940
gattattgta ttattatttg attatataag cctatatatt aagcttaaaa tcaagtagac    39000
taaatgctct cactttattc ttattttttca aaattgtttt agctattcta aaacctttttc    39060 ttttctatat acattttaga ataatcttgt gtatatctac aaaaaaatct tactgaaact    39120
ttgacaggaa ttgctgtata tcaaccatac ctaaacactg atttagggag gattgtcatc    39180
tttactatgt tgggtcttct aatctatgaa catggtatgt ctcttcattt atttagattt    39240
tctttgatgt ctttcatagt ggttgtgtag ttttcagcat gcaagttctg tatatcaaaa    39300
aaatttacat ctagttattt aatttttgag tgatttcaat agcattgtat ttttaatttt    39360
tatgttcaca tgtttactac taatacatag aaatacaatc agttttgtat atttatcttg    39420
tctgtcacct tgctgaacta acttattagt ttctgggagg tattgtttat gtagattcat    39480
tgggattttc cacagcgata atcatgttat ctatttttatt tctcctttct catatgtatg    39540
gcttttgaat tcatgttaat tattctgcaa agaattggta caattgtcca gtaaaatcat    39600
ccaggcttgg agatttctga aatgatgtct ttaatttcct taatagttat aaggctatgc    39660
aaattatcta tttcatattg ggtgagttgt ggttaagaag ttgatttatc taagttgtca    39720
aatttatgtg tgtagagtgg ctcatagtat tctatttttat cttttgatg tctgcagggt    39780 ctgtaatgat attcccggtt tcattcttca tgttggcaat ttgcatcttc tcctcctttt    39840
tttcgttatc agtcttgcta gaagtgtgtc cattttattg ttctcttcaa agagacagct    39900
cttttttcat tgattttatt ttttttcaat tttattcatg tctgctgttc tctattatt    39960 cttctttctg ctttctttgg gttgattttt ctcttctttc tctagtttct tgaggtggga    40020
acttagacta tggttttgag gcttttcctt ctttttgatc ataggtatt tgtagtataa    40080 ttttctcctct cagcattgtt ttagctgtgt cacacaaaca ctagtgtgtt gtattttcat    40140
tttcattaag ttcaatgtat ttttctgtct tccttgaaac ttcctcttttg atccaaagat    40200 aatttagaag tgtgttgttt agtttccaag tgttcagaga ttttcctgtt atctttctgt    40260
tactgatttc tagtttgatt tcattgtgtt tggagaacat accctgtatg atttatattt    40320
tttaaagttt tttagattgc tttatggccc aggatatggt ctatctattt tacatgagca    40380
cttgaaaaga atgcatattt ttctgttatt gaggggaatg tgttgtaaat attgattaga    40440
```

```
tcctgggagt tgacagtgtt gagtgtttta gtattcttgt tgattttctg tctagttcta    40500
tcaattgtag agagaaaagt gttgaaattt ctaactctaa ttctgtactt gtctattttt    40560
cctttcagtt ttctcagttt ttcttttggtg ctttgaagac ttttttctgt ctttagtttt    40620
cagaagttta attagtatgt gtcttggtgt ggatttcttt ggtttatcct atttacggtt    40680
tgttcagctt cttgaatctg taagtttgtg tctcttcaca aatttaggaa gtttccagcc    40740
attatttctg taagcatttt ttcactatca tgctctttct cctttccttc tggaactcca    40800
gaaacttaaa tattagattt tttgttgtgt ttcttgactc ttggttcctt ttgttgtgtc    40860
cctgaggctc tgttattttt tatttcagtc tcttttctct gtgttgttca gattcagtaa    40920
tttctgttat tctgtctccc acttcactct ttcctctgtc ctttccattc ttctgttcaa    40980
ggtgtcagtg aatttttcat ttctcatact gtattttttca gttctaaaat tttccatttg    41040
gttcttctta tcttctatttt cattgcaaag ctttctatt ttttatttgc ttcaagtgta    41100
ttcataattg atcctggaag cattctgtca tggctacttt aattattttc aggtaactct    41160
aacatctctg tcatcttggt gttggcacct attgattgtt gtttttcatg cagcttgaga    41220
tcttcatgat tcttggtatg atgtgtgatt tccagttgaa actgggatgt ttctgtatta    41280
tttagatcct gtggttcatc tggattgttt ttcttttgac attgctttgg caagagaagg    41340
gggtctgctg cctcattatt gataggtgga ggtaaaatta attttggtgc atggtataaa    41400
ttagaggtag gagttcattt tccccccattg gctctctggt ctccccagca ttatttactg    41460
aaaagatcac ccttcctttc ccttgattac agttgtcctt atgtcttaaa tcagaagact    41520
gtgtaggtga gggtcagctc tagactcatt gcttcattgc tagtgtcaac tatgggccag    41580
gatccagggc ttggaaccaa gaacctcttt ggattaatgc ctattaagat aatattgaaa    41640
atgaagtaag tgcaatggag actcatcatt gcattacaga gacagaaggg gcccccaaac    41700
taatctggag tggtgtacag gatcaggaaa gttgccctga agttgataag cagaatgtgg    41760
aaggatgggc aggagttgtc taagagaaga gtgtggcaat agaagggcac cctgggccac    41820
agggaacaaa ccatagctga aagatgagga gtcaagaaat attctggcac ccatggggta    41880
ctattagcag tttaacttta caggagctga aaatttaaga aggggaatgt caagagatga    41940
ggctgaacct tggcagggat ggatccttgg accacatcat gtagttgacc ctgtcacata    42000
gcttggactt caccttgtgg gtgacaggag gccaccaggg ctgacagtag aggaagaaca    42060
tggccatgga atccttggga gaagtggtgt gggttcattg aaaaggccag ggcagaggct    42120
gaaagactca tcagggggaat gtagcagtga tccgcagggg ttgtttaggg accagtcatg    42180
actgtggcat ggggctggga aaatggggcc atgatggcac ctgttttcac ttgtggtatg    42240
attggacttt aatgtggttc ctatggtcat cctggttgca gagctggagt agacaccaga    42300
tcatctcact gcagtcctct caacacacag agacagagga tgaccatggg ggtcagggge    42360 aaagtgagga aagttctcta accccctggg agaatagcag caccatcaat gggcagatct    42420
gtattagggc tctccagaga aacagaacca ataagatgtg tacatataca gaaatatata    42480
tatatgtatg tgtgtgtgtg tgtgtgtgtg tgtgtgtgtg tgtgtatagt atactagatg    42540
aggctgacct acattaggga gggcaatctg ctttactcag tctatggatt ttaatgttca    42600
tctcatccag caacaccctc acagacatac ccagaatgta tgaccaaata tctgggcacc    42660
ctgtggccca gttaagttga caaataaaat taattattat gagtccactc tttcccatcc    42720
ctgtcagagg cagcagggtg cactagggac cacagactct gttcttctca gcattgacat    42780
attccatatt tatttatttg ttctgtgtct cctcccagat gggacgtcag ctctctgagg    42840
```

```
gcagggattt tggctgagat aaccgtgcag agactctggg ttctgaatgg gttcagaggg    42900
gaagggaacc atgatgggga ttatcctctt caacatggaa taatgatgat gaggatggag    42960
acagtaatga tattattgta tgatcactac acaacatgtc tggttcaggc actttatgtg    43020
tattaaacta tgaattcctt caacaacctt ataaggcaga tatcactctt agccccactt    43080
tacagatgag gaaaccatgg cccagagaga gccagtaact tgctggggaa cttggttttt    43140
gagtggcaga gctgggattc agacctagaa agtctggctc cagaacccat acactgatag    43200
agtatatttc tgttcaatat ttattaaact cctgcatgtg tttgacactc tgctaggcac    43260
cagggattta ggatggaaag gacagtcatt tccttgcctg ccctcatgga gcttctgatt    43320
tgtggatgga aggcatgaac ataggtgtgg tggtcatggt gcctcccacc catcatgaac    43380
ttgaaccaaa acaggaattc ttttgtcagt tttttctatc ggttttgggg aagttttat    43440 tggaaaaaaa acttctaaac aaaagcttaa aaagtatgct ttattgtctt ttacccttat    43500
tatcgaacca gtggaaaatc agaaaaatac aagtgcttac accagcaata aaaaaatatg    43560
gttctcatca acaccaccct ttgccccgag ccctagagtg tctttctcca agttgtctaa    43620
atttcccttc agttcctggg accagctgag aggacaggga gcccacactt ggccccacat    43680
gagacctggt tccatttctc tccttgggc actctacaac ttcccactct gcccgggtca    43740
tgtgtggagc tgactagata cttaaaaaca acaacaacaa caacaacaac aacaacaaca    43800
aacaatgtta ttttgtaaga gcagttttaa gttcacagca aaaatgagtg gaaagtagag    43860
cattcccaca ggtcctctct ccccacgtgc gcagccccgg ttatcaacac gcccaccaga    43920
ctggtgcatt tgttacaact gacgcagcta cactgacacg tcatttccag tgaagtccag    43980
agtctgcatt agggttccct attggggctg cgccattttt ctcaccagca gtgaatgaga    44040
gttctgctgc tccacatgct cagcagcctt tggtgccatc agtgttctgg attggaccat    44100
tccctaacga catacgatgt ggggcaccct ttcaaatgct tacttgcatc tgtacatctt    44160
ctctggcgaa gtgtctgttc aggtcttttg cccattgttt aactgagttg tgctgaccag    44220
gtactttgag gaactccaga cttgtggcta tggcatcatc ctggggcccc ataggccagt    44280
tcaggagggt ggctggtgag cgatcctgct tgctggcctg tgcaaaattt gttaatgtag    44340
catgcgactg gctgctggga cagtgctgac aggctgattt tgggtgaccc cactcgtgtt    44400
gggtgtgggg tgagctcagg gctctgagct tcccatgctc ctctgcccac actcgagttt    44460
gaacacatgt ggcctgttgt gggccccac ctgtctgtgc tgttactgtg aggcctcctc    44520
tggctcccag ccccctctct gctgctgggc tgggctcagg tctgaagtca gggcagcact    44580
acaggtggcc tctgactcca gcttcatgca tctctgcagc attaccaact ggatacacta    44640
ggcaaaaggc ctaccagaca tggggagatg gctggagcct aaagcttttg catctcccag    44700
gcctttcaat tctcaagcaa aggagacaga acccacatca ggtcaagtgt gagcctgcat    44760
gaatggtcag atgagcacgg ctggtgatgg tggatggtgg atttgtgagc agagttcccc    44820
acagtgctcg gggtgggaga aaacagttta ttcagtttct gactttcaaa tatggaccct    44880
gaaccttgct ttggctacac acttgccacc tgaaaggagg atgtgccaca tgtggtattg    44940
acttcaatgg gtatctttct agtacccttc tcttagaact ggcctctcct ggaatctcat    45000
tcgggtgccc taccaatggt cctggatgtt tctcttcatc accatctccc gccatgacaa    45060
atggagccag gatggacacc tgaccccacc tgtgttggtt gggttatttc tgagctggtt    45120
tcttgaccac gagaattgaa atggccactt cccaactgcc aagtgctcca agaagcagag    45180
aacacaggag taaaagaag cacagaaggg acagaggttc cagttcttct tgaggcctgc    45240
```

```
tgtcccatcc ttgggttttg agagacacct ctgtgtcctt gcagagaatt caccactttg    45300
ttcaaaccag tctgagaaag cttctttatt gtggtccca  agtgcagctg ctgcaatgac    45360
cactgttaac ttccccgcct tggcaaaata actgatactc caaactgcta agagtcccag    45420
gactgcacca gttagctatt actgtgtaac aaattgtccc ccgatacagc agcttcaaac    45480
agccataaat atttattacc tcccaggttc tgagggccag gcatctggga gtggcttgga    45540
ggggtgtttc tggctcaggg tctcatgagg ctgcagtcat actgtccctg aggctgcatc    45600
gtctgaaggc ttggctgggg ctgaaggatc cacttccaag ctcccatgca tgcttgtgga    45660
cacgtctcag gttcccactg ctgttggcca gaggcttcag tggcttacac agggcatctc    45720
cacggggctg cagtgtgctt cccccagagt cagagatgag agagggaggg agggagtggg    45780
gttagagaga gagacgggt  gtggggcagg agattgaagc tgcaatcttt cataacctaa    45840
gcttggaagt gctattccat cacttctgcc acgggctgct ggtcacttgg accatccctg    45900
gggaaaggaa actacacagg gtgtgaaaac caggaggcgg ggctcactgg gggtctctga    45960
gaatctggct accagcaaga tcttgcagga agtgatggac agccccaggt ggacgcgtgg    46020 catagggtc  tgctgcctcc tcctcgtatt atcttatctt ctgagagctg ctcctgggtg    46080
aacaggtgct cactgcctct ttttctgggt tcacatggac ctgggttaga aagctgcctc    46140
taacatttac tagcaagtga cttctctatg cctctatttt cttatctgca aaatcgggag    46200
aaaaatattg tcctcatcga gttttctga  accttaaatg cagagatctt atcagaaagt    46260
tcttggccgt tgtctcagaa actcagagtc tctcctgctt tagggcaac  gaaagttcat    46320 tcacctacct gtacatctgt ccgtccatct gtacgggagg ctgtccatct cacacaggtc    46380
tactgagcac ccccaatgtg tcaggcatgg tgtcaaacac aagccagcac tggagagaaa    46440
atgggctgtg tgctcagagt gtgaccagga ggcccaggct ctgggctgcc cgagcccacg    46500
tggccaggct gggaggggct atgaaggag  gagcatcagg gaggcttcag gagctgagct    46560
ttaaggccag taggatgggg agaggccagg tgacaggagg aggatgggag agaagtcagg    46620
gaatggaggc aaagcacaga gatgaggaa  gacctgccat attctgcagt gttgcccagg    46680
tcctaatgat gagagatgca gctgtcaagg aaggtgggaa gctcacgcag gccagtatc     46740 ttgctaaggg actagagggt ggggacttct ggggggtgct ggaaactcaa aaggtttaag    46800
caggtgaaca acaatttcag ataactccca ggtgagtgtg tagacattgg aactggaaac    46860
cctgcaaggt gggggcaggg agatactttt attgttccct gtttgcagaa gtagaagttg    46920
aggcttgaga ggtgaagaag cttgtgggag gtgtcacagg cctaggtgtg gagtgcggct    46980
ttaagccttg gctgttgggc ccctagcaca ggcccccacc caactgccct gagcacctgc    47040
tgtaggttaa atcgtgtctt tcaaaaagat atgttcatat cctaaccct  ggtacctttg    47100 actgtgacct tatctggaaa tagcgtctgt gcagatgtaa tcttgagatg agatcattct    47160
gggtttaggg tgggctctaa atccaatgac tgatgtcctt acaagagaaa tgaagggaga    47220
cttcaggcag acacagagga aaggccatg  tgaagatgga ggcagacatg ggtgatgcgc    47280
ctacaagcct gagaatacca gcaccagaag ctggagagag gctgggtg   attctctcag    47340 agcctccaga aggaaccacc ctgctttaca ccttcatttc agacttctgg catctggaac    47400
tgcaagagaa tgaattattg ttgttctaag ccacctggtt tttgatcatt tttgttagaa    47460
cagccctagg atatgaatct agcctccaaa gcccctcct  ggggataagc cggcctcctg    47520
gcctgccaca actcccggag tttccagcca ctcaacaaga aagcagggaa gattctgagc    47580
cccagaccca ggtggagga  tggaggggct cctcctcttg cctgctctca ccaggaaaat    47640
```

```
tccgcgatgt cacctgcttc tccagggcat gatctgagct cctacaaaca gagagataga   47700
gagaggcaga cagatagtca ccaggcagag caggaggggc accctgtctg ggacagtgg    47760 ctctgaaacc ttagtgtcta aagagtcat ctggagcgct tgaaatacat ccttgagccc    47820 ccaccccag cggttctgat tcagtcagtg tgaggtgggg cctgggaata tgtatgtctc    47880
cccagttccc agcaaccttg acactgctgg tttggggacc acactttgag tagcactgtt   47940
ccaggcagag ggggctactt ggatagaggc tgggagaaaa gagcagaggc gcagtctggg   48000
cagacagcag ctatcacgga gcttggtaat gacgttacaa gtgggacagg tcatgcggag   48060
gagggcaggt gctcgccaag gccaggatgg tagcaccagg gtctgcctga gggaagggga   48120
gccatgcatg ggccagcgca tacggaacat agaacttggg caaccaagtg gcagatgggg   48180
gccttcagtc aagggccttg agtgaacatg aaggtcagcg gctgccgaca tgggggttta   48240
gagagggaac cccatcctca ggccggcggg cgggggggttg tcagctcacg aacatcagtt   48300
ccctcaacag tggcccccatt atccaaactg ggtgccaaaa cttcttaga aactccagcc    48360 tgcaacctgc agtgcccagg ctcacaggtg gactttgctg agagaggccc agatgctgat   48420
acactgaaac cgatcaagaa gcttggaggg caagcaggcc ccattccccc tttgagttct   48480
tctcaaaaga gaagactcct tccatctgca atgccaggcc ccagctttgc caatgccgcc   48540
caccccccat ggagcctggc tgggcccaga gtgcttaatg cagtacgcag gcccctccac   48600
agacctttcc cagctggtaa gagctgtttt ctttccct ctaagaggtt tgttcctggt    48660
cataaattct gcaggcccgg tcggccagac taggatgtac acgttggtaa acactgtagt   48720
tcaaaacacg cttcacgctt cacggctgaa aaaggcagcc ccgacaatgg agccttgtcc   48780
ccggcagcaa ctctaacggc caccttcttt cattccttaa ccttgctgtg ggcttgtatg   48840
aaattggtcc cattctctgg ggtccatcaa acgtgcattt aaacgacttc attagcatct   48900
tcctctgatc cataaccact gggcaaatcc aaaagtcatt tcggtgaggg cagccgcggt   48960
tttctatctg gtgaacatct aaaactcctt gacaaagttc cttttaaaat ttacttcttt   49020
tgttccgtct tcgtcttctg ttgagatctt tagtggccaa tgtactccga gatgacttgg   49080
ggacaaaaat cccgtctggc ccagacagta aatctagcct ccattcagac ggcttaaatg   49140
catgctttat gcctattgtc cccggctctc caaaagctcc tgcgccttca agggtttcct   49200
acaataaatt aagcccatcc aagacggtgg agggaaagag ggcctgcctg gatgctgtcg   49260
gaaggccagg ctgggccggg ccccgacaca gcccacccat cgccctggac ctctggcctc   49320
taggtatctg ggattctcct ttgtgagagg caaaaaaaaa aaaaaaaacc caaccaaaaa   49380 aaaccccccaa aaaaaccccca acttgaagtg gattcagcca caatgtattg gatggtgaac   49440
acgaagggca ggaggaaggg gggggggtgg gggtggtagg gaggggcctg gttcaggccc   49500
cacaggccct aggacgctgg tgccctctcc ccctctggcc acaccctcca gggctctgct   49560 gaccctccc cagcttcccc cctgcattcg taccatggcg ggagcagtgc aagcctcacg   49620
tctagtagga agcagcagga gtctttccca gcattcccca acaagagtct cattggctgt   49680
ggttggggca catgacagtc cctgaccaat cactgaggcc tggtctgat tggctaggct    49740 tgggtcacat ggcccacttt tggcccagtg ggtgaagcca ctcttgaaat ggatcctggc   49800
caggaggagt cctccttata ggaaagttgg gttacggttc ccagaagagg tgggaaggga   49860
tgctgggtag ccagaactga cactggctgt gatctctaac caagggcatt gcgtttgtcc   49920
cacattccga aattcacagt ggcaggtggt ggctcagagg ctggaacctg gccctgagag   49980
acccattgcc tttctctgtt ctgtaacctc ttcccataga gattttatc ctgtaaccct    50040
```

```
gtggtcatca ccatgcctcc catttatgtg cagttcctat gggctcctga tgctttcctg    50100
gatttctccc aggagaggct gttgggtgtt ggggtgttgg ggaagagaat tagtgttctg    50160
cagtctggag ttcactggtc tgcagactgc taaaagtctg ggggctgcgt ctgccaggga    50220
tagtggctct ggctggtatg gggaccaagg gcaaaaggat cagtgatttc agcagatgcc    50280
tttgagcccc gagtctctgg ctgtggacta gtccagtaga aagagtgtct tggagtgtgg    50340
cagagtccca gtcccctgtc tttcttactg tcaaaaccaa ggtttgggca atcgatgatc    50400
tagctaaaaa aacgatgttt ttcagcctgt cctttctggg ctcctcctgt cccaaacaca    50460
gatgtgaagc aatgtgcgag aattcctatt ctacaatcgc tgtgtatatt taacactatg    50520
aagcttctct ttttttgccag tctgacggat atgatggggc atcgcttact gctttcattc    50580
ccatttcctt catcatcatt gaggttggtt gtagtgtcta ttctggtttc tttcgctata    50640
ttttgactcg ttgtatcctt tgaccatggt tttaaaattt gtagacattt ttaatatatt    50700
ctaatacaaa tcctttgtca attataagta ttgcatatat cttcttcttt gtgcctgttc    50760
tcttcatttt tcccacagta tctttggtca tactaaagtt ttttttgttg tgtgttttt    50820 ttttttaca tttgatacag ttaaattaaa tcttgttttg attgtacttt ttgtgttagt     50880
ttaatacata atttcttatc ttggtgtcag aaaggcattc tatcagaatt tatttttcaaa   50940 ttgtatagat tttccgtgta cagtttggtc tttggctcaa ctgaaattta tttcttttttg   51000 taggtgtaag gaaaggatat attttttatct tgttttcctt tgtaaagcca tttgtcccca   51060
atccatgtat tgaattcttt ttcttttttt tctacagata tattcttata tattgtttcc    51120
ataaaattcc tctctatttt gtcccatcaa tctatttatt catgcactaa taccacacaa    51180
ttttaattat gatagtttta ctgttaatct ttatctttgg tatgactctt tctcactcgt    51240
tccttccttc cctaccttct tttcctcgtc ttccttttc aagaccttct tcctgttttt    51300
agcaccttaa tcattcacat aaattttagg attaccttgt taagttttat gaaataatct    51360
gttggaattt tggttagact tgccttaatt catacattaa ctggagtaga attgtcatct    51420
ttaccatact gagttctact caggagcatg acatatctct taatttattt aatgcttcct    51480
ttgtgtcttt ccatgaagat ttagaatttt ctccataggt cttgcatgtc ttttgttaga    51540
cttcttccta ggtgccgctc tttatttaat gctattttaa gtgttatctt tttaaagtta    51600 cttttttatga ttgttgatga attagaatgt aattgaatct acttagattt tcttacaaga   51660
aaataattca ctggtaaata atggcaaata gacatagtta attaagtcaa cagagaaata    51720
gaatttcaaa aaatattcta ttaaggacca aatggaacaa aaaaaggaa aggataaaca    51780 taggggaata taaaagagaa gacaaatgga cctaaattca actatatata aaattatgct    51840
aaaaaattta acattctgag agagagagag agaggaagaa gactcaacct gctgtcaaca    51900
agagacacat tttaagtata aagacacaga tagattgaaa gtaaataggt ggaaaatgat    51960
ataccataca aacgataagc ataagaaggt tggttgaagg ggttatatta aatcagataa    52020
aataaacttc taggcaaggt gcaataactg gtataaagag gaacatttca taaaaaacat    52080
aataacacat gtaataaatt acttaatagc aaagggacat tcataaggaa gatacaatag    52140
gctatatata tatatctgtt aatggatctt caacatgaat gaagcaaaat ttgacaaaat    52200
tgcagggtga aaaatatcc acaaatatga ttggaaattt tagtacctat ctgtcagcaa     52260
ttgatagaac aactagacag aaactgagag aagacatgga aaagctaagc ataagtatcc    52320
tattaactgc ctttgttgaa ttgatactta taaaaatcaa catccccaag gagagaatac    52380 acacttttttt catattcatt atgatggact atatgctgca ccatacatga aaattgttac    52440
```

```
tgttcttgtc ttttttccctc tgtgtataat gtgtcttttt ctctggctgc tttcaagatt    52500
ttctctttat cacttgtttg attacaatat gccttggtgt agttgtcttt acctttatc     52560 ctgcgtggga ttccttaggc ttcttgggtc tgtgggttta gagtttacat tatatttgga    52620
aaattttcaa ccattgtttc ttcagatatt tttcctgtcc cctttgtatt gatcatctta    52680
tgctacataa atatttaccc caaaacttag tggcttgaaa caataagcat attatctcac    52740
gcagtgttct gtgggtcaga aatttggtag aagctgagct gggcacccct ggatcaaggt    52800
ctctcataat aagtttacaa tcaaagtgtt gggctgcaga catctaaaag taatagttct    52860
ttcccagatg ggcctgttta gagggctgct tgagtgctct catgacatga tggaggcttc    52920
cccaagaatg aatgattcaa gagagaataa gacagaagcc acaatgtctt ttatcggctt    52980
gctttccttt ctaggagttt gctttggtca agttggttga ttgtgttaag ttgtctgtgt    53040
tcctcttaat tttctgtgga gttgttctgc cagttagtga gagagaagtg ttaaaatctt    53100
tgcctaaaat tgtggatttt tacatttctt ttttcagttt tgtctgtttt tgcttagtgt    53160
gttttgaaac actcttattc attgcgtaca catttagaat ggttatatct tggttaagtg    53220
actttagcat tatgaaacat ccctctttat atcttttttcc gtccttttac tttaacctat    53280
gtgtatatgt gtatttaaag tggatttctt gtatacagca catagctggg tgttgatctt    53340
ttattcagcc tgacaacatc catgcagaat tttgatggtg acttaaactt tcctctaagt    53400
caaaattgcc acaatatgtt ctgtgtcaca tttttttcagg acttcagagg atatgtctct    53460
ctagaggatg tgtcatcatt gcaaatccgt cctctgcagt cagcagggat gcttccattt    53520
tatagatgag ggtattgagc ttccacgagg ggaggtgaag tacttgagtc cactcccacg    53580
gccaccagag gttgaagcac gactctctgg ctcctggcca gccttccttt tcccatcaca    53640
gctgcagctg tggggaagga ggatgattct gaactgaccc tgtgggttga gatggagacc    53700
tccagcttcc tgggaagagt tcttccttct ttgcaaaaat aaatgaattg atataggcca    53760
ttttgtattc aaattagatt ggtcagggc tatttaagca accacatcag aaggctcatt    53820 ttccctttg acattaaagt gtcttttcca gaaactgtag gaggtggggt ttccctagaa    53880
tgagttgaca gcttgtacct attgttaaaa aaagcaaaaa aaagaaaagc cttgtacacc    53940
tcttcccaca tcttcaatgg taacagaatg agcataatcg aaagaggttt gtgatgatta    54000
tttttttttt aagagaaaac actcacagcc ttctgcctgg tgtaaggctg aaataggcca    54060 aaagggaaa ctgagcatga gcagggcata gaatatcaaa ggcagtaagt ccttttggcc    54120
acatctggac tcttctccca tcccacagaa aacctcccca gccagtctgg aggtgggtgg    54180
atggcgaggg tccccttca taggtcactt gatccgctcc ttgcccaccc ctcctgccca    54240
ccctctgccg gcttaggtta cccctggaaa ccacccacat ttttcatctg tccagagaaa    54300
tcaggagggg acgaacacct ctgttgggtt ttccaatcaa acactggggg aacggagcat    54360
tttaatcctc aagaatctcc ccaccagcga agtgaacccc tgagaggcac tgtggatgtg    54420
caaaggcaag ccctgtcccc gatggcccag cactaagtgg tagagatgac atggtcatga    54480
caacaccgag gctcaggcat gagaggtgtg tcagccccat cctgggacac tgcgacagtg    54540
gggacaagga agactgctgg tcagaaacag ggttcagagg caggcccgac tgacattgac    54600 aaagctccttt tcatgtgctg ctataggagg caggtgggct ctgggatcat ttggcagctt    54660
gtacctattg ttaaaagagg aaaacaggcc aggcgcagtg gcttacgcct gtaatcccag    54720
cactttggga ggcccgaggc aggcggatca cgaggtcagg agatcgagac catcctggcc    54780
aacatggtaa aaccctgtct ctactaaaaa tacaaaaatt agctgggcgt ggtgacgtgt    54840
```

```
gtctgtaatc ccagctactc gggaggctga ggcaggagaa tcggttgagc ccgggaggtg    54900
gaggttgcag tgagccgaga tcgcgccact gcactccagc ctggtgacag agtaggactc    54960
cttctcaaaa aaaaaaaaa gaaaaaaaaa aaaaggaaaa caaaatatgg taaatatctt    55020
gtcacctctt cgatgtagga tggcatgaga tgacataagc ccagttcttc caaatgtccc    55080
cattttacag cagaggaaac tgagggtcag gatctctttg ggcacggttg caaagaaagg    55140
cctcctagag aaaggggcct gtgtgcaagc ccagggggat gggggggtgag gcttagagca    55200 tttcccgtgg gtggaaacag tgaacaggcc tctggaatca agctagccca taacctgccc    55260
ggggcacagc aagtggtatg gcgagaacag accaagtttt gggtgccgaa taaggatgag    55320
gtaaaccagg ggcagagttt tggaatctca gcccaaagga gtggcctgag tccaaggctg    55380
ggggagcatg cacctgctgg ttgctgacac aggtgatcct ggctgtgttt ttgttaagac    55440
tggctttgtc gtagctccat ggatctgggc acaatccaga gatgttgtct tcttgcacac    55500
tcattttaca gatgaagaaa tcaaggcttg gggtagtaga gaacttttcca gaagtacagg    55560 gcaagtttgt gtctaagcaa agctgagccc tctgcccct tgtggtgatc tcctcagccc    55620
cgttctcatc cttccagggc aatagtcttt ccttgggagt aaagttcaac ctcagtttgg    55680
cccagacatt tggctttttcc cagtggtggc agaatttgtg ggatcagtgt gtgtgtgtgg    55740
tgggggcagg gcaggggct gagttaggga gcttagggat gggcagcttc tcccacatcc    55800
ataaaattgg ggcgtttacc aattcccaca gctggtataa ataccctccc tggtgcttag    55860
caaaggctgc tgggagtggg gttgcccctg cccgactcag attctcttaa agacccagga    55920
gaaacacttg cattgcaatg aggtctctat gtcctcaacc attggactga gcacctccgc    55980
atgggaatgt ctggaattgc aggttttgaa ggcctaaatt agggctgtga atgattttct    56040
tcaaaattca ggggcctgtg ggcatggcca caaccctcac ctggatgcct gtcctctgtt    56100
caccctctgt tctctttcca gcagaacatt cagcccagcc ttgggtgtca ggcatgtgcc    56160
tgcctctctg acctcatctg gtggccaggc tgtgggaagg gaaaactgga ggagtctttg    56220
ggggctgagc ctctgggcat ttgtaggagg caccaccagg gtgtcaatga agataatgac    56280
gctgaagctc caggcccttc atttgcatgg gcccatccca cagttcagcg tgggcttccc    56340
tgcccctacg ctgaaggatg ctccttgact gtgagtggga ctgtgggctg tggcaacctg    56400
gtaggtggac ctcatggatc actgactctc tctcttggct ccaaggagga agatgaagca    56460
gtcgctgctg cgcttcctgc tcagggccat ggtgcccagg ctttatggcc atctcttccc    56520
tccaggacca gagggaatga gggcctggct cagttggctt ggttgcccaa ctgtggtcat    56580
caggagggtg aatgatgtca agaactggt gtctcttaca gataccctgc ccaggcaaga    56640
aattgtagag gacatttcag atacggcctt gccaataaca acacatgtaa ttgaaagaaa    56700
tttccctaag acatcaaaag taaacaaact gcttttaaac aaaacaaaca aacaaaaaac    56760
atgtgctgga ggacagactg aagcatttt tattcgctct gtggaaaatc atattacgaa    56820
atcattgtca tacaaataag caatcaaaga atatgcagcc aaaaaaaatg taggaaaagg    56880
gtattataga ggtggccgag gcagttactt acttgtggaa tcatatgcta tttttctgat    56940
ttgatactta tggtttgttc agctttttac aaatttgtca tttctttctc attctaaatg    57000 atttttttt ttttgcactt tgtagctgtt aatttggtgt tattttttctt aaataagccc    57060 tccagattgc ataacgttta ggccccaaa gtccagacca ctccagttcc cagcctcacc    57120
atttgttcag aaatgagctg cttgcttcct gctttcactc aagaccttgg gtgaaagcag    57180
gaagcaaggc cgaggctgtg tattattgca cttcccgtaa gggggtctgc ttgaaagaat    57240
```

```
atttcccatc ctcctaaaag gaacaaaagc tgttgcaagt attgaattcc ctagtcacag   57300
ggtttgtggg gatctggggt ccacacagag gcctctgggg agaggaacag agggaggcag   57360
aggggtgggg gaagggctct gtgagagctg ggtcagacca gatggcagag caggtggtca   57420
ggtgagaagg gccagggata tcctcccctc ccacttccct ggggatctcc aggccttgcc   57480
ctttcccagc tcaggacaag atgccagggg aagctggcct tgtgtggcac tactagcccc   57540
agtgaggcta acatggggt atgcaggctg ctttatgaca gcagtgtcct gatgtctggg   57600
gcatgtgagc atccttgtgg tgtgtcccca tgtgcacaca tgcatgtgtg cccacatgtg   57660
agaaggaggt gggggcattg ctgccaggag atggatcatg gggagagaaa gaaactcttt   57720
ttaccaactc ttggaatcag gcctgttcat acatgatggc attgctggat ctggggatgt   57780
gtctgtagat gaatttcaag gtctctcttg gcttaaaatt tctaagaatc ccaagcaatt   57840
accttgcagg agaaatatgg gaaaagccct tttttagtct gtccattcat gcatcttttt   57900
attcaatcac ctatccgttc actgacttag gcatccatct acccactcac acattcaccc   57960
attcactcat ccatccaacc attcatctac tcatccaacc attcatctac ccatccattc   58020
agtcatccat tcacttgccc attgaccac ccatccatcc atccacccat ccatccaacc   58080
atccatccac ccacccatcc atccatccat ccacccatcc atccatccat ccatccatcc   58140
acccacccac ccatccatcc atccatccat ccacccatcc atccatccat cccccccactc   58200 aactgatgct cattgaacca cacattgtgc tgaaacatgc tctggctgct gagtgttggg   58260
gacataggtg agtcagacat ggtctttact ctgagtctta gtgccattct gaagaaagat   58320
caggggagaa acaattgcaa caggacaggg tccatggttt ggttgaggcc agtgaaatgg   58380 gaacccagg gagctcctaa ctcatcctga gatagaccca ggaggaattc acagagcagc   58440
aggccaaggg agacagctct gctcagcctc tagggacaga tgaagtatgt ggcagtcagc   58500
tccaagtcca tgttggtcac ctgttggcat tcacaccctt gtgtggtgtc cttccacctt   58560
gagcccaggt tggtctgtat gatggagtca gtgcagcaga ggtgacagca tgtgtctagg   58620
ccataaaagg cattaagctt ctgctttggc ctcatgaatc cctctctctg agggaaacca   58680
gctgctatga catcaggaca ctcaagaggc acattggcgg ggaactgagg attcctacca   58740
gcagccagca ctcactagcc atgagggagc tgctttggaa gcagatcctc tggcctggtc   58800
aaacctccag aggactaccc ctccagctga catctgcttg tatcttcatg agagaccctc   58860
agccagcact gcctagccca gccctgtgat ccacagaaac tgtgagagta gcaaatgtct   58920
attgtttaac cctccatgat gggggaattt gttacacagc aatgaataac tgatacatgg   58980
ggcatggagg gaaacctggc gatgccctgg tgcagtcccc atgggggtga ggtggaaggg   59040
atgtagcttg ggagggcctt ccctgctgag ttggggacct caccctcag cctctgggcc   59100 ctgtggagcc atggcaagct gatgcatgat aagcttttgt ttaatgaagg tcactctgta   59160 caggggtcg ttcactccag gaagctatcc ttgaccacct ccctgtatca ggcccgggctg   59220 cctgcctta taggatcccc aagccctgaa cttgccctgc actgcacctg ttattagtca   59280
atattgtgat ggtccagctg actatatgtc cccactactg gactatgtgc ttggggtgaa   59340
gtgttagtgt agacagggca gtaaatatgt ctgtcttgct cacggtgtaa ccccagtacc   59400
atgtatagga cctgctatgc agtacggact ttgatgatgt ttggctctgt gtccccaccc   59460
aactttcatc tggaattata atccccatgt gtcgagggag ggaccaggtg ggaggtgatt   59520
ggatcgtgaa ggcagtttcc cccatgccgt tcttgtgata gtgagtgcgt tctcatgagc   59580
tctgatggtt ttataaggca gtcttccctg ctcttgctag ctctctcttt cctgctgcca   59640
```

```
tgtgaagaag gtctttgcct cccccttcacc ttctgccatg attgtaagtt tcctgaggcc   59700
tccccaacca tgcagaacta tgagtcaatt aagcttttt cttcataaat tacccagtct     59760
cgggaagttc tttatagtaa tgtgaaaaca gactaataca gacttttac atgttactga     59820 gcagacacag gatgagttac aatctgatgg gccctctggg ctgtagggca agagtctctg    59880
gcatcctcat tttacagctg tgacccagga gggaggatct cctacactgg gcaactgcag    59940
cttccagccc tgcaggctgt gactcctctt ggatctcatc cccaatccct ggactttcct   60000
cctctgcacc acccaccttg acacccatct ggctgccacg agtagtttcc atcagagcca    60060
gagtttgggt gaaaggagtt tccagaaggt gtcccctact cattcagtag atattcactc    60120
agggcccact gtcctggaga acaaagaag tgagtgctag gaagagagat taactaggat    60180
gaggggctgg gggtgtctgg gggtgggtgt ggggctgtc tgagtcatgg tgtcagggcg    60240
tgctgtactg acaaggggca tttgaataga tccctgagaa atgtctgaga gtgagccctg    60300
ttggtacctg gggaggagtg ctcctggcta cggcagccac agtgtgtgca aaggccctga    60360
ggcaggagtt tgcttggtgt gttggaggag cagcaagggg atcagtgtgg ctgcagcaga    60420
gtgagtgcaa ccgagagctg atgaggtcag gaggtggggg ccaggcaggc cagggagggc    60480
ctcgtgatgt ggctggagaa ggtgaagtgc ttgttcctgg cctgggagct tatctcaacg    60540
gttcctatgc tcccagctct ctgacattgg cccacggcag ccccagaatg gatgctttgc    60600
aacatctaac agtttggggg ctaaaattag gtgccaagct gggttagggc cagcagaatg    60660
ccactacata tgcttggcat ctgcatggca aggggaaaat gttgctgctg cctcttgtcc    60720
atgttgctgt acctcagcga cttccagagt aaaattcaac gtctgcggcc tggagttgga    60780
ggctcttctg tgtctagtcc cagcttgtgt ttcagcctg agcccacctt gcaggctgaa    60840
cttcccctcc cctccaagct gtgagctgag gtccaggcta ctgcctccct cttcctaaaa    60900 tgctcttct ggctaccttg cctgttctcc cccttggagt ctgagctcaa gggcacctgc     60960
tccgtgacgc ttccctacac cccagcccaa caggtggcgg gtctttttc tgccgcgcag    61020 ctcccgccgc acactggttt cttctggctt gtattgtttc tgatgagatg tcttcatcat    61080
tcttatcttt gtctccctgt aagtaatgtg tagtttttg ctactttatt gaggtataat    61140
ttatatcctg tcaagttaat gcttttgagt gtatacttct gtgagttctg acaaacacac    61200
acagttgttt aattacctgc acagtcaaga tacagaatgt ttccatcacc cctgagggtg    61260
cctcattccc accctcaact cctagaaacc acttaatatt agtctgttgg ggctgctaca    61320
aagaagacca tagaccaggg gctttaaaca acagacattt attttgctc gttctggagg    61380 ctaaaagtcc aagatcaatg tgtgattagg gttggtttct attttctctc tctctctttt    61440 tttttttt gagacagtct tgctctgtca cccaggctgg agtgccgtgg tgagatcttg      61500
actcactgca acctctgcct cctgggttca agtgattgtc ctgcctcagc ctcctaggta    61560
gctgggatta caggtgcctg ccaccatgcc tggctaattt tgtgtgtgtg tgtgtatttt   61620
tagtagagat ggggtttgc tatgttggcc aggctggtct cgaactcctg acatctgagc    61680
ctggccaggt tgggttctt gtgagtcctc tcttcctggc ttggagatgg gtgtctttct    61740
gctgtgtctt cacatggtgg gaagagagaa agagagaaag agagaaagag agagaaagag    61800
atatggtatg tcttcttctt cttcttcttt ttttttccg agacggagtc tagctctgct    61860
gccaggctgg agtgcagtgg tgcaatcttg actcactgca acctcctcct cctgggttca    61920
agggattctc ctgcctcagc ctcccgagta gctgggatta caggcatgcg ccaccacgcc    61980
tggctaattt ttgtattttt agtagagaag ggggtttcacc atgttggcca ggctggtctc   62040
```

```
aaactcctga cctcaggtga tcctctggcc tctcaagtgt tgggattaca ggcgtgagcc   62100
accatgcccg gccaagattg tgtcttaatt caacactgtg tacctttcat gttgtgcagt   62160
gccaggcatg ttgctgtgtt tgtttattac ttgtaattta ctagattctt ctatttcttg   62220
accttctgga attgaacaca atcaattgct attagttatt tatttatttg cttttttatt   62280
gttttcttaa gcttgtgagg tctttaggtg agagtgggaa gggagtggct tccaacacac   62340
gaaacatcca aggaagaagt cagagttcca tgtataaaac ctaaagaaat gcttcttttt   62400
tctattttaa gcaaggtagt ggagatgttc tgttctgaag gttgcagtca acactatcac   62460
aaggtacagg gacaggctgg agaattcctt tctatcaaag tcttagacca gtagagttag   62520
cactaagagg aatgcaaccc attcatttta ctgatgagga gacagaaggt caaggtggac   62580
catggtgggg tttcactcaa cattctggat tccccatcct gatagttcct tctgtatcac   62640
agatcctagc ttacaataca aagtccaatt tttcaaaaag gcatgtaatt aaaaaaaagt   62700
cccaacactc aggtgtctga cccctgattc ctcatttctt cctgtgtgcc gagatgcctt   62760
tggcagacct aggggagct tctccccact ctatgggaa aggagcacca gctccttcct   62820
cctctgggtc ccctcaagga ggccaaaatg cccatcatga ccctgatatt tttctcccca   62880
ctcctctgga acctcacttc ctcatcccag gtggtacctg ggtttctaat gccccaaaca   62940
ttcataaatt taacacatat ttattgagaa cgtactgtat actagcccct tgttaggtac   63000
tgtgactaca gcagccagca agacagtctg ggacccaggc ctgctcatac attcactctt   63060
tcctcttcac tagggtctgg gagagagctt tgggatcgag actcagccca aggtaagtcc   63120
tggacggtac tcagccctga tgtggacctt gtggatattt tttaaaaaat tatttaaata   63180
ttttttattt acagagtgat tgaacagatc gtacatagag ttccatatac ctcccaccct   63240
ctctgtttcc cctattacta acatcctgca ttggtgtggt atgcttgtta caatcgatga   63300
gccagtattg atacattact gagtcctaat ttttttacta ggataatcac taaaatccat   63360
atttaggtta gagttcactc tttgtgttgt acaatccgtg ggttttgaaa aatgcataat   63420
gacatccatc caccatgata gtatcaaaca gaagacctcc actgccctag agacccttga   63480
tgctcctcct gttcctccct cccttctaac ccctggcaac cattgctgtc tttactgtct   63540
ccacggtttg gccctttcta gaacatcaca gagtggaaac catgcggtgg ggagccttt   63600 cagattggct tctttctcgg ctcacaggaa gaaatgatga attggggatc agacacctga   63660
gagttgggat tttttttttta attacatgcc ttttgaaaa actggacttt gtatttataa   63720
gctaggatct gtgatacaga aggaaccatc gggatgggga atccagaatg ttgagtcaaa   63780
ccccaccgtg gtccaccttg accttctgtc tcctcatcag taaaatgaat gggttgcatt   63840
cctcttagtc ctaactctac ctaagacttt gatggagagg aattctccaa cctgtccctg   63900
tacctcgtga tagtgttgat ttcacttcac actcctccat gtcttgttgc agcttgccgg   63960
ctcatttctt cttattcctg aataacgtgg gagtcttctc tacagatcct cccaggtggt   64020
tccacggggg agctgagtgg agcttctgtg atctagtgac ctagtcccca gcatggagtg   64080
ctcggaagtg ccctccttga acatgtaaac atcccaccaa gttgcctccc ttctcttgct   64140
attttgatgt agctttcttt tcaatggtct tatttctggg tctagccccc agacacactt   64200
tccaccccat gtcctaacct acactctgca gcacatcgca cctgtgcagg gtgatcggtg   64260
attgcaggcc tgggtccacg tctctgctct gcttcttgct ggccacgagg ctgcgtgctc   64320
cttactggcc cctgcgtgct catctgtaca gtgtgcagga gcaggagcat ctgccggcag   64380
acttcttgtg agattctagt tctgaggcct ccagacggcg tgggtgcacc gcctgagtcc   64440
```

```
tgctgcattc tgtctgctgc agacccaagc ctggttcctg cgtggggtcc ctcacgggtg   64500
gtgtgtgttt cacagggcag cagggagcca aggggctggg gctgcccgtg gggagtgtgt   64560
gaatcaaagg agcagaccgc agctggagcc acctcgcctg gattcctgaa cgcagactct   64620
tgacagaccg attgtgtaac ggcattcctc ccaaggaaac acgcctgccc cctccaagaa   64680
ggtgcgagag cttcccagac acagaaaggg ccctgctggg taaatcagtt cttcattatt   64740
ccgttcccga ggctctccta ttggccaagt gcccggcacc agcagacgtc tgcccgcacg   64800
gggtcggtcc gcatggggtc ggtccgcacg cagctgacgc tgaggctcag gtagtctctt   64860
tggtcccact aagcggagga tgcattcaaa aggatgcaaa tttccatcca tttcctgtcc   64920
cccctgcctg ggataagggg cctgttgtgg ctgtgcaagc tggctttctg gtatctaaat   64980
acttctctgg tgaggacaca cctgttcaca tctgcctgca caccacaggc aagctggctt   65040
tctggtatct aaatactcct ctggtgagga cacacctgtt catatcctgc ctgcacacca   65100
caggcaagct ggctttctgg tatctaaata cttctctggt gaggacacac ctgttcacgt   65160
cctgcctgca caccacaggt ggggtttatt gtgtggggct gggatttggc cagccgactt   65220
ctggaactca ttgtttatct ctccatcact gcaacaaata accccagac ccggaaatgc    65280 caccttcgac taaggcctca gtgtggggtc atcaaaaatg gcaagctggc cagccccgag   65340
gtgggtgagg accagtgcag gccttgtcct cttggagtca ggtagggctg ctactggcag   65400
gtggcatgag gtctctaccg cctccgaatg accccgcacc ccttctcctt tcctttctgc   65460
ccctcccttt ttcattcagg atggaggcag aagaggtgct gagtctgaa cccatggctg     65520 ctgcggacga ggagctgggt gatgcttgcc tgggcaccgt atcgctctca tcctgttttc   65580
tcgcctgtga aatgggaatg gcgctcatgc ttctctgtgg gatgctggga aggaacatg    65640 agggcgtcca tggaagtgtt tgaggcatgc ctgctccagg gggaagctcc agaaatgaca   65700
cctatgatct cccagctgtg ttccctttaa gttaacaaac actcgtctgg tctgggctg    65760 gggtacagcg atgaggatga cctggtccga gccccaggaa tgtgggccgt aggaagggca   65820
tgggcatgaa agacgtgctc aggggacccc ttccaggtgt caccaaagag ccctgggttg   65880
tggtgtcggc gggagcaggg caggtgggag gcggtggggg tgggcaaggt ctcggacgcc   65940
agatgcctgg gttcacagcc caggcctgcc tgttaccagc tgtgtgattt cacctttctg   66000
aacctcagct tccccaaatg tgaaatggag tcgatgctga tagcagcttc tcctggggtt   66060
gttgtgaggc tgaaacgagt atttgcacaa tacacaaata cttgatgcct ggcaaaaggt   66120
atctaagtgt gttaaatatg tagctgtgtc tacacatcag ggggccaacc tcactgtgct   66180
gagaggcaaa aatggagaaa aaagggaggt tgccaagatt ttgctcctgg tggccccagg   66240
ctttggagtt tcagagacgg gtgagagagg gagtcggggc agtcaggacc ctggtgtgag   66300
tagcatgctt cgtaaaagtg actgggagaa accttgggac gtccttgtct aaactagact   66360
cctggcctgc ggagagccac gccccacctc cctcagtccc taccattcgc tatctttctg   66420
ggctgcctgt acatcctgct gcagccttcc gagggccacc cggcagggaa accggagctg   66480
caggcaggag gcacaggccg tttcatccac ccggggatgg gagcgagtta caggtgtggc   66540
cattgttcct gagcacaggt ggggataatg catgctgaca gcccaaggat gggcccctgg   66600
cagcctccat cggcctggcc cgagcccag ggcagccctc atgggcaccc aaattacaaa    66660
acgtcctgtg aactctcccc acggtcccgg cctcttcatg tgcttccaac gccggcggct   66720
tggacacacc tgggagcagc cacggcccat tcacgaagca ctttggtgaa ggtcaccaac   66780
tgcagggaca gagcgggtat tgtcaaggac gccagcctag cctttgtgcc ccgccgtctg   66840
```

| | | | | | |
|---|---|---|---|---|---|
| ccccgaccac | aggaattcct | cacactcacc | ctcattcaca | ccaggagggt | gcccactgcc | 66900 |
| actgggggcg | gcctccctcc | ctccctcccc | atgctatttt | caggcaggag | gctggagcct | 66960 |
| cggccaaagg | aacctcaccc | acgattttcc | aaaacctgat | tgccgtggct | gtgtctgtga | 67020 |
| tgggcacaga | cccagggggcc | gggcctgcca | agactctccc | cgtgtgaata | cctgcacagg | 67080 |
| gcacctcctg | tgggaaccgg | gagtcacaca | gagcctggca | tttgtcccca | gcctgtcttg | 67140 |
| tgacattagg | tagatcaaag | ccccattgta | aaaagtcatg | ttgcctctgt | tcatctgctt | 67200 |
| ggagcctgtg | tcctaggacg | gcccttccct | cggctctggc | tcgggaggg | agctgaccgc | 67260 |
| caacacatct | gctcccattt | gggtcctagt | gttcctcctg | gaaggagccc | caccgaaagt | 67320 |
| gaaattgcct | ttcatgggtc | tgaggctggg | gcacaccctg | agaaagaatg | agaaagcatg | 67380 |
| gggcagcgca | gctcctctcc | aaagtcttca | gaggaacaag | ttcctacttg | gctctactac | 67440 |
| ggaacagcaa | gaaggcagag | aaaaatgtca | ctgatgccaa | aatcctggag | gcttcctgaa | 67500 |
| tcggcgatga | ggggtgggga | gttggcagag | gctggggtgg | gggcagcctc | tgtccagcag | 67560 |
| cccccttgggg | catggcaggg | aaggaggtga | tggaaggagg | tgagaagaca | cgaggctttg | 67620 |
| acaatcctga | attgtgagtg | gtggggcgag | gtcagatcct | tccagaggga | cagcttcccc | 67680 |
| ttgactccca | agcctgaccg | ttgtgtgtca | aatgaggggc | agtcaaattg | ctcaaccacc | 67740 |
| tgagtggtag | gtaacttgtg | agctggaggg | atctttaccc | accttacagt | ccttaggtag | 67800 |
| tccattggta | tgggctgcct | ggagcatgtc | tgagatggga | ggaaaatgtg | ccaagatgga | 67860 |
| ttagtaatgt | ctggatggct | gccagtctct | tagtgatggt | gtgtgtgtca | tgtgtttgcc | 67920 |
| atctctggta | tgttagtcag | gataagctag | gttttgctgc | cataacaaat | aaatctccaa | 67980 |
| acctcaattg | cttattgctg | tgagaactta | ttttctctca | ctcaaatccc | aaagtgaagg | 68040 |
| gggtgacttg | ttaggacagc | tgtgctctac | atagtgattc | agggatccag | cctgtttgca | 68100 |
| tctcatgtgc | taatgagggg | tcacatggtg | cttctcatgg | cctcagcctg | gaagtgacac | 68160 |
| acacgtctct | ttttactttt | catcatccag | aactgcttct | gtgcaatctg | atccctgact | 68220 |
| ccctcagaag | gcagcagggg | tccaggaggg | aagaaagtgg | gatgggtctg | tggggcaaag | 68280 |
| aacattatct | ctaccacact | cagacccatc | ctctttgtta | tagaggattg | ggtttctata | 68340 |
| actcaatagg | gatgtgggat | gtggtttcta | gacaagaaag | tgacttgaac | aaagtcaaca | 68400 |
| aggggtgttg | gcaccgttgg | gaccagccta | actaccatgt | aggcattttt | tttgatgtac | 68460 |
| catagtgcca | aattgtctaa | gtcattttt | caatctatct | ctcatctttc | ttgtgaattt | 68520 |
| tgtcatcccc | agaggtgatt | tctcttactg | gaaagtctag | tggagggacc | atgtcccttg | 68580 |
| gcggactctg | ccaatggggtg | cccttcttag | aagcaccgtg | tcctctttgc | tggggtaaag | 68640 |
| ccattcagta | ctggatgact | tgatgaaggt | aaaccatagc | tgcccagggt | cctggacaca | 68700 |
| tgaggcctgc | tcttgattaa | tctatatccc | ttattcccca | aagagaatgg | caaaatcctg | 68760 |
| gagctatgct | catgtttgag | ttctgtattg | gacaggacca | ttttgggtgc | aattggcttg | 68820 |
| tgcatttgtg | tacttgaaaa | gctcagggat | ttcagcttca | ggaatggctg | gattcagaag | 68880 |
| ctcaaatgat | atcagaactc | gatctcactt | tctccatttc | ccgtttctgt | cttcctctga | 68940 |
| gaaggcttta | atccctggat | ccactttgat | tggtgagact | ggggtcgtat | gcccaaccct | 69000 |
| aaaccagcta | ccatggccag | gggaataaga | aacactgatt | gaccaacctg | gatcttgcaa | 69060 |
| acctcctttg | cccctcttga | tcctcctggt | ctgaaaaagg | cttgcactgg | aatggggccc | 69120 |
| tgatgcacaa | gacacggtgc | cccactttgc | tctcacctgt | tgctagtgat | acacgttcca | 69180 |
| gggcttctgt | gctggagagg | tagaagatca | tactgcagaa | gtccagtggg | aggaggtgct | 69240 |

```
cactctgccc aggaaatgga tcatcaggga aggcttcctg gaggagatat gtttaccaga  69300
cagccaaagg ggaatgagga gggcatagca gcagtggaaa cagcaggggc aaaggcagga  69360
gggcaaaaag accaccctaa ccagaggact ctggttgctc agtgtgatgg tgacttgttg  69420
gggtggaggg gagggtagca gggggaggga catacaggac ccaggctgg tgaggctgtc   69480 tggggcctgt tctgaccatg ccttgagatt gggtgagctg ggtgggaacc ctgaggagca  69540
aaagcaaact taaattccaa ggggagaaga atgggatgtg ggctagtgta gacctcagat  69600
ggctgagcag agagtaggtg atgggcattt cttaattgtg accctggggc agagatggat  69660
ctggtgccca aagaggctgg tcaggccagg aagctccttg aaagtcggcc agaggagcta  69720
gggtgtatcc tccccaaatg aagacccact gaagggtttc aagcatgtgg gactgttttc  69780
tgtgtggaca tatcattgag gctgctgtgg tgtatggtat gggttggagg aggcaaggcc  69840
agccggagag aggtaagggg ctagtgctaa tggccgactt catgttcact aagtgcatat  69900
taggctcaga actaggagct gggttttggta gatctgggag ctgggcaca gcgagggatg   69960 aagggagggt ggagggttag aagagtcact aaccccagc tttgagaatt tcagccactc   70020
cgtccgcaga caagatgcat gaaggaagca gacaaggcat gaggtttcac aaatgctctg  70080
cactaatatg cccgccttac agtcatagcc tggttactct ttctttatat aaaattataa  70140
cggatattct aaacttcttt tcctactcta tagtaaatta ggagctcata cattggaaat  70200
ggtgtgtgtg tgtgtgtgtg tgtgtatgag agagagagag attcagggg tgcgagagaa   70260 gggagcaata aaggcagcag ctgagatgga gataaagttc tcctaaagac atcccatgaa  70320
ctcataaagc tcggcatttt gggccactgg tgtaaaggtg atagttttct ataactcagt  70380
cctacagaag aacatcccat tagaagatgg gaacattagc aagtgttggt agttgctcca  70440
tctggccact tcaaggcaag caagtcttct tggctttgcc cagagtatcc acgatgctgg  70500
cacatcctgg tgattgccaa gtgggtgaat gggtgaatgg atgcacgttc caatgacacc  70560
tgcgttcttt gagcaattga tcctgtgggg gaaactgaca tcccagaaga tctgtcgggc  70620
tgctgcctgc ccccaacccc aatgcagtgc cctcgataag gaaagtgagc tccatggctt  70680
ctgtttagga agatggggaa gctgcaatgc aatgaggaaa aaaaaatccc accccaaacg  70740
ggtttgcatt ttaggaagtg ttttgttgtc cctgccaagt gacagtgtgg actcagggtg  70800
ggggaggact ctagacttgg caaaccaggt gtattagtct gttctcacac tgctataaag  70860
atactacctg agactggata atttatgaag aaaagaggtt taattgactc acagttcccc  70920
atggctgggg aggcctcagg aaacttacaa tcatggcaga aggtgaaggg gaggcaaggc  70980
acatcttcac aaggcggcag gagagagagc gcgaggaagg aagtgccaca ttttaaatc   71040 atcagatctc atgagaactt actcaatatc atgagaacaa catggggaa attgccccca   71100 taatccaatc acctcctacc aggttccttc ctaacacatg ggaattataa ttcaagatga  71160
gatttgggtg gggacacagc caaaccatat caccagggga caaggagtgg ttcagagcaa  71220
agctgtcatc gcagcttggg tggccgtagg agatggaaat accccactct gcttaagcct  71280
ctctgatgcc aggcaccctg tgactgcagc caacccactt cttaatccct gggaactgtg  71340
aatacatgac cttacatggc aaaagggact ttgcagttgt gataaagtga aggatcttga  71400
cacgggagag gaccctgggt tgggagggtg ccctccctt atgagaggga ggaaggggga   71460
gttggagcca gaggagatgt gcagatggga gcagggcttg gagagctgta ctttgaagaa  71520
cgagggagag ggccaccagt gcagagggag gggggcca ccagcgcaga gggagggaga    71580
ggccaccagc acagggattt gggtgacctc taaaagcaga aagacaagaa caagaattct  71640
```

-continued

```
ccttgagggc ctccagaagg aacatgactc cattgaggac ttctgacctc caggattctg    71700
ggatcaataa atgtgtgctg tttagaagct gctaagtatg tggtcattta ttacagcagc    71760
aattggaaac aagtatacaa gtcccagcta acacacctgc cacattccca agtgagaggc    71820
agagcctggt aatggaaggg cccagtggtt tgggtcctgg gtctgccccg gctcaagtgc    71880
cctgggtgct gctcacccct ggacatcatg ctcctttcat ccaccgggag ctctgcttct    71940
ctcttccttg gatacctgcc attcactcac tcacgacttt ttcattcccc tattaaggcc    72000
accgagtgca gggatgcagg aatggaggaa aagaagagga ccaaaacctg ctggtcccag    72060
gtcccctgcc tcttccttct ggtgggaggg cctgggggtg caaacccaat gctgggcctc    72120
cagctcccca gcacacagct gcatatgaga ggctcctgca gacaggtgcc gtcatgggct    72180
gaattgtgtt ccccaaaatt tatgtgttgc agctctaacc ctcaaaacct ctgcatatga    72240
ctgcatttgg agatagggct ttaaagaggc aattaagttt aaatgaggtc gttagggtgg    72300
actcgtgtct ttataagaaa aggagattag gacacacaca gagggattga gagcagactg    72360
gcccctgtga ggactctgag ggacagagcc ctgttcctgg agcctctgca tgccctggga    72420
agtgtgggga gtaggcaggg cccccagcca aggctgaggc tgtccctcct aggcttcctg    72480
ccttgcaaag ccagagtcac cctgcgggtc cttgactcac tctgtagagc cccttcctac    72540
cttggccaag ctttgtctgg gctagcatca gtgagaagat acttgggaag agtttttacc    72600
cactaagggc agcttaggag gaaggaaagg cagaggtaga gtgagcactg ggggtttgag    72660
tcacaggcag gcacaggagg aggccaccag agttccatct ttgtgacgca gcaccatgga    72720
gttcctgtgt tggtctctga gtctttgccc atgttattcc ctctacctgg aaggcttgcc    72780
ccttctctgg gccagctcgg atcctcctca tcaagacagg aagagagtag ggactactgt    72840
ctgccagatc tctgcccaca ccattggcac cttgtccaca aagcactcct gtgaccgccc    72900
agtgccttcc tcaagccatg cacctgggct catgggacc actcatgccc aggggatggg    72960
agtagagcct tattttaga cccagggttg atttcgtgag actttctggg aaagtattta    73020
ttgaaagggg aagtcctaag agattagaaa tttacccagt aattgacgaa tctgatactt    73080
agagaaaaac cccctttccca caagggctt gtatctgctg accctgcaca cttgtctgtt    73140
cctggcattc actgtttatc tgctgtgaat tagaaacaaa acaaaacaaa aaagacagct    73200
attagcatgc aaaccccagg agaactggcc ccctgtgatt tgcatgagaa caaaagctct    73260
ttccaatgtc ctggggctca agtcttcagg atagccttaa cttccaaacc aggcagggct    73320
tcaaagccgg aactggggaa ctcc                                          73344
```